(12) United States Patent
Chen et al.

(10) Patent No.: US 6,600,015 B2
(45) Date of Patent: Jul. 29, 2003

(54) SELECTIVE LINEAR PEPTIDES WITH MELANOCORTIN-4 RECEPTOR (MC4-R) AGONIST ACTIVITY

(75) Inventors: Li Chen, Westfield, NJ (US); Adrian Wai-Hing Cheung, Glen Rock, NJ (US); Xin-Jie Chu, Livingston, NJ (US); Waleed Danho, Wayne, NJ (US); Joseph Swistok, Nutley, NJ (US); Keith Alan Yagaloff, HoHokus, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/811,964

(22) Filed: Mar. 19, 2001

(65) Prior Publication Data

US 2001/0056179 A1 Dec. 27, 2001

Related U.S. Application Data

(60) Provisional application No. 60/194,450, filed on Apr. 4, 2000.

(51) Int. Cl.[7] ................................................. C07K 5/08
(52) U.S. Cl. .......................... 530/331; 530/330; 514/18
(58) Field of Search ................................. 530/330, 331; 514/17, 18

(56) References Cited

FOREIGN PATENT DOCUMENTS

| WO | WO 99 64002 | 12/1999 |
|----|-------------|---------|

OTHER PUBLICATIONS

Bednarek M A, et al., *Biochemical and Biophysical Research Communications, Academic Press Inc.*, vol. 261, No. 1, pp. 209–213 (1999).
Adan E.A., *European Journal of Pharmacology*, vol. 378, pp. 249–258 (1999).
Fan et al., *Nature*, vol. 385, pp. 165–168 (1997).
Cone et al., *Rec. Prog. Hormone Research*, vol. 51, pp. 287–318 (1996).
Haskell–Luevano et al., *Peptides*, vol. 17, No. 6, pp. 995–1002 (1996).
R. B. Merrifield, *J. Amer. Chem. Soc.*, vol. 85, pp. 2149–2154 (1963).
Barany et al., *The Peptides, Analysis, Synthesis and Biology*, vol. 2, E. Gross and J. Meienhofer, Eds. Academic Press, pp. 1–284 (1980).
Kaiser et al., *Anal. Biochem.*, 34, pp. 595–598 (1970).
Obrecht et al., *Helv. Chim. Acta*, vol. 75, pp. 1666–1696 (1992).
Freeman et al., *J. Org. Chem.*, vol. 54, pp. 782–789 (1989).

*Primary Examiner*—Christopher S.F. Low
*Assistant Examiner*—David Lukton
(74) *Attorney, Agent, or Firm*—George W. Johnston; Dennis P. Tramaloni; Eileen M. Ebel

(57) ABSTRACT

Peptides that selectively stimulate melanocortin-4 (MC-4) receptor activity are disclosed. In one embodiment, the peptides are of formula I:

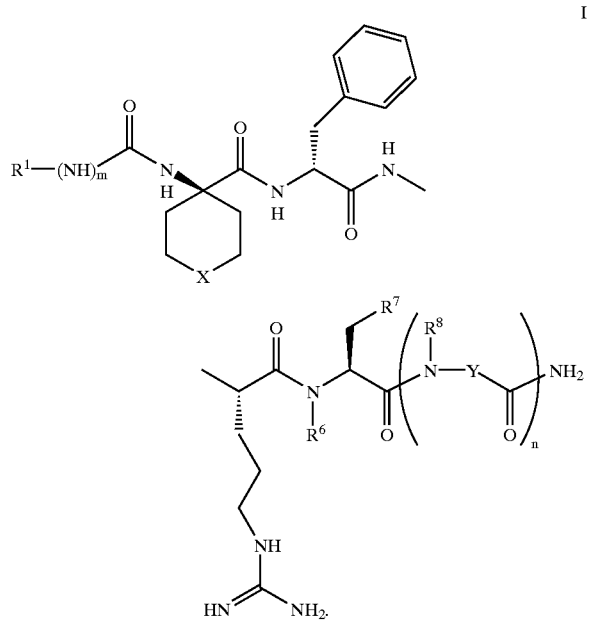

117 Claims, No Drawings

SELECTIVE LINEAR PEPTIDES WITH MELANOCORTIN-4 RECEPTOR (MC4-R) AGONIST ACTIVITY

PRIORITY TO PROVISIONAL APPLICATION(S) UNDER 35 U.S.C. §119(e)

This application claims priority under 35 U.S.C. §119(e) of provisional application(s) Ser. No. 60/194,450, filed Apr. 4, 2000.

BACKGROUND OF THE INVENTION

Obesity is widely recognized as a serious health problem for the developed countries, and has reached epidemic status in the United States. More than 50% of the U.S. population is considered overweight, with >25% diagnosed as clinically obese and at considerable risk for heart disease, non-insulin dependent diabetes mellitus (NIDDM), hypertension, and certain cancers. This epidemic presents a significant burden on the health care system as projected obesity treatment costs of more than $70 billion annually are expected in the U.S. alone. Strategies for treating obesity include reducing food intake or enhancing the expenditure of energy.

It has been demonstrated that, when injected into the third ventricle of the brain or intraperitoneally, a cyclic heptapeptide analog of α-melanocyte stimulating hormone (αMSH) having melanocortin-4 receptor (MC4-R) agonist activity caused long lasting inhibition of food intake in mice. This effect was reversible when co-administered with a MC4-R antagonist. (Fan, et al., Nature (1997) 385: 165–168) Therefore, agonists of MC4-R activity would be useful in treating or preventing obesity.

There are five known melanocortin receptors based on sequence homology that ranges from 35–60% homology between family members ((Cone, et al., Rec. Prog. Hormone Res. (1996) 51: 287–318), but these receptors differ in their functions. For example, the MC1-R is a G-protein coupled receptor that regulates pigmentation in response to the αMSH, which is a potent agonist of MC1-R. (Cone, et al., ibid.). Agonism of the MC1-R receptor results in stimulation of the melanocytes which causes eumelanin and increases the risk for cancer of the skin. Agonism of MC1-R can also have neurological effects. Stimulation of MC2-R activity can result in carcinoma of adrenal tissue. The effects of agonism of the MC3-R and MC5-R are not yet known. All of the melanocortin receptors respond to the peptide hormone class of melanocyte stimulating hormones (MSH). These peptides are derived from pro-opiomelanocortin (POMC), a prohormone of 131 amino acids that is processed into three classes of hormones; the melanocortins (α, β and γ), adrenocorticotropin hormone (ACTH), and various endorphins (e.g. lipotropin) (Cone, et al., ibid.). Because of their different functions, simultaneous agonism of the activities of multiple melanocortin receptors has the potential of causing unwanted side effects. Therefore it is desirable that an agonist of MC4-R be more selective for the MC4-R than for one or more of the other melanocortin receptors.

Haskell-Luevano, et al. (Peptides (1996) 17(6): 995–1002) disclose peptides that contain the tripeptide (D)Phe-Arg-Trp and exhibit melanotropic (skin darkening) activity in the frog (*Rana pipiens*) skin bioassay. Haskell-Luevano, et al. (ibid.) do not disclose any compound of formula I, II or III described below.

SUMMARY OF THE INVENTION

This invention provides a compound of the formula:

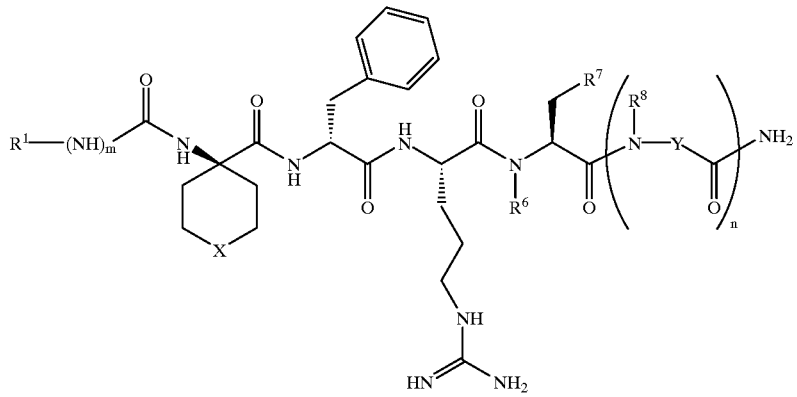

I

In compounds of formula I m is 0 or 1. n is 0 or 1. $R^1$ is an unsubstituted linear or branched alkyl having from 1 to 8 carbon atoms; linear or branched alkyl having from 1 to 8 carbon atoms mono-substituted by phenyl or carboxyl; unsubstituted phenyl; or phenyl mono-substituted by fluoro, chloro or linear or branched alkyl having from 1 to 4 carbon atoms. X is

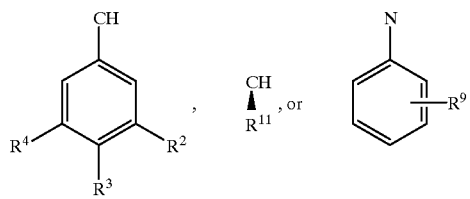

$R^2$, $R^3$ and $R^4$ are independently hydrogen or a linear or branched alkoxy having from 1 to 4 carbon atoms, wherein when $R^3$ is alkoxy, $R^2$ and $R^4$ are both hydrogen. $R^9$ is hydrogen, linear or branched alkyl having from 1 to 3 carbons, linear or branched alkoxy having from 1 to 3 carbons, or unsubstituted phenoxy. $R^{11}$ is cyclohexyl, cycloheptyl, or a branched alkyl having from 3 to 8 carbon atoms. $R^6$ is hydrogen or methyl. $R^7$ is

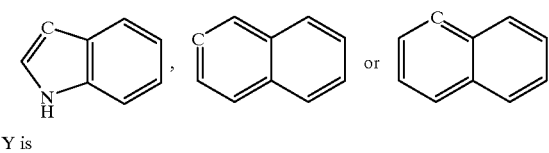

Y is

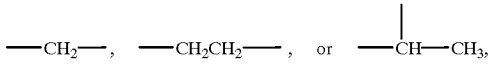

and R⁸ is hydrogen or methyl; or
Y is

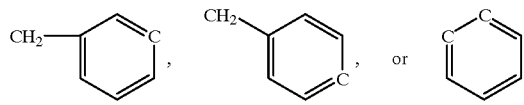

and R⁸ is hydrogen.

This invention provides a compound of the formula:

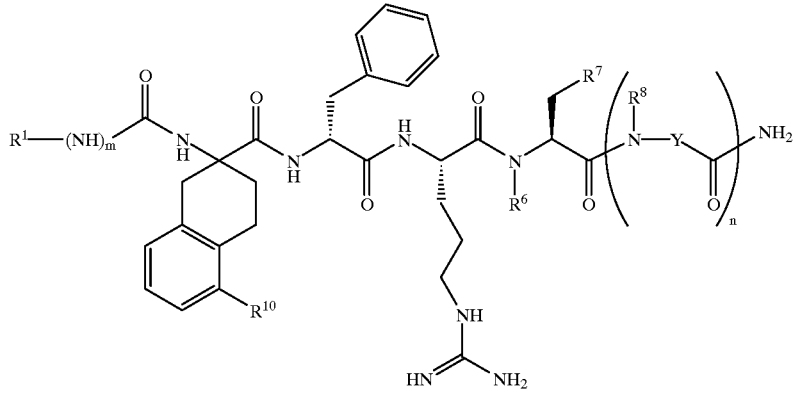

In the compounds of formula II m is 0 or 1. n is 0 or 1. $R^1$ is an unsubstituted linear or branched alkyl having from 4 to 8 carbon atoms; linear or branched alkyl having from 1 to 8 carbon atoms mono-substituted by phenyl or carboxyl; or unsubstituted phenyl; or phenyl mono-substituted by fluoro, chloro or linear or branched alkyl having from 1 to 4 carbon atoms. $R^7$ is

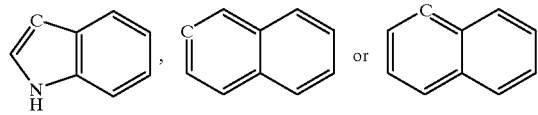

Y is

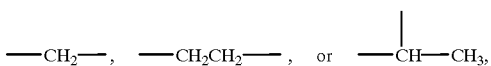

and $R^8$ is hydrogen or methyl; or

Y is

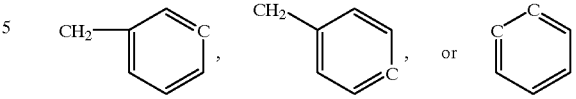

and $R^8$ is hydrogen.

$R^{10}$ is hydrogen, halo, linear or branched alkyl having from 1 to 3 carbon atoms, linear or branched alkoxy having from 1 to 3 carbon atoms, or $-NR^{12}N^{13}$ wherein $R^{12}$ and $R^{13}$ are each independently a linear or branched alkyl having from 1 to 3 carbons or together are $-(CH_2)_q-$ wherein q is 3, 4 or 5.

This invention provides a compound of the formula:

III

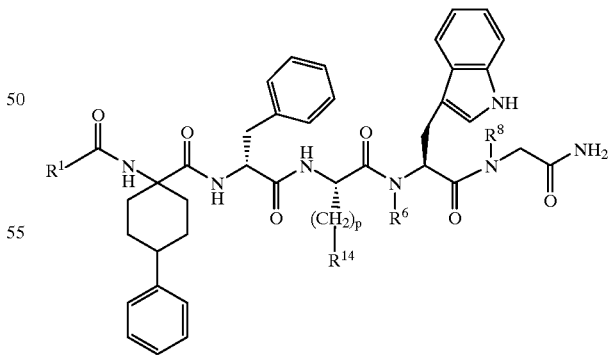

In the compounds of formula III, $R^1$ is unsubstituted linear or branched alkyl having from 4 to 8 carbon atoms. $R^6$ is hydrogen or methyl. $R^8$ is hydrogen or methyl. p is 2, 3 or 4 and $R^{14}$ is

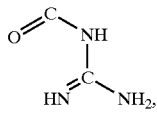

or p is 4 and $R^{14}$ is

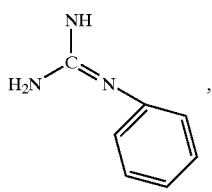

or p is 3 and $R^{14}$ is

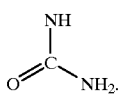

The compounds of formulae I, II and III as well as Penta-Adpc-(D)Phe-Arg-Trp-Gly-NH$_2$ and Penta-Ape-(D)Phe-Arg-Trp-Gly-NH$_2$ are agonists of the MC4-R. It is known that agonists of MC4-R activity cause reduction of food intake in a mouse model of human obesity. Therefore the compounds of formula I are useful in the treatment or prevention of obesity.

All of the compounds of formulae I, II and III exemplified below as well as Penta-Adpc-(D)Phe-Arg-Trp-Gly-NH$_2$ and Penta-Ape-(D)Phe-Arg-Trp-Gly-NH$_2$ were tested for MC4-R agonist activity and MC1-R agonist activity in the in vitro assay described below in Biological Activity Example A. All of the tested compounds had an EC50 for MC4-R agonist activity of less than 500 nM, and all exhibited at least 10-fold greater MC4-R agonist activity than MC1-R agonist activity. In contrast, the compound Bu-His-(D)Phe-Arg-Trp-Gly-NH$_2$ (Example 30) exhibited greater MC1-R agonist activity than MC4-R agonist activity.

DETAILED DESCRIPTION OF THE INVENTION

Nomenclature and Abbreviations

The nomenclature used to define the peptides is that typically used in the art wherein the amino group at the N-terminus appears to the left and the carboxyl group at the C-terminus appears to the right. By natural amino acids is meant one of the naturally occurring amino acids found in proteins, i.e., Gly, Ala, Val, Leu, Ile, Ser, Thr, Lys, Arg, Asp, Asn, Glu, Gln, Cys, Met, Phe, Tyr, Pro, Trp, and His. Where the amino acid has isomeric forms, it is the L form of the amino acid that is represented unless otherwise explicitly indicated.

The following abbreviations or symbols are used to represent amino acids, protecting groups, solvents, reagents and the like.

| Symbol | Meaning |
| --- | --- |
| β-Ala | beta-Alanine |
| (2)-Nal | (2)-Naphthylalanine |
| Atc | 2-Aminotetraline-2-carboxylic acid |
| 5-BrAtc | 5-Bromo-2-aminotetraline-2-carboxylic acid |
| 5-ClAtc | 5-Chloro-2-aminotetraline-2-carboxylic acid |
| 5-MeOAtc | 5-Methoxy-2-aminotetraline-2-carboxylic acid |
| 5-EtOAtc | 5-Ethoxy-2-aminotetraline-2-carboxylic acid |
| 5-iPrOAtc | 5-Isopropoxy-2-aminotetraline-2-carboxylic acid |
| 5-MeAtc | 5-Methyl-2-aminotetraline-2-carboxylic acid |
| 5-EtAtc | 5-Ethyl-2-aminotetraline-2-carboxylic acid |
| 5-iPrAtc | 5-Isopropyl-2-aminotetraline-2-carboxylic acid |
| 5-DmaAtc | 5-Dimethylamino-2-aminotetraline-2-carboxylic acid |
| Sar | Sarcosine (N-methylglycine) |
| Cit | Citrulline |
| Apc | 1-Amino-4-phenylcyclohexane-1-carboxylic acid |
| 4-HOApc | 1-Amino-4-(4-hydroxyphenyl)cyclohexane-1-carboxylic acid |
| 4-MeOApc | 1-Amino-4-(4-methoxyphenyl)cyclohexane-1-carboxylic acid |
| 3-MeOApc | 1-Amino-4-(4-methoxyphenyl)cyclohexane-1-carboxylic acid |
| 4-EtOApc | 1-Amino-4-(4-ethoxyphenyl)cyclohexane-1-carboxylic acid |
| 4-iPrOApc | 1-Amino-4-(4-isopropoxyphenyl)cyclohexane-1-carboxylic acid |
| 4-MeApc | 1-Amino-4-(4-methylphenyl)cyclohexane-1-carboxylic acid |
| 4-ClApc | 1-Amino-4-(4-chlorophenyl)cyclohexane-1-carboxylic acid |
| Appc | 4-Amino-1-phenylpiperidine-4-carboxylic acid |
| 2-MeAppc | 4-Amino-1-(2-methylphenyl)piperidine-4-carboxylic acid |
| 2-iProAppc | 4-Amino-1-(2-isopropoxyphenyl)piperidine-4-carboxylic acid |
| 3-MeAppc | 4-Amino-1-(3-methylphenyl)piperidine-4-carboxylic acid |
| 3-MeOAppc | 4-Amino-1-(3-methoxyphenyl)piperidine-4-carboxylic acid |
| 4-MeAppc | 4-Amino-1-(4-methylphenyl)piperidine-4-carboxylic acid |
| 4-ClAppc | 4-Amino-1-(4-chlorophenyl)piperidine-4-carboxylic acid |
| 4-PhOAppc | 4-Amino-1-(4-phenoxyphenyl)piperidine-4-carboxylic acid |
| Achc | 1-Amino-4-cyclohexylcyclohexane-1-carboxylic acid |
| Adpc | 1-Amino-4-diphenylcyclohexane-1-carboxylic acid |
| Ape | 1-Amino-4-phenylcyclohex-3-ene-1-carboxylic acid |
| Abc | 1-Amino-4-tert-butylcyclohexane-1-carboxylic acid |
| 3-Amb | 3-Aminomethyl benzoic acid |
| 4-Amb | 4-Aminomethyl benzoic acid |
| 2-Aba | 2-Aminobenzoic acid |
| Bu | Butyl |
| Penta | Pentyl |
| Fmoc | 9-Fluorenylmethoxycarbonyl |
| Pmc | 2,2,5,7,8-Pentamethylchroman-6-sulfonyl |
| CH$_2$Cl$_2$ | Methylene chloride |
| CH$_3$CN | Acetonitrile |
| DMF | Dimethylformamide |
| DIPEA | N,N-Diisopropylethylamine |
| TFA | Trifluoroacetic acid |
| HOBT | N-Hydroxybenzotriazole |
| DIC | N,N'-Diisopropylcarbodiimide |
| BOP | Benzotriazol-1-yloxy-tris-(dimethylamino)phosphonium Hexafluorophosphate |
| PyBroP | Bromo-tris-pyrrolidino-phosphonium hexafluorophosphate |
| HBTU | 2-(1H-Benzotriazol-1-yl)-1,1,3,3-tetramethyluronium Hexafluorophosphate |
| FAB-MS | Fast atom bombardment mass spectrometry |
| ES-MS | Electrospray mass spectrometry |
| NBSC | 2-Nitrobenzenesulfonyl chloride |
| DEAD | N,N-diethylazodicarboxylate |
| Ph | Phenyl |

Setting forth the substituted amino acid, in parentheses indicates analogs of the peptide sequence. Derivatization of the N-terminal amino group, is indicated to the left of the N-terminal substitution, separated by a hyphen. That is, for example, Ac-His-(D)Phe-Arg-Trp-Gly-NH$_2$ indicates a peptide having an amino acid sequence in which an acetyl group has been substituted for hydrogen at the N-terminus. The suffixes "—OH" and "—NH$_2$" following the hyphen or the parentheses refer to the free acid and amide forms of the polypeptide, respectively.

DETAILED DESCRIPTION OF COMPOUNDS

In compounds of formula I, it is generally preferred that $R^6$ and $R^8$ are both hydrogen, n is 1 and $R^7$ is either the first or the second of the substructures shown above. Also preferred are compounds of formuae IA, IB or IC as shown below.

Compounds of formula IA, are represented as follows:

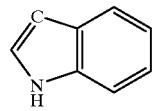

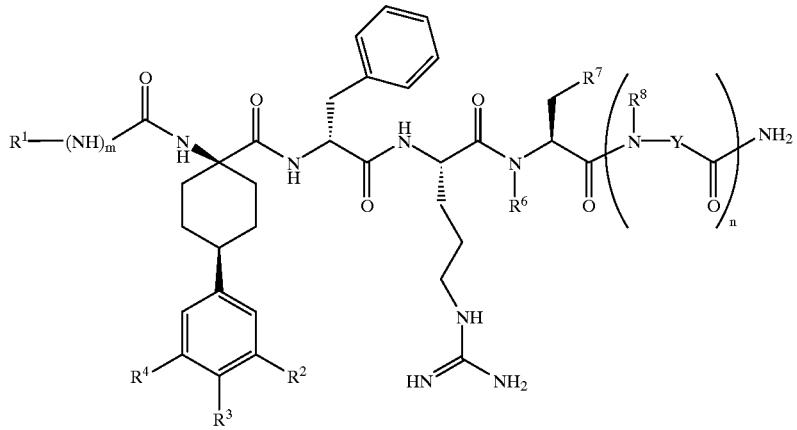

IA

In the compound of formula IA, m is 0 or 1. n is 0 or 1. $R^1$ is an unsubstituted linear or branched alkyl having from 1 to 8 carbon atoms; linear or branched alkyl having from 1 to 8 carbon atoms mono-substituted by phenyl or carboxyl; unsubstituted phenyl; or phenyl mono-substituted by fluoro, chloro or linear or branched alkyl having from 1 to 4 carbon atoms. $R^2$, $R^3$ and $R^4$ are independently hydrogen; a linear or branched alkyl having from 1 to 4 carbon atoms; hydroxy, a linear or branched alkoxy having from 1 to 4 carbon atoms; or chloro, wherein when $R^3$ is alkyl, hydroxy, alkoxy or chloro, $R^2$ and $R^4$ are both hydrogen. $R^6$ is hydrogen or methyl. $R^7$ is

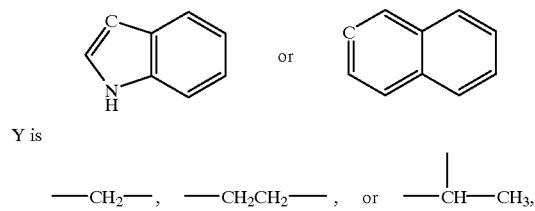

Y is

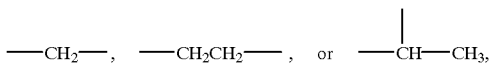

and $R^8$ is hydrogen or methyl; or
Y is

$R^8$ is hydrogen.

In the compounds of formula IA, $R^7$ can be either a tryptophan side chain or a 1- or 2-naphthyl group. In compounds of formula IA in which $R^7$ is a tryptophan side chain, i.e.

n can be either 0 or 1. Examples of such compounds in which n is 0 include Penta-Apc-(D)Phe-Arg-Trp-NH$_2$ and Penta-Apc-(D)Phe-Arg-N-methylTrp-NH$_2$. In compounds of formula IA in which $R^7$ is a tryptophan side chain and n is 1, Y can be a linear or branched alkyl group selected from methylene, ethylene or methyl-substituted methylene, i.e.

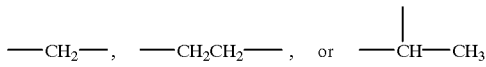

or one of the aryl-containing moieties shown above. In compounds of formula IA in which $R^7$ is a tryptophan side chain and n is 1, Y is methylene, ethylene or methyl-substituted methylene, m can be 0 or 1. Examples of such compounds in which m is 1 include Bu-Carbamoyl-Apc-(D)Phe-Arg-Trp-Gly-NH$_2$, Bu-carbamoyl-Apc-(D)Phe-Arg-Trp-Ala-NH$_2$, and Bu-Carbamoyl-Apc-(D)Phe-Arg-Trp-β-Ala-NH$_2$. In compounds of formula IA in which $R^7$ is a tryptophan side chain, n is 1, Y is methylene, ethylene or methyl-substituted methylene and m is 0, the phenyl ring of the Apc group can be either unsubstituted (i.e. $R^2$, $R^3$ and $R^4$ are hydrogen) or substituted. In such compounds in which the phenyl ring of the Apc group is unsubstituted, $R^1$ can be, for example, an unsubstituted linear alkyl such as in the compounds Penta-Apc-(D)Phe-Arg-Trp-Gly-NH$_2$, Penta-Apc-(D)Phe-Arg-Trp-Sar-NH$_2$, Penta-Apc-(D)Phe-Arg-N-methylTrp-Gly-NH$_2$, Bu-Apc-(D)Phe-Arg-Trp-Ala-NH$_2$, or Bu-Apc-(D)Phe-Arg-Trp-β-Ala-NH$_2$; or unsubstituted phenyl such as in the compounds Phenylacetyl-Apc-(D)Phe-Arg-Trp-Gly-NH$_2$, Phenylacetyl-Apc-(D)Phe-Arg-Trp-Ala-NH$_2$, or Phenylacetyl-Apc-(D)Phe-Arg-Trp-Ala-NH$_2$. In such compounds in which the phenyl ring of the Apc group is substituted, one preferred substitution pattern is wherein $R^3$ is alkyl, hydroxy, alkoxy or chloro (more preferably $R^3$ is hydroxy or alkoxy) and $R^2$ and $R^4$ are hydrogen. Examples include Penta-4-ClApc-(D)Phe-Arg-Trp-Gly-NH$_2$, Penta-4-MeApc-(D)Phe-Arg-Trp-Gly-NH$_2$, Penta-4-HOApc-(D)Phe-Arg-Trp-Gly-NH$_2$, Penta-4-MeOApc-(D)

Phe-Arg-Trp-Gly-NH$_2$, Penta-4-EtOApc-(D)Phe-Arg-Trp-Gly-NH$_2$, and Penta-4-iPrOApc-(D)Phe-Arg-Trp-Gly-NH$_2$. Another preferred substitution pattern is wherein R$^2$ is alkoxy, R$^3$ is hydrogen and R$^4$ is hydrogen, for example in the compound Penta-3-MeOApc-(D)Phe-Arg-Trp-Gly-NH$_2$. In compounds of formula IA in which R$^7$ is a tryptophan side chain and n is 1, and Y is

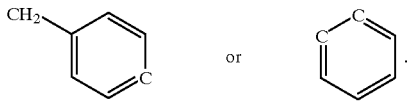

m can be 0 or 1. Examples of such compounds in which m is 1 include Bu-carbamoyl-Apc-(D)Phe-Arg-Trp-2-Aba-NH$_2$ and Bu-carbamoyl-Apc-(D)Phe-Arg-Trp-3-Amb-NH$_2$. Examples of such compounds in which m is 0 include Bu-Apc-(D)Phe-Arg-Trp-2-Aba-NH$_2$, Phenylacetyl-Apc-(D)Phe-Arg-Trp-2-Aba-NH$_2$, Bu-Apc-(D)Phe-Arg-Trp-3-Amb-NH$_2$, Phenylacetyl-Apc-(D)Phe-Arg-Trp-3-Amb-NH$_2$, Bu-Apc-(D)Phe-Arg-Trp-4-Amb-NH$_2$, and Phenylacetyl-Apc-(D)Phe-Arg-Trp-4-Amb-NH$_2$.

In compounds of formula IA in which R$^7$ is 2-naphthyl, i.e.

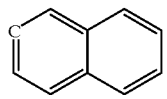

it is preferred that R$^2$, R$^3$ and R$^4$ are hydrogen. Examples of such compounds include Penta-Apc-(D)Phe-Arg-N-methyl (2)Nal-NH$_2$ and Bu-Carbamoyl-Apc-(D)Phe-Arg-(2)Nal-Gly-NH$_2$. In compounds of formula IA in which R$^7$ is 2-naphthyl, it is preferred that n is 1 and m is 0. In compounds of formula IA in which R$^7$ is 2-naphthyl, n is 1 and m is 0, and Y is methylene, ethylene or methyl-substituted methylene, R$^1$ can be, for example an unsubstituted linear alkyl. Examples of such compounds include, Penta-Apc-(D)Phe-Arg-(2)Nal-Gly-NH$_2$, Bu-Apc-(D)Phe-Arg-(2)Nal-Gly-NH$_2$, Ac-Apc-(D)Phe-Arg-(2)Nal-Gly-NH$_2$, Penta-Apc-(D)Phe-Arg-N-methyl (2)Nal-Gly-NH$_2$, Bu-Apc-(D)Phe-Arg-(2)Nal-Ala-NH$_2$, and Bu-Apc-(D)Phe-Arg-(2)Nal-beta-Ala-NH$_2$. Alternatively R$^1$ can be, for example, unsubstituted phenyl, or alkyl substituted by phenyl or carboxyl. Examples of such compounds include Benzoyl-Apc-(D)Phe-Arg-(2)Nal-Gly-NH$_2$, 3-carboxylpropanoyl-Apc-(D)Phe-Arg-(2)Nal-Gly-NH$_2$, and 3-carboxylpropanoyl-Apc-(D)Phe-Arg-(2)Nal-Gly-NH$_2$. In compounds of formula IA in which R$^7$ is 2-naphthyl, n is 1 and m is 0, and Y is

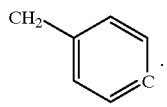

It is preferred that R$^1$ is unsubstituted lower alkyl. Examples of such compounds include Bu-Apc-(D)Phe-Arg-(2)Nal-3-Amb-NH$_2$, Bu-Apc-(D)Phe-Arg-(2)Nal-2-Aba-NH$_2$, and Bu-Apc-(D)Phe-Arg-(2)Nal-4-Amb-NH$_2$.

Compounds of formula IB are represented as follows:

IB

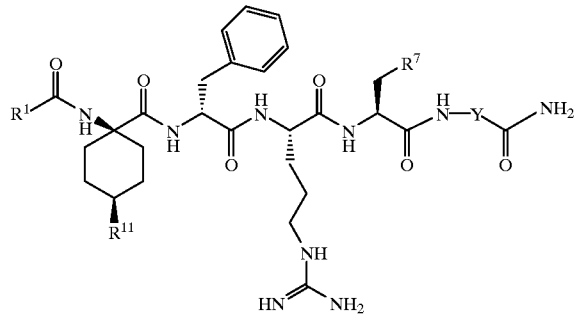

In the compound of formula IB, R$^1$ is an unsubstituted linear or branched alkyl having from 1 to 8 carbon atoms. R$^7$ is

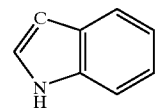

R$^{11}$ is cyclohexyl, or a branched alkyl having from 3 to 8 carbon atoms. Y is methylene, i.e. —CH$_2$—. Examples of compounds of formula IB include Penta-Abc-(D)Phe-Arg-Trp-Gly-NH$_2$ and Penta-Achc-(D)Phe-Arg-Trp-Gly-NH$_2$.

Compounds of formula IC are represented as follows:

IC

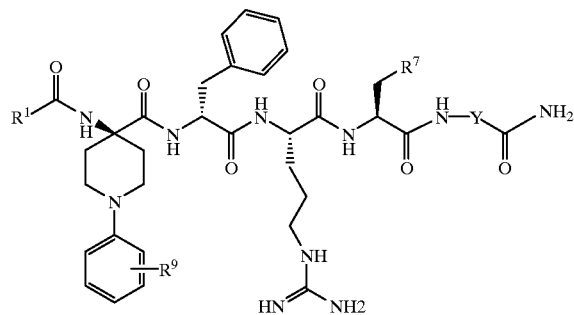

In the compound of formula IC, R$^1$ is an unsubstituted linear or branched alkyl having from 1 to 8 carbon atoms. R$^7$ is

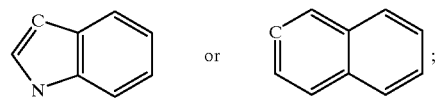

Y is

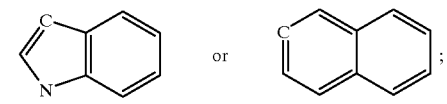

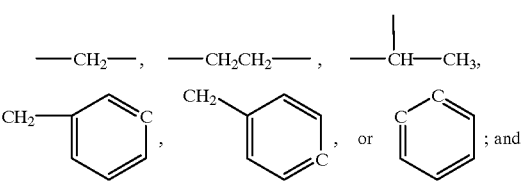

R$^9$ is hydrogen, a linear or branched alkyl having from 1 to 3 carbon atoms, a linear or branched alkoxy having from 1 to 3 carbon atoms, fluoro, chloro, or unsubstituted phenoxy. Examples of compounds of formula IC in which R$^9$ is hydrogen include Penta-Appc-(D)Phe-Arg-Trp-Gly-NH$_2$ and Penta-Appc-(D)Phe-Arg-(2)Nal-Gly-NH$_2$. Examples of compounds of formula IC in which R$^9$ is a linear or branched alkyl having from 1 to 3 carbon atoms include Penta-2-MeAppc-(D)Phe-Arg-Trp-Gly-NH$_2$, Penta-2-iPrAppc-(D) Phe-Arg-Trp-Gly-NH$_2$, Penta-3-MeAppc-(D)Phe-Arg-Trp-Gly-NH$_2$ and Penta-4-MeAppc-(D)Phe-Arg-Trp-Gly-NH$_2$. Examples of compounds of formula IC in which R$^9$ is a linear or branched alkoxy having from 1 to 3 carbon atoms or unsubstituted phenoxy include Penta-3-MeOAppc-(D) Phe-Arg-Trp-Gly-NH$_2$ and Penta-4-PhOAppc-(D)Phe-Arg-Trp-Gly-NH$_2$. Examples of compounds of formula IC in which R$^9$ is chloro include Penta-4-ClAppc-(D)Phe-Arg-Trp-Gly-NH$_2$.

In the compound of formula II it is generally preferred that R$^6$ and R$^8$ are hydrogen. R$^7$ can be, for example a tryptophan side chain, i.e.

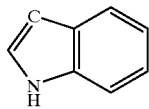

or 2-naphthyl. When R$^7$ is a tryptophan side chain it is generally preferred that n is 1. Among the compounds of formula II in which R$^6$ and R$^8$ are hydrogen; R$^7$ is a tryptophan side chain, and n is 1, are included compounds in which Y is —CH$_2$— and m is 0. Examples of such compounds in which R$^{10}$ is hydrogen or a linear or branched alkyl having from 1 to 3 carbon atoms are included Bu-Atc-(D)Phe-Arg-Trp-Gly-NH$_2$, Penta-5-Me-(D,L)Atc-(D)Phe-Arg-Trp-Gly —NH$_2$, Penta-5-Et-(D,L)Atc-(D)Phe-Arg-Trp-Gly -NH$_2$ and Penta-5-iPr-(D,L)Atc-(D)Phe-Arg-Trp-Gly-NH$_2$. Examples of such compounds in which R$^{10}$ is halo include Penta-5-Br-(D,L)Atc-(D)Phe-Arg-Trp-Gly-NH$_2$, Penta-5-Br-Atc-(D)Phe-Arg-Trp-Gly-NH$_2$ and Penta-5-Cl-(D,L)Atc-(D)Phe-Arg-Trp-Gly-NH$_2$. Examples of such compounds in which R$^{10}$ is linear or branched alkoxy having from 1 to 3 carbon atoms include Penta-5-MeO-(D,L)Atc-(D)Phe-Arg-Trp-Gly —NH$_2$, Penta-5-EtO-(D,L)Atc-(D) Phe-Arg-Trp-Gly —NH$_2$ and Penta-5-iPrO-(D,L)Atc-(D) Phe-Arg-Trp-Gly-NH$_2$. Examples of such compounds in which R$^{10}$ is —NR$^{12}$R$^{13}$ wherein R$^2$ and R$^{13}$ are each methyl include Penta-5-DmaAtc-(D)Phe-Arg-Trp-Gly-NH$_2$.

Among the compounds of formula II in which R$^6$ and R$^8$ are hydrogen; R$^7$ is a tryptophan side chain, and n is 1, are included compounds in which Y is

and R$^{10}$ is halo. Examples of such compounds include Bu-(D,L)5-BrAtc-(D)Phe-Arg-Trp-2-Aba-NH$_2$, Bu-carbamoyl-(D,L)-5-BrAtc-(D)Phe-Arg-Trp-2-Aba-NH$_2$ and Phenylacetyl-(D,L)-5-BrAtc-(D)Phe-Arg-Trp-2-Aba-NH$_2$.

In compounds of formula II in which wherein R$^6$ and R$^8$ are hydrogen; R$^7$ is 2-naphthyl i.e.

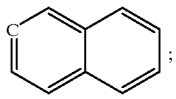

it is generally preferred that R$^{10}$ is halo. Examples of such compounds include Penta-(D,L)-5-BrAtc-(D)Phe-Arg-(2) Nal-Gly-NH$_2$, 3-carboxylpropanoyl-(D,L)-5-BrAtc-(D) Phe-Arg-(2)Nal-Gly-NH$_2$, Phenylacetyl-(D,L)-5-BrAtc-(D) Phe-Arg-(2)Nal-Gly-NH$_2$ and Bu-(D,L)-5-BrAtc-(D)Phe-Arg-(2)Nal-2-Aba-NH$_2$.

Examples of compounds of formula III include Bu-Apc-(D)Phe-PhenylhomoArg-Trp-Gly-NH$_2$, Penta-Apc-(D)Phe-Cit-Trp-Gly-NH$_2$, Penta-Adpc-(D)Phe-Arg-Trp-Gly-NH$_2$ and Penta-Ape-(D)Phe-Arg-Tip-Gly-NH$_2$.

Chemical Synthesis

The compounds of this invention can be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected.

The synthesis of these compounds may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods [Merrifield, R. B., J. Amer. Chem. Soc. 1963, 85, 2149–2154; Barany et al., The Peptides, Analysis, Synthesis and Biology, Vol. 2, Gross, E. and Meienhofer, J., Eds. Academic Press 1–284 (1980)].

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group of an amino acid or fragment while that entity reacts at the carboxyl group, followed by the selective removal of the alpha amino protecting group and allow a subsequent reaction to take place at that site. While specific protecting groups are mentioned below in regard to the solid phase synthesis method, it should be noted that each amino acid can be protected by any protective group conventionally used for the respective amino acid in solution phase synthesis.

For example, alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc)

and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Herein, Fmoc is the most preferred for alpha amino protection.

Guanidino groups may be protected by a suitable protecting group selected from nitro, p-toluenesulfonyl (Tos), Z, pentamethylchromanesulfonyl (Pmc), adamantyloxycarbonyl, and Boc. Pmc is the most preferred for arginine (Arg).

In the examples all solvents, isopropanol (iPrOH), methylene chloride ($CH_2Cl_2$), dimethylformamide (DMF) and N-methylpyrrolidinone (NMP) were purchased from Fisher or Burdick and Jackson and were used without additional distillation. Trifluoroacetic acid was purchased from Halocarbon or Fluka and used without further purification. Diisopropylcarbodiimide (DIC) and diisopropylethylamine (DIPEA) was purchased from Fluka or Aldrich and used without further purification. Hydroxybenzotriazole (HOBT) dimethylsulfide (DMS) and 1,2-ethanedithiol (EDT) were purchased from Sigma Chemical Co. and used without further purification. Protected amino acids were generally of the L configuration and were obtained commercially from Bachem, Advanced ChemTech, or Neosystem. Purity of these reagents was confirmed by thin layer chromatography, NMR and melting point prior to use. Benzhydrylamine resin (BHA) was a copolymer of styrene—1% divinylbenzene (100–200 or 200–400 mesh) obtained from Bachem or Advanced Chemtech. Total nitrogen content of these resins were generally between 0.3–1.2 meq/g.

High performance liquid chromatography (HPLC) was conducted on a LDC apparatus consisting of Constametric I and III pumps, a Gradient Master solvent programmer and mixer, and a Spectromonitor III variable wavelength UV detector. Analytical HPLC was performed in reversed phase mode using Vydac Clg columns (0.4×30 cm). Preparative HPLC separations were run on Vydac columns (2×25 cm).

Peptides were prepared using solid phase synthesis following the principles and general method described by Merrifield, [*J. Amer. Chem. Soc.*, 1963, 85, 2149], although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-[(R,S)-α-[1-(9H-fluoren-9-yl)-methoxyformamido]-2,4-dimethyloxybenzyl]-phenoxyacetic acid (Rink linker) to a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

In general, the amino acids or mimetics are coupled onto the Fmoc-Linker-BHA resin using the Fmoc protected form of amino acid or mimetic, with 2–5 equivalents of amino acid and a suitable coupling reagent. After couplings, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions.

Piperidine, piperazine or morpholine (20–40% v/v) in DMF may be used for this purpose. Preferably 40% piperidine in DMF is utilized Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino) phosphonium hexafluorophosphate (BOP), Bromo-tris-pyrrolidino-phosphonium hexafluorophosphate (PyBroP), 2-(1H-Benzotriazole-1-yl)-1,1,3,3-tetramethyluronium hexafluorophosphate (HBTU), and diisopropylcarbodiimide (DIC). Preferred here are HBTU and DIC. Other activating agents as described by Barany and Merrifield [The Peptides, Vol. 2, J. Meienhofer, ed., Academic Press, 1979, pp 1–284] may be utilized. Various reagents such as 1-hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle is as follows:

Protocol 1

| Step | Reagent | Time |
| --- | --- | --- |
| 1 | DMF | 2 × 30 sec |
| 2 | 40% piperidine/DMF | 1 min |
| 3 | 40% piperidine/DMF | 15 min |
| 4 | DMF | 2 × 30 sec |
| 5 | iPrOH | 2 × 30 sec |
| 6 | DMF | 3 × 30 sec |
| 7 | coupling | 60 min–18 hours |
| 8 | DMF | 2 × 30 sec |
| 9 | iPrOH | 1 × 30 sec |
| 10 | DMF | 1 × 30 sec |
| 11 | $CH_2Cl_2$ | 2 × 30 sec |

Solvents for all washings and couplings were measured to volumes of 10–20 ml/g resins. Coupling reactions throughout the synthesis were monitored by the Kaiser ninhydrin test to determine extent of completion [Kaiser et at. *Anal. Biochem.* 1970, 34, 595–598]. Slow reaction kinetics was observed for Fmoc-Arg (Pmc) and for couplings to secondary amines by sterically hindered acids. Any incomplete coupling reactions were either recoupled with freshly prepared activated amino acid or capped by treating the peptide resin with acetic anhydride as described above. The fully assembled peptide-resins were dried in vacuum for several hours.

For each compound, the blocking groups were removed and the peptide cleaved from the resin by the following procedure. Generally, the peptide-resins were treated with 100 μL ethanedithiol, 100 μL dimethylsulfide, 300 μL anisole, and 9.5 mL trifluoroacetic acid, per gram of resin, at room temperature for 120 min. The resin is filtered off and the filtrates are precipitated in chilled ethyl ether. The precipitates are centrifuged and the ether layer is decanted. The residue was washed with two or three volumes of $Et_2O$ and recentrifuged. The crude products are dried under vacuum.

Purification of Crude Peptide Preparations

Purification of the crude peptides was carried out by preparative HPLC. The peptides were applied to the columns in a minimum volume of either AcOH/H2O or 0.1%

TFA/H2O. Gradient elution was generally started at 10% B buffer, 10%–60% B in 90 minutes, (buffer A: 0.1% TFA/H₂O, buffer B:0.1% TFA/CH₃CN) at a flow rate of 8 mL/min. UV detection was made at 280 nm. Fractions were collected at 1.0–2.5 minute intervals and inspected by analytical HPLC. Fractions judged to be of high purity were pooled and lyophilized.

Purity of the final products was checked by analytical HPLC on a reversed phase column as stated above. Purity of all products was judged to be approximately 95–99%. All final products were also subjected to fast atom bombardment mass spectrometry (FAB-MS) or electrospray mass spectrometry (ES-MS). All products yielded the expected parent M+H ions within acceptable limits.

Utilizing the techniques described above, the compounds of this invention can be synthesized in accordance with the following reaction schemes.

Scheme A

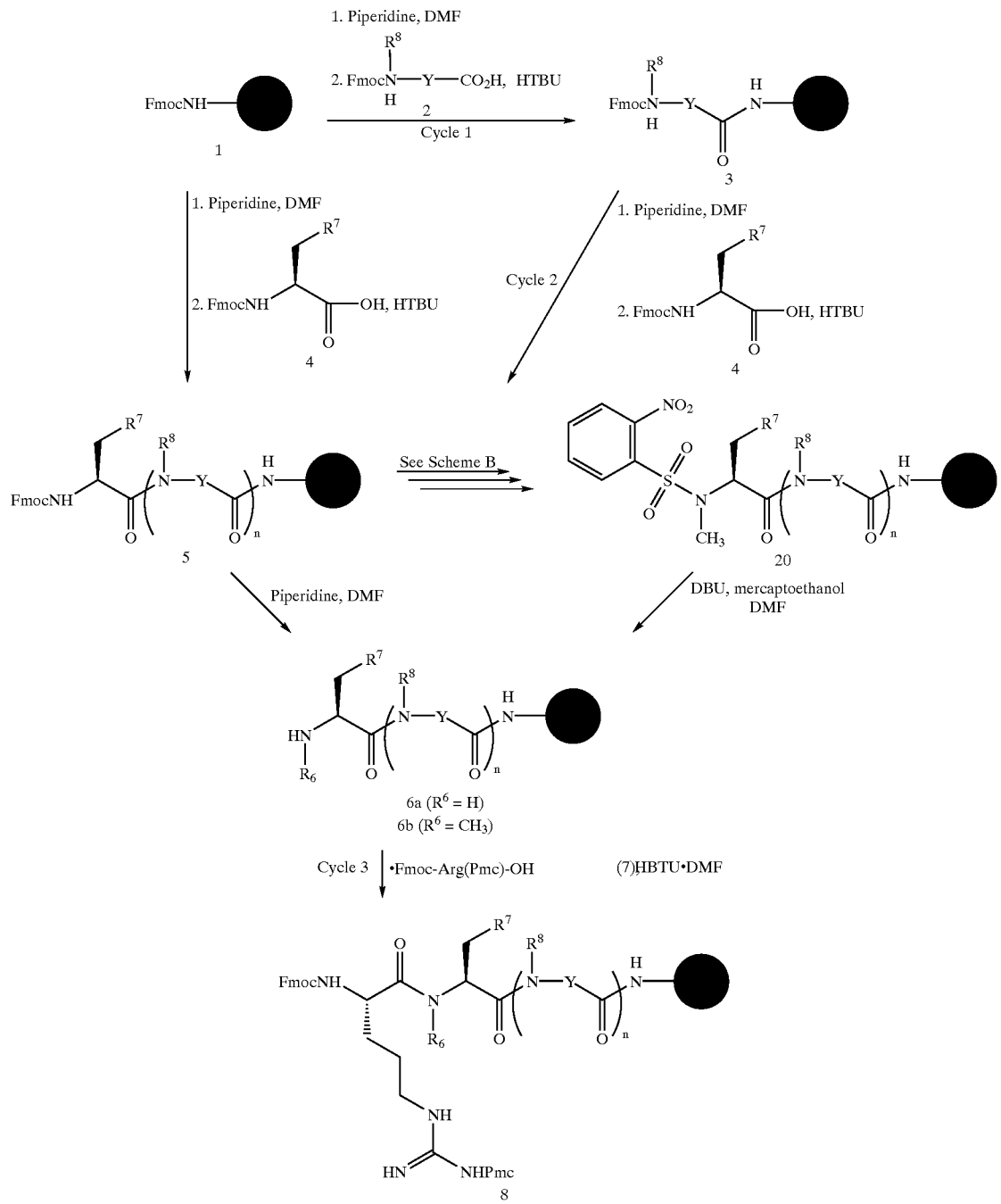

$R^6$, $R^7$, $R^8$, Y and n are as previously described.

Scheme B
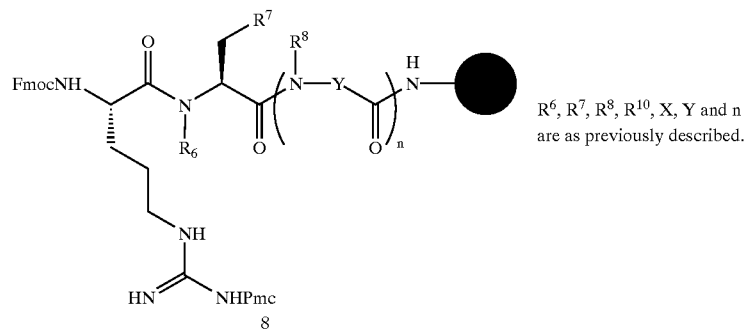
R[6], R[7], R[8], R[10], X, Y and n are as previously described.
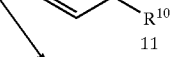
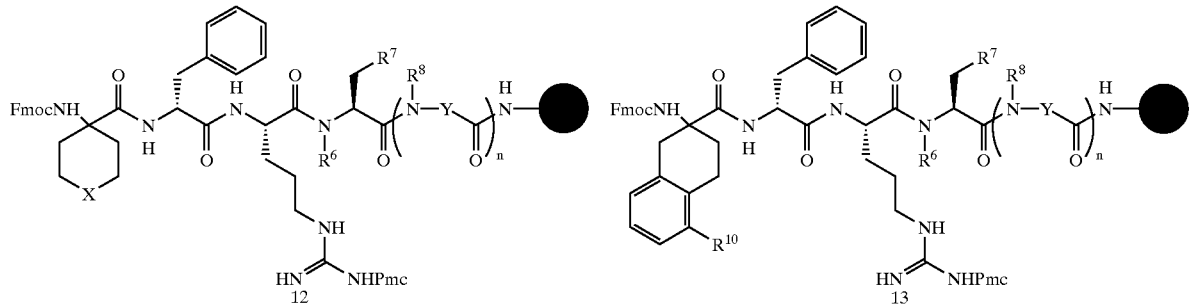
Scheme C
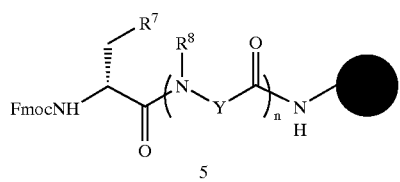
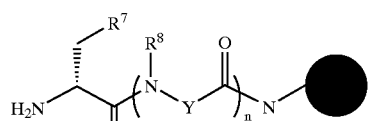

-continued
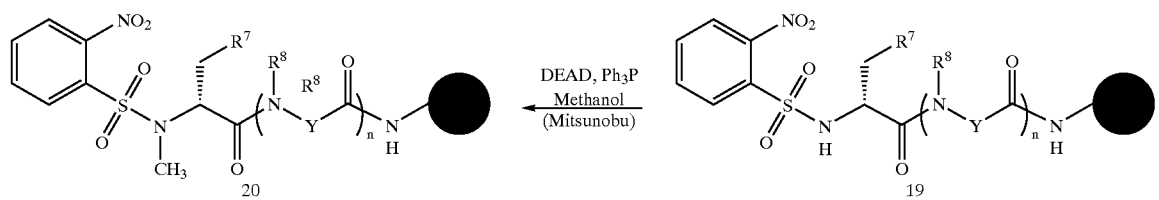
$R^7$, $R^8$, Y and n are as previously described.
Scheme D
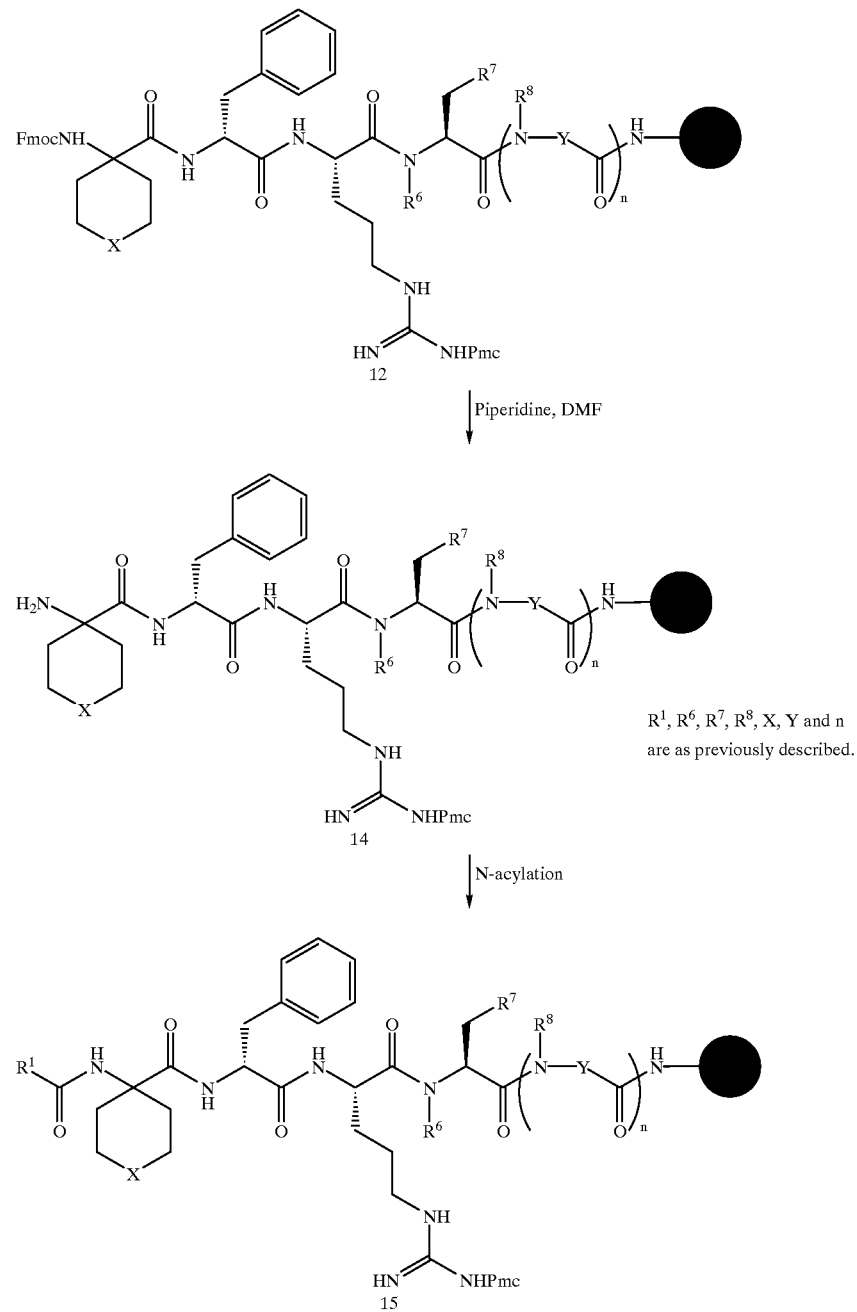

-continued
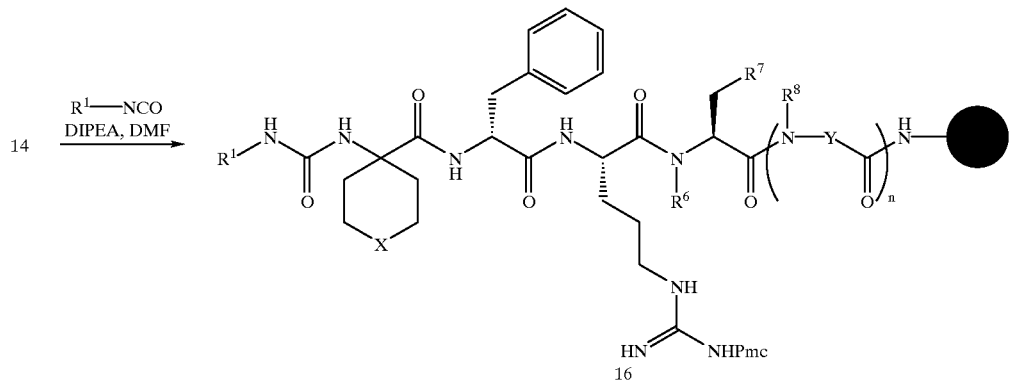
Scheme E
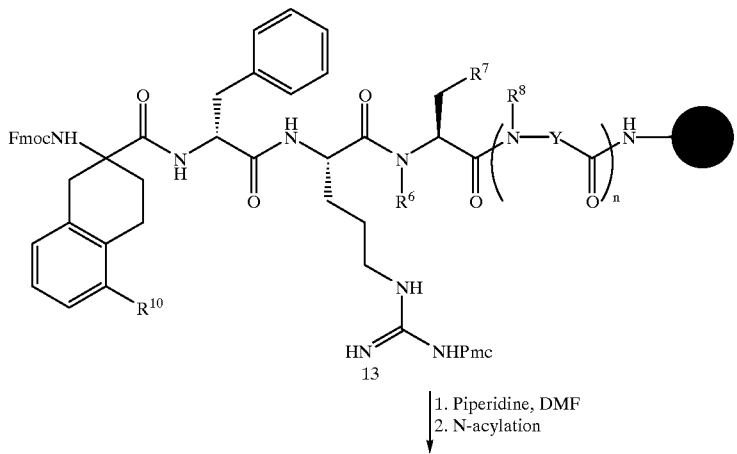
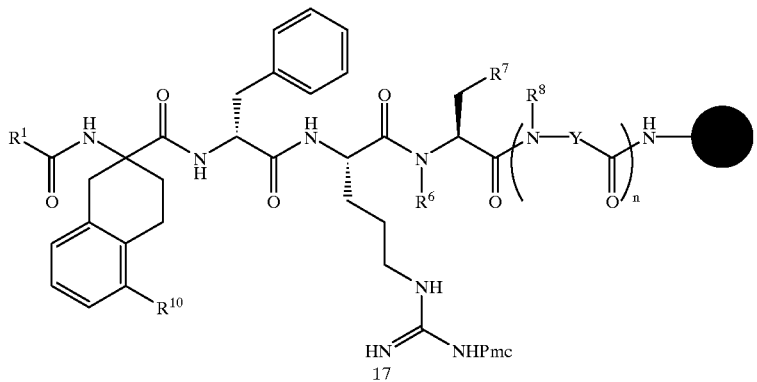
$R^1$, $R^6$, $R^7$, $R^8$, $R^{10}$, Y and n are as previously described.
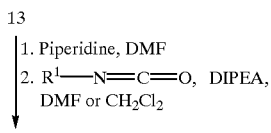

-continued
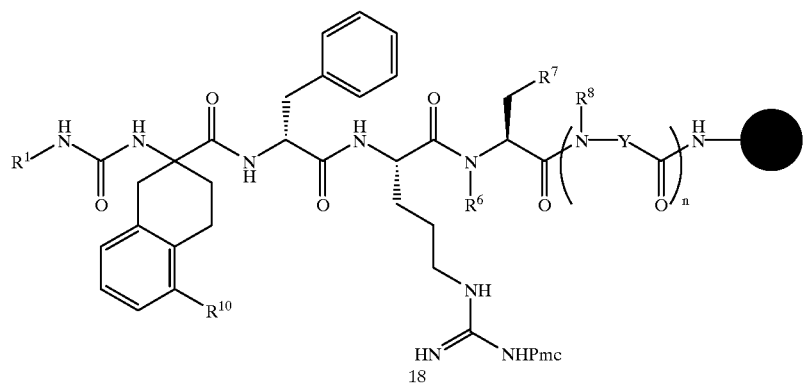
18
Scheme F
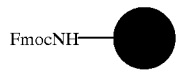
1
1. (a) Piperidine, DMF
   (b) FmocAA (2), HBTU, DMF
2. (a) Piperidine, DMF
   (b) FmocAA (4), HBTU, DMF
3. (a) Piperidine, DMF
   (b) Fmoc-Glu(ally)-OH (21), HBTU
4. (a) Piperidine, DMF
   (b) FmocAA (9), HBTU, DMF
5. (a) Piperidine, DMF
   (b) FmocAA (10), HBTU, DMF
6. (a) Piperidine, DMF
   (b) R$_1$—CO$_2$H, HBTU, DMF
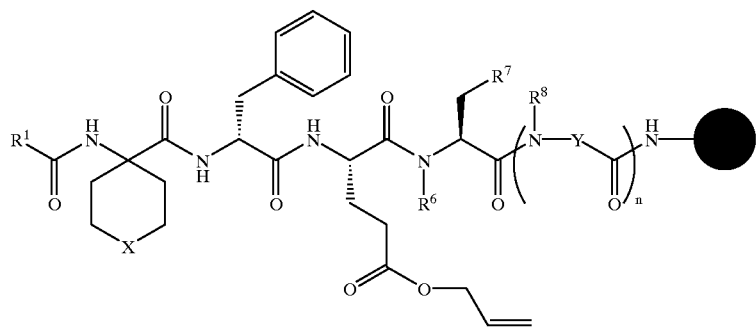
22
1. PdCl$_2$, Ph$_3$P, tri-n-butyltin hydride, DMF
2. Boc-guanidine•HCl, HBTU -continued
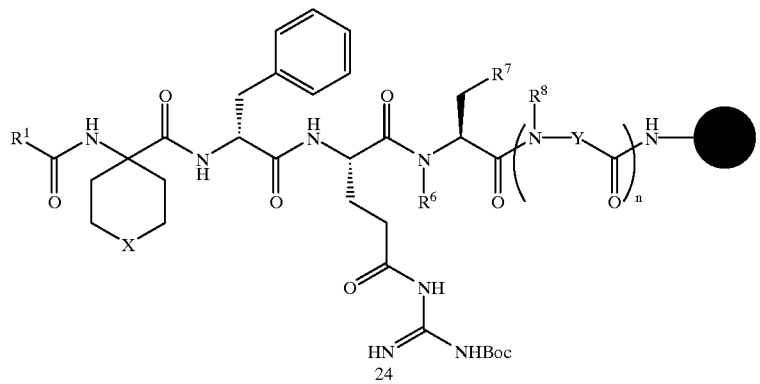
$R^1, R^6, R^7, R^8, X, Y$ and n are as previously described.
Scheme G
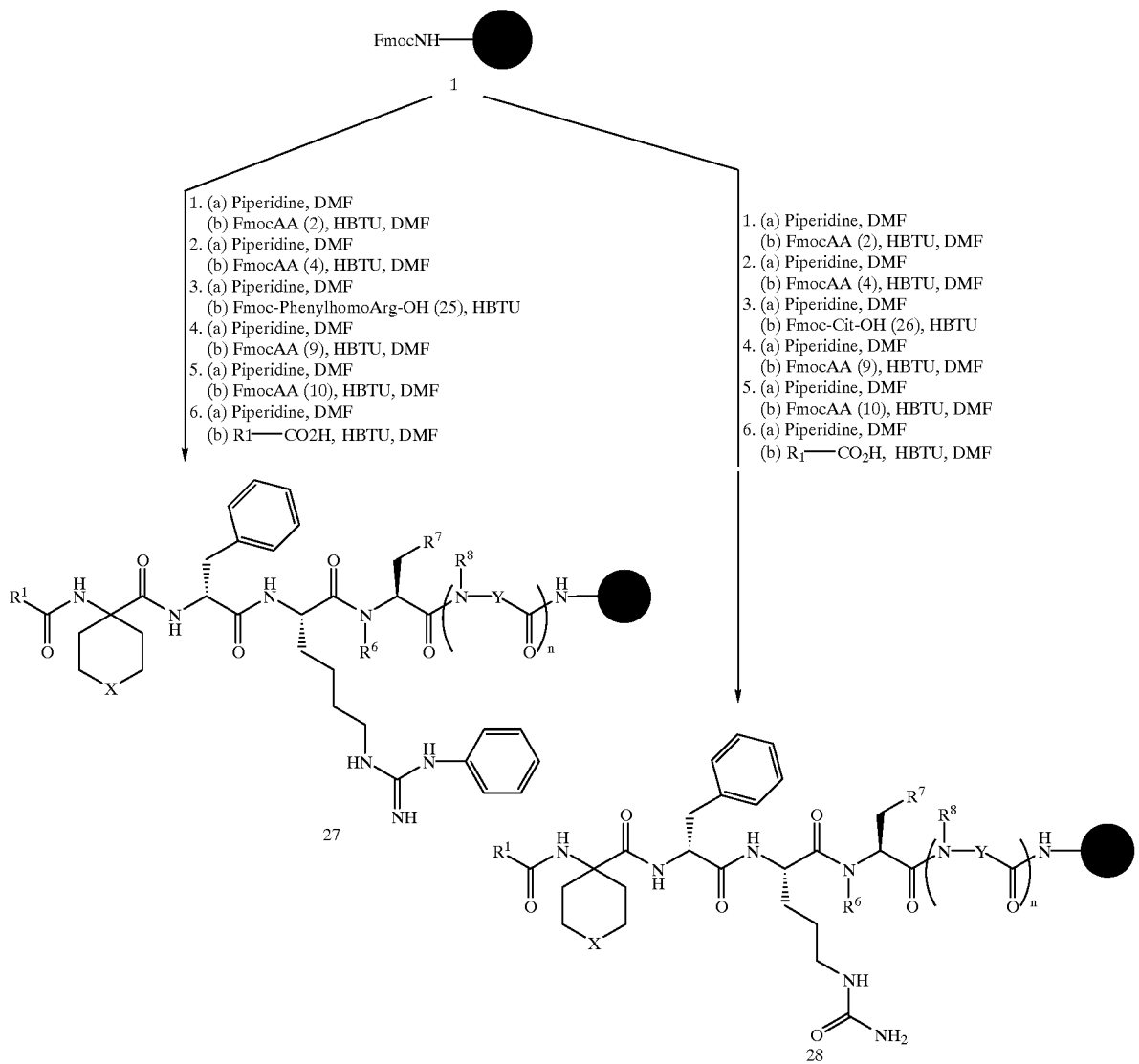
$R^1, R^6, R^7, R^8, X, Y$ and n are as previously described.

Scheme H
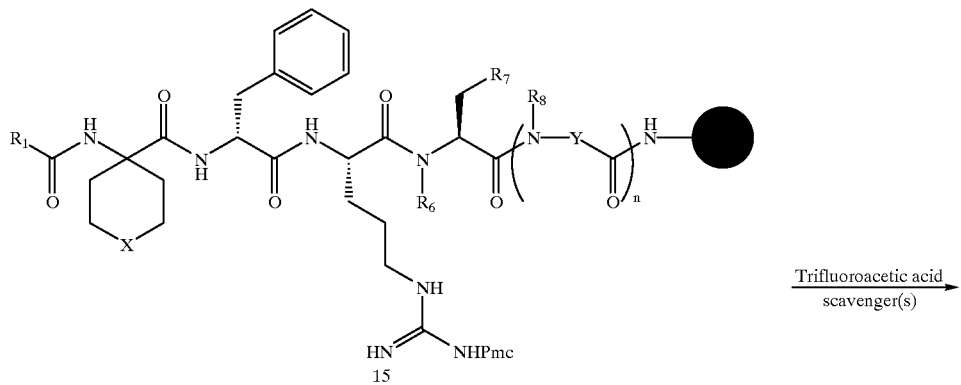
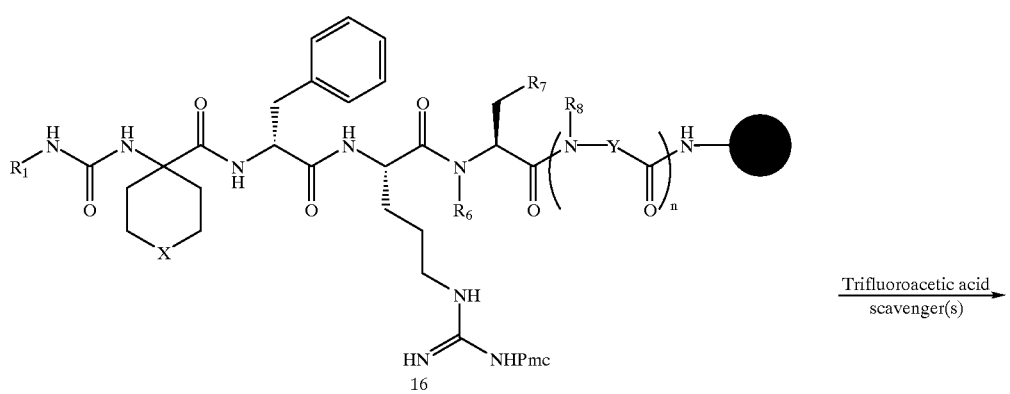
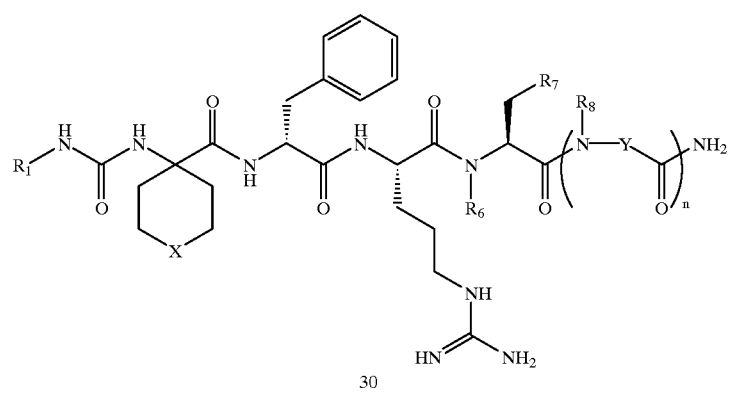

-continued
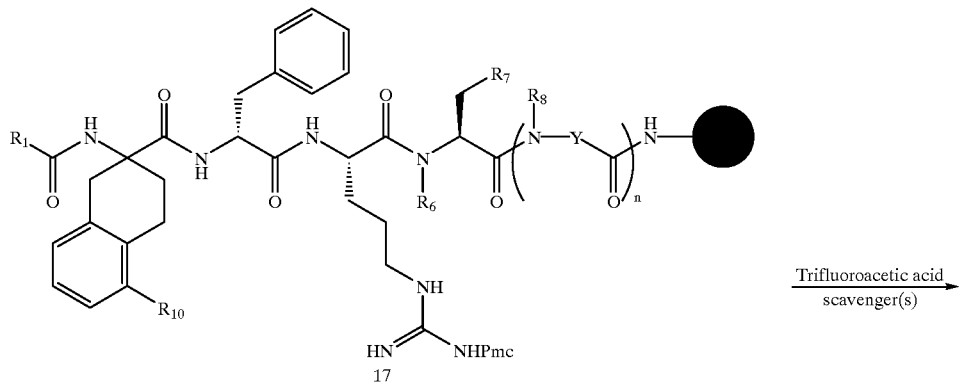
Trifluoroacetic acid
scavenger(s)
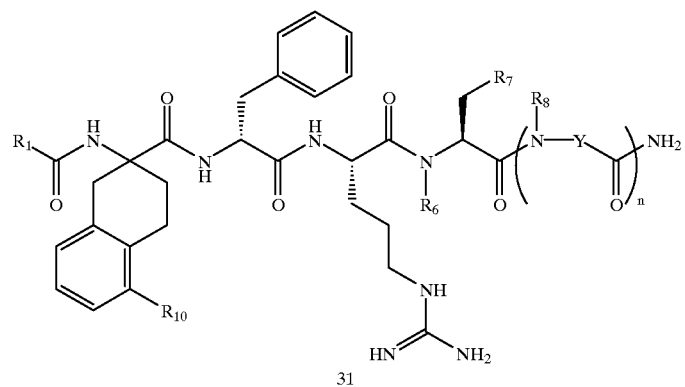
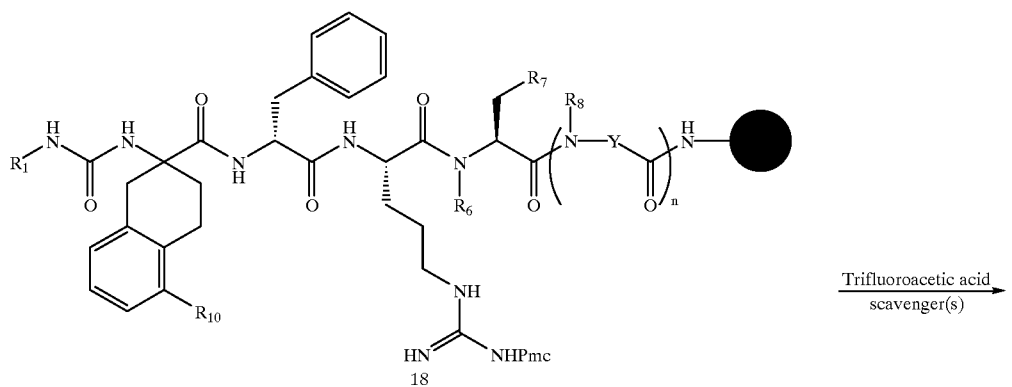
Trifluoroacetic acid
scavenger(s)
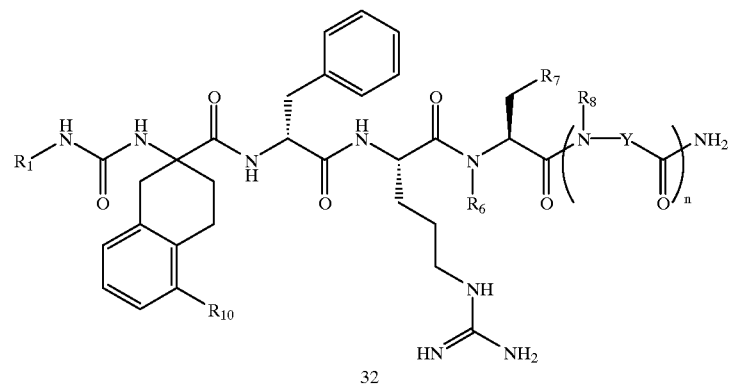
$R_1$, $R_6$, $R_7$, $R_8$, $R_{10}$, X, Y and n are as previously described.

-continued
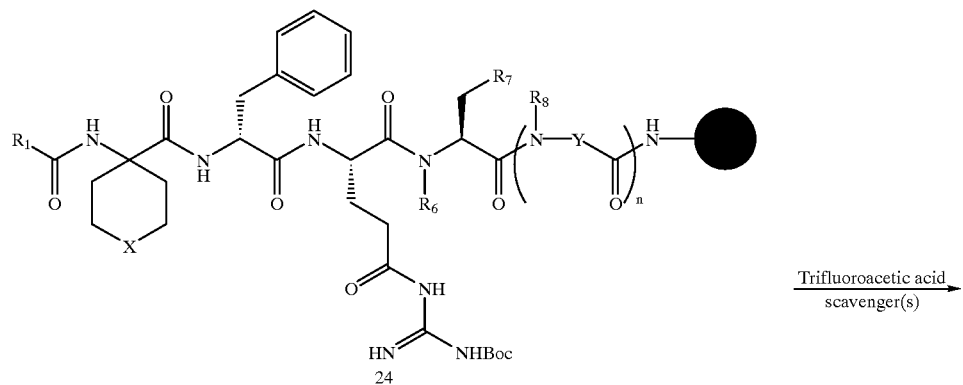
24
Trifluoroacetic acid
scavenger(s) →
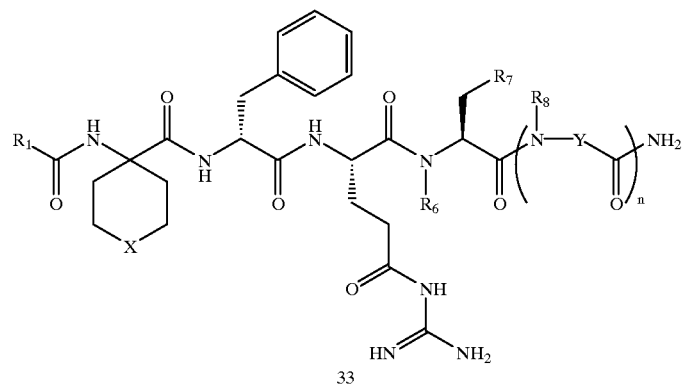
33
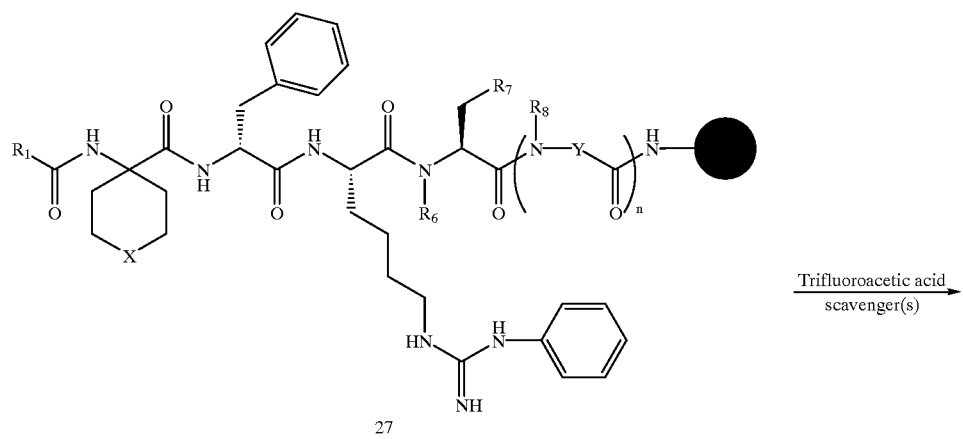
27
Trifluoroacetic acid
scavenger(s) →
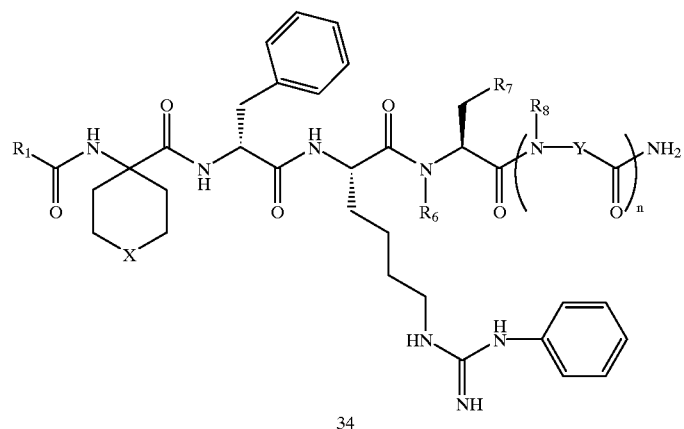
34

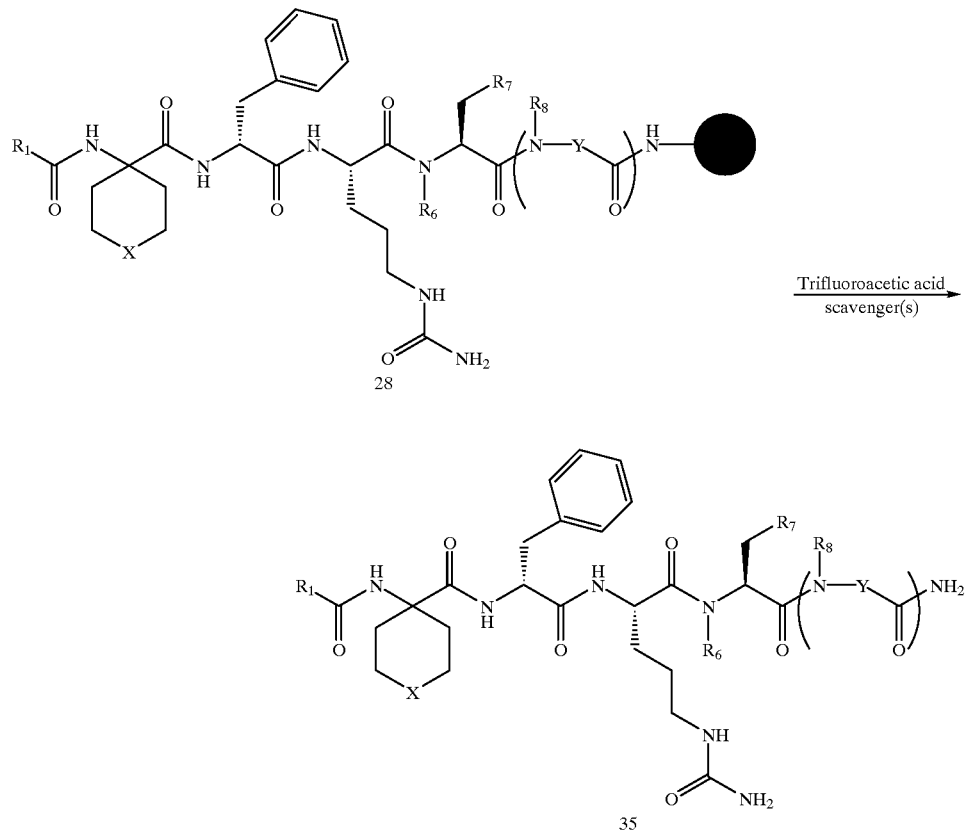
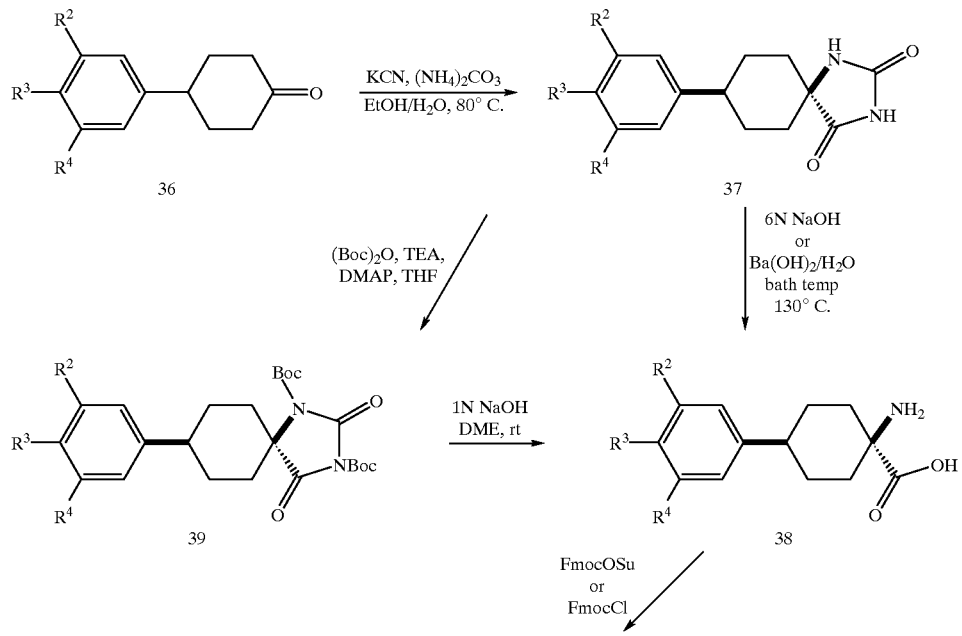
$R_1$, $R_6$, $R_7$, $R_8$, $R_{10}$, X, Y and n are as previously described.

-continued
$R^2$, $R^3$, $R^4$, $R^9$, $R^{10}$, and $R^{11}$ are as previously described.
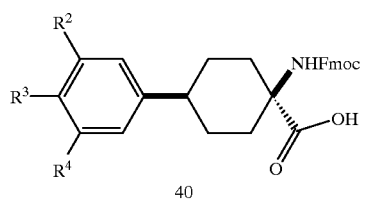
40
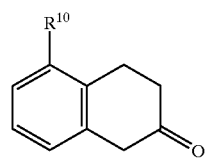
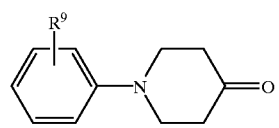
41
42
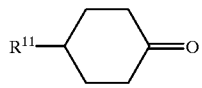
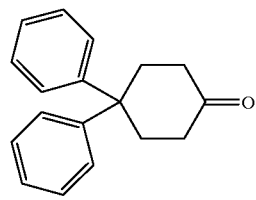
43
44
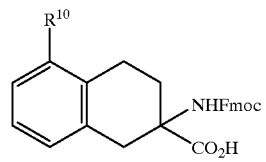
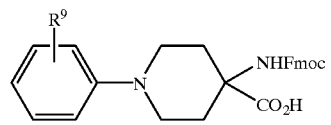
11
45
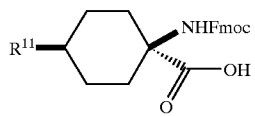
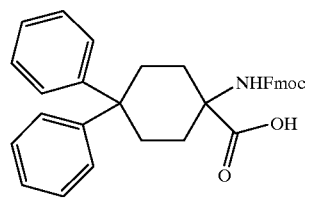
46
47
Scheme J
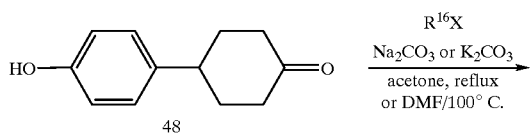
48
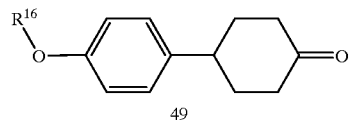
49

Scheme K
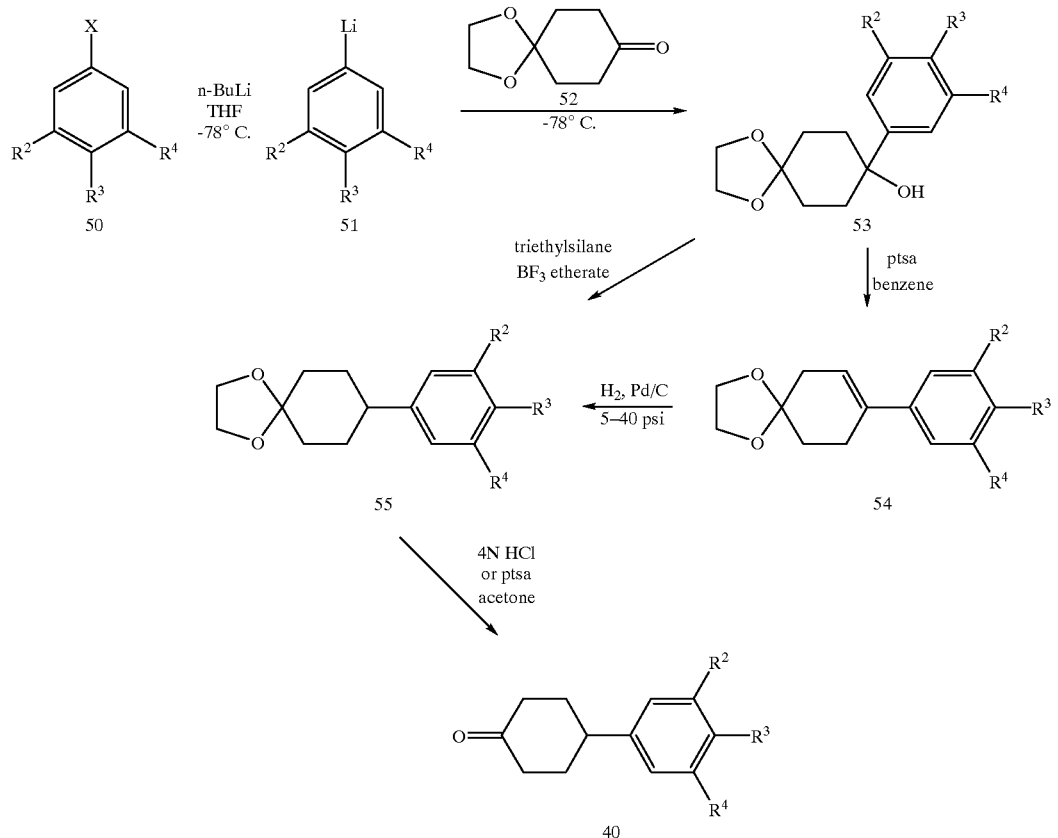
$R^2$, $R^3$ and $R^4$ are as previously described.
Scheme L
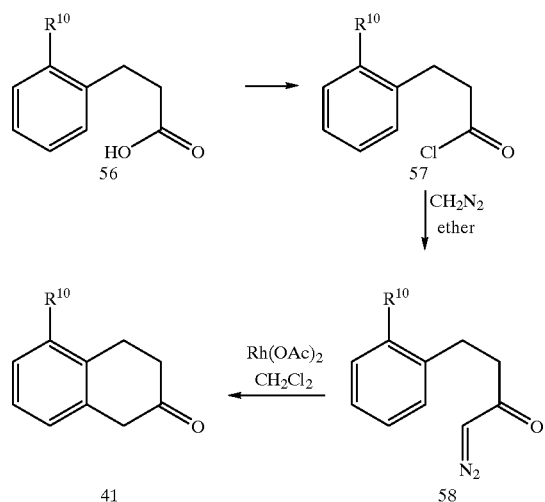
$R^{10}$ is as previously described.

Scheme M

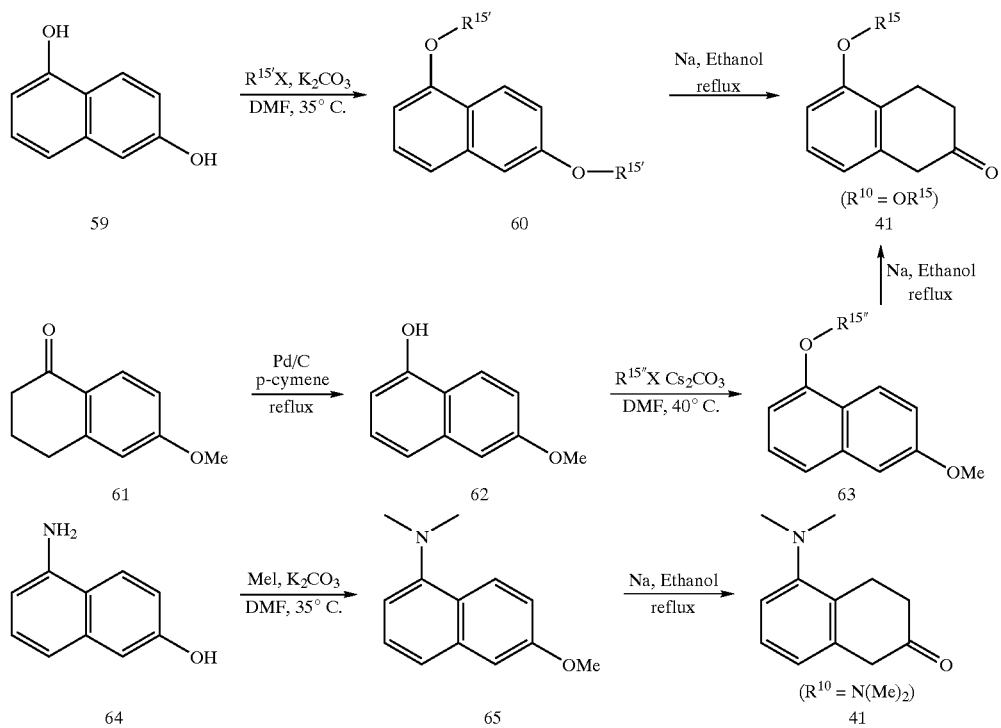

Scheme N

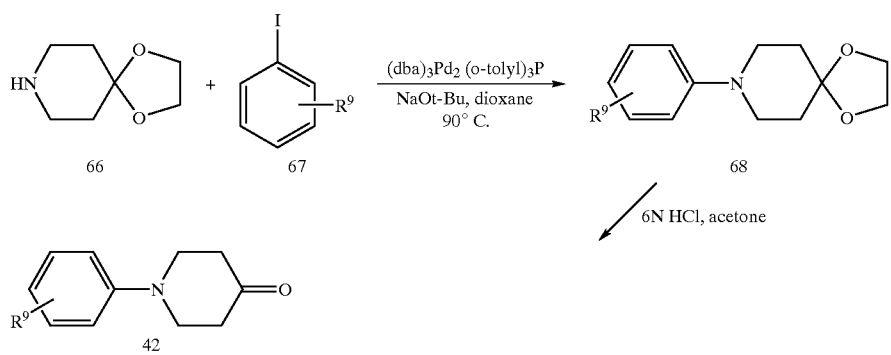

$R^9$ is as previously described.

The synthetic peptides of the current invention are prepared by using conventional solid phase peptide synthesis methodology discussed in the previous section. Each cycle consists of two procedures; the initial cleavage of the Fmoc protecting group from the terminal nitrogen in the resin bound chain followed by acylation of the amine function with an Fmoc protected amino acid. The cycle is generally carried out in accordance with the stepwsize procedures outlined in Protocol 1. The deprotection is accomplished by using an organic base, for example piperazine, morpholine or piperidine, preferably piperidine in a suitable inert solvent, for example N,N-dimethylformamide (DMF) or Nmethylpyrrolidone (NMP). The coupling reaction can be carried out by one of the many conditions developed for amide bond formation, for example O-benzotriazol-l-yl N,N,N',N'-tetramethyluronium hexafluorophosphate (HBTU) in the presence of an organic base, for example diisopropylethylamine (DIPEA) in an inert solvent, for example DMF. Alternatively in the present instance, the amide group can be formed using a carbodiimide, for example, diisopropylcarbodiimide (DIC) along with an activating agent such as 1-hydroxybenzotriazole (HOBT) in a suitable inert solvent such as DMF.

In Scheme A, in the first cycle, the Fmoc-Linker-BHA Resin represented by structure 1 is deprotected and condensed with Fmoc-amino acids of structure 2 to give the resin bound compounds of structure 3. A second cycle incorporates the Fmoc-amino acids 4 to give the compounds of structure 5 (n=1). Compounds of structure 5 in which n=0 are prepared by eliminating the first cycle, and by coupling Fmoc-amino acids of structure 4 directly to the deprotected Fmoc-Linker-BHA Resin. In the third cycle, treatment of the resin linked peptide furnishes the intermediates of structure 6a where $R^6$ represents hydrogen. The intermediates of structure 6b where $R^6$ represents methyl are synthesized as shown in Scheme C. Compounds of structure 6a, prepared by treating compounds of structure 5 as prescribed in steps 1–5 of Protocol 1, are reacted with an arylsulfonyl chloride, preferably 2-nitrobenzenesulfonyl chloride. The reaction is carried out in the presence of a proton acceptor, for example pyridine, triethylamine (TEA) or DIPEA, preferably DIPEA in a suitable inert solvent, preferably DMF. N-methylation of the formed sulfonamide group in the washed resin bound compounds of structure 19 is accomplished under Mitsunobu conditions. Thus the sulfonamides of structure 19 are reacted with methanol in the presence of diethyl azodicarboxylate (DEAD) and triphenylphosphine using methanol as solvent. After the reaction is complete, the resin bound N-methylsulfonamide of structure 20 is washed free of residual reagents and byproducts. The 2-nitrobenzenesulfonyl residue is removed by reacting 20 with 2-mercaptoethanol and the strong organic base 1,8-diazabicyclo[5.4.0]undec-7-ene (DBU) in a suitable solvent, preferably DMF to give the resin bound intermediate of structure 6b. The third cycle is completed by coupling compounds of either structures 6a and 6b with Fmoc-Arg (Pmc)-OH (7) to give the resin bound compounds of structure 8. Two additional cycles (Scheme B) are carried out on peptides of structure 8 where the amino acid Fmoc-(D)-Phe-OH (9) followed by either one of the amino acid derivatives of structure 10 or 11 are sequentially incorporated into the resin bound peptide to give the resin bound polypeptides of structures 12 and 13.

Removal of the Fmoc from the resin bound polypeptides 12 is carried out by treatment of 12 with piperidine in DMF to give the compounds of structure 14 using the reaction conditions outlined in Steps 1–5 of Protocol 1. The polypeptide is then N-capped by reaction with an acylating agent to form the resin bound amides of structure 15 or by reaction with an isocyanate to form the ureas of structure 16 (Scheme D). The acylation is carried out under a variety of methods well known to one skilled in the art. Among the methods used are:

(i) reaction of the compounds of structure 14 with a carboxylic acid $R^1$—$CO_2H$ in a suitable solvent, such as DMF in the presence of HBTU, and an organic base, preferably DIPEA and (ii) reaction of the compounds of structure 14 with a carboxylic acid chloride $R^1$—COCl in a suitable solvent, such as dichloromethane in the presence an organic base, such as pyridine, TEA and DIPEA, preferably DIPEA and (iii) reaction of the compounds of structure 14 with a carboxylic acid anhydride ($R^1$—$CO_2CO$—$R^1$ in a suitable solvent, such as dichloromethane or DMF in the presence an organic base, preferably DIPEA.

The reaction of the compounds of structure 14 with an isocyanate $R^1$—NCO is carried out in a suitable solvent, such as dichloromethane or DMF in the presence an organic base, preferably DIPEA.

When the acylation and urea forming reactions are complete, the resin bound products 15 and 16 are washed free of residual reagents and byproducts.

Using the same conditions, the resin bound polypeptides of structure 13 are converted to the N-acylated compounds of structure 17 and the ureas of structure 18 (Scheme E).

In Scheme F, the sequencing is carried out as in Scheme A except that Fmoc-Glu(allyl)-OH (21) is incorporated into the resin bound polypeptide instead of Fmoc-Arg(Pmc)-OH (7) to give the resin bound N-capped polypeptides of structure 22. The allyl group is removed by treatment of 22 with tributyltin hydride, palladium chloride and triphenylphosphine in an inert solvent, for example DMF to give the resin bound polypeptide of structure 23. Coupling of 23 with Boc-guanidine gave the acylguanidine resin bound compounds of structure 24. The reaction can be carried out by using standard amide forming reaction methods, for example in the presence of HBTU and an organic base, preferably DIPEA in a suitable solvent, such as DMF.

In Scheme G, the sequencing is carried out as in Scheme A except that either FmocPhenylhomoArg-OH (25) or Fmoc-citrulline (26) is incorporated into the resin bound polypeptide in the place of Fmoc-Arg(Pmc)-OH (7) to give the resin bound N-capped polypeptides of structures 27 and 28 respectively.

As shown in Scheme H, the cleavage of remaining protecting groups in the N-capped polypeptides 15–18, 24, 27 and 28 and the concomitant cleavage of the peptides from the solid support is carried out by using a strong organic acid, preferably trifluoroacetic acid, optionally in the presence of an inert solvent such as dichloromethane and a trace (1%) of water. The reaction is conveniently carried out with or without the presence of one or more carbocation scavengers, for example ethanedithiol, dimethyl sulfide, triethylsilane and anisole. The polypeptide cleavage solution is filtered free from the solid support, then is diluted with a suitable solvent, preferably diethyl ether. The solid polypeptides of structures 29–35 produced in this manner is purified by reversed phase chromatography over a preparative C18 column. If convenient, in those cases where a racemic Fmoc-amino acid 11 is sequenced into the polypeptide, the individual stereoisomers are separated during the purification procedure. The Fmoc-amino acids 2, 4, 7, 9, 21, 25 and 26 as well as the acylating agents and isocyanates used to N-cap the polypeptides are known compounds that are commercially available.

The Fmoc-amino acids 10 and 11 are prepared as described herein by methods that are well known to those of ordinary skill in the practice of organic chemistry. In Scheme I, the preparation of Fmoc-amino acids from cyclic ketones is outlined. The 4-phenylcyclohexanones of formula 36 are converted to the hydantoins of formula 37 by treatment with ammonium carbonate and potassium cyanide. The reaction is conveniently carried out an aqueous ethanol mixture at a temperature of from 50° C. to 90° C., preferably between 80° C. and 90° C. Direct hydrolysis of the hydantoins to the amino acids of structure 38 require a prolonged treatment with strong base, for example with 6N sodium hydroxide solution or with barium hydroxide at reflux temperature. Alternatively, compounds of structure 37 can be converted to the bis-Boc derivatives of structure 39. The reaction is carried out using tert-butyl dicarbonate [(Boc)$_2$O] in an inert solvent, preferably tetrahydrofuran (THF), in the presence of an organic amine base, preferably TEA and a catalyst, 4-dimethylaminopyridine (DMAP) at a temperature of from zero degrees to room temperature, preferably at room temperature. The bis-Boc hydantoins of structure 39 are readily converted to the amino acids of structure 38. The reaction is accomplished using 1N sodium hydroxide in an inert solvent, preferably dimethoxyethane (DME) at from zero degrees to 50° C., preferably at about room temperature. Protection of the amino functionality with an Fmoc group in a compound of structure 38 is carried out under a variety of reaction conditions to give 40. The reaction may conveniently be performed by treatment of a solution of the amino acid 38 in a mixture of THF or dioxane, preferably dioxane and aqueous sodium carbonate with 9-fluorenylmethoxychloroformate (FmocCl) at a temperature of from zero degrees to room temperature, preferably at room temperature. Alternatively, N-(9-fluorenylmethoxycarbonyloxy)succinimide (FmocOSu) is added to a solution of the amino acid 38 in aqueous acetonitrile containing an organic tertiary amine base, preferably TEA. The reaction is run at from zero degrees to room temperature, preferably at room temperature. In another variation of the procedure, DME is evaporated from the hydrolysis mixture in the conversion of 39 to 38 and the reaction is adjusted to ~pH 11. The resulting solution of the sodium salt of 38 is then treated in situ with FmocOSu or FmocCl in dioxane at a temperature of from zero degrees to room temperature, preferably at room temperature.

In the same manner, the tetralones 41, the N-aryl-4-ketopiperidines 42, and the cyclohexanone derivatives 43 and 44 are converted to the corresponding Fmoc-amino acids of structures 11 and 45–47.

Compounds of structure 40 where $R^3$ represents a linear or branched lower alkoxy and $R^2$ and $R^4$ is hydrogen, as in the sub genus structure 49, may be prepared by 0-alkylation of the compound of structure 48 (Scheme J). Where $R^{16}$ represents an unbranched lower alkyl moiety, the alkylation is carried out by using a primary alkyl halide of structure $R^{16}X$ in the presence of an alkali metal carbonate, for example, sodium or potassium carbonate. The alkyl halide may be a chloro, bromo or iodo derivative, preferably an alkyl iodide (X=I). The reaction may be conveniently carried out in an inert solvent that promotes Sn2 displacement reactions, for example acetone, 2-butanone or N,N-dimethylformamide, preferably acetone, at a temperature of from room temperature to the reflux temperature of the solution, preferably the reflux temperature. When $R^{16}$ represents a branched lower alkyl group, e.g., 2-propyl, the alkylation is carried out by using a secondary alkyl halide of structure $R^{16}X$ in the presence of an alkali metal carbonate, e.g., potassium carbonate. The secondary alkyl halide is preferably a secondary alkyl iodide, for example, 2-iodopropane (X=I). The reaction may be conveniently carried out in an inert solvent, preferably N,N-dimethylformamide, at a temperature of from room temperature to the reflux temperature of the solution, preferably at about 100° C.

Compounds of structure 40 can be prepared by methods that are well known to one of ordinary skill in the practice of organic chemistry. As outlined in Scheme K), treatment of the aryl halides of structure 50 (X' represents bromo or iodo) with an alkyl metal reagent, preferably t-butyl lithium, results in a transmetalation reaction to give the corresponding aryl lithium of structure 51. The reaction is conveniently carried out at −78° C. by the addition of a solution of the alkyl lithium in to a solution of compounds of structure 50 an inert anhydrous solvent, such as diethyl ether or tetrahydrofuran, preferably tetrahydrofuran. The aryl lithium of structure 51, is then reacted in situ with a solution of the monoketal of cyclohexane-1,4-dione (52) in an suitable inert solvent, for example tetrahydrofuran, while the reaction temperature is maintained below −60° C., preferably at about −78° C. to give the carbinols of structure 53. The compounds of structure 54 are obtained by the dehydration of the carbinols of structure 53. The reaction is conveniently carried out using a strong organic acid catalyst, preferably p-toluenesulfonic acid in an inert solvent, for example benzene or toluene, preferably benzene, at the reflux temperature of the solvent. The formed water is removed from the reaction mixture by means of a Dean Stark apparatus to enable the reaction to go to completion. Compounds of structure 55 are produced by hydrogenation of the olefins of structure 54. The reaction is conveniently carried out using a noble metal catalyst, for example palladium on carbon, in a hydrogen atmosphere in an inert solvent, for example ethanol or ethyl acetate. The hydrogenation is usually carried out at room temperature and 40 psi of hydrogen, however if the aryl ring in structure 54 contains a group prone to hydrogenolysis, e.g., if $R^2$, $R^3$ or $R^4$ represents chloro, the reaction pressure is kept at about 5 psi. Compounds of structure 55 may be also obtained directly from carbinols of structure 53 by reductive elimination of the hydroxyl group. In this reaction a solution of the compound of structure 53 ($R^2=R^3=H$ and $R^4=OMe$) in an inert solvent, for example dichloromethane, is treated with a Lewis acid, such as boron trifluoride etherate, and a reducing agent, for example triethylsilane, at a temperature of from zero degrees to room temperature. Removal of the ketal protecting group in compounds of structure 55 gives the ketone of formula 40. The reaction is conveniently carried out in acetone or 2-butanone, preferably acetone under acid catalysis, for example 4N hydrochloric acid or p-toluenesulfonic acid at from room temperature to the reflux temperature of the reaction mixture, preferably at the reflux temperature.

5-Substituted-beta-tetralones of structure 41 are generally known compounds, or if they are not known they can be prepared by methods that are well known to one of ordinary skill in the field of organic chemistry. In the present instance, compounds of structure 41 are prepared by two methods outlined in Schemes L and M.

As shown in Scheme L, a 2-substituted hydrocinnamic acid of structure 56 ($R^{10}$=bromo, chloro or a linear or branched alkyl group of from 1 to 3 carbons) is converted to the corresponding carboxylic acid chloride of structure 57. This conversion can be carried out by several methods, for example by treatment of the hydrocinnamic acid with oxalyl chloride, optionally in the presence of a catalytic amount of N,N-dimethylformamide, in an inert solvent, such as benzene or dichloromethane, preferably dichloromethane. The reaction may be conveniently carried out at a temperature of from zero degrees to room temperature, preferably at room temperature. Alternatively the compound of structure 56 is reacted with an acyl chloride forming reagent such as sulfuryl chloride in an inert solvent, for example benzene or toluene, preferably toluene at a temperature between room temperature to the reflux temperature of the solution, preferably at the reflux temperature.

The diazoketone of structure 58 is prepared by treatment of the thus formed acyl halide of structure 57 in an inert solvent, e.g., dichloromethane with an excess of a freshly prepared ethereal solution of diazomethane. The combination of reagents is conveniently carried out at ice bath temperature and the reaction is then allowed to proceed at a temperature of from zero degrees to room temperature, preferably at room temperature. Cyclization of the diazoketone of structure 58 to furnish the tetralone of structure 41 is promoted by rhodium (II) acetate dimer in an inert solvent, e.g., dichloromethane. The reaction is normally carried out at from room temperature to the reflux temperature of the solution, preferably at the reflux temperature.

Compounds of structure 41, wherein $R^{10}$ represents a linear or branched lower alkoxy group or a dialkylamino substituent, are prepared as shown in Scheme M. The compounds of structure 60 ($R^{15'}$=an unbranched lower alkyl moiety) are prepared by per-O-alkylation of the naphthalenediol of structure 59 with a primary alkyl iodide or bromide, preferably an iodide, in the presence of a base such as an alkali metal carbonate, for example, sodium or potassium carbonate. The reaction may be carried out in an inert solvent, preferably N,N-dimethylformamide at a temperature of from room temperature to 100° C., preferably at 35° C. The compounds of structure 63 ($R^{15''}$ represents a branched lower alkyl) are prepared in two steps from the 2-tetralone of structure 61. The tetralone of structure 61 is subjected to dehydrogenation in the presence of a noble metal catalyst, such as palladium metal (10% on carbon) in a suitable high boiling solvent such as p-cymene to give the aromatized compound of structure 62. The naphthol of structure 62 is then 0-alkylated with a secondary alkyl iodide in the presence of a base such as an alkali metal carbonate, preferably cesium carbonate to furnish the compound of structure 63. The reaction may be conveniently carried out in an inert solvent, preferably N,N-dimethylformamide at a temperature of from room temperature to 100° C., preferably at about 40° C. The compound of structure 65 is prepared by alkylation of 5-amino-2-naphthol (64) with methyl iodide in the presence of a base such as an alkali metal carbonate, preferably potassium carbonate. The reaction may be carried out in an inert solvent, for example acetone or 2-butanone, preferably acetone, at a temperature between room temperature and the reflux temperature of the solution, preferably at the reflux temperature.

The tetralones of structures 41 are produced by reduction of the compounds of structures 60, 63 and 65 under dissolving metal conditions, followed by the acid catalyzed hydrolysis of the intermediate enol ethers. The transformation is conveniently carried out by the portionwise addition of a large excess of an alkali metal, such as sodium or potassium, preferably sodium, to a boiling solution of the substrate in an lower alcohol, preferably alcohol until the starting material is consumed. The tetralones of structures 41 are obtained by treatment of a solution of the isolated intermediate enol ethers with a strong acid catalyst, preferably p-toluenesulfonic acid. The hydrolysis may conveniently carried out in a mixture of a lower alcohol, preferably ethanol, and water at a temperature of between room temperature and the reflux temperature of the solution, preferably at the reflux temperature.

Compounds of structure 68 are can be prepared by reactions that are known per se. For example, they can be prepared by coupling a secondary amine of structure 66 with an aryl bromide or iodide, preferably an aryl iodide of structure 67 (Scheme N). The coupling reaction is catalyzed by a noble metal catalyst, preferably tri(dibenzylideneacetone)-dipalladium, in the presence of a chelating phosphine ligand, preferably tri-o-tolylphosphine, and a hindered alkoxide base such as sodium tert-butoxide. The reaction is conveniently carried out in an inert atmosphere using an anhydrous solvent such as dioxane or toluene, preferably dioxane, at a temperature of from 60° C. to the reflux temperature, preferably at 90° C. Compounds of structure 56 and 66 are generally known compounds and are can be obtained from commercial sources. Removal of the carbonyl protecting group in compound 67 to give compounds of structure 42 can be carried out by a variety of methods well known in the field of organic chemistry. For example, the deprotection can be achieved by treatment of a solution of compound 68 in a low boiling ketone such as acetone or 2-butanone with an aqueous mineral acid solution, for example 6N hydrochloric acid. The reaction can be run at a temperature of from room temperature to the reflux temperature of the mixture, preferably at the reflux temperature.

The cyclohexanone derivatives of structures 63 are commercially available compounds and the 4,4-diphenylcyclohexanone (64) is prepared by published procedures.

This invention will be better understood by reference to the following examples, which illustrate but do not limit the invention described herein.

EXAMPLE 1

Preparation of Fmoc-1-amino-4-phenylcyclohexane-1-carboxylic acid (Fmoc-Apc-OH)

Step 1:

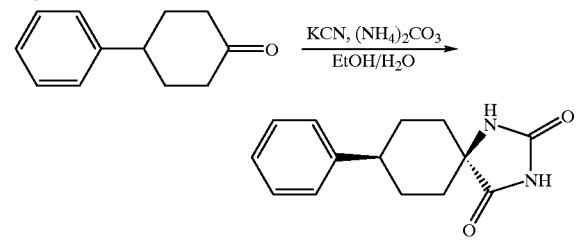

To a solution of 4-phenylcyclohexanone (10.0 g, 57.5 mmol) in ethanol (100 mL) and water (33 mL) in a glass pressure bottle, were added ammonium carbonate (33 g, 344 mmol, 6 equiv.) and potassium cyanide (5.6 g, 86.2 mmol, 1.5 equiv.). The mixture was heated at 80–90° C. for 24 hrs. The cooled reaction mixture was added to icy water (400 ml) and stirred vigorously for 30 min. The resulting precipitate was suction filtered, washed thoroughly with water and dried to yield the hydantoin as a white solid (14.0 g, 100% yield). $^1$H NMR (DMSO-$d_6$): 8.63 (s, 1H), 7.23–7.36 (m, 4), 7.15 (m, 1), 2.50 (m, 1H), 2.10 (m, 1H), 1.85 (d, 1H) and 1.55–1.80 (m, 6H).

Step 2:

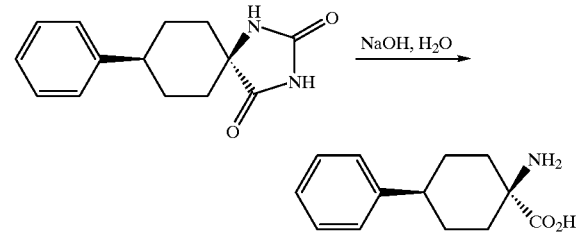

The hydantoin (10.0 g) was suspended in aqueous NaOH (6N, 350 mL) and heated at 130° C. for 2–3 days. Upon the completion of the hydrolysis, the reaction mixture was neutralized with conc. HCl to slightly acidic (pH~6). The resulting slurry was filtered, washed with water and dried to give 1-amino-4-phenylcyclohexane carboxylic acid (APC) as a white solid (25 g, >100% yield. contaminated with inorganic salt) which was used directly for next step. Small portion of the crude product was purified on HPLC. $^1$H NMR (DMSO-$d_6$): 7.23~7.7.35 (m, 2), 7.10–7.19 (m, 3H), 2.45 (m, 1H), 1.92–2.18 (m, 3H), 1.56–1.78 (m, 4H) and 1.20 (m, 1H); LRMS (electrospray) m/e 220 (M+1)$^+$, Calcd for $C_{13}H_{17}NO_2$, 219.

Step 3:

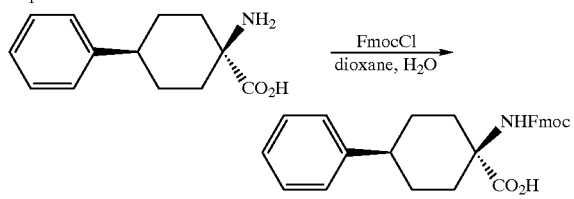

The crude APC from the last step (25 g) was treated with Fmoc-Cl (13.2 g., 1.25 equiv) in dioxane (300 mL) and aqueous 10% Na$_2$CO$_3$ (150 ml) and stirred vigorously overnight. The reaction mixture was concentrated to remove dioxane, neutralized with 6N HCl to slightly acidic (pH 5–6) and extracted with EtOAc. The combined organic extracts were washed with brine and dried over Na$_2$SO$_4$. Removal of the solvent gave the crude product which was then purified on flash chromatography (hexane/EtOAc to CH$_2$Cl$_2$/MeOH) to give pure Fmoc-cis-APC (18.2 g, 72% overall yield for two steps) and Fmoc-trans-APC (2.1 g, 8%). The structure of cis Fmoc-APC was confirmed by single crystal X-ray analysis of its derivative. Fmoc-cis-APC, $^1$H NMR (CD$_3$OD), 7.79 (d, 2H), 7.72 (d, 2H), 7.37 (t, 2), 7.24–7.32 (m, 4), 7.14–7.23 (m, 3), 4.37 (d, 2H), 4.24 (t, 1H), 2.55 (m, 1H), 2.28 (m, 2H), 1.84–1.96 (m, 2H) and 1.64–1.73 (m, 4H).

EXAMPLE 2

Preparation of Fmoc-1-amino-4-(4-methoxyphenyl) cyclohexane-1-carboxylic acid (Fmoc-4-MeOApc-OH)

Step 1:

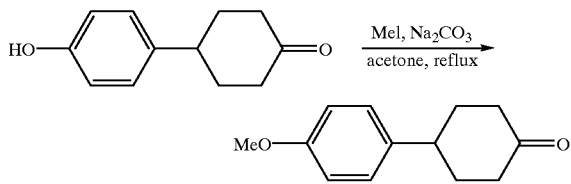

A solution of 4-(4-hydroxyphenyl)cyclohexanone (5.0 g, 26.3 mmol) in acetone (100 mL) was treated with K$_2$CO$_3$ (14.5 g, 105 mmol, 4 equiv) and iodomethane (4.9 mL, 11.2 g, 78.6 mmol, 3 equiv.). The reaction was heated at 65° C. overnight. After the solvent was removed, the residue was treated with H$_2$O and extracted with EtOAc. The organic extracts were combined and washed with brine, dried over Na$_2$SO$_4$ and concentrated in vacuum to give the spectroscopically pure 4-(4-methoxyphenyl)cyclohexanone (5.34 g, 100%). $^1$H NMR(CDCl$_3$) 7.16 (dt, 2H), 6.87 (dt, 2H), 3.78 (s, 3H), 2.99 (tt, 1H), 2.47–2.53 (m, 4H), 2.20 (m, 2H) and 1.83–1.98 (m, 2H); MS (electrospray) m/e, 205 (M+1)$^+$, Calcd for C$_{13}$H$_{16}$O$_2$, 204.

Step 2:

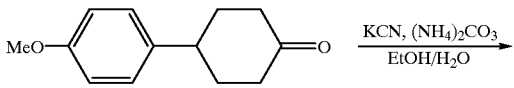

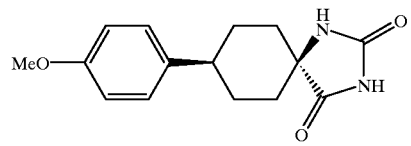

To a solution of the ketone (3.86 g, 18.9 mmol) in ethanol (50 mL) and water (15 mL) in a glass pressure bottle, were added ammonium carbonate (14.5 g, 151 mmol, 8 equiv.) and potassium cyanide (2.0 g, 30.7 mmol, 1.6 equiv.). The mixture was heated at 80–90° C. for 24 hrs. The cooled reaction mixture was added to icy water (300 ml) and stirred vigorously for 30 min. The resulting precipitate was suction filtered, washed thoroughly with water and dried to yield the hydantoin as a white solid (4.75 g, 91% yield). MS (electrospray) m/e 273 (M-H), Calcd for C$_{15}$H$_{18}$N$_2$O$_3$, 274.

Step 3:

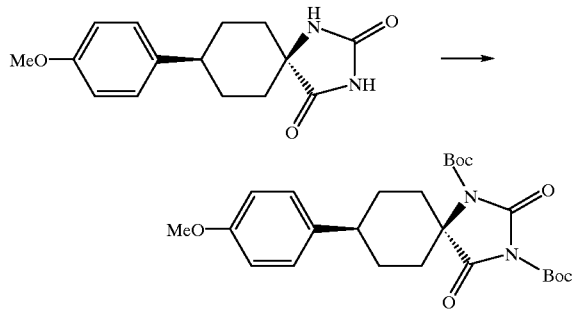

To a suspension of the hydantoin (18.7 g, 68.25 mmol) in dry THF (450 mL) were added di-tert-butyl dicarbonate (37.2 g, 170.5 mmol, 2.5 equiv), triethylamine (10.5 mL, 7.59 g, 75.0 mmol, 1.1 equiv) and DMAP (460 mg, 3.65 mmol) in succession. About 15 minutes after the addition, the reaction turned into a clear yellow solution and was stirred overnight at room temperature. The reaction mixture was concentrated under reduced pressure to yield a solid that was then taken up in EtOAc (800 mL), washed with 1N HCl (3×50 mL), saturated aqueous Na$_2$CO$_3$ (2×50 mL) and brine (2×50 mL), dried over anhydrous Na$_2$SO$_4$ and concentrated under reduced pressure. The crude light yellow product was purified through flash chromatography (hexane/EtOAc, 90/10→70/30) to give the pure bis-Boc hydantoin as a white solid (27.6 g, 87%). $^1$H NMR (CDCl$_3$): 7.28 (dt, 2H), 6.88 (dt, 2H), 3.79 (s, 3H), 2.14–2.24 (m, 2H), 1.59 (s, 9H) and 1.38 (s, 9H); MS (electrospray) m/e 538 (M+MeCN+Na)$^+$, Calcd for C$_{25}$H$_{34}$N$_2$O$_7$, 474.

Step 4:

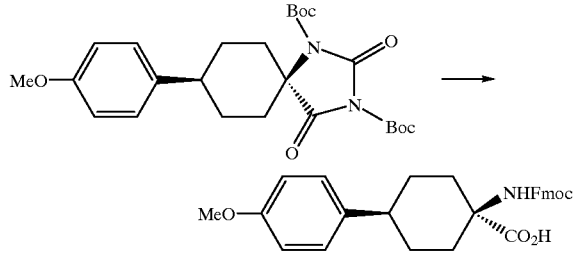

The bis-Boc hydantoin (15.08 g, 31.78 mmol) was dissolved in DME (500 mL) to give a clear solution. To this solution was added 1N NaOH (290 mL, 290 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-methoxyphenyl)cyclohexane carboxylic acid (4-MeOAPC) was treated with 6N HCl to adjust the pH to 11–12. To this solution (~300 mL) were added DME (300 mL) and a solution of Fmoc-OSu (16.7 g, 49.42 mmol) in DME (200 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography ($CH_2Cl_2$/MeOH, 98/2→90/10) to give the pure product Fmoc-4-MeOAPC as a white solid (12.4 g, 83% yield from the bis-Boc hydantoin). $^1H$ NMR (DMSO-$d_6$), 7.88 (d, 2H), 7.76 (d, 2H), 7.40 (t, 2H), 7.30 (t, 2H), 7.11 (d, 2H), 6.85 (d, 2H), 3.71 (s, 3H); MS (electrospray) m/e 470 (M−H), Calcd for $C_{29}H_{29}NO_5$, 471.

EXAMPLE 3

Preparation of Fmoc-1-amino-4-(4-ethoxyphenyl) cyclohexane-1-carboxylic acid (Fmoc-4-EtOApc-OH)

Step 1:

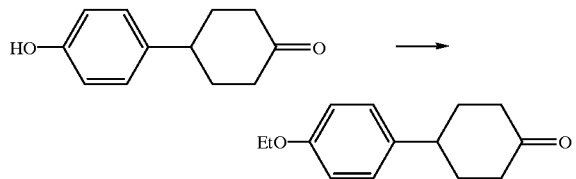

A solution of 4-(4-hydroxyphenyl)cyclohexanone (5.0 g, 26.3 mmol) in acetone (100 mL) was treated with $K_2CO_3$ (14.5 g, 105 mmol, 4 equiv) and iodoethane (10.5 mL, 20.5 g, 131 mmol, 5 equiv.). The reaction was heated at 65°C. overnight. After the solvent was removed, the residue was treated with $H_2O$ and extracted with EtOAc. The organic extracts were combined and washed with brine, dried over $Na_2SO_4$ and concentrated in vacuum to give the spectroscopically pure 4-(4-ethoxyphenyl)cyclohexanone (5.74 g, 100%). $^1H$ NMR ($CDCl_3$) 7.15 (dt, 2H), 6.86 (dt, 2H), 4.02 (q, 2H), 2.99 (tt, 1H), 2.46–2.54 (m, 4H), 2.16–2.24 (m, 2H), 1.83–2.00 (m, 2H) and 1.41 (t, 3H); MS (electrospray) m/e, 219 (M+1)$^+$, Calcd for $C_{14}H_{18}O_2$, 218.

Step 2:

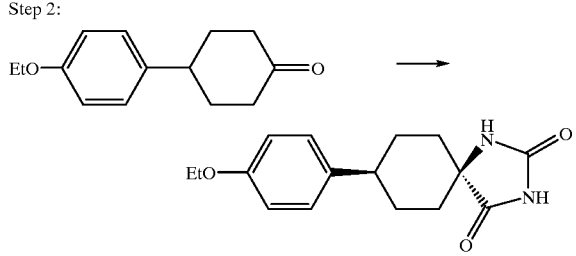

To a solution of the ketone (4.15 g, 19.01 mmol) in ethanol (50 mL) and water (15 mL) in a glass pressure bottle, were added ammonium carbonate (14.5 g, 151 mmol, 8 equiv.) and potassium cyanide (2.05 g, 31.42 mmol, 1.6 equiv.). The mixture was heated at 80–90° C. for 19 hrs. The cooled reaction mixture was added to icy water (300 ml) and stirred vigorously for 30 min. The resulting precipitate was suction filtered, washed thoroughly with water and dried to yield the hydantoin as a white solid (5.17 g, 94% yield). MS (electrospray) m/e 287 (M−H), Calcd for $C_{16}H_{20}N_2O_3$, 288.

Step 3:

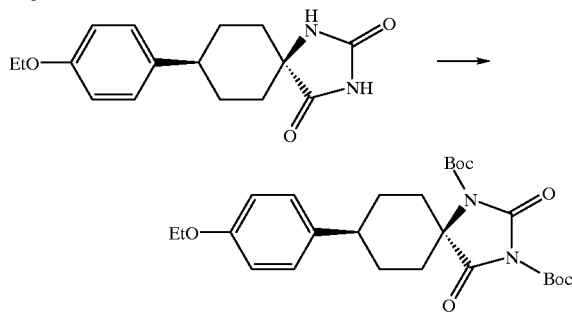

To a suspension of the hydantoin (4.22 g, 14.65 mmol) in dry THF (100 mL) were added di-tert-butyl dicarbonate (7.98 g, 36.60 mmol, 2.5 equiv), triethylamine (2.3 mL, 1.63 g, 16.11 mmol, 1.1 equiv) and DMAP (89.4 mg, 0.73 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with 1N HCl (3×20 mL), saturated aqueous Na2CO3 (2×20 mL) and brine (2×20 mL), dried over anhydrous $Na_2SO_4$ and concentrated under reduced pressure. The crude light yellow product was purified through flash chromatography (hexane/EtOAc, 90/10→70/30) to give the pure bis-Boc hydantoin as a white solid (7.01 g, 98%). $^1$NMR ($CDCl_3$):7.27 (dt, 2H), 6.87 (dt, 2H), 4.02 (q, 2H), 1.59 (s, 9H), 1.43 (t, 3H) and 1.38 (s, 9H); MS (electrospray) m/e 999 (2M+Na)$^+$, Calcd for $C_{26}H_{36}N_2O_7$, 488.

Step 4:

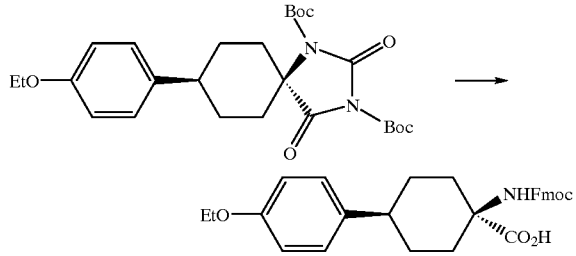

The bis-Boc hydantoin (6.58 g, 13.46 mmol) was dissolved in DME (200 mL) to give a clear solution. To this solution was added 1N NaOH (121 mL, 121 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-ethoxyphenyl)cyclohexane carboxylic acid (4-EtOAPC) was treated with 6N HCl to adjust the pH to 11–12. To this solution (~130 mL) were added DME (100 mL) and a solution of Fmoc-OSu (6.83 g, 20.24 mmol) in DME (30 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous Na$_2$SO$_4$ and concentrated. The crude product was purified through flash chromatography (CH$_2$Cl$_2$/MeOH, 98/2→90/10) to give the pure product as a white solid (5.56 g, 85% yield from the bis-Boc hydantoin). $^1$H NMR (DMSO-d$_6$), 7.88 (d, 2H), 7.74 (d, 2H), 7.40 (td, 2H), 7.30 (td, 2H), 7.11 (d, 2H), 6.84 (d, 2H), 3.97 (q, 2H) and 1.29 (t, 3H); MS (electrospray) m/e 484 (M−H), Calcd for C$_{30}$H$_{31}$NO$_5$, 485.

EXAMPLE 4

Preparation of Fmoc-1-amino-4-(4-hydroxyphenyl) cyclohexane-1-carboxylic acid (Fmoc-4-HOApc-OH)

Step 1:

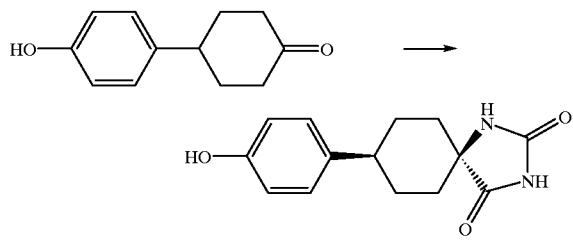

To a solution of 4-(4-hydroxyphenyl)cyclohexanone (2.00 g, 10.52 mmol) in ethanol (30 mL) and water (10 mL) in a glass pressure bottle, were added ammonium carbonate (6.17 g, 64.2 mmol, 6 equiv.) and potassium cyanide (1.07 g, 15.8 mmol, 1.5 equiv.). The mixture was heated at 80–90° C. overnight. The cooled reaction mixture was added to icy water (200 ml) and stirred vigorously for 30 min. The resulting precipitate was suction filtered, washed thoroughly with water and dried to yield the hydantoin as a white solid (2.56 g, 94% yield). MS (electrospray) m/e 261 (M+H)$^+$, Calcd for C$_{14}$H$_{16}$N$_2$O$_3$, 260.

Step 2:

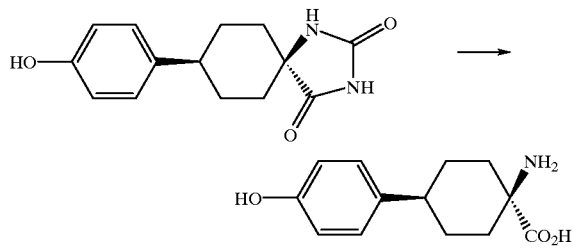

The hydantoin (2.10 g, 8.06 mmol) was suspended in aqueous NaOH (6N, 100 mL) and heated at 130° C. for 2–3 days. Upon the completion of the hydrolysis, the reaction mixture was neutralized with conc. HCl to slightly acidic (pH~6). The resulting slurry was filtered, washed with water and dried to give 1-amino-4-(4-hydroxyphenyl)cyclohexane carboxylic acid (4-HOAPC) as a white solid (3.1 g, >100% yield. contaminated with inorganic salt). MS (electrospray) m/e 236 (M+H)$^+$, Calcd for C$_{13}$H$_{17}$NO$_3$, 235.

Step 3:

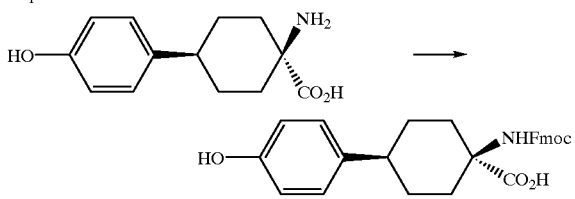

The crude APC from the last step (3.1 g) was treated with Fmoc-Cl (2.6 g, 1.25 equiv) in dioxane (100 mL) and aqueous 10% Na$_2$CO$_3$ (50 ml) and stirred vigorously overnight. The reaction mixture was concentrated to remove dioxane, neutralized with 6N HCl to slightly acidic (pH 5–6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$/MeOH) to give pure Fmoc-4-HOAPC (2.76 g, 75% overall yield for two steps). $^1$H NMR(CD$_3$OD), 7.78 (d, 2H), 7.72 (d, 2H), 7.38 (t, 2H), 7.30 (td, 2H), 7.04 (d, 2H), 6.72 (dt, 2H), 4.38 (d, 2H), 4.25 (t, 1H), 2.46 (m, 1H), 2.24–2.34 (m, 2H) and 1.81–1.92 (m, 6H); MS (electrospray) m/e 456 (M−H), Calcd for C$_{28}$H$_{27}$NO$_5$, 457.

EXAMPLE 5

Preparation of Fmoc-1-amino-4-(4-isopropoxyphenyl)cyclohexane-1-carboxylic acid (Fmoc-4-iPrOApc-OH)

Step 1:

A solution of 4-(4-hydroxyphenyl)cyclohexanone (6.0 g, 31.6 mmol) in DMF (90 mL) was treated with K$_2$CO$_3$ (21 g, 158 mmol, 5 equiv) and 2-iodopropane (15 mL, 26.8 g, 158 mmol, 5 equiv.). The reaction was heated at 100° C. overnight. After the solvent was removed, the residue was treated with H$_2$O and extracted with EtOAc. The organic extracts were combined and washed with brine, dried over Na$_2$SO$_4$ and concentrated in vacuum to give the spectroscopically pure 4-(4-isopropoxyphenyl)cyclohexanone (7.02 g, 95%). $^1$ H NMR (CDCl$_3$): 7.14 (dt, 2H), 6.84 (dt, 2H), 4.3 (septet, 1H), 2.97 (tt, 1H), 2.46–2.52 (m, 4H), 2.16–2.24 (m, 2H), 1.83–1.98 (m, 2H) and 1.33 (d, 6H).

Step 2:

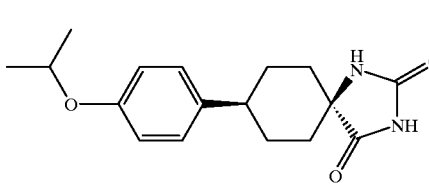

To a solution of the ketone (5.1 g, 21.98 mmol) in ethanol (90 mL) and water (30 mL) in a glass pressure bottle, were added ammonium carbonate (12.6 g, 131 mmol, 6 equiv.) and potassium cyanide (2.14 g, 32.9 mmol, 1.5 equiv.). The mixture was heated at 80–90° C. for 24 hrs. The cooled reaction mixture was added to icy water (400 ml) and stirred vigorously for 30 mm. The resulting precipitate was suction filtered, washed thoroughly with water and dried to yield hydantoin as a white solid (6.60 g, 99% yield). $^1$H NMR (DMSO-d$_6$): 10.60 (s, 1H), 8.65 (s, 1H), 7.18 (d, 2H), 6.80 (d, 2H), 4.52 (septet, 1H), 2.43 (m, 1H), 1.85–2.15 (m, 2H), 1.56–1.80 (m, 6H) and 1.22 (d, 6H); MS (electrospray) m/e 301 (M–H), Calcd for $C_{17}H_{22}N_2O_3$, 302.

Step 3:

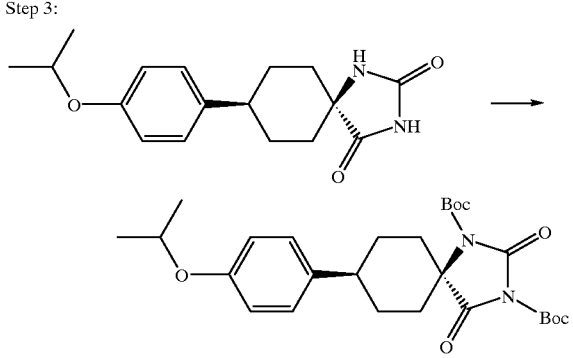

To a suspension of the hydantoin (5.8 g, 19.20 mmol) in dry THF (180 mL) were added di-tert-butyl dicarbonate (10.46 g, 48.0 mmol, 2.5 equiv), triethylamine (2.9 mL, 2.13 g, 21.12 mmol, 1.1 equiv) and DMAP (140 mg, 1.15 mmol) in succession. About 15 minutes after the addition, the reaction turned into a clear yellow solution and was stirred overnight at room temperature. The reaction mixture was concentrated under reduced pressure to yield a solid that was then taken up in EtOAc (600 mL), washed with 1N HCl (3×40 mL), saturated aqueous Na$_2$CO$_3$ (2×40 mL) and brine (2×40 mL), dried over anhydrous Na$_2$SO$_4$ and concentrated under reduced pressure. The crude light yellow product was purified through flash chromatography (hexane/EtOAc, 90/10→80/20) to give the pure bis-Boc hydantoin as a white solid (9.4 g, 98%). $^1$H NMR (CDCl$_3$): 7.27 (dt, 2H), 6.87 (dt, 2H), 4.02 (q, 2H), 2.98 (t, 1H), 2.26–2.56 (m, 4H), 2.14–2.24 (m, 2H), 1.76–1.86 (m, 2H), 1.59 (s, 9H), 1.43 (t, 3H) and 1.38 (s, 9H); MS (electrospray) m/e 999 (2M+Na)$^+$, Calcd for $C_{26}H_{36}N_2O_7$, 488.

Step 4:

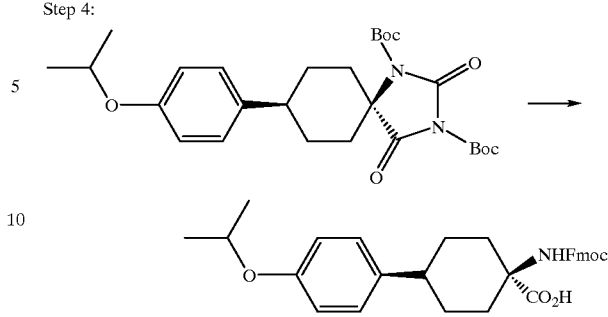

The bis-Boc hydantoin (4.34 g, 8.64 mmol) was dissolved in DME (100 mL) to give a clear solution. To this solution was added 1N NaOH (78 mL, 78 mmol) and the reaction was stirred overnight at room temperature, giving a fairly clear mixture. HPLC showed completion of the reaction. The reaction mixture was concentrated under reduced pressure to remove DME and extracted with Et$_2$O. Without purification, the resulting aqueous layer containing 1-amino-4-(4-isopropoxyphenyl)cyclohexane carboxylic acid (4-iPrOAPC) was treated with 6N HCl to adjust the pH to 11–12. To this solution (~90 mL) were added DME (120 mL) and a solution of Fmoc-OSu (3.49 g, 10.34 mmol, 1.2 equiv) in DME (20 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous Na$_2$SO$_4$ and concentrated. The crude product was purified through flash chromatography (hexane/EtOAc→CH$_2$Cl$_2$/MeOH) to give the pure product as a white solid (3.23, 75% yield from bis-Boc hydantoin). $^1$H NMR(DMSO-d$_6$), 7.76 (d, 2H), 7.60 (d, 2H), 7.39 (t, 2H), 7.31 (t, 2H), 7.08 (d, 2H), 6.84 (d, 2H), 4.24 (m, 1H) and 1.34 (d, 6H); MS (electrospray) m/e 498 (M–H), Calcd for $C_{31}H_{33}NO_5$, 499.

EXAMPLE 6

Preparation of Fmoc-1-amino-4-(4-methylphenyl)cyclohexane-1-carboxylic acid (Fmoc-4-MeApc-OH)

Step 1:

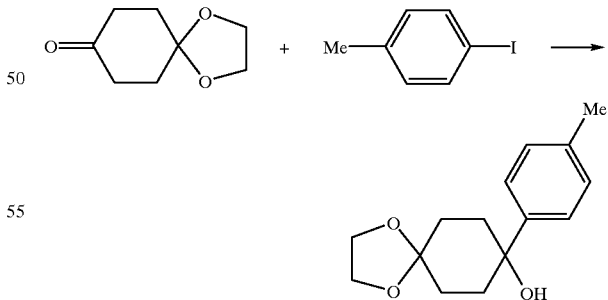

To a solution of 4-iodotoluene (10.9 g, 50.0 mmol) in dry THF (180 mL) at −78° C. was added a solution of n-BuLi (1.6 M, 31.0 mL, 50 mmol) in hexane over 20 min. The reaction was stirred for another 20 min before a solution of 1,4-cyclohexanedione mono-ethylene ketal (6.0 g, 38.46 mmol) in dry THF (100 mL) was added dropwise. After stirred for 2 h at −78° C., the reaction was quenched with aqueous NH₄Cl and extracted with EtOAc. The combined organic extracts were washed with brine, dried over Na₂SO₄, concentrated in vacuo to give the spectroscopically pure product as a white solid (9.34 g, 98% yield). ¹H NMR (CDCl₃): 7.41 (m, 2H), 7.16 (d, 2H), 3.98 (m, 4H), 2.34 (s, 3H); MS (EI) m/e 248 (M⁺), Calcd for $C_{15}H_{20}O_3$, 248.

Step 2:

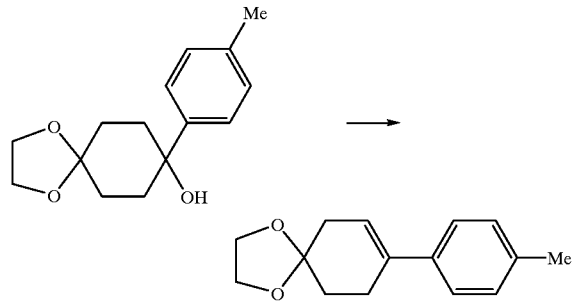

To a solution of the alcohol (9.10 g, 36.65 mmol) in dry benzene (200 mL) in a flask equipped with a Dean-Stark trap, was added p-toluenesulfonic acid monohydrate (650 mg) and the reaction was heated at 100° C. for 3 hrs. The reaction was cooled to rt, diluted with EtOAc (500 mL) and washed with aqueous Na₂CO₃ (50 mL), brine (3×50 mL), dried over Na₂SO₄ and concentrated under reduced pressure to give the spectroscopically pure product (8.36 g, 100 yield), which was used for next step without purification. MS (EI) m/e 230 (M⁺), 190 (M−OCH₂CH₂O), Calcd for $C_{15}H_{18}O_2$, 230.

Step 3:

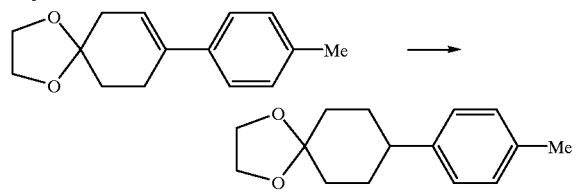

To a solution of the olefin (7.49 g) in EtOAc (180 mL) was added Pd/C (5 wt % on carbon, 800 mg) and the reaction was run under 40 psi of hydrogen for 3 hrs at room temperature. The catalyst was filtered off and the filtrate was concentrated to give the spectroscopically pure product as a colorless oil (7.40 g, 100% yield). MS (EI) m/e 232 (M⁺), 188 (M−OCH₂CH₂), Calcd for $C_{15}H_{20}O_2$, 232.

Step 4:

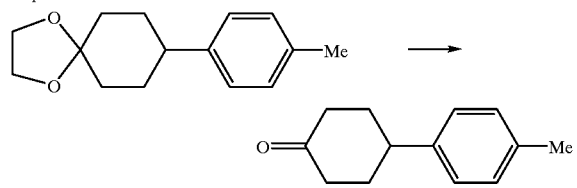

A solution of the ketal (6.90 g) in acetone (140 mL) was treated with 4N HCl (60 mL) and heated at 65° C. for 4 hrs. Solvent was removed and the residue was diluted with EtOAc and neutralized with 4N HCl. The aqueous was extracted with EtOAc. The combined organic extracts were washed with brine, dried and concentrated. The resulting crude product was used for next step without without purification (5.57 g, quantitative yield). MS (EI) m/e 188 (M⁺), Calcd for $C_{13}H_{16}O$, 188.

Step 5:

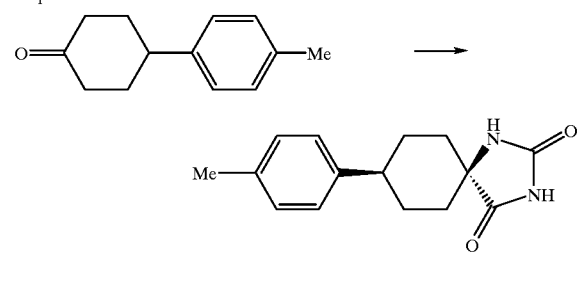

To a solution of 4-(4-methylphenyl)cyclohexanone (5.32 g, 28.3 mmol) in ethanol (90 mL) and water (30 mL) in a glass pressure bottle, were added ammonium carbonate (16.3 g, 169.8 mmol, 6 equiv.) and potassium cyanide (3.68 g, 56.5 mmol, 2 equiv.). The mixture was heated at 80–90° C. overnight. The cooled reaction mixture was added to icy water (400 ml) and stirred vigorously for 30 min. The resulting precipitate was suction filtered, washed thoroughly with water and dried to yield the hydantoin as a white solid (6.3 g, 86% yield). MS (electrospray) m/e 517 (2M+H), Calcd for $C_{15}H_{18}ClN_2O_2$, 258

Step 6:

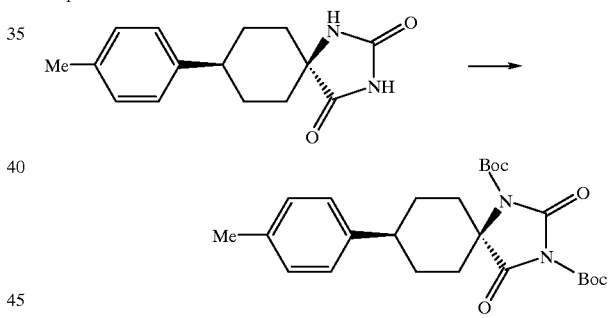

To a suspension of the hydantoin (5.82 g, 22.55 mmol) in dry THF (250 mL) were added di-tert-butyl dicarbonate (12.3 g, 56.4 mmol, 2.5 equiv), triethylamine (3.5 mL, 2.5 g, 24.7 mmol, 1.1 equiv) and DMAP (275 mg, 2.25 mmol) in succession. The reaction turned into a clear yellow solution and was stirred overnight at room temperature. The reaction mixture was concentrated under reduced pressure to yield a solid that was then taken up in EtOAc (500 mL), washed with 1N HCl (3×50 mL), saturated aqueous Na₂CO₃ (2×50 mL) and brine (2×50 mL), dried over anhydrous Na₂SO₄ and concentrated under reduced pressure. The crude light yellow product was purified through flash chromatography (hexane/EtOAc, 90/10→70/30) to give the pure bis-Boc hydantoin as a white solid (10.03 g, 100% yield). ¹H NMR (CDCl₃): 7.26 (d, 2H), 6.87 (d, 2H), 3.00 (m, 1H), 2.32 (s, 3H), 1.59 (s, 9H) and 1.37 (s, 9H).

Step 7:

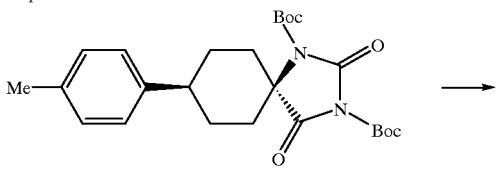

The bis-Boc hydantoin (6.40 g, 13.97 mmol) was dissolved in DME (200 mL) to give a clear solution. To this solution was added 1N NaOH (120 mL, 120 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-methylphenyl)cyclohexane carboxylic acid (4-MeAPC) was treated with 6N HCl to adjust the pH to 11–12. To this solution (~140 mL) were added DME (240 mL) and a solution of Fmoc-OSu (5.10 g, 15.13 mmol, 1.1 equiv) in DME (40 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography ($CH_2Cl_2$/MeOH, 98/2→90/10) to give the pure product as a white solid (4.35 g, 69% yield from bis-Boc hydantoin). $^1H$ NMR (DMSO-$d_6$): 7.88 (d, 2H), 7.75 (d, 2H), 7.24–7.43 (m, 4H), 7.02–7.14 (m, 4H), 4.25 (m, 3H), 2.24 (s, 3H).

EXAMPLE 7

Preparation of Fmoc-1-amino-4-(4-chlorophenyl)cyclohexane-1-carboxylic acid (Fmoc-4-ClApc-OH)

Step 1:

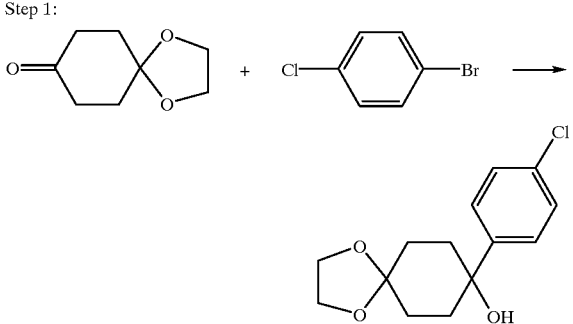

A solution of 4-chlorophenylbromide (7.5 g, 39.2 mmol) in dry THF (180 mL) was cooled to −78° C. and treated dropwise with a solution of n-BuLi (1.6 M, 25 mL, 40 mmol) in hexane over 20 min. The reaction was stirred for a further 30 min before a solution of 1,4-cyclohexanedione mono-ethylene ketal (6.0 g, 38.46 mmol) in dry THF (100 mL) was added dropwise. After stirred for 1 hr at −78° C., the reaction was quenched with aqueous $NH_4Cl$ and extracted with EtOAc. The combined organic extracts were washed with brine, dried over $Na_2SO_4$, concentrated in vacuo to give the spectroscopically pure product as a white solid (9.40 g, 91% yield). $^1H$ NMR (CDCl$_3$): 7.45 (m 2H), 7.31 (m, 2H), 3.99 (m, 4H), 2.02–2.20 (m, 4H), 1.75–1.82 (m, 2H), 1.66–1.73 (m, 2H), 1.54 (s, 1H); MS (EI) m/e 268 ($M^+$), 251 (M–OH), 250 (M–$H_2O$), Calcd for $C_{14}H_{17}ClO_3$, 268.

Step 2:

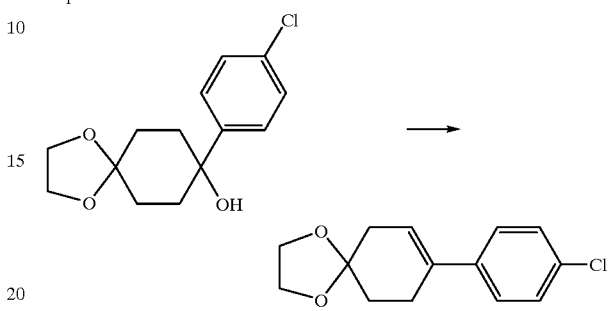

To a solution of the alcohol (6.78 g, 25.30 mmol) in dry benzene (120 mL) in a flask equipped with a Dean-Stark trap, was added p-toluenesulfonic acid monohydrate (960 mg) and the reaction was heated at reflux for 3 hrs. The reaction was cooled to rt, diluted with EtOAc (500 mL) and washed with aqueous $Na_2CO_3$ (50 mL), brine (3×50 mL), dried over $Na_2SO_4$ and concentrated under reduced pressure to give the spectroscopically pure product (6.30 g, 100% yield), which was used for next step without purification. MS (EI) m/e 250 ($M^+$), 190 (M–$OCH_2CH_2O$), Calcd for $C_{14}H_{15}ClO_2$, 250.

Step 3:

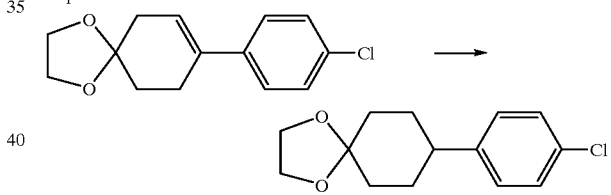

To a solution of the olefin (6.11 g) in EtOAc (120 mL) was added Pd/C (5 wt % on carbon, 600 mg) and the reaction was run under 5 psi of hydrogen for 3 hrs at room temperature. The catalyst was filtered off and the filtrate was concentrated to give the spectroscopically pure product as a colorless oil (6.10 g, 100% yield). MS (EI) m/e 252($M^+$), Calcd for $C_{14}H_{17}ClO_2$, 252.

Step 4:

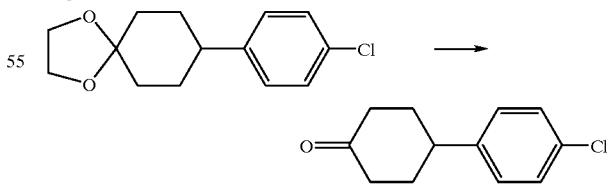

A solution of the ketal (5.81 g, 23.06 mmol) in acetone (200 mL) was treated with p-toluenesulfonic acid monohydrate (876 mg) and heated at 60° C. overnight. Solvent was removed and the residue was taken up in EtOAc, washed with aqueous $Na_2CO_3$ solution, brine, dried and concentrated to give the crude product as a yellow oil (5.38 g, >100% yield). Purification through flash chromatography (heaxane/EtOAc, 80/20→60/40) provided the ketone as a light yellow oil (4.54 g, 95% yield). MS (EI) m/e 208 (M+), Calcd for $C_{12}H_{13}ClO_2$, 208.

Step 5:

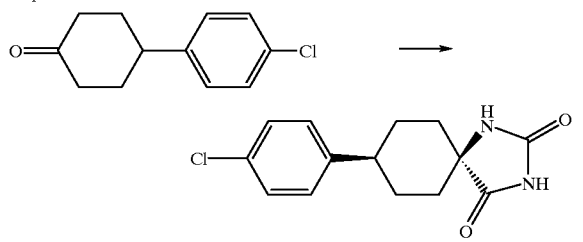

To a solution of 4-(4-chlorophenyl)cyclohexanone (4.26 g, 20.48 mmol) in ethanol (90 mL) and water (30 mL) in a glass pressure bottle, were added ammonium carbonate (13.8 g, 144 mmol, 7 equiv) and potassium cyanide (3.56 g, 54.77 mmol, 2.5 equiv). The mixture was heated at 80–90° C. overnight. The cooled reaction mixture was added to icy water (400 ml) and stirred vigorously for 30 min. The resulting precipitate was suction filtered, washed thoroughly with water and dried to yield the hydantoin as a white solid (5.58 g, 98% yield). MS (electrospray) m/e 277 (M–H), Calcd for $C_{14}H_{15}ClN_2O_2$, 278

Step 6:

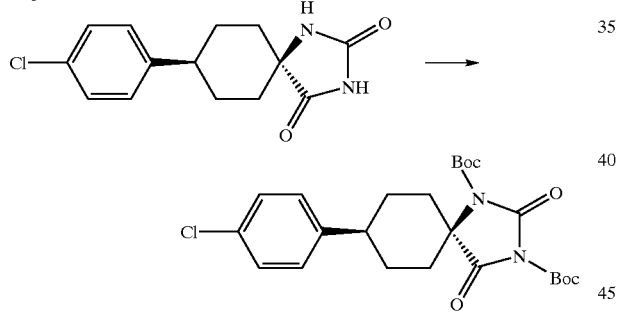

To a suspension of the hydantoin (5.15 g, 18.5 mmol) in dry THF (250 mL) were added di-tert-butyl dicarbonate (10.1 g, 46.3 mmol, 2.5 equiv), triethylamine (2.8 mL, 2.07 g, 20.45 mmol, 1.1 equiv) and DMAP (226 mg, 1.85 mmol) in succession. The reaction turned into a clear yellow solution and was stirred overnight at room temperature. The reaction mixture was concentrated under reduced pressure to yield a solid that was then taken up in EtOAc (500 mL), washed with 1N HCl (3×50 mL), saturated aqueous $Na_2CO_3$ (2×50 mL) and brine (2×50 mL), dried over anhydrous $Na_2SO_4$ and concentrated under reduced pressure. The crude light yellow product was purified through flash chromatography (hexane/EtOAc, 90/10→70/30) to give the pure bis-Boc hydantoin as a white solid (8.05 g, 91% yield). MS (electrospray) m/e 542 (M+Ma+MeCN), Calcd for $C_{24}H_{31}ClN_2O_6$, 478

Step 7:

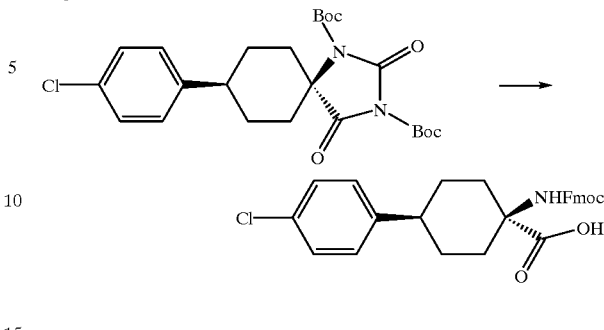

The bis-Boc hydantoin (6.41 g, 13.97 mmol) was dissolved in DME (200 mL) to give a clear solution. To this solution was added 1N NaOH (120 mL, 120 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-chlorophenyl)cyclohexane carboxylic acid (4-ClAPC) was treated with 6N HCl to adjust the pH to 11–12. To this solution (~180 mL) were added DME (240 mL) and a solution of Fmoc-OSu (5.31 g, 15.74 mmol, 1.1 equiv) in DME (30 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography ($CH_2Cl_2$/MeOH, 98/2→90/10) to give the pure product as a white solid (5.04 g, 76% yield from the bis-Boc hydantoin). $^1H$ NMR (DMSO-$d_6$), 7.88 (d, 2H), 7.74 (d, 2H), 7.19–7.42 (m, 8H), 4.20–4.31 (m, 3H); MS (electrospray) m/e 474 (M–H), Calcd for $C_{28}H_{26}ClNO_4$, 475.

EXAMPLE 8

Preparation of Fmoc-1-amino-4-(3-methoxyphenyl) cyclohexane-1-carboxylic acid (Fmoc-3-MeOApc-OH)

Step 1:

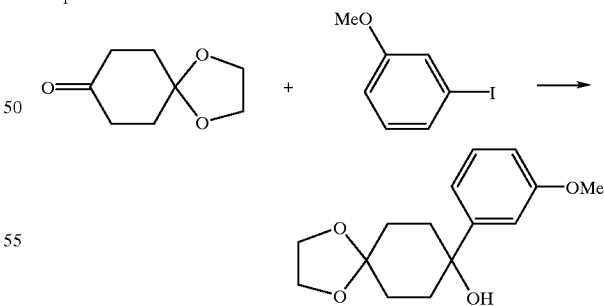

To a solution of 3-iodoanisole (11.7, 50.0 mmol, 1.3 equiv) in dry THF (180 mL) at −78° C. was added a solution of n-BuLi (1.6 M, 31.0 mL, 50 mmol, 1.3 equiv) in hexane over 25 min. The reaction was stirred for another 30 min before a solution of 1,4-cyclohexanedione mono-ethylene ketal (6.0 g, 38.46 mmol) in dry THF (100 mL) was added dropwise. After stirred for 2 h at −78° C., the reaction was quenched with aqueous $NH_4Cl$ and extracted with EtOAc.

The combined organic extracts were washed with brine, dried over Na$_2$SO$_4$, concentrated in vacuo to give the spectroscopically pure product as a white solid (9.34 g, 98% yield). $^1$H NMR (CDCl$_3$): 7.26 (dd, 1H), 7.06–7.11 (m, 2H), 6.79 (dd, 1H), 3.98 (m, 4H), 3.81 (s, 3H).

Step 2:

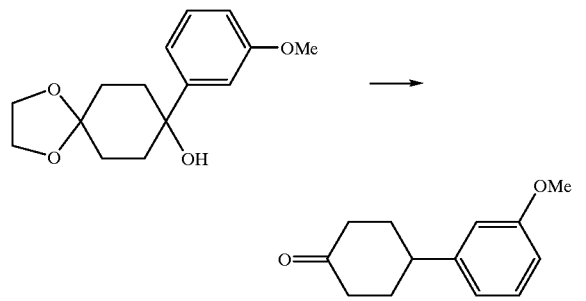

To a stirred solution of the alcohol (5.6 g, 21.21 mmol) in dry CH$_2$Cl$_2$ (200 mL) under a nitrogen atmosphere at salt-ice bath temperature, were added in succession triethylsilane (10.2 mL, 7.4 g, 63.63 mmol, 3 equiv) and boron trifluoride etherate (21.5 mL, 24.1 g, 169.7 mmol, 8 equiv). The reaction mixture was then allowed to warm to room temperature and stirred for 3 hrs before washed with 10% aqueous K$_2$CO$_3$ solution and H$_2$O, dried over Na$_2$SO$_4$, and concentrated in vacuo to give the deoxygenation compound as an oil (4.91 g), which was sufficiently pure for direct use.

This crude intermediate was dissolved in acetone (130 mL) and treated with 4N HCl (60 mL) and heated at 65° C. for 4 hrs. Solvent was removed under reduced pressure and the residue was diluted with EtOAc and neutralized with 4N NaOH solution. The aqueous layer was extracted with EtOAc and the combined organic extracts were washed with brine, dried and concentrated. The resulting residue was purified by flash chromatography on silica gel (80/20→60/40) to give the ketone (3.67 g, 85% overall yield) as a yellow oil. $^1$H NMR (CDCl$_3$): 7.25 (dt, 1H), 6.75–6.86 (m, 3H), 3.81 (s, 3H), 3.00 (tt, 1H); MS (EI) m/e 204 (M+), Calcd for C$_{13}$H$_{16}$O$_2$, 204.

Step 3:

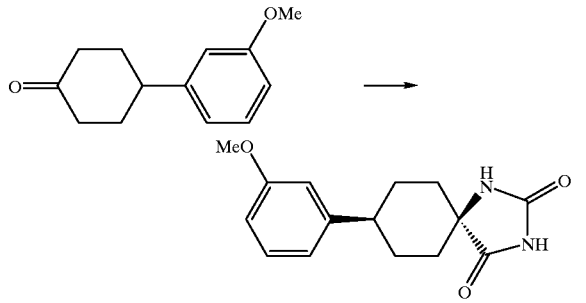

To a solution of 4-(3-methoxyphenyl)cyclohexanone (3.10 g, 15.20 mmol) in ethanol (60 mL) and water (20 mL) in a glass pressure bottle, were added ammonium carbonate (8.75 g, 91.20 mmol, 6 equiv) and potassium cyanide (1.98 g, 30.40 mmol, 2 equiv.). The mixture was heated at 80–90° C. overnight. The cooled reaction mixture was added to icy water (300 ml) and stirred vigorously for 30 min. The resulting precipitate was suction filtered, washed thoroughly with water and dried to yield the hydantoin as a white solid (4.08 g, 98% yield). $^1$H NMR (DMSO-d$_6$): 7.11 (d, 1H), 6.70–6.94 (m, 3H), 3.72 (s, 3H); MS (electrospray) m/e 316 (M+MeCN+H), Calcd for C$_{15}$H$_{18}$N$_2$O$_3$, 274.

Step 4:

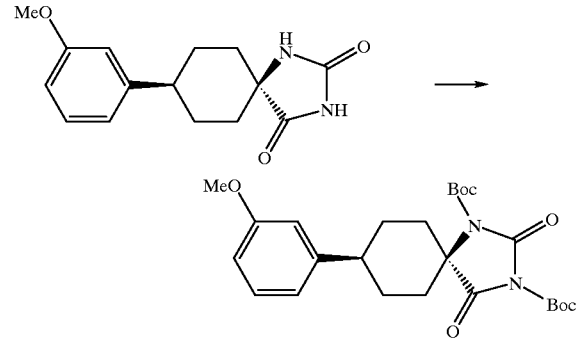

To a suspension of the hydantoin (5.29 g, 19.30 mmol) in dry THF (250 mL) were added di-tert-butyl dicarbonate (10.5 g, 48.16 mmol, 2.5 equiv), triethylamine (3.0 mL, 2.17 g, 21.52 mmol, 1.1 equiv) and DMAP (235 mg, 1.92 mmol) in succession. The reaction turned into a clear yellow solution and was stirred overnight at room temperature. The reaction mixture was concentrated under reduced pressure to yield a solid that was then taken up in EtOAc (500 mL), washed with 1N HCl (3×50 mL), saturated aqueous Na$_2$CO$_3$ (2×50 mL) and brine (2×50 mL), dried over anhydrous Na$_2$SO$_4$ and concentrated under reduced pressure. The crude light yellow product was purified through flash chromatography (hexane/EtOAc, 80/20→60/40) to give the pure bis-Boc hydantoin as a white solid (8.70 g, 95% yield). MS (electrospray) m/e 538 (M+MeCN+Na), Calcd for C$_{25}$H$_{34}$N$_2$O$_7$, 474.

Step 5:

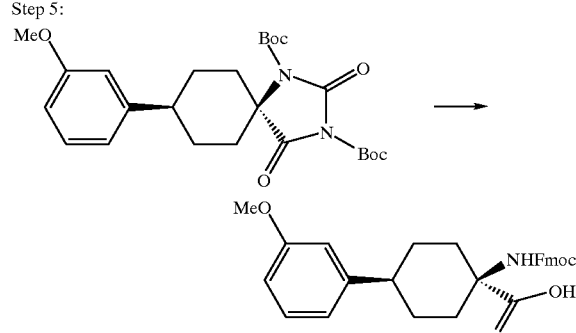

The bis-Boc hydantoin (2.30 g, 4.84 mmol) was dissolved in DME (80 mL) to give a clear solution. To this solution was added 1N NaOH (44 mL, 44 mmol) and the reaction was stirred overnight at room temperature, giving a slightly cloudy mixture. HPLC showed completion of the reaction. The reaction mixture was concentrated under reduced pressure to remove DME and extracted with Et$_2$O. Without purification, the resulting aqueous layer containing 1-amino-4-(3-methoxyphenyl)cyclohexane carboxylic acid (3-MeOAPC) was treated with 6N HCl to adjust the pH to 11–12. To this solution (~40 mL) were added dioxane (80 mL) and Fmoc-Cl (1.73 g, 6.76 mmol, 1.4 equiv) and the reaction was stirred overnight at room temperature. The reaction mixture was then concentrated under reduced pressure to remove DME, neutralized with 3N HCl and extracted with EtOAc. The combined organic extracts were washed with brine, dried over anhydrous Na$_2$SO$_4$ and concentrated. The crude product was purified by flash chromatography on silica gel (CH$_2$Cl$_2$/MeOH, 98/2→90/10) to give the pure product as a white solid (1.98 g, 87% yield from bis-Boc hydantoin). $^1$H NMR (DMSO-d$_6$), 7.88 (d, 2H), 7.75 (d, 2H), 7.40 (td, 2H), 7.30 (td, 2H), 7.21 (m, 1H), 6.71–6.80 (m, 3H), 3.72 (s, 3H); MS (electrospray) m/e 494 (M+Na), Calcd for C$_{29}$H$_{29}$NO$_5$, 471.

EXAMPLE 9

Preparation of Fmoc-(D,L)-5-bromo-2 aminotetraline-2-carboxylic acid (Fmoc-(D,L) 5-Br-Atc-OH)

Step 1:

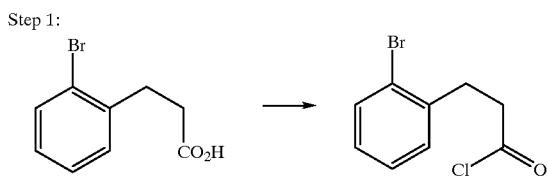

A mixture of 3-(2-bromophenyl)propanoic acid (prepared in 2 steps from 2-bromobenzyl bromide, 2.0 g, 8.73 mmole), oxalyl chloride (1.14 ml, 13.1 mmole) and methylene chloride (20 ml) was cooled in an ice bath and N,N-dimethylformamide (34 μL, 0.44 mmole) was added dropwise. The mixture was stirred at room temperature for 3 hours. Concentration in vacuo gave 3-(2-bromophenyl)propanoyl chloride which was taken up in methylene chloride and used in the next step as a crude.

Step 2:

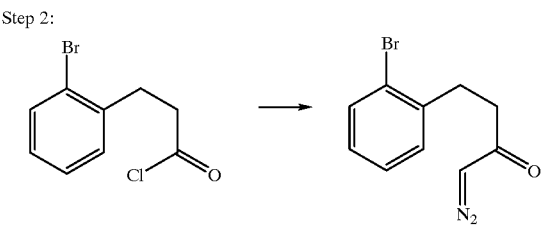

A solution of the above acid chloride (crude, 8.73 mmole) in methylene chloride was slowly added to a solution of diazomethane (generated from 5.70 g of 1-methyl-3-nitro-1-nitrosoguanidine) in ether (40 ml) cooled in an ice bath. The mixture was then warmed up to room temperature and stirred overnight. The mixture was concentrated in vacuo and purified by column chromatography (10→20% ethyl acetate/hexanes) to give 1-diazo-4-(2-bromophenyl)butan-2-one (1.88 g, 85% over 2 steps). $^1$H NMR (CDCl$_3$) δ7.50 (1H, d, phenyl), 7.24 (2H, m, phenyl), 7.06 (1H, m, phenyl), 5.21 (1H, broad s, diazo), 3.05 (2H, t, benzylic), 2.62 (2H, m).

Step 3:

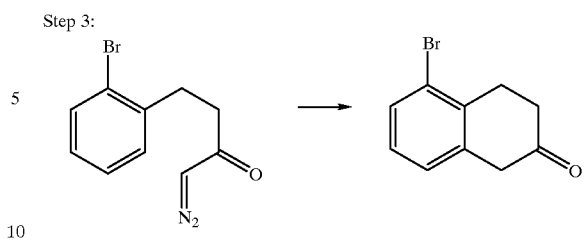

To a mixture of rhodium (II) acetate dimer (15 mg, 0.068 mmole) in methylene chloride (120 ml) under reflux was slowly added a solution of 1-diazo-4-(2-bromophenyl)butan-2-one (1.74 g, 6.85 mmole) in methylene chloride (30 ml). After the addition was complete, the mixture was refluxed for an extra twenty minutes. The mixture was cooled to room temperature, trifluoroacetic acid (1.5 ml) was added and the mixture was stirred at room temperature for an hour. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a brown oil. Purification by column chromatography (10→15% ethyl acetate/hexanes) gave 5-bromo-β-tetralone (1.18 g, 77% yield) as a colorless oil. $^1$H NMR (CDCl$_3$) δ7.46 (1H, t, phenyl), 7.05–7.09 (2H, m, phenyl), 3.58 (2H, s, benzylic), 3.22 (2H, t, benzylic), 2.54 (2H, t).

Step 4:

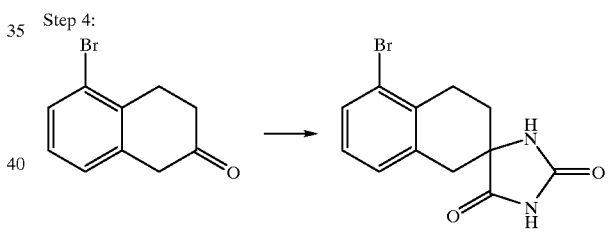

A mixture of 5-bromo-β-tetralone (1.18 g, 5.24 mmole), potassium cyanide (512 mg, 7.86 mmole), ammonium carbonate (3.0 g, 31.22 mmole), ethanol (25 ml) and water (5 ml) in a sealed, thick walled pressure flask was heated in a 80° C. oil bath for 4 days. After cooling to room temperature, the white slurry was poured into ice-water and stirred at room temperature for a couple of hours. Filtration followed by air-drying gave hydantoin (1.31 g, 85%). $^1$H NMR (DMSO-d$_6$) δ10.71 (1H, broad, NH), 8.28 (1H, broad s, NH), 7.0–7.5 (3H, m, phenyl). LRMS (Electrospray): C$_{12}$H$_{11}$BrN$_2$O$_2$, calc. 294; observed: 293 (M–H), 295 (M–H).

Step 5:

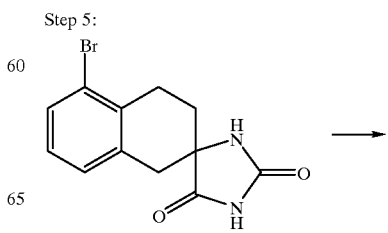

-continued

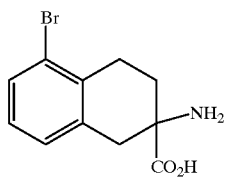

A mixture of hydantoin (1.287 g, 4.36 mmole), Ba(OH)$_2$·H$_2$O (4.20 g, 22.2 mmole) in water (25 ml) in a sealed, thick walled pressure flask was heated in a 125° C. oil bath for 4 days. The reaction mixture was cooled to room temperature, acidified to ~pH 3 using 4N sulfuric acid while being stirred vigorously. The suspension was stirred in a boiling water bath for one hour and cooled to room temperature. The white suspension was filtered and the precipitates rinsed with water. The combined filtrate and washings were concentrated in vacuo to ~20 ml. Neutralization with concentrated ammonium hydroxide solution gave white precipitate which were filtered, washed with water and dried in vacuo overnight to give racemic 5-bromo-2 aminotetraline-2-carboxylic acid (893 mg, 76% yield). LRMS (Electrospray): C$_{11}$H$_{12}$BrNO$_2$, calc. 269; observed: 270 (M+H), 272 (M+H), 268 (M−H), 270 (M−H).

Step 6:

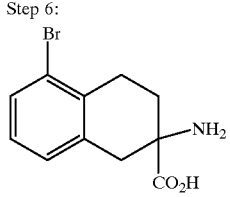  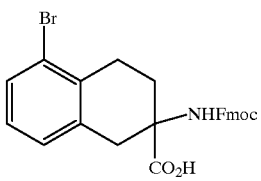

A mixture of racemic 5-bromo-2 aminotetraline-2-carboxylic acid (882 mg, 3.27 mmole), triethylamine (0.60 ml, 4.30 mmole), 9-fluorenylmethyl succinimidyl carbonate (Fmoc-OSu, 1.32 g, 3.91 mmole) in acetonitrile (30 ml) and water (30 ml) was stirred at room temperature overnight. TLC analysis of the reaction the next day indicated the presence of starting material amino acid. 9-fluorenylmethyl succinimidyl carbonate (0.25 g), triethylamine (0.6 ml) and acetonitrile (5 ml) was added and the mixture was stirred at room temperature for another day. The reaction mixture was concentrated in vacuo to remove most of the acetonitrile, acidified to pH ~3 with 10% aqueous citric acid solution, and the white emulsion extracted twice with methylene chloride. The combined organic layers were washed with water, brine, dried over magnesium sulfate. Filtration and concentration gave a crude oil which was purified by column chromatography (eluted with 2→5→10% methanol/methylene chloride) to give racemic Fmoc-5-bromo-2 aminotetraline-2-carboxylic acid (1.09 g, 68% yield) as a white solid. HRMS (FAB): C$_{26}$H$_{22}$BrNNaO$_4$ (M+Na) calc. 514.0630; observed: 514.0643.

EXAMPLE 10

Preparation of Fmoc-(D,L)-5-chloro-2 aminotetraline-2-carboxylic acid (Fmoc-(D,L) 5-ClAtc-OH)

Step 1:

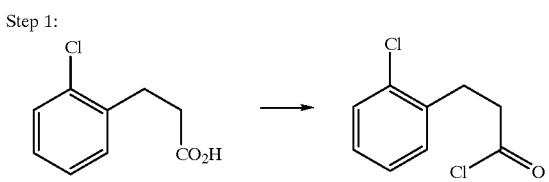

A mixture of 3-(2-chlorophenyl)propanoic acid (5.0 g, 27.1 mmole), thionyl chloride (10.9 ml, 149 mmole) and toluene (75 ml) was refluxed for two hours. Concentration in vacuo gave 3-(2-chlorophenyl)propanoyl chloride which was taken up in methylene chloride and used in the next step without further purification.

Step 2:

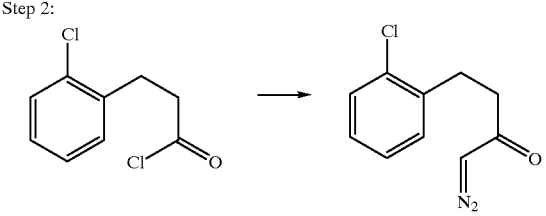

A solution of the above acid chloride (crude, 27.1 mmole) in methylene chloride was slowly added to a solution of diazomethane (generated from 17.8 g of 1-methyl-3-nitro-1-nitrosoguanidine) in ether (120 ml) cooled in an ice bath. The mixture was then warmed up to room temperature and stirred overnight. The mixture was concentrated in vacuo to give 1-diazo-4-(2-chlorophenyl)butan-2-one (5.87 g, >100% over 2 steps) as a bright yellow oil. The compound was used in the next step without further purification. $^1$H NMR (CDCl$_3$) δ7.05–7.32 (4H, m, phenyl), 5.13 (1H, broad s, diazo), 3.00 (2H, t, benzylic), 2.57 (2H, m).

Step 3:

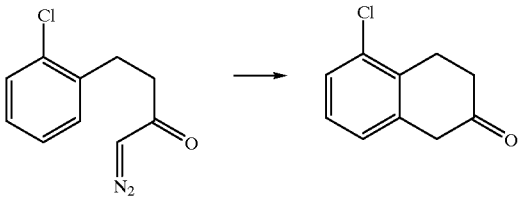

To a mixture of rhodium (II) acetate dimer (60 mg, 0.27 mmole) in methylene chloride (400 ml) under reflux was slowly added a solution of crude 1-diazo-4-(2-bromophenyl)butan-2-one (5.87 g, 27.1 mmole theoretical) in methylene chloride (50 ml). After the addition was complete, the mixture was refluxed for an extra twenty minutes. The mixture was cooled to room temperature, trifluoroacetic acid (6.0 ml) was added and the mixture was stirred at room temperature for two hours. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a brown oil. Purification by column chromatography (10→15% ethyl acetate/hexanes) gave 5-chloro-β-tetralone (3.32 g, 68% yield for steps a through c) as a light brown oil. $^1$H NMR (CDCl$_3$) δ7.30 (1H, m, phenyl), 7.15 (1H, t, phenyl), 7.05 (1H, d, phenyl), 3.60 (2H, s, benzylic), 3.22 (2H, t, benzylic), 2.56 (2H, t).

Step 4:

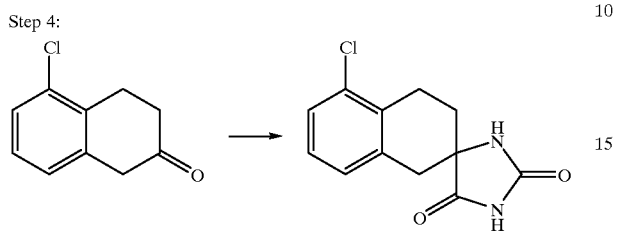

A mixture of 5-chloro-β-tetralone (880 mg, 4.87 mmole), potassium cyanide (500 mg, 7.67 mmole), ammonium carbonate (2.85 g, 29.7 mmole), ethanol (24 ml) and water (6 ml) in a sealed, thick walled pressure flask was heated in a 80° C. oil bath for 66 hours. After cooling to room temperature, the slurry was poured into ice-water and stirred at room temperature for a couple of hours. Filtration followed by air-drying gave hydantoin (0.92 g, 75%) as a light beige solid. $^1$H NMR (DMSO-d$_6$) δ10.70 (1H, broad, NH), 8.25 (1H, broad s, NH), 7.0–7.3 (3H, m, phenyl). LRMS (Electrospray): C$_{12}$H$_{11}$ClN$_2$O$_2$, calc. 250; observed: 249 (M–H), 251 (M–H).

Step 5:

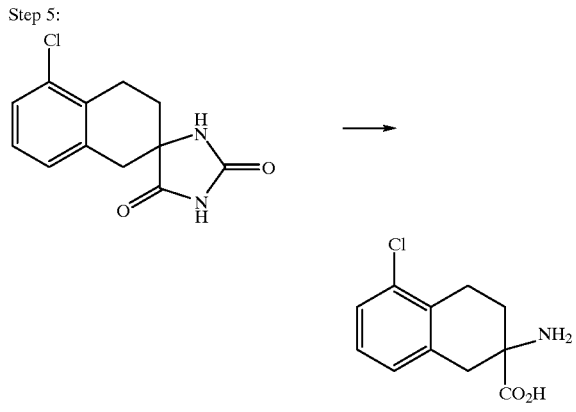

A mixture of hydantoin (880 mg, 3.51 mmole), Ba(OH)$_2$·H$_2$O (3.40 g, 18.0 mmole) in water (50 ml, too dilute) in a sealed, thick walled pressure flask was heated in a 125° C. oil bath for 2 days. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and dried in vacuo overnight to give racemic 5-chloro-2-aminotetraline-2-carboxylic acid (788 mg, 99% yield). LRMS (Electrospray): C$_{11}$H$_{12}$ClNO$_2$, calc. 225; observed: 226 (M+H), 228 (M+H), 224 (M–H), 226 (M–H).

Step 6:

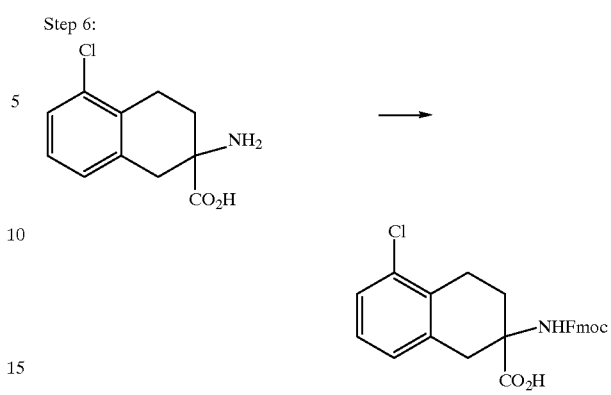

A mixture of racemic 5-chloro-2-aminotetraline-2-carboxylic acid (402 mg, 1.78 mmole), triethylamine (0.38 ml, 2.73 mmole), 9-fluorenylmethyl succinimidyl carbonate (Fmoc-OSu, 904 mg, 2.68 mmole) in acetonitrile (20 ml) and water (20 ml) was stirred at room temperature for two days. TLC analysis of the reaction after two days indicated the presence of starting material amino acid. 9-fluorenylmethyl succinimidyl carbonate (0.12 g) and triethylamine (0.1 ml) was added and the mixture was stirred at room temperature for another day. The reaction mixture was concentrated in vacuo to remove most of the acetonitrile, acidified to pH~3 with 10% aqueous citric acid solution, and the white emulsion extracted three times with ethyl acetate. The combined organic layers were washed with water, brine, dried over magnesium sulfate. Filtration and concentration gave a crude oil which was purified by column chromatography (eluted with 3→6→8% methanol/methylene chloride) to give racemic Fmoc-5-chloro-2-aminotetraline-2-carboxylic acid (540 mg, 68% yield) as a white solid. HRMS (EI): C$_{26}$H$_{22}$ClNO$_4$ (M) calc. 447.1237, observed: 447.1234.

EXAMPLE 11

Preparation of Fmoc-(D,L)-5-methoxy-2-aminotetraline-2-carboxylic acid (Fmoc-(D,L) 5-MeOAtc-OH)

Step 1:

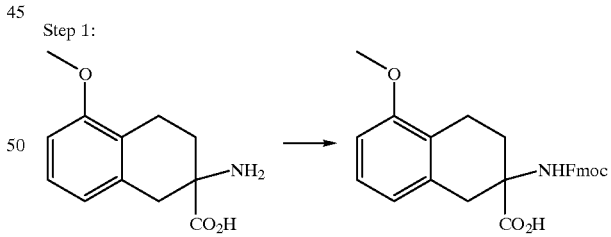

A mixture of racemic 5-methoxy-2-aminotetraline-2-carboxylic acid (prepared according to Obrecht, D. et. al. *Helv. Chim Acta.* 1992, 75, 1666) (802 mg, 3.62 mmole), triethylamine (0.62 ml, 4.45 mmole), 9-fluorenylmethyl succinimidyl carbonate (Fmoc-OSu, 1.47 g, 4.36 mmole) in acetonitrile (25 ml) and water (25 ml) was stirred at room temperature for 30 hours. TLC analysis of the reaction indicated the presence of starting material amino acid. 9-fluorenylmethyl succinimidyl carbonate (370 mg) and triethylamine (0.6 ml) were added and the mixture was stirred at room temperature for another 24 hours. The reaction mixture was concentrated in vacuo to remove most of the acetonitrile, acidified to pH~3 with 10% aqueous citric acid solution, and the white emulsion was extracted three times with ethyl acetate. The combined organic layers were washed with water, brine and dried over magnesium sulfate. Filtration and concentration gave a crude oil which was purified by column chromatography (eluted with 1→3→5→10% methanol/methylene chloride) to give racemic Fmoc-5-methoxy-2-aminotetraline-2-carboxylic acid (1.14 g, 71% yield) as an off-white solid. HRMS (FAB): $C_{27}H_{26}NO_5$ (M+H) calc. 444.1812; observed: 444.1814.

EXAMPLE 12

Preparation of Fmoc-(D,L)-5-ethoxy-2-aminotetraline-2-carboxylic acid (Fmoc-(D,L) 5-EtOAtc-OH)

Step 1:

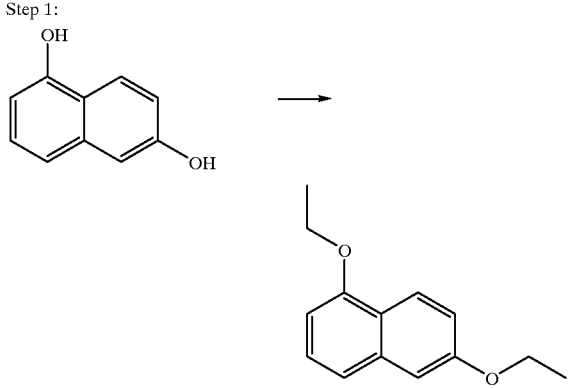

A mixture of 1,6-dihydroxynaphthalene (5.02 g, 31.3 mmole), anhydrous potassium carbonate (52.0 g, 376 mmole), N,N-dimethylformamide (50 ml) and iodoethane (15 ml, 188 mmole) was stirred in a 35° C. oil bath for 24 hours. The reaction mixture was filtered and the solid residue was rinsed thoroughly with ethyl ether. The filtrate and the washings were combined and concentrated in vacuo to remove most of the solvents. The brown residue was partitioned between water and ether and the layers were separated. The ether layer was washed with water. The combined aqueous layers were back extracted with ether. The ether extracts were combined, washed with brine and dried over magnesium sulfate. Filtration and concentration gave a crude brown solid (6.74 g, 99% yield). Recrystallization of the crude product from hot methanol gave 1,6-diethoxynaphthalene (4.36 g, 64% yield, first crop) as a light brown solid. $^1H$ NMR (CDCl$_3$) δ8.20 (1H, d, phenyl), 7.06–7.36 (4H, m, phenyl), 6.66 (1H, dd, phenyl), 4.10–4.23 (4H, 2 sets of q, 2 CH$_2$), 1.45–1.56 (6H, 2 sets if t, 2 CH$_3$).

Step 2:

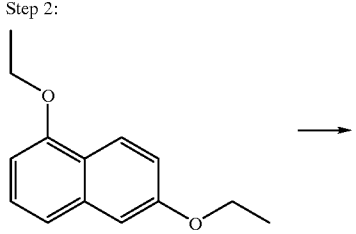

-continued

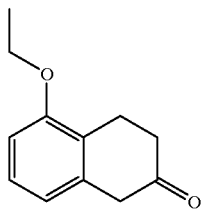

To a refluxing solution of 1,6-diethoxynaphthalene (4.15 g, 19.2 mmole) in absolute ethanol (100 ml) was carefully added small pieces of sodium metal (6.8 g, 296 mmole) over 60 minutes. The mixture was refluxed for another 90 minutes. TLC indicated the presence of unreacted starting material. Extra sodium metal (1.0 g, 43.5 mmole) was added and the reaction mixture was refluxed for another 60 minutes. The reaction was cooled to room temperature, quenched with water and acidified with concentrated hydrochloric acid. The mixture was concentrated in vacuo to remove most of the ethanol. The aqueous mixture was extracted three times with ether. The combined organic layers were washed with water and dried over sodium sulfate. Filtration and concentration gave a brown solid which was dissolved in 1:1 ethanol/water (200 ml), then p-toluenesulfonic acid (400 mg) was added. The mixture was refluxed for 210 minutes. Extra p-toluenesulfonic acid (100 mg) was added and the mixture was refluxed for another 60 minutes. After cooling to room temperature, most of the ethanol was removed under reduced pressure. The aqueous mixture was extracted three times with ether and the combined organic layers were washed with water, saturated sodium chloride solution and dried over sodium sulfate. Filtration and concentration gave a brown oil which was purified by column chromatography (7% ethyl acetate/hexanes) to give 5-ethoxy-β-tetralone (2.43 g, 67% yield) as a light yellow oil. $^1H$ NMR (CDCl$_3$) δ7.15 (1H, t, phenyl), 6.76 (1H, d, phenyl), 6.72 (1H, d, phenyl), 4.05 (2H, q, CH$_2$), 3.56 (2H, s, benzylic), 3.10 (2H, t, benzylic), 2.53 (2H, t), 1.44 (3H, t, CH$_3$).

Step 3:

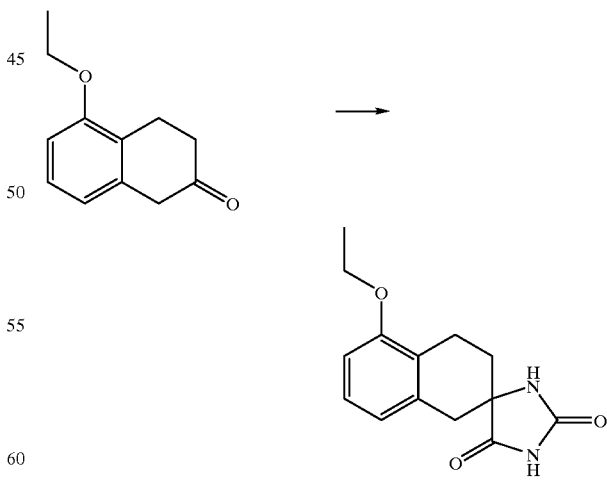

A mixture of 5-ethoxy-β-tetralone (2.23 g, 11.7 mmole), potassium cyanide (1.20 g, 18.4 mmole), ammonium carbonate (6.75 g, 70.2 mmole), ethanol (80 ml) and water (20 ml) in a sealed, thick walled pressure flask was heated in a 80° C. oil bath for 3 days. After cooling to room temperature, the slurry was poured into ice-water and stirred at room temperature for a couple of hours. Filtration followed by air-drying gave hydantoin (2.69 g, 88%) as a beige solid. $^1$H NMR (DMSO-$d_6$) δ10.65 (1H, broad s, NH), 8.22 (1H, broad s, NH), 7.06 (1H, t, phenyl), 6.75 (1H, d, phenyl), 6.65 (1H, d, phenyl), 3.98 (2H, q, $CH_2$), 1.32 (3H, t, $CH_3$). LRMS (Electrospray): $C_{14}H_{16}N_2O_3$, calc. 259; observed: 258 (M−H).

Step 4:

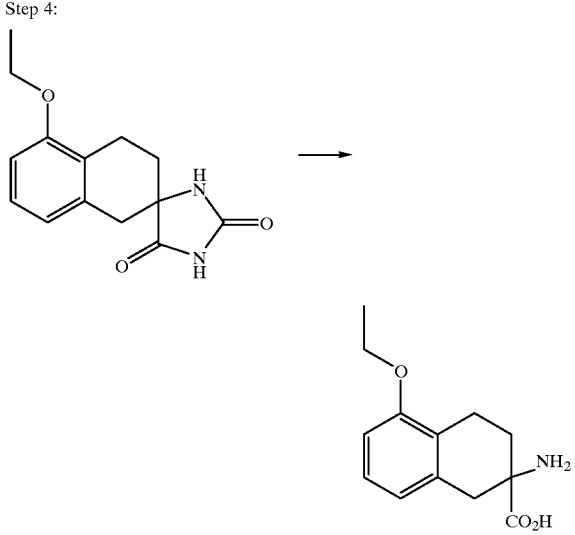

A mixture of hydantoin (2.57 g, 9.87 mmole), Ba(OH)$_2$.H$_2$O (9.40 g, 49.6 mmole) in water (200 ml, too dilute) in a sealed, thick walled pressure flask was heated in a 105° C. oil bath for 39 hours. Extra Ba(OH)$_2$. H$_2$O (9.40 g, 49.6 mmole) was added and the mixture was heated in a 125° C. oil bath for an additional 21 hours. The reaction mixture was cooled to room temperature, acidified to ~pH 3 using 4N sulfuric acid while being stirred vigorously. The suspension was stirred in a boiling water bath for one hour and cooled to room temperature. The white suspension was filtered and the precipitates rinsed with water. The combined filtrate and washings were concentrated in vacuo to ~75 ml. Neutralization with concentrated ammonium hydroxide solution gave white precipitate which were filtered, washed with water and air-dried to give racemic 5-ethoxy-2-aminotetraline-2-carboxylic acid (2.34 g, quantitative yield) as a light beige solid. LRMS (Electrospray): $C_{13}H_{17}NO_3$, calc. 235; observed: 236 (M+H), 234 (M−H).

Step 5:

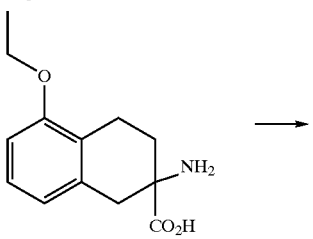

-continued

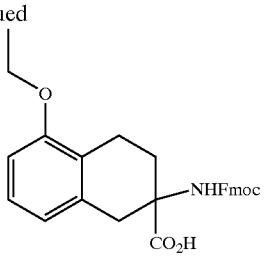

A mixture of racemic 5-ethoxy-2-aminotetraline-2-carboxylic acid (2.22 g, 9.44 mmole), triethylamine (2.00 ml, 14.3 mmole), 9-fluorenylmethyl succinimidyl carbonate (Fmoc-OSu, 4.81 g, 14.3 mmole) in acetonitrile (75 ml) and water (75 ml) was stirred at room temperature for two days. TLC analysis of the reaction indicated the presence of starting material amino acid. 9-fluorenylmethyl succinimidyl carbonate (645 mg) and triethylamine (1.0 ml) was added and the mixture was stirred at room temperature for another day. The reaction mixture was concentrated in vacuo to remove most of the acetonitrile, acidified to pH~3 with 10% aqueous citric acid solution, and the white emulsion extracted three times with ethyl acetate. The combined organic layers were washed with water, brine, dried over magnesium sulfate. Filtration and concentration gave a crude oil which was purified by column chromatography (eluted with 3→5→10% methanol/methylene chloride) to give racemic Fmoc-5-ethoxy-2-aminotetraline-2-carboxylic acid (4.66 g, >quantitative yield) as a white solid. HRMS (FAB): $C_{28}H_{28}NO_5$ (M+H) calc. 458.1967; observed: 458.1985.

EXAMPLE 13

Preparation of Fmoc-(D,L)-5-isopropoxy-2-aminotetraline-2-carboxylic acid (Fmoc-(D,L) 5-iPrOAtc-OH)

Step 1:

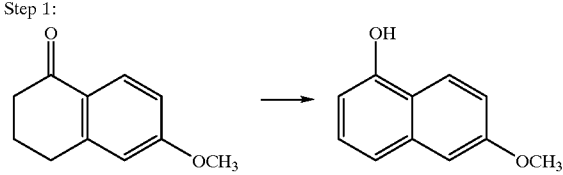

A mixture of 6-methoxy-1-tetralone (5.07 g, 28.8 mmole), 10% Pd/C (3.53 g, 3.32 mmole) in dry p-cymene (250 ml) was heated to reflux under argon for 38 hours. The reaction mixture was cooled to room temperature, filtered over celite and the residue rinsed thoroughly with p-cymene. The filtrate and the washings were combined and extracted twice with 1N sodium hydroxide solution (2×70 ml). The combined aqueous extracts were acidified with 6N hydrochloric acid to pH ~3 and extracted three times with ether. The combined organic layers were washed with water, dried over anhydrous sodium sulfate. Filtration and concentration gave crude 5-hydroxy-6-methoxynaphthalene (2.31 g, 46% yield) as a light brown solid which was used in the next step without further purification. LRMS (Electrospray): $C_{11}H_{10}O_2$, calc. 174; observed: 173 (M−H).

Step 2:

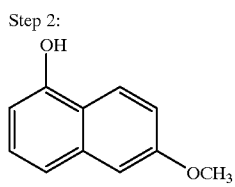

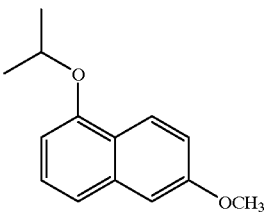

A mixture of 5-hydroxy-6-methoxynaphthalene (2.10 g, 12.1 mmole), cesium carbonate (19.7 g, 60.5 mmole), N,N-dimethylformamide (12 ml) and 2-bromopropane (3.50 ml, 36.9 mmole) was stirred in a 40° C. oil bath overnight. The reaction mixture was filtered and the solid residue was rinsed thoroughly with ethyl ether. The filtrate and the washings were combined and concentrated in vacuo to remove most of the solvents. The brown residue was partitioned between water and ether and the layers were separated. The ether layer was washed with water. The combined aqueous layers were back extracted with ether. The ether extracts were combined, washed with brine and dried over sodium sulfate. Filtration and concentration gave a crude which was purified by column chromatography (2.5→5% ethyl acetate/hexanes) to give 1-isopropoxy-6-methoxynaphthalene (2.23 g, 86% yield) as a light brown oil. $^1$H NMR (CDCl$_3$) δ8.17 (1H, d, phenyl), 7.05–7.38 (4H, m, phenyl), 6.72 (1H, dd, phenyl), 4.73 (1H, m, CH of iPr), 3.92 (3H, s, OCH$_3$), 1.42 (6H, d, 2 CH$_3$ of iPr).

Step 3:

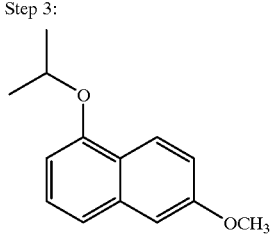

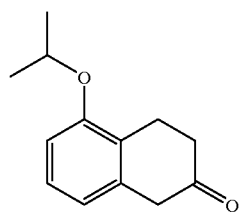

To a refluxing solution of 1-isopropoxy-6-methoxynaphthalene (2.23 g, 10.3 mmole) in absolute ethanol (50 ml) was carefully added small pieces of sodium metal (3.6 g, 157 mmole) over 45 minutes. The mixture was refluxed for a further 120 minutes. The reaction was cooled to room temperature, quenched with water and acidified with concentrated hydrochloric acid. The mixture was concentrated in vacuo to remove most of the ethanol. The aqueous mixture was extracted three times with ether. The combined organic layers were washed with water and dried over sodium sulfate. Filtration and concentration gave a reddish oil which was dissolved in 1:1 ethanol/water (90 ml), then p-toluenesulfonic acid (200 mg) was added. The mixture was refluxed for 60 minutes. After cooling to room temperature, most of the ethanol was removed under reduced pressure. The aqueous mixture was extracted twice with ether and the combined organic layers were washed with water, saturated sodium chloride solution and dried over sodium sulfate. Filtration and concentration gave a reddish oil which was purified by column chromatography (8→15% ethyl acetate/hexanes) to give 5-isopropoxy-β-tetralone (1.37 g, 65% yield) as a colorless oil. $^1$H NMR (CDCl$_3$) δ7.16 (1H, t, phenyl), 6.78 (1H, d, phenyl), 6.71 (1H, d, phenyl), 4.53 (1H, m, CH of iPr), 3.56 (2H, s, benzylic), 3.08 (2H, t, benzylic), 2.50 (2H, t), 1.37 (6H, d, 2 CH$_3$ of iPr).

Step 4:

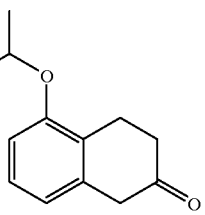

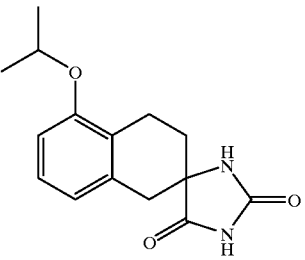

A mixture of 5-isopropoxy-β-tetralone (1.37 g, 6.71 mmole), potassium cyanide (660 mg, 10.1 mmole), ammonium carbonate (3.87 g, 40.3 mmole), ethanol (44 ml) and water (9 ml) in a sealed, thick walled pressure flask was heated in a 80° C. oil bath for 42 hours. After cooling to room temperature, the slurry was poured into ice-water and stirred at room temperature for a couple of hours. Filtration followed by air-drying gave hydantoin (1.64 g, 89%).

Step 5:

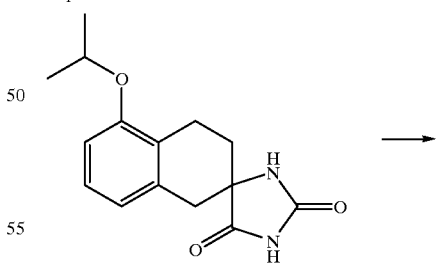

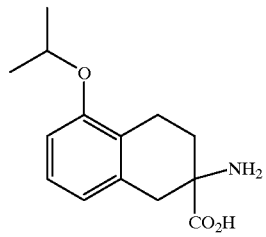

75

A mixture of hydantoin (1.64 g, 5.98 mmole), Ba(OH)$_2$·H$_2$O (5.66 g, 29.9 mmole) in water (25 ml) in a sealed, thick walled pressure flask was heated in a 100° C. oil bath for 70 hours. The reaction mixture was cooled to room temperature, neutralized to ~pH 7 using 4N sulfuric acid while being stirred vigorously. The suspension was stirred in a boiling water bath for one hour and cooled to room temperature. Basified with 1N sodium hydroxide solution and the white suspension was filtered and the precipitates rinsed with water. The combined filtrate and washings were concentrated in vacuo to ~75 ml. Neutralization with concentrated hydrochloric acid solution gave white precipitate which were filtered, washed with water and air-dried to give racemic 5-isopropoxy-2-aminotetraline-2-carboxylic acid (3.48 g, wet and containing inorganic salt, >quantitative yield). LRMS (Electrospray): C$_{14}$H$_{19}$NO$_3$, calc. 249; observed: 248 (M−H).

Step 6:

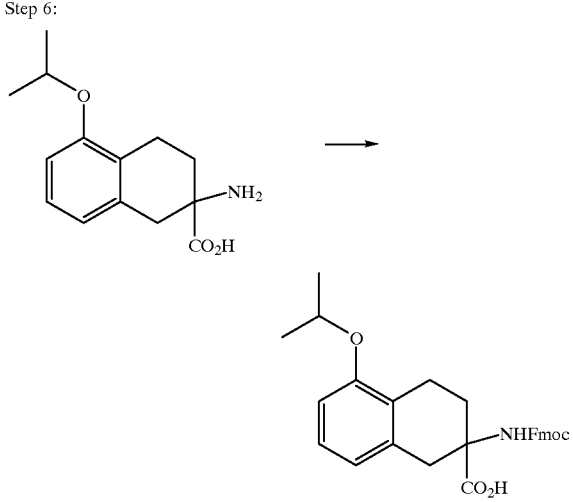

A mixture of racemic 5-isopropoxy-2-aminotetraline-2-carboxylic acid (3.48 g, 5.98 mmole theoretical), triethylamine (1.10 ml, 7.89 mmole), 9-fluorenylmethyl succinimidyl carbonate (Fmoc-OSu, 2.62 g, 7.77 mmole) in acetonitrile (30 ml) and water (30 ml) was stirred at room temperature for one day. TLC analysis of the reaction indicated the presence of starting material amino acid. 9-fluorenylmethyl succinimidyl carbonate (500 mg) was added and the mixture was stirred at room temperature for another day. The reaction mixture was concentrated in vacuo to remove most of the acetonitrile, acidified to pH~3 with 10% aqueous citric acid solution, and the white emulsion extracted three times with methylene chloride. The combined organic layers were washed with water, brine, dried over magnesium sulfate. Filtration and concentration gave a crude oil which was purified by column chromatography (eluted with 1→2→5→8% methanol/methylene chloride) to give racemic Fmoc-5-isopropoxy-2-aminotetraline-2-carboxylic acid (0.50 g, 18% yield over 2 steps) as a white solid. HRMS (FAB): C$_{29}$H$_{30}$NO$_5$ (M+H) calc. 472.2124; observed: 472.2117.

76

EXAMPLE 14

Preparation of Fmoc-(D,L)-5-dimethylamino-2-aminotetraline-2-carboxylic acid (Fmoc-(D,L) 5-DmaAtc-OH)

Step 1:

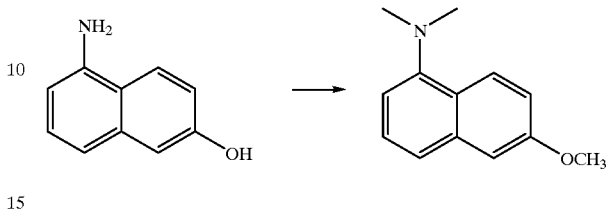

A mixture of 5-amino-2-naphthol (2.97 g, 18.6 mmole), potassium carbonate (37.0 g, 268 mmole), acetone (100 ml) and iodomethane (10.0 ml, 161 mmole) was refluxed for 2 days. The reaction mixture was cooled to room temperature, filtered and the solid residue was rinsed thoroughly with ethyl ether and acetone. The filtrate and the washings were combined and concentrated in vacuo to remove most of the solvents. The brown residue was partitioned between water and ether and the layers were separated. The ether layer was washed with water. The combined aqueous layers were back extracted with ether. The ether extracts were combined, washed with brine and dried over sodium sulfate. Filtration and concentration gave crude 1-dimethylamino-6-methoxynaphthalene (3.54 g, 94% yield) as a dark brown oil. $^1$H NMR (CDCl$_3$) δ8.16 (1H, t, phenyl), 7.30–7.50 (2H, m, aromatic), 7.10–7.20 (2H, m, aromatic), 6.96 (1H, d, aromatic), 3.93 (3H, s, OCH$_3$), 2.89 (6H, s, N(CH$_3$)$_2$).

Step 2:

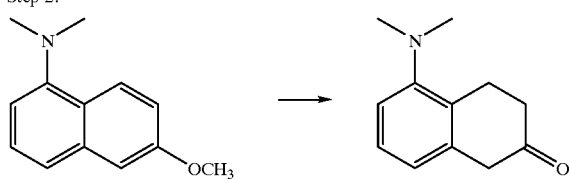

To a refluxing solution of 1-dimethylamino-6-methoxynaphthalene (2.99 g, 14.9 mmole) in absolute ethanol (100 ml) was carefully added small pieces of sodium metal (5.76 g, 251 mmole) over 45 minutes. The mixture was refluxed for another 45 minutes. TLC indicated the presence of unreacted starting material. Extra sodium metal (7.09 g, 308 mmole) was added and the reaction mixture was refluxed until TLC indicated the complete consumption of all the starting material. The reaction was cooled to room temperature and pH adjusted to ~9–10 with concentrated hydrochloric acid. The mixture was concentrated in vacuo to remove most of the ethanol. The aqueous mixture was extracted four times with ethyl acetate. The combined organic layers were washed with saturated sodium bicarbonate and dried over sodium sulfate. Filtration and concentration gave a dark brown oil which was dissolved in 1:1 ethanol/water (150 ml), then p-toluenesulfonic acid (3.05 g) was added to bring the pH to ~2–3. The mixture was refluxed for 3 hours. After cooling to room temperature, most of the ethanol was removed under reduced pressure. The pH of the mixture was adjusted to ~9–10 with 2N sodium hydroxide solution and the aqueous mixture was extracted four times with ethyl acetate. The combined organic layers were washed with saturated sodium bicarbonate solution and dried over sodium sulfate. Filtration and concentration gave a dark brown oil which was purified by column chromatography (15% ethyl acetate/hexanes) to give 5-dimethylamino-p-tetralone (834 mg, 30% yield) as a brown oil. $^1$H NMR (CDCl$_3$) δ7.18 (1H, t, phenyl), 6.96 (1H, d, phenyl), 6.82 (1H, d, phenyl), 3.57 (2H, s, benzylic), 3.10 (2H, t, benzylic), 2.70 (6H, s, N(CH$_3$)$_2$), 2.48 (2H, t). LRMS (Electrospray): C$_{12}$H$_{15}$NO, calc. 189; observed: 190 (M+H).

Step 3:

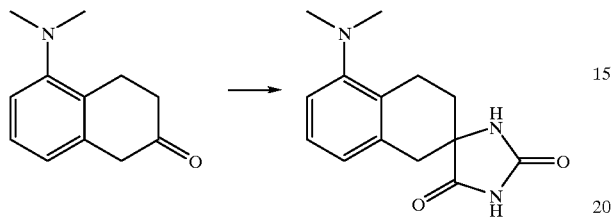

A mixture of 5-dimethylamino-β-tetralone (0.97 g, 5.13 mmole), potassium cyanide (510 mg, 7.82 mmole), ammonium carbonate (2.98 g, 31.0 mmole), ethanol (40 ml) and water (10 ml) in a sealed, thick walled pressure flask was heated in a 80° C. oil bath for 29 hours. After cooling to room temperature, the dark brown slurry was poured into ice-water and stirred at room temperature for a couple of hours. Filtration followed by air-drying gave hydantoin (885 mg, 67%) as a dark brown solid. LRMS (Electrospray): C$_{14}$H$_{17}$N$_3$O$_2$, calc. 259; observed: 260 (M+H), 258 (M−H).

Step 4:

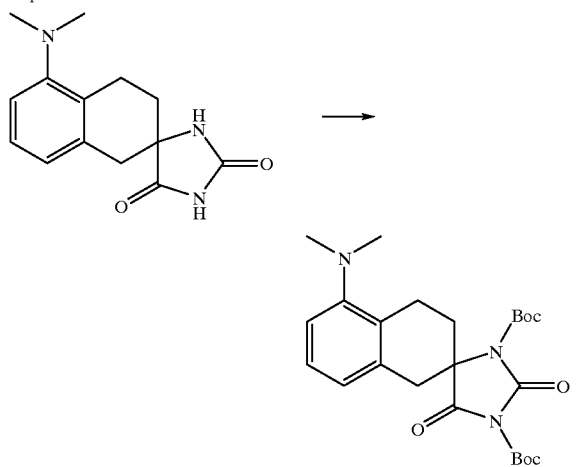

To a solution of hydantoin (832 mg, 3.21 mmole) in THF (25 ml) was added di-t-butyl dicarbonate (2.51 g, 11.5 mmole), triethylamine (0.50 ml, 3.59 mmole) and 4-dimethylaminopyridine (17 mg, 0.14 mmole). The mixture was stirred at room temperature overnight. The solvents were removed in vacuo and the crude was purified using column chromatography (15% ethyl acetate/hexanes) to give bis-Boc hydantoin (1.02 g, 69% yield) as a yellow foam. LRMS (Electrospray): C$_{24}$H$_{33}$N$_3$O$_6$, calc. 459; observed: 919 (2M+H).

Step 5:

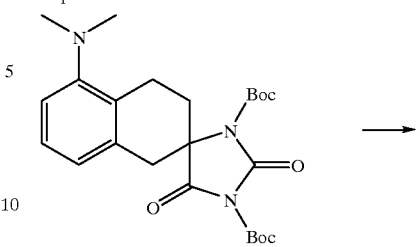

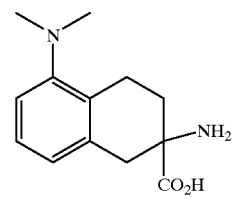

To a solution of bis-Boc hydantoin (988 mg, 2.15 mmole) in dimethoxyethane (15 ml) was added 1N sodium hydroxide solution (20 ml). The mixture was stirred at room temperature overnight. The reaction mixture was concentrated in vacuo to remove most of the solvents and water was added to the resulting light brown mixture. The aqueous mixture was extracted twice with methylene chloride and twice with ethyl acetate. The aqueous layer was concentrated to ~20 ml, neutralized to pH~7 with 1N hydrochloric acid to give a slurry. The slurry was filtered to give racemic 5-dimethylamino-2-aminotetraline-2-carboxylic acid (1.33 g, still wet, >quantitative yield) as a off-white solid. LRMS (Electrospray): C$_{13}$H$_{18}$N$_2$O$_2$, calc. 234; observed: 235 (M+H).

Step 6:

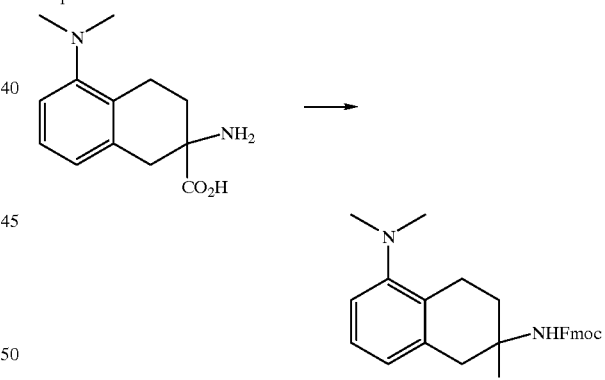

A mixture of 5-dimethylamino-2-aminotetraline-2-carboxylic acid (1.33 g, 2.15 mmole theoretical), triethylamine (0.40 ml, 2.87 mmole), 9-fluorenylmethyl succinimidyl carbonate (Fmoc-OSu, 0.92 g, 2.73 mmole) in acetonitrile (10 ml) and water (10 ml) was stirred at room temperature for one day. TLC analysis of the reaction indicated the presence of starting material amino acid. 9-fluorenylmethyl succinimidyl carbonate (400 mg) and triethylamine (0.2 ml) were added and the mixture was stirred at room temperature for another day. The reaction mixture was concentrated in vacuo to remove most of the acetonitrile and the almost neutral mixture was extracted three times with ethyl acetate. The combined organic layers were washed with water, brine, dried over sodium sulfate.

Filtration and concentration gave a crude which was purified by column chromatography (eluted with 2.5→6→10→15→20% methanol/methylene chloride) to give racemic Fmoc-5-dimethylamino-2-aminotetraline-2-carboxylic acid (602 mg, 61% yield over 2 steps) as an off-white solid. HRMS (FAB): $C_{28}H_{28}N_2O_4$ (M) calc. 456.2049; observed: 456.2056.

EXAMPLE 15

Preparation of Fmoc-(D,L)-5-methyl-2-aminotetraline-2-carboxylic acid (Fmoc-(D,L) 5-MeAtc-OH)

Step 1:

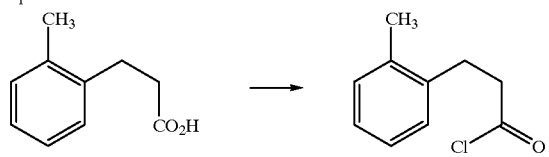

A mixture of 2-methylhydrocinnamic acid (3.0 g, 18.3 mmole), oxalyl chloride (3.19 ml, 36.6 mmole) and methylene chloride (30 ml) was cooled in an ice bath and N,N-dimethylformamide (0.14 ml, 1.81 mmole) was added dropwise. The mixture was stirred at room temperature overnight. Concentration in vacuo gave 3-(2-methylphenyl)propanoyl chloride which was taken up in methylene chloride and used in the next step as a crude.

Step 2:

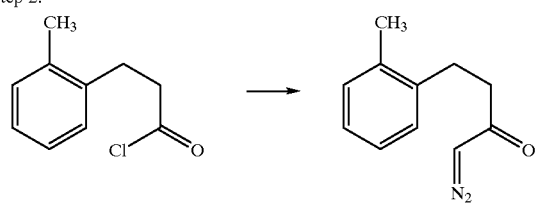

A solution of the above acid chloride (crude, 18.3 mmole) in methylene chloride was slowly added to a solution of diazomethane (generated from 11.9 g of 1-methyl-3-nitro-1-nitrosoguanidine) in ether (80 ml) cooled in an ice bath. The mixture was then warmed up to room temperature and stirred overnight. The mixture was concentrated in vacuo and purified by column chromatography (10→20% ethyl acetate/hexanes) to give 1-diazo-4-(2-methylphenyl)butan-2-one (2.08 g, 60% over 2 steps) as a bright yellow oil.

Step 3:

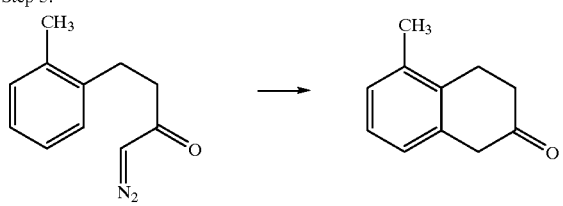

To a mixture of rhodium (II) acetate dimer (24 mg, 0.109 mmole) in methylene chloride (200 ml) under reflux was slowly added a solution of 1-diazo-4-(2-methylphenyl)butan-2-one (2.08 g, 11.1 mmole) in methylene chloride (50 ml) over 180 minutes. After the addition was complete, the mixture was refluxed for an extra twenty minutes. The mixture was cooled to room temperature, trifluoroacetic acid (2.40 ml) was added and the mixture was stirred at room temperature for an hour. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a crude brown oil. Purification by column chromatography (15% ethyl acetate/hexanes) gave 5-methyl-β-tetralone (1.48 g, 84% yield) as a light brown oil. $^1$H NMR (CDCl$_3$) δ6.90–7.20 (3H, m, phenyl), 3.58 (2H, s, benzylic), 3.03 (2H, t, benzylic), 2.55 (2H, t), 2.34 (3H, s, CH$_3$).

Step 4:

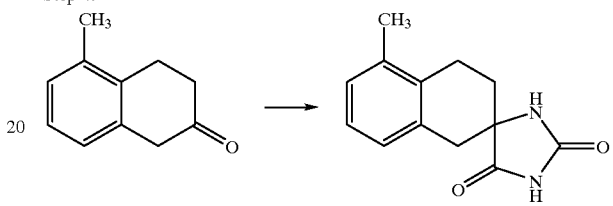

A mixture of 5-methyl-β-tetralone (1.48 g, 9.24 mmole), potassium cyanide (902 mg, 13.9 mmole), ammonium carbonate (5.33 g, 55.5 mmole), ethanol (45 ml) and water (9 ml) in a sealed, thick walled pressure flask was heated in a 80° C. oil bath for 3 days. After cooling to room temperature, the slurry was poured into ice-water and stirred at room temperature for a couple of hours. Filtration followed by air-drying gave crude hydantoin (1.81 g, 85% yield) as a beige solid. $^1$H NMR (DMSO-d$_6$) δ10.66 (1H, broad s, NH), 8.22 (1H, broad s, NH), 6.85–7.05 (3H, m, phenyl), 2.17 (3H, s, CH$_3$).

Step 5:

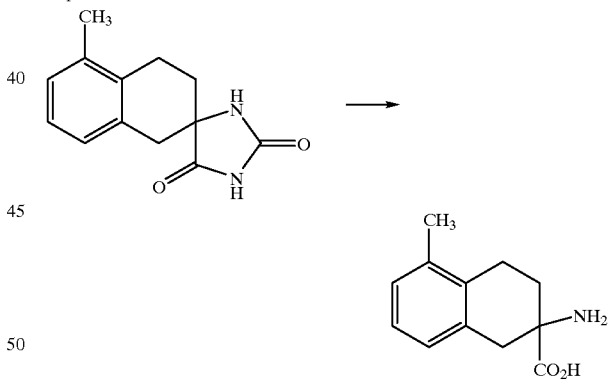

A mixture of hydantoin (1.80 g, 7.82 mmole), Ba(OH)$_2$·H$_2$O (7.40 g, 39.1 mmole) in water (28 ml) in a sealed, thick walled pressure flask was heated in a 125° C. oil bath for 88 hours. The reaction mixture was cooled to room temperature, acidified to ~pH3 using 4N sulfuric acid while being stirred vigorously. The suspension was stirred in a boiling water bath for an hour and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and air-dried to give racemic 5-methyl-2-aminotetraline-2-carboxylic acid (1.05 g, 65% yield) as a beige solid. LRMS (Electrospray): $C_{12}H_{15}NO_2$, calc. 205; observed: 206 (M+H).

Step 6:

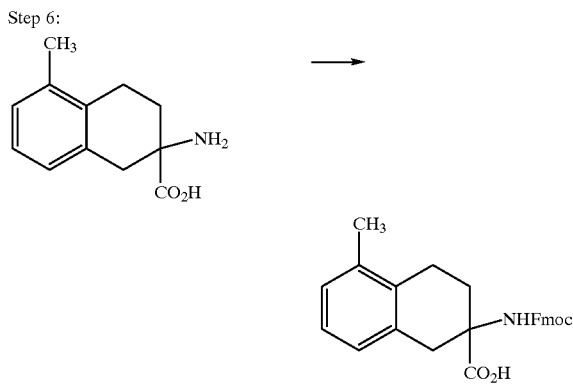

A mixture of racemic 5-methyl-2-aminotetraline-2-carboxylic acid (1.05 g, 5.12 mmole), triethylamine (0.93 ml, 6.67 mmole), 9-fluorenylmethyl succinimidyl carbonate (Fmoc-OSu, 2.24 g, 6.64 mmole) in acetonitrile (30 ml) and water (30 ml) was stirred at room temperature for 2 days. TLC analysis of the reaction indicated the presence of starting material amino acid. 9-fluorenylmethyl succinimidyl carbonate (520 mg) was added and the mixture was stirred at room temperature for another 24 hours. The reaction mixture was concentrated in vacuo to remove most of the acetonitrile, acidified to pH~3 with 10% aqueous citric acid solution, and the white emulsion was extracted twice with methylene chloride. The combined organic layers were washed with water, brine and dried over magnesium sulfate. Filtration and concentration gave a crude oil which was purified by column chromatography (eluted with 2→5→8% methanol/methylene chloride) to give racemic Fmoc-5-methyl-2-aminotetraline-2-carboxylic acid (1.62 g, 74% yield) as an light brown solid. HRMS (FAB): $C_{27}H_{26}NO_4$ (M+H) calc. 428.1862; observed: 428.1844.

EXAMPLE 16

Preparation of Fmoc-(D,L)-5-ethyl-2 aminotetraline-2-carboxylic acid (Fmoc-(D,L) 5-EtAtc-OH)

Step 1:

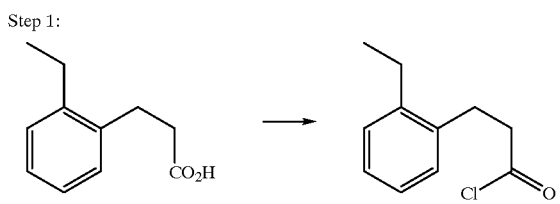

A mixture of 3-(2-ethylphenyl)propanoic acid (prepared in 3 steps from 1-ethyl-2-iodobenzene, 4.24 g, 23.8 mmole), thionyl chloride (9.50 ml, 130 mmol) and toluene (100 ml) was refluxed for 2 hours. Concentration in vacuo gave 3-(2-ethylphenyl)propanoyl chloride which was taken up in methylene chloride and used in the next step as a crude.

Step 2:

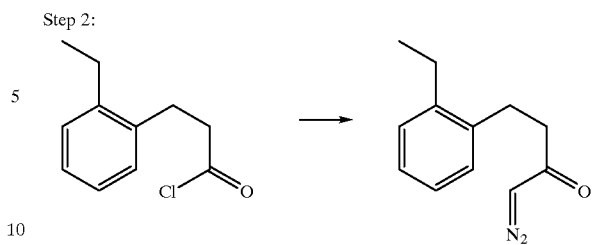

A solution of the above acid chloride (crude, 23.8 mmole) in methylene chloride was slowly added to a solution of diazomethane (generated from 15.6 g of 1-methyl-3-nitro-1-nitrosoguanidine) in ether (100 ml) cooled in an ice bath. The mixture was then warmed up to room temperature and stirred overnight. The mixture was concentrated in vacuo and purified by column chromatography (10→20% ethyl acetate/hexanes) to give 1-diazo-4-(2-ethylphenyl)butan-2-one (3.47 g, 72% over 2 steps). $^1$H NMR (CDCl$_3$) δ7.1–7.2 (4H, m, phenyl), 5.21 (1H, broad s, diazo), 2.97 (2H, m, CH$_2$ of ethyl), 1.20 (3H, t, CH$_3$).

Step 3:

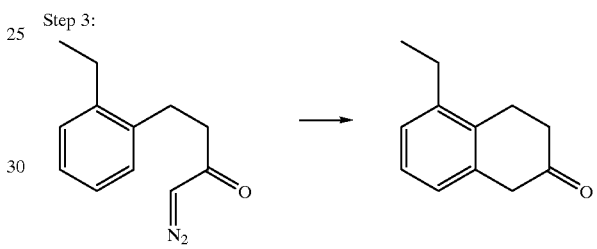

To a mixture of rhodium (II) acetate dimer (38 mg, 0.172 mmole) in methylene chloride (300 ml) under reflux was slowly added a solution of 1-diazo-4-(2-ethylphenyl)butan-2-one (3.47 g, 17.2 mmole) in methylene chloride (50 ml) over 90 minutes. After the addition was complete, the mixture was refluxed for an extra twenty minutes. The mixture was cooled to room temperature, trifluoro acetic acid (3.75 ml) was added and the mixture was stirred at room temperature for an hour. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give crude 5-ethyl-β-tetralone (3.09 g, >quantitative yield) as a reddish-brown oil. The compound was used in the next step without further purification. $^1$H NMR (CDCl$_3$) δ6.9–7.2 (3H, m, phenyl), 3.58 (2H, s, benzylic), 3.08 (2H, s, benzylic), 2.70 (2H, q, CH$_2$ of ethyl), 2.52 (2H, t, benzylic), 1.20 (3H, t, CH$_3$ of ethyl).

Step 4:

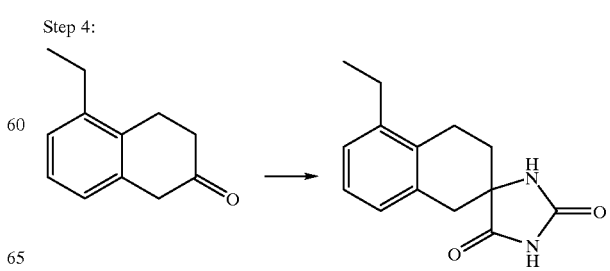

A mixture of 5-ethyl-β-tetralone (3.09 g, 17.7 mmole), potassium cyanide (1.73 g, 26.6 mmole), ammonium carbonate (10.2 g, 106 mmole), ethanol (80 ml) and water (16 ml) in a sealed, thick walled pressure flask was heated in a 80° C. oil bath for 48 hours. After cooling to room temperature, the white slurry was poured into ice-water and stirred at room temperature for a couple of hours. Filtration followed by air-drying gave hydantoin (3.85 g, 92% yield over 2 steps) as a light beige solid. $^1$H NMR (DMSO-$d_6$) δ10.67 (1H, broad s, NH), 8.26 (1H, broad s, NH), 6.8–7.1 (3H, m, phenyl), 1.13 (3H, t, $CH_3$). LRMS (Electrospray): $C_{14}H_{16}N_2O_2$, calc. 244; observed: 243 (M–H).

Step 5:

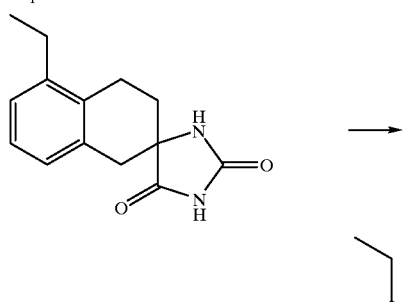

A mixture of hydantoin (1.00 g, 4.09 mmole), Ba(OH)$_2$·H$_2$O (4.00 g, 21.1 mmole) in water (20 ml) in a sealed, thick walled pressure flask was heated in a 125° C. oil bath for 48 hours. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and dried in vacuo overnight to give racemic 5-ethyl-2-aminotetraline-2-carboxylic acid (796 mg, 89% yield). LRMS (Electrospray): $C_{13}H_{17}NO_2$, calc. 219; observed: 220 (M+H).

Step 6:

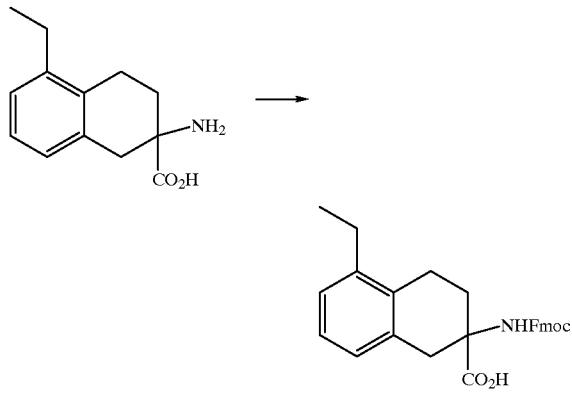

A mixture of racemic 5-ethyl-2-aminotetraline-2-carboxylic acid (765 mg, 3.49 mmole), triethylamine (1.0 ml, 7.17 mmole), 9-fluorenylmethyl succinimidyl carbonate (Fmoc-OSu, 1.79 g, 5.31 mmole) in acetonitrile (40 ml) and water (40 ml) was stirred at room temperature for 2 days. The reaction mixture was concentrated in vacuo to remove most of the acetonitrile, acidified to pH~3 with 10% aqueous citric acid solution, and the white emulsion extracted twice with methylene chloride, twice with ethyl acetate. The methylene chloride extracts were washed with water, brine and dried over magnesium sulfate. The ethyl acetate extracts were washed with water, brine and dried over magnesium sulfate. Filtration and concentration gave a crude oil which was purified by column chromatography (eluted with 2→5→8% methanol/methylene chloride) to give racemic Fmoc-5-ethyl-2-aminotetraline-2-carboxylic acid (330 mg, 21% yield) as a white solid. HRMS (FAB): $C_{28}H_{28}NO_4$ (M+H) calc. 442.2018; observed: 442.2010.

EXAMPLE 17

Preparation of Fmoc-(D,L)-5-isopropyl-2-aminotetraline-2-carboxylic acid (Fmoc-(D,L) 5-iPrAtc-OH)

Step 1:

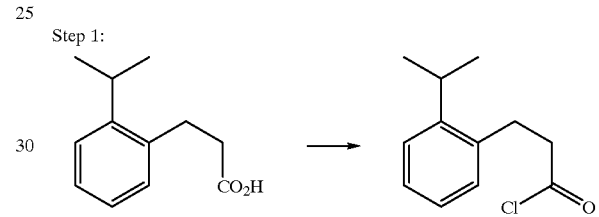

A mixture of 3-(2-isopropylphenyl)propanoic acid (prepared in 3 steps from 1-isopropyl-2-iodobenzene, 2.01 g, 10.5 mmole), thionyl chloride (4.30 ml, 59.0 mmole) and toluene (40 ml) was refluxed for 2 hours. Concentration in vacuo gave 3-(2-isopropylphenyl)propanoyl chloride which was taken up in methylene chloride and used in the next step as a crude.

Step 2:

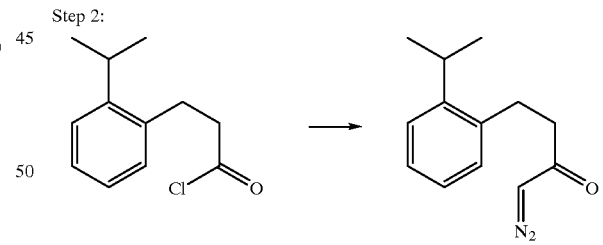

A solution of the above acid chloride (crude, 10.5 mmole) in methylene chloride was slowly added to a solution of diazomethane (generated from 6.95 g of 1-methyl-3-nitro-1-nitrosoguanidine) in ether (50 ml) cooled in an ice bath. The mixture was then warmed up to room temperature and stirred overnight. The mixture was concentrated in vacuo and purified by column chromatography (20% ethyl acetate/hexanes) to give 1-diazo-4-(2-isopropylphenyl)butan-2-one (1.87 g, 82% over 2 steps) as a bright yellow oil. $^1$H NMR (CDCl$_3$) δ7.10–7.30 (4H, m, phenyl), 5.21 (1H, broad s, diazo), 3.15 (1H, m, CH of iPr), 3.00 (2H, t, benzylic), 2.57 (2H, m), 1.24 (6H, d, 2 $CH_3$ of iPr).

Step 3:

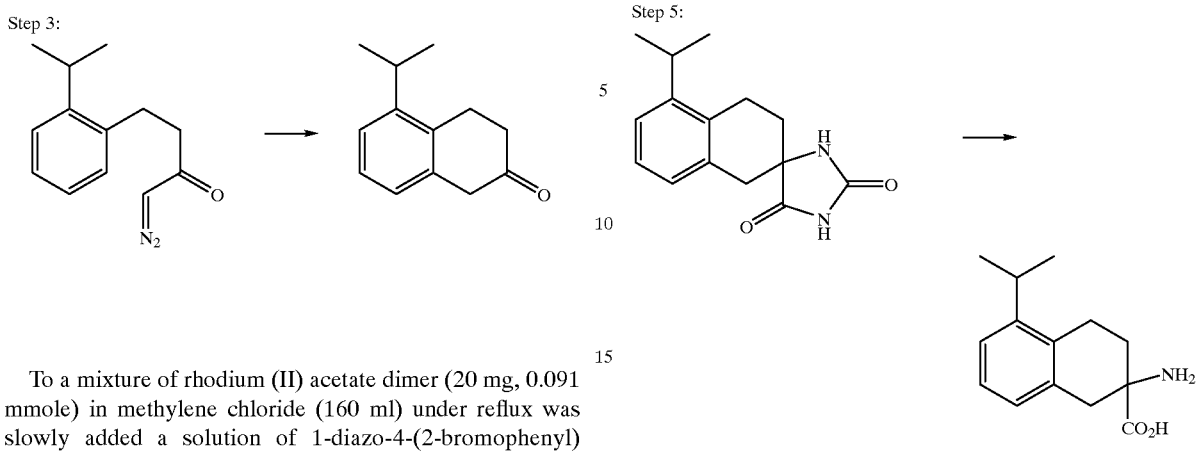

To a mixture of rhodium (II) acetate dimer (20 mg, 0.091 mmole) in methylene chloride (160 ml) under reflux was slowly added a solution of 1-diazo-4-(2-bromophenyl)butan-2-one (1.87 g, 8.65 mmole) in methylene chloride (25 ml) over 60 minutes. After the addition was complete, the mixture was refluxed for an extra fifteen minutes. The mixture was cooled to room temperature, trifluoroacetic acid (1.90 ml) was added and the mixture was stirred at room temperature for 45 minutes. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a crude brown oil. Purification by column chromatography (5% ethyl acetate/hexanes) gave 5-isopropyl-β-tetralone (1.57 g, 96% yield) as a light yellow oil. $^1$H NMR (CDCl$_3$) δ6.93–7.22 (3H, m, phenyl), 3.59 (2H, s, benzylic), 3.24 (1H, m, CH of iPr), 3.12 (2H, t, benzylic), 2.52 (2H, t), 1.27 (6H, d, 2 CH$_3$ of iPr).

Step 4:

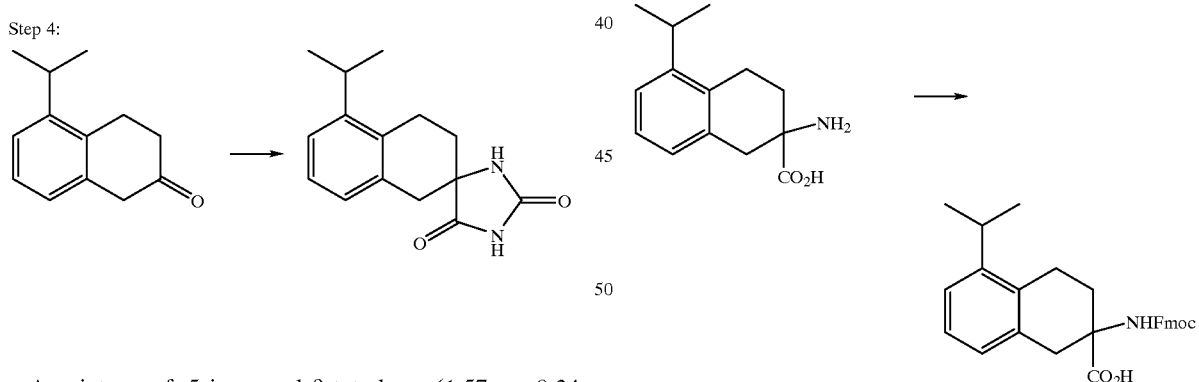

A mixture of 5-isopropyl-β-tetralone (1.57 g, 8.34 mmole), potassium cyanide (0.82 g, 12.6 mmole), ammonium carbonate (4.81 g, 50.1 mmole), ethanol (40 ml) and water (10 ml) in a sealed, thick walled pressure flask was heated in a 80° C. oil bath for 48 hours. After cooling to room temperature, the brown slurry was poured into ice-water and stirred at room temperature for a couple of hours. Filtration followed by air-drying gave crude hydantoin as a beige solid which was used in the next step without further purification. $^1$H NMR (DMSO-d$_6$) δ10.69 (1H, broad s, NH), 8.30 (1H, broad s, NH), 6.85–7.32 (3H, m, phenyl), 1.15 (6H, t, CH$_3$). LRMS (Electrospray): C$_{15}$H$_{18}$N$_2$O$_2$, calc. 258; observed: 539 (2M+Na).

Step 5:

A mixture of hydantoin (crude, 8.34 mmole theoretical), Ba(OH)$_2$·H$_2$O (7.90 g, 41.7 mmole) in water (40 ml) in a sealed, thick walled pressure flask was heated in a 125° C. oil bath for 38 hours. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and dried in vacuo overnight to give racemic 5-isopropyl-2-aminotetraline-2-carboxylic acid (1.23 g, 63% yield over 2 steps) as a beige solid. LRMS (Electrospray): C$_{14}$H$_{19}$NO$_2$, calc. 233; observed: 232 (M–H).

Step 6:

A mixture of racemic 5-isopropyl-2-aminotetraline-2-carboxylic acid (250 mg, 1.07 mmole), triethylamine (1.2 ml, 8.61 mmole), 9-fluorenylmethyl succinimidyl carbonate (Fmoc-OSu, 2.70 g, 8.00 mmole) in acetonitrile (30 ml) and water (30 ml) was stirred at room temperature for 2 days. The reaction mixture was concentrated in vacuo to remove most of the acetonitrile, acidified to pH~3 with 10% aqueous citric acid solution, and the white emulsion was extracted with ethyl acetate. The organic layer was washed with water, brine and dried over sodium sulfate. Filtration and concentration gave a crude oil which was purified by column chromatography (eluted with 2→5→8% methanol/ methylene chloride) to give racemic Fmoc-5-isopropyl-2-aminotetraline-2-carboxylic acid (208 mg, 43% yield) as an off-white foam. HRMS (FAB): $C_{29}H_{30}NO_4$ (M+H) calc. 456.2175; observed: 456.2184.

EXAMPLE 18

Preparation of Fmoc-4-amino-1-phenylpiperidine-4-carboxylic acid (Fmoc-Appc-OH)

Step 1:

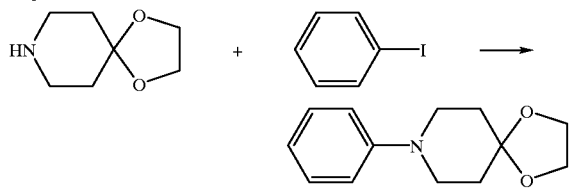

To a solution of iodobenzene (6.37 g, 3.5 mL, 31.2 mmole), 1,4-dioxa-8-azaspiro[4.5]decane (10.32 g, 9.3 mL, 72.2 mmole, 2.3 equiv) and sodium tert-butoxide (8.0 g, 83.3 mmole, 2.7 equiv) in dry dioxane (120 mL) were added tris(dibenzylideneacetone)dipalladium(0) (91 mg, 0.1 mmol) and tri-o-tolylphosphine (180 mg, 0.591 mmol). The reaction was heated at 90° C. for 26 hrs. The resulting reaction mixture was concentrated to remove solvent. The residue was treated with water and extracted with EtOAc. The combined organic extracts were combined, washed with brine, dried over $Na_2SO_4$ and concentrated to give a brown oil. This crude product was purified on flash chromatography (hexane/EtOAc, 95/5 to 75/25) to provide the pure product as a slightly yellow solid (6.08 g, 89%). $^1$H NMR ($CDCl_3$), 7.25 (ddt, 2H), 6.95 (dd, 2H), 6.84 (t, 1H), 4.00 (s, 4H), 3.32 (t, 4H) and 1.84 (t, 4H); MS (electrospray) m/e 220 (M+H), Calcd for $C_{13}H_{17}NO_2$, 219.

Step 2:

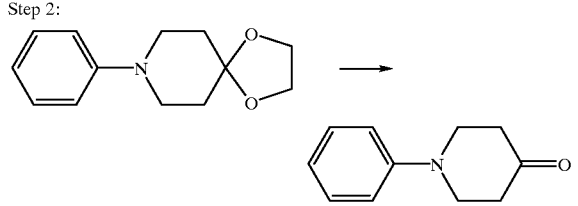

To a solution of the ketal (3.22 g, 15.16 mmol) in acetone (100 mL) was added 6N hydrochloric acid (50 mL) and the reaction was heated at reflux overnight. The resulting reaction mixture was concentrated to remove solvent. The residue was taken up in EtOAc and neutralized with aqueous 6N NaOH solution. The layers were separated and the aqueous layer was extracted with EtOAc. The combined organic extracts were washed with brine, dried over $Na_2SO_4$ and concentrated. The crude product was purified on flash chromatography (hexane/EtOAc, 80/20→60/40) to give the product as a yellow oil (2.58 g, 97%). MS (electrospray) m/e 176 (M+H), Calcd for $C_{11}H_{13}NO$, 175.

Step 3:

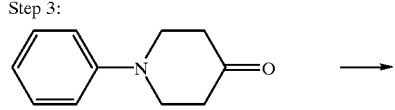

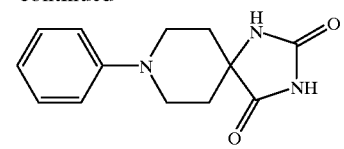

To a solution of the ketone (2.53 g, 14.46 mmol) in ethanol (75 mL) and water (25 mL) in a glass pressure bottle, were added ammonium carbonate (12.9 g, 134.3 mmole, 9 equiv.) and potassium cyanide (2.11 g, 32.5 mmol, 2 equiv.). The mixture was heated at 80–90° C. for 18 hrs. The cooled reaction mixture was concentrated in vacuo and the residue was treated with water, extracted with EtOAc (4×). The combined organic extracts were washed with water, dried over anhydrous $Na_2SO_4$ and concentrated to give the spectroscopically pure hydantoin as a white solid (3.36 g, 95% yield). MS (electrospray) m/e 246 (M+H), Calcd for $C_{13}H_{15}N_3O_2$, 245.

Step 4:

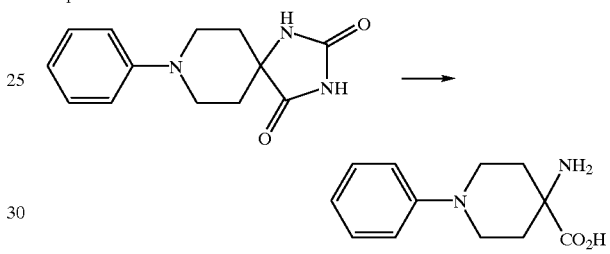

The hydantoin (3.36 g) was suspended in aqueous NaOH (6N, 100 mL) and heated at 130° C. for 2–3 days. Upon completion (by HPLC) of the hydrolysis, the reaction mixture was neutralized with conc. HCl to slightly acidic (pH~6). The resulting slurry was filtered, washed with water and dried to give 4-amino-1-phenylpiperidine-4-carboxylic acid (APPC) as a white solid (5.26 g, >100% yield, wet and contaminated with inorganic salt), which showed a single peak on HPLC and used directly for the next step. MS (electrospray) m/e 221 (M+H), Calcd for $C_{12}H_{16}N_2O_2$, 220.

Step 5:

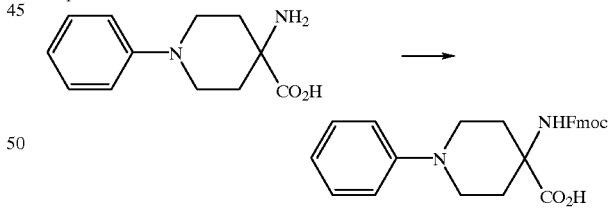

The crude amino acid APPC from the last step was suspended in dioxane (80 mL) and aqueous 10% $Na_2CO_3$ (40 ml), treated with Fmoc-Cl (5.3 g, 20.57 mmole, 1.5 equiv) and was stirred vigorously overnight. The reaction mixture was then concentrated to remove dioxane, neutralized with 6N HCl to slightly acidic (pH 6) and extracted with EtOAc. The combined organic extracts were washed with brine and dried over $Na_2SO_4$. Removal of the solvent gave the crude product which was purified on flash chromatography hexane/EtOAc to $CH_2Cl_2$/MeOH) to give pure APPC (4.91 g, 81% overall yield for two steps). $^1$H NMR(DMSO-$d_6$), 7.88 (d, 2H), 7.74 (d, 2H), 7.19–7.42 (m, 8H), 4.20–4.31 (m, 3H); HRMS m/z 465.1788, Calcd for $C_{27}H_{26}N_2O_4Na$, 465.1791

EXAMPLE 19

Preparation of Fmoc-4-amino-1-(4-methylphenyl)piperidine-4-carboxylic acid (Fmoc-4-MeAppc-OH)

Step 1:

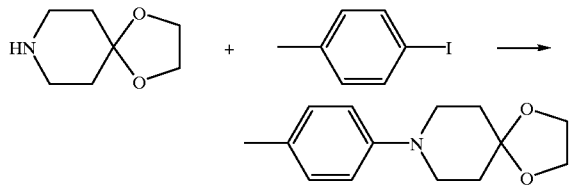

To a solution of 4-iodotoluene (2.12 g, 9.7 mmol), 1,4-dioxa-8-azaspiro[4.5]decane (2.8 mL, 3.12 g, 21.82 mmol, 2.2 equiv) and sodium tert-butoxide (2.6 g, 27.08 mmol, 2.8 equiv) in dry dioxane (40 mL) were added tris(dibenzylideneacetone)dipalladium (0) (44.4 mg, 0.0485 mmol) and tri-o-tolylphosphine (59.0 mg, 0.194 mmol). The reaction was heated at 90° C. for 26 hrs. The resulting reaction mixture was concentrated to remove solvent. The residue was treated with water and extracted with EtOAc. The combined organic extracts were combined, washed with brine, dried over $Na_2SO_4$ and concentrated to give brown oil. This crude product was purified on flash chromatography (hexane/EtOAc, 95/5 to 75/25) to provide the pure product as a slightly yellow solid (1.937 g, 85%). $^1$H NMR ($CDCl_3$), 7.06 (d, 2H), 6.87 (d, 2H), 3.99 (s, 4H), 3.26 (t, 4H), 2.26 (s, 3H) and 1.85 (t, 4H).

Step 2:

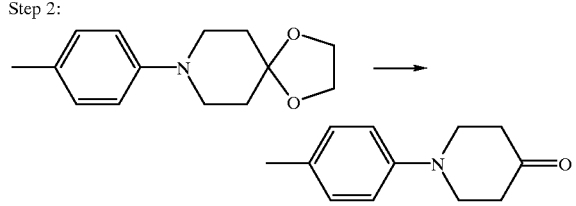

To a solution of the ketal (1.58 g, 6.79 mmol) in acetone (50 mL) was added 6N hydrochloric acid (25 mL) and the reaction was heated at reflux overnight. The resulting reaction mixture was concentrated to remove solvent. The residue was taken up in EtOAc and neutralized with aqueous 6N NaOH solution. The layers were separated and the aqueous layer was extracted with EtOAc. The combined organic extracts were washed with brine, dried over $Na_2SO_4$ and concentrated. The crude product was purified on flash chromatography (hexane/EtOAc, 90/10→70/30) to give the product as a yellow oil (1.27 g, 998%). MS (electrospray) m/e 190 (M+H), Calcd for $C_{12}H_{15}NO$, 189.

Step 3:

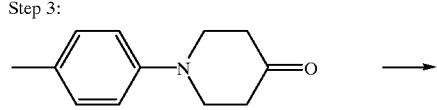

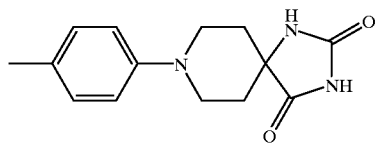

To a solution of the ketone (1.17 g, 6.18 mmol) in ethanol (60 mL) and water (20 mL) in a glass pressure bottle, were added ammonium carbonate (4.74 g, 49.44 mmole, 8 equiv.) and potassium cyanide (1.01 g, 15.54 mmol, 2.5 equiv.). The mixture was heated at 90° C. for 22 hrs. The cooled reaction mixture was concentrated in vacuo and the residue was treated with water, extracted with EtOAc (4×). The combined organic extracts were washed with water, dried over anhydrous $Na_2SO_4$ and concentrated to give the spectroscopically pure hydantoin as a white solid (1.554 g, 97% yield). MS (electrospray) m/e 260 (M+H), Calcd for $C_{14}H_{17}N_3O_2$, 259.

Step 4:

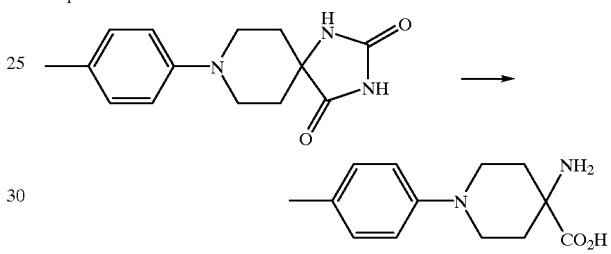

The hydantoin (1.502 g) was suspended in aqueous NaOH (6N, 40 mL) and heated at 130° C. for 4 days. Upon completion (by HPLC) of the hydrolysis, the reaction mixture was neutralized with conc. HCl to slightly acidic (pH~6). The resulting slurry was filtered, washed with water and dried to give 4-amino-1-(4-methylphenyl)piperidine-4-carboxylic acid (4-MeAPPC) as a white solid (2.10 g, >100% yield, wet and contaminated with inorganic salt), which showed a single peak on HPLC and used directly in the next step. MS (electrospray) m/e 235 (M+H), Calcd for $C_{13}H_{18}N_2O_2$, 234.

Step 5:

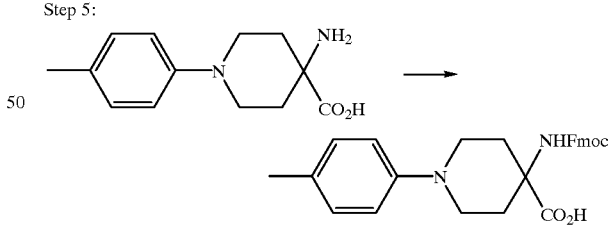

The crude amino acid 4-MeAPPC from the last step was suspended in dioxane (80 mL) and aqueous 10% $Na_2CO_3$ (40 ml), treated with Fmoc-Cl (2.2 g, 8.59 mmole, 1.5 equiv) and was stirred vigorously overnight. The reaction mixture was then concentrated to remove dioxane, neutralized with 6N HCl to slightly acidic (pH 6) and extracted with EtOAc. The combined organic extracts were washed with brine and dried over $Na_2SO_4$. Removal of the solvent gave the crude product which was purified on flash chromatography (hexane/EtOAc to $CH_2Cl_2$/MeOH) to give pure Fmoc-4-MeAPPC (2.16 g, 82% overall yield for two steps). $^1$H NMR (DMSO-d$_6$): 7.88 (d, 2H), 7.72 (d, 2H), 7.39 (t, 2H), 7.30 (td, 2H), 6.99 (d, 2H), 6.82 (d, 2H), 2.18 (s, 3H); MS (electrospray) m/e 457 (M+H), Calcd for C$_{28}$H$_{28}$N$_2$O$_4$, 456.

EXAMPLE 20

Preparation of Fmoc-4-amino-1-(4-chlorophenyl) piperidine-4-carboxylic acid (Fmoc-4-ClAppc-OH)

Step 1:

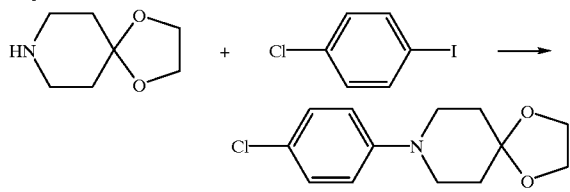

To a solution of 1-chloro-4-iodobenzene (2.38 g, 10.0 mmole), 1,4-dioxa-8-azaspiro[4.5]decane (3.1 mL, 3.44 g, 24.0 mmole, 2.4 equiv) and sodium tert-butoxide (2.68 g, 28.0 mmole, 2.8 equiv) in dry dioxane (40 mL) were added tris(dibenzylideneacetone)dipalladium(0) (45.5 mg, 0.0497 mmol) and tri-o-tolyl-phosphine (61 mg, 0.20 mmol). The reaction was heated at 90° C. for 9 hrs. The resulting reaction mixture was concentrated to remove solvent. The residue was treated with water and extracted with EtOAc. The combined organic extracts were combined, washed with brine, dried over Na2SO4 and concentrated to give a brown oil. This crude product was purified on flash chromatography (hexane/EtOAc, 95/5 to 75/25) to provide the pure product as a slightly yellow solid (2.17 g, 86%). $^1$H NMR (CDCl$_3$), 7.18 (dt, 2H), 6.85 (dt, 2H), 3.98 (s, 4H), 3.28 (t, 4H) and 1.82 (t, 4H).

Step 2:

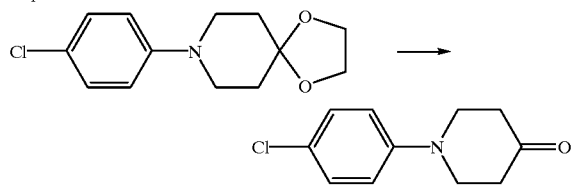

To a solution of the ketal (2.123 g, 8.39 mmole) in acetone (75 mL) was added 6N hydrochloric acid (30 mL) and the reaction was heated at reflux overnight. The resulting reaction mixture was concentrated to remove solvent. The residue was taken up in EtOAc and neutralized with aqueous 6N NaOH solution. The layers were separated and the aqueous layer was extracted with EtOAc. The combined organic extracts were washed with brine, dried over Na$_2$SO$_4$ and concentrated. The crude product was purified on flash chromatography (hexane/EtOAc, 95/5→70/30) to give the product as a yellow solid (1.515 g, 86%). MS (electrospray) m/e 210 (M+H), Calcd for C$_{11}$H$_{12}$ClNO, 209.

Step 3:

-continued

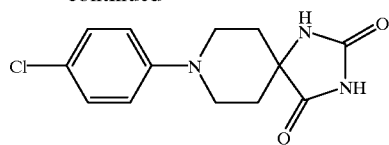

To a solution of the ketone (1.465 g, 6.986 mmole) in ethanol (75 mL) and water (25 mL) in a glass pressure bottle, were added ammonium carbonate (5.36 g, 55.88 mmole, 8 equiv.) and potassium cyanide (1.135 g, 17.46 mmol, 2.5 equiv.). The mixture was heated at 80–90° C. for 18 hrs. The cooled reaction mixture was concentrated in vacuo and the residue was treated with water, extracted with EtOAc (4×). The combined organic extracts were washed with water, dried over anhydrous Na$_2$SO$_4$ and concentrated to give the spectroscopically pure hydantoin as a white solid (1.817 g, 93% yield). MS (electrospray) m/e 280 (M+H), Calcd for C$_{13}$H$_{14}$ClN$_3$O$_2$, 279.

Step 4:

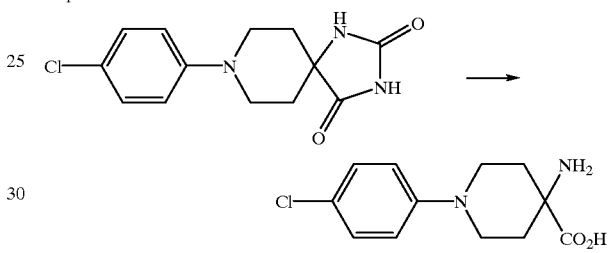

The hydantoin (1.768 g) was suspended in aqueous NaOH (6N, 50 mL) and heated at 130° C. for 4 days. Upon the completion (by HPLC) of the hydrolysis, the reaction mixture was neutralized with conc. HCl to slightly acidic (pH~6). The resulting slurry was filtered, washed with water and dried to give 4-amino-1-(4-chlorophenyl)piperidine-4-carboxylic acid (4-ClAPPC) as a white solid (2.05 g, >100% yield, wet and contaminated with inorganic salt), which showed a single peak on HPLC and used directly for the next step. MS (electrospray) m/e 253 (M−H), Calcd for C$_{12}$H$_{15}$ClN$_2$O$_2$, 254.

Step 5:

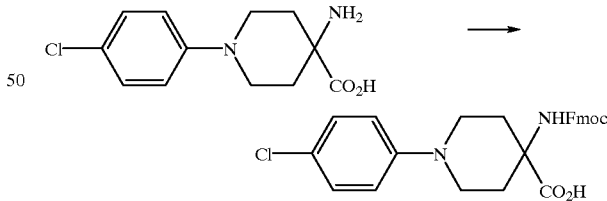

The crude amino acid 4-ClAPPC from the last step was suspended in dioxane (100 mL) and aqueous 10% Na$_2$CO$_3$ (50 ml), treated with Fmoc-Cl (2.0 g, 7.75 mmole, 1.2 equiv) and was stirred vigorously overnight. The reaction mixture was then concentrated to remove dioxane, neutralized with 6N HCl to slightly acidic (pH 6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$/MeOH) to give pure Fmoc-4-ClAPPC (1.18 g, 81% overall yield for two steps). $^1$H NMR (DMSO-d$_6$): 7.87 (d, 2H), 7.71 (d, 2H), 7.39 (td, 2H), 7.30 (td, 2H), 7.20 (d, 2H), 6.92 (d, 2H), 3.44 (d, 2H), 2.93 (t, 2H); MS (electrospray) m/e 477 (M+H), Calcd for C$_{27}$H$_{25}$N$_2$O$_4$, 476.

EXAMPLE 21

Preparation of Fmoc-4-amino-1-(4-phenoxyphenyl) piperidine-4-carboxylic acid (Fmoc-4-PhOAppc-OH)

Step 1:

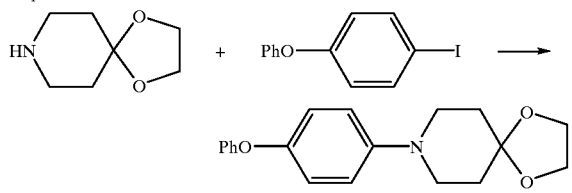

To a solution of 1-iodo-4-phenoxybenzene (3.15 g, 10.6 mmol), 1,4-dioxa-8-azaspiro[4.5]decane (3.3 mL, 3.66 g, 25.6 mmole, 2.4 equiv) and sodium tert-butoxide (2.85 g, 29.7 mmol, 2.8 equiv) in dry dioxane (40 mL) were added tris (dibenzylideneacetone) dipalladium (0) (48.5 mg, 0.053 mmol) and tri-o-tolyl- phosphine (64 mg, 0.4 mmol). The reaction was heated at 90° C. for 9 hrs. The resulting reaction mixture was concentrated to remove solvent. The residue was treated with water and extracted with EtOAc. The combined organic extracts were combined, washed with brine, dried over Na$_2$SO$_4$ and concentrated to give a brown oil. This crude product was purified on flash chromatography (hexane/EtOAc, 95/5 to 80/20) to provide the pure product as a slightly yellow solid (2.805, 85%). $^1$H NMR (CDCl$_3$), 7.26–7.32 (m, 2H), 7.03 (t, 1H), 6.92–6.97 (m, 6H), 4.00 (s, 4H). 3.26 (t, 4H), 1.86 (t, 4H).

Step 2:

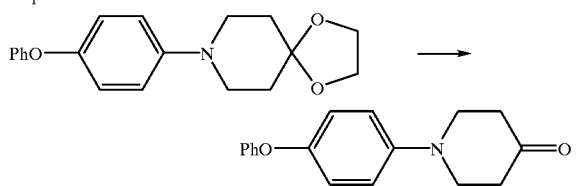

To a solution of the ketal (2.755 g, 8.86 mmol) in acetone (90 mL) was added 6N hydrochloric acid (45 mL) and the reaction was heated at reflux overnight. The resulting reaction mixture was concentrated to remove solvent. The residue was diluted with EtOAc and neutralized with aqueous 6N NaOH. The layers were separated and the aqueous layer was extracted with EtOAc. The combined organic extracts were washed with brine, dried over Na$_2$SO$_4$ and concentrated to give the crude product which was purified on flash chromatography (hexane/EtOAc, 90/10 to 70/30) to give the product as a yellow oil (2.21 g, 93%). MS (electrospray) m/e 268 (M+H), Calcd for C$_{17}$H$_{17}$ClNO$_2$, 267.

Step 3:

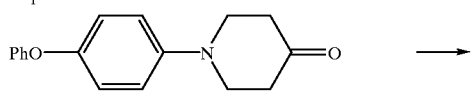

-continued

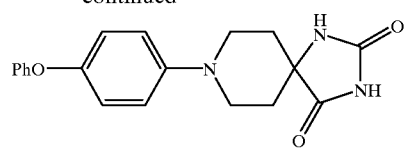

To a solution of the ketone (2.01 g, 7.52 mmol) in ethanol (80 mL) and water (25 mL) in a glass pressure bottle, were added ammonium carbonate (5.78 g, 60.0 mmol, 8 equiv.) and potassium cyanide (1.22 g, 18.80 mmol, 2.5 equiv.). The mixture was heated at 80–90° C. for 18 hrs. The cooled reaction mixture was concentrated in vacuo and the residue was treated with water, extracted with EtOAc (4x). The combined organic extracts were washed with water, dried over anhydrous Na$_2$SO$_4$ and concentrated to give the spectroscopically pure hydantoin as a white solid (2.34 g, 95% yield). MS (electrospray) m/e 338 (M+H), Calcd for C$_{19}$H$_{19}$N$_{3l}$ $_{O3}$, 337.

Step 4:

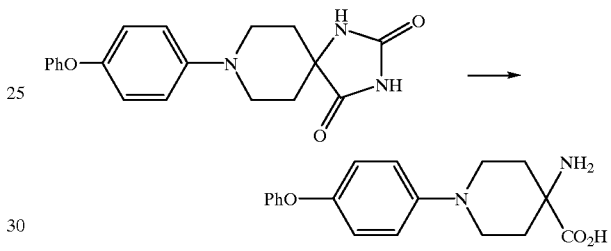

The hydantoin (2.28 g, 6.76 mmole) was suspended in aqueous NaOH (6N, 60 mL) and heated at 130° C. for 4 days. Upon completion (by HPLC) of the hydrolysis, the reaction mixture was neutralized with conc. HCl to slightly acidic (pH~6). The resulting slurry was filtered, washed with water and dried to give 4-amino-1-(4-phenoxyphenyl) piperidine-4-carboxylic acid (4-PhOAPPC) as a white solid (2.53 g, >100% yield, wet and contaminated with inorganic salt), which showed a single peak on HPLC and used directly for the next step. MS (electrospray) m/e 313 (M+H), Calcd for C$_{18}$H$_{20}$N$_2$O$_3$, 312.

Step 5:

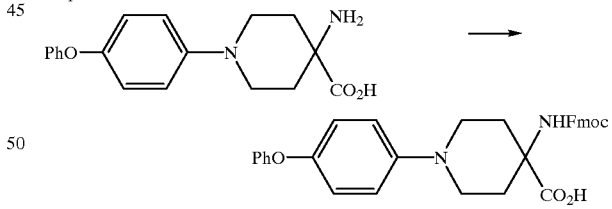

The crude 4-PhOAPPC from the last step was treated with Fmoc-Cl (2.6 g, 1.25 equiv) in dioxane (50 L) and aqueous 10% Na$_2$CO$_3$ (50 ml) and stirred vigorously overnight. The reaction mixture was concentrated to remove dioxane, neutralized with 6N HCl to slightly acidic (pH 6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$/MeOH) to give pure 4-PhOAPPC (2.18 g, 60% overall yield for two steps). $^1$H NMR (DMSO-d$_6$): 7.87 (d, 2H), 7.72 (d, 2H), 7.38 (t, 2H), 7.30 (td, 4H), 7.02 (dt, 1H), 6.86–6.96 (m, 6H), 3.35 (m, 2H), 2.94 (t, 2H); MS (electrospray) m/e 535 (M+H), Calcd for C$_{33}$H$_{30}$N$_2$O$_5$, 534.

EXAMPLE 22

Preparation of Fmoc-4-amino-1-(2-methylphenyl)piperidine-4-carboxylic acid(Fmoc-2-MeAppc-OH)

Step 1:

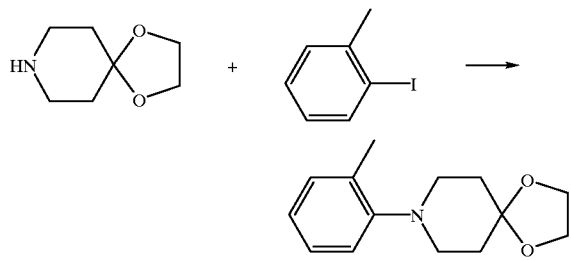

To a solution of 2-iodotoluene (4.36 g, 2.5 mL, 20.0 mmol), 1,4-dioxa-8-azaspiro[4.5]decane (6.88 g, 6.2 mL, 48.1 mmol, 2.4 equiv) and sodium tert-butoxide (5.3 g, 55.2 mmol, 2.8 equiv) in dry dioxane (80 mL) were added tris(dibenzylideneacetone)dipalladium(0) (91 mg, 0.1 mmol) and tri-o-tolylphosphine (122 mg, 0.4 mmol). The reaction was heated at 90° C. for 26 hrs. The resulting reaction mixture was concentrated to remove solvent. The residue was treated with water and extracted with EtOAc. The combined organic extracts were combined, washed with brine, dried over $Na_2SO_4$ and concentrated to give brown oil. This crude product was purified on flash chromatography (hexane/EtOAc, 95/5 to 75/25) to provide the pure product as a slightly yellow solid (2.66 g, 57%). $^1$H NMR ($CDCl_3$), 7.12–7.18 (m, 2H), 6.94–7.06 (m, 2H), 4.01 (s, 4H), 2.98 (t, 4H) and 1.88 (t, 4H).

Step 2:

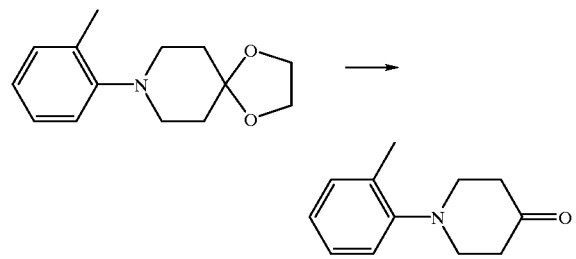

To a solution of the ketal (2.66 g, 11.4 mmol) in acetone (70 mL) was added 6N hydrochloric acid (35 mL) and the reaction was heated at 85° C. overnight. The resulting reaction was concentrated to remove solvent. The residue was diluted with EtOAc and neutralized with aqueous NaOH (6N). The layers were separated and the aqueous layer was extracted with EtOAc. The combined organic extracts were washed with brine, dried over $Na_2SO_4$ and concentrated. The crude product was purified on flash chromatography (hexane/EtOAc, 90/10 to 70/30) to give the product as a yellow oil (2.04 g, 95%). MS (electrospray) m/e 190 (M+H), Calcd for $C_{12}H_{15}NO$, 189.

Step 3:

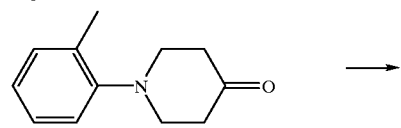

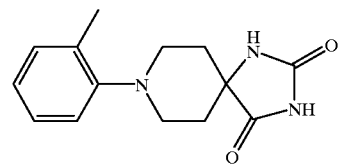

To a solution of the ketone (1.54 g, 8.15 mmol) in ethanol (60 mL) and water (20 mL) in a glass pressure bottle, were added ammonium carbonate (4.69 g, 48.9 mmol, 6 equiv.) and potassium cyanide (800 g, 12.2 mmol, 1.5 equiv.). The mixture was heated at 80–90° C. for 18 hrs. The cooled reaction mixture was added to icy water (300 ml) and stirred vigorously for 30 min. The resulting precipitate was suction filtered, washed thoroughly with water and dried to yield the hydantoin as a white solid (2.01 g, 95% yield). MS (electrospray) m/e 260 (M+H), Calcd for $C_{14}H_{17}N_3O_2$, 259.

Step 4:

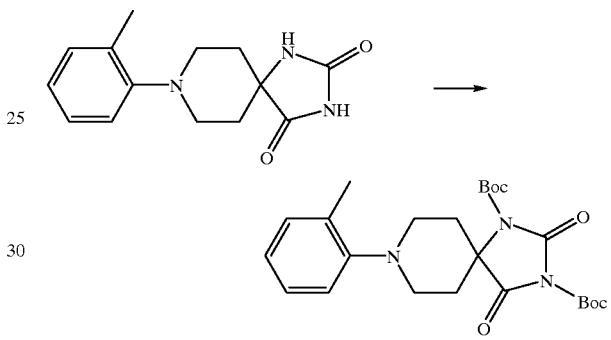

To a suspension of the hydantoin (1.07 g, 4.13 mmol) in dry THF (25 mL) were added di-tert-butyl dicarbonate (2.25 g, 10.32 mmol, 2.5 equiv), triethylamine (0.63 mL, 460 mg, 4.54 mmol, 1.1 equiv) and DMAP (36 mg, 0.29 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with 1N HCl (3×30 mL), saturated aqueous $Na_2CO_3$ (2×30 mL) and brine (2×30 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin as a white solid (1.71 g, 90%). MS (electrospray) m/e 460 (M+H), Calcd for $C_{24}H_{33}N_3O_6$, 459.

Step 5:

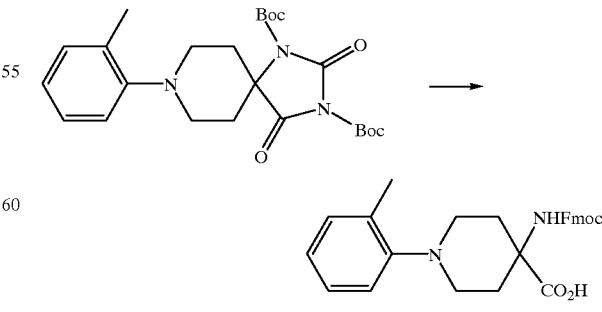

The bis-Boc hydantoin (1.71 g, 3.72 mmol) was dissolved in DME (23 mL) to give a clear solution. To this solution was added 1N NaOH (33 mL, 33 mmol) and the reaction was stirred overnight at room temperature, giving a fairly clear mixture. HPLC showed completion of the reaction. The reaction mixture was concentrated under reduced pressure to remove DME and extracted with Et$_2$O. Without purification, the resulting aqueous layer containing 4-amino-1-(2-methylphenyl)piperidine-4-carboxylic acid (2-MeAPPC) was treated with 6N HCl to adjust the pH to 11–12. This solution (30 mL) was then diluted with 1,4-dioxane (30 mL) and treated with Fmoc-Cl (1.28 g, 4.96 mmol, 1.3 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous Na$_2$SO$_4$ and concentrated. The crude product was purified through flash chromatography (hexane/EtOAc→CH$_2$Cl$_2$/MeOH) to give the pure product as a white solid (1.09 g, 64% yield from the bis-Boc hydantoin). $^1$H NMR (DMSO-d$_6$): 7.87 (d, 2H), 7.74 (d, 2H), 7.40 (td, 2H), 7.31 (td, 2H), 7.12 (m, 2H), 6.97 (d, 1H), 6.92 (td, 1H), 2.72–2.88 (m, 4H) and 2.22 (s, 3H); MS (electrospray) m/e 457 (M+H), Calcd for C$_{28}$H$_{28}$N$_2$O$_4$, 456.

EXAMPLE 23

Preparation of Fmoc-4-amino-1-(2-isopropylphenyl)piperidine-4-carboxylic acid (Fmoc-2-iPrAppc-OH)

Step 1:

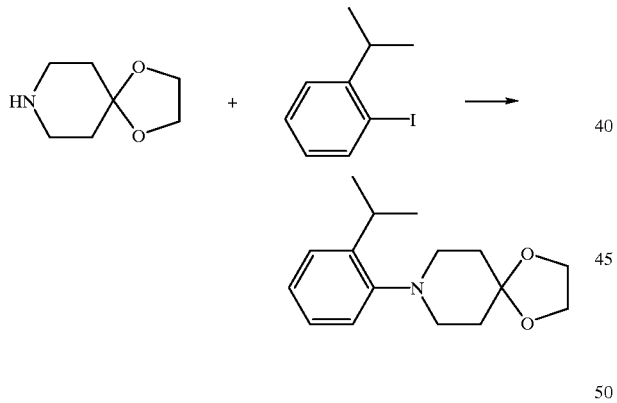

To a solution of 1-iodo-2-iso-propylbenzene (10.0 g, 40.7 mmol), 1,4-dioxa-8-azaspiro[4.5]decane (12.0 mL, 13.3 g, 93.0 mmol, 2.3 equiv) and sodium tert-butoxide (10.0 g, 104.2 mmol, 2.6 equiv) in dry dioxane (160 mL) were added tris(dibenzylideneacetone)dipalladium(0) (180 mg, 0.197 mmol) and tri-o-tolyl-phosphine (244 mg, 0.80 mmol) and the reaction was heated at 90° C. for 26 hrs. The resulting reaction mixture was concentrated to remove solvent, treated with water and extracted with EtOAc. The combined organic extracts were combined, washed with brine, dried over Na$_2$SO$_4$ and concentrated to give a brown oil. This crude product was purified on flash chromatography (hexane/EtOAc, 95/5→75/25) to provide the pure product as a slightly yellow solid (3.61 g, 35% yield). MS m/z 262 (M+H), Calcd for C$_{16}$H$_{23}$NO$_2$, 261.

Step 2:

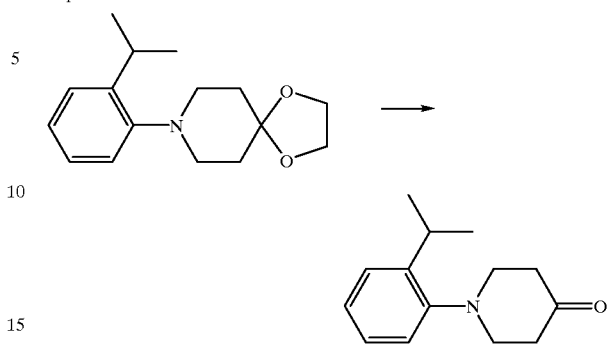

To a solution of the ketal (3.24 g, 12.4 mmol) in acetone (90 mL) was added 6N hydrochloric acid (45 mL) and the reaction was heated at reflux overnight. The resulting reaction mixture was concentrated to remove solvent and the residue was diluted with EtOAc, neutralized with aqueous NaOH (6N). The layers were separated and the aqueous layer was extracted with EtOAc. The combined organic extracts were washed with brine, dried over Na$_2$SO$_4$ and concentrated. The crude product was purified on flash chromatography (hexane/EtOAc, 90/10→70/30) to give the product as a yellow oil (2.42 g, 89%). $^1$H NMR (CDCl$_3$): 7.27 (m, 1H), 7.04–7.19 (m, 3H), 3.58 (m, 1H), 3.20 (t, 4H), 2.60 (t, 4H) and 1.25 (d, 6H); MS m/z 218 (M+H), Calcd for C$_{14}$H$_{19}$NO, 217.

Step 3:

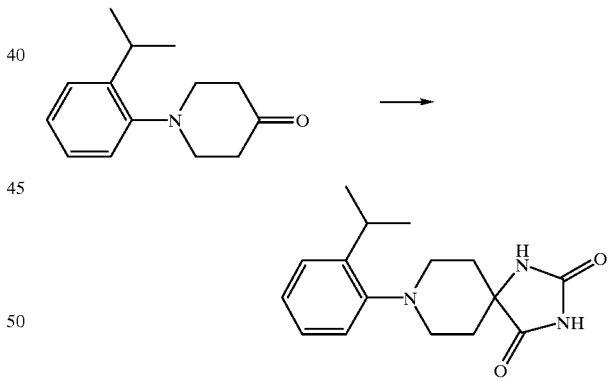

To a solution of the ketone (2.30 g, 10.6 mmol) in ethanol (90 mL) and water (20 mL) in a glass pressure bottle, were added ammonium carbonate (8.1 g, 84.3 mmol, 8 equiv) and potassium cyanide (1.72 g, 26.5 mmol, 2.5 equiv). The mixture was heated at 80–90° C. for 18 hrs. The cooled reaction mixture was added to icy water (400 ml) and stirred vigorously for 30 min. The resulting precipitate was suction filtered, washed thoroughly with water and dried to yield the hydantoin as a white solid (2.78 g, 91% yield). MS m/z 288 (M+H), Calcd for C$_{16}$H$_{21}$N$_3$O$_2$, 287.

Step 4:

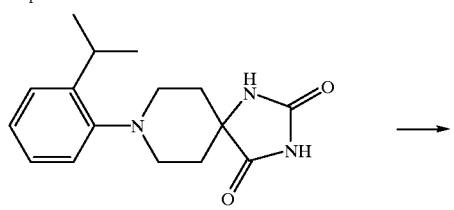

To a suspension of the hydantoin (2.74 g, 9.54 mmol) in dry THF (100 mL) were added di-tert-butyl dicarbonate (5.2 g, 24.24 mmol, 2.5 equiv), triethylamine (1.5 mL, 1.07 g, 10.5 mmol, 1.1 equiv) and DMAP (46 mg, 0.29 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with brine (3×30 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin as a white solid (4.39 g, 94% yield). MS m/z 488 (M+H), Calcd for $C_{26}H_{37}N_3O_6$, 487.

Step 5:

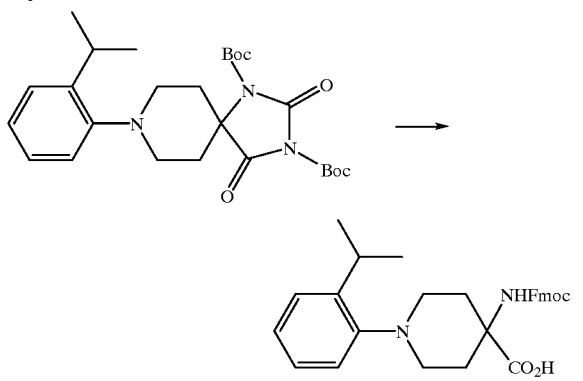

The bis-Boc hydantoin (2.34g, 4.8 mmol) was dissolved in DME (30 mL) to give a clear solution. To this solution was added 1N NaOH (45 mL, 45 mmol) and the reaction was stirred overnight at room temperature, giving a fairly clear mixture. HPLC showed completion of the reaction. The reaction mixture was concentrated under reduced pressure to remove DME and extracted with $Et_2O$. Without purification, the resulting aqueous layer containing 4-amino-1-(2-isopropylphenyl)piperidine-4-carboxylic acid (2-iPrAPPC) was treated with 6N HCl to adjust the pH to 11–12. This solution (~45 mL) was then diluted with 1,4-dioxane (45 mL) and treated with Fmoc-Cl (1.78 g, 6.89 mmol, 1.5 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous $Na_2SO_4$ and concentrated. The crude product was purified through flash chromatography (hexane/EtOAc→$CH_2Cl_2$/MeOH) to give the pure product as a white solid (1.46 g, 63% yield from the bis-Boc hydantoin). HRMS m/z 507.2263, Calcd for $C_{30}H_{32}N_2O_4Na$, 507.2260.

EXAMPLE 24

Preparation of Fmoc-4-amino-1-(3-methylphenyl) piperidine-4-carboxylic acid (Fmoc-3-MeAppc-OH)

Step 1:

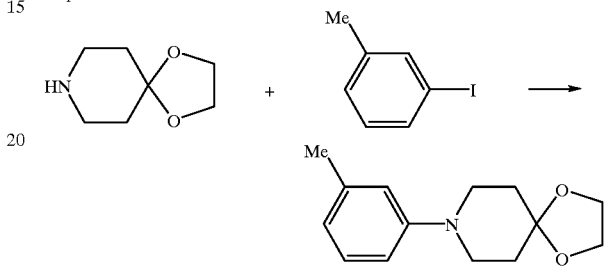

To a solution of 3-iodotoluene (4.36 g, 2.6 mL, 20.0 mmol), 1,4-dioxa-8-azaspiro[4.5]decane (6.88 g, 6.2 mL, 48.1 mmol, 2.4 equiv) and sodium tert-butoxide (5.3 g, 55.2 mmol, 2.8 equiv) in dry dioxane (80 mL) were added tris (dibenzylideneacetone) dipalladium (0) (91 mg, 0.1 mmol) and tri-o-tolylphosphine (122 mg, 0.4 mmol). The reaction was heated at 90° C. for 26 hrs. The resulting reaction mixture was concentrated to remove solvent. The residue was treated with water and extracted with EtOAc. The combined organic extracts were combined, washed with brine, dried over $Na_2SO_4$ and concentrated to give a brown oil. This crude product was purified on flash chromatography (hexane/EtOAc, 95/5 to 75/25) to provide the pure product as a slightly yellow solid (3.21 g, 69%).

Step 2:

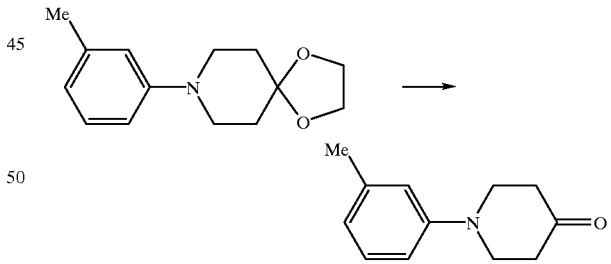

To a solution of the ketal (1.25 g, 5.36 mmol) in acetone (20 mL) was added 6N hydrochloric acid (10 mL) and the reaction was heated at reflux overnight. The resulting reaction was concentrated to remove solvent. The residue was diluted with EtOAc and neutralized with aqueous NaOH (6N). The layers were separated and the aqueous layer was extracted with EtOAc. The combined organic extracts were washed with brine, dried over $Na_2SO_4$ and concentrated. The crude product was purified on flash chromatography (hexane/EtOAc, 90/10 to 70/30) to give the product as a yellow oil (843 mg, 83% yield). MS m/z 190 (M+H), Calcd for $C_{12}H_{15}NO$, 189.

Step 3:

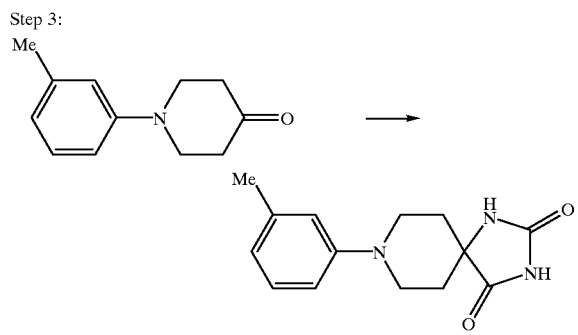

To a solution of the ketone (763 g, 4.03 mmol) in ethanol (45 mL) and water (15 mL) in a glass pressure bottle, were added ammonium carbonate (3.09 g, 32.21 mmol, 8 equiv) and potassium cyanide (675 mg, 10.38 mmol, 2.5 equiv). The mixture was heated at 80–90° C. for 18 hrs. The cooled reaction mixture was added to icy water (200 ml) and stirred vigorously for 30 min. The resulting precipitate was suction filtered, washed thoroughly with water and dried to yield the hydantoin as a white solid (930 mg, 89% yield). MS m/z 260 (M+H), Calcd for $C_{14}H_{17}N_3O_2$, 259.

Step 4:

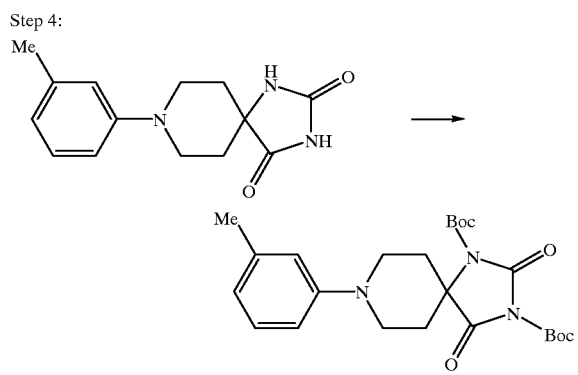

To a suspension of the hydantoin (780 mg, 3.012 mmol) in dry THF (22 mL) were added di-tert-butyl dicarbonate (1.64 g, 7.52 mmol, 2.5 equiv), triethylamine (0.42 mL, 305 mg, 3.01 mmol, 1.0 equiv) and DMAP (20 mg, 0.164 mmol) in succession. About 5 minutes after the addition, the reaction turned into a clear yellow solution and was stirred overnight at room temperature. The reaction mixture was concentrated under reduced pressure to yield a solid that was then taken up in EtOAc (300 mL), washed with brine (3×30 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin as a white solid (1.37 g, quantitative). HRMS m/z 482.2261 (M+Na), Calcd. for $C_{24}H_{33}N_3O_6Na$, 482.2267.

Step 5:

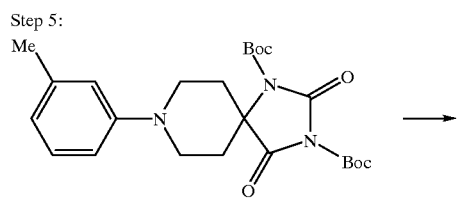

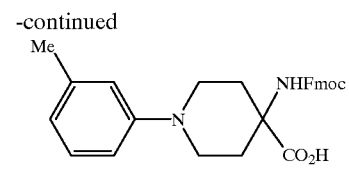

The bis-Boc hydantoin (1.29 g, 2.818 mmol) was dissolved in DME (20 mL) to give a clear solution. To this solution was added 1N NaOH (25 mL, 25 mmol) and the reaction was stirred overnight at room temperature, giving a fairly clear mixture. HPLC showed completion of the reaction. The reaction mixture was concentrated under reduced pressure to remove DME and extracted with $Et_2O$. Without purification, the resulting aqueous layer containing 4-amino-1-(3-methylphenyl)piperidine-4-carboxylic acid (3-MeAPPC) was treated with 6N HCl to adjust the pH to 11–12. This solution (30 mL) was then diluted with 1,4-dioxane (30 mL) and treated with Fmoc-Cl (1.46 mg, 5.65 mmol, 2.0 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous $Na_2SO_4$ and concentrated. The crude product was purified through flash chromatography (hexane/EtOAc→$CH_2Cl_2$/MeOH) to give the pure product as a white solid (1.002 g, 78% yield from the bis-Boc hydantoin). HRMS m/z 479.1940 (M+Na), Calcd. for $C_{28}H_{28}N_2O_4Na$, 479.1947.

EXAMPLE 25

Preparation of Fmoc-4-amino-1-(3-methoxyphenyl) piperidine-4-carboxylic acid (Fmoc-3-MeOAppc-OH)

Step 1:

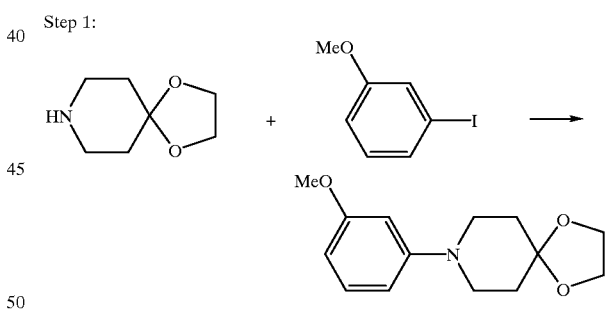

To a solution of 3-iodoanisole (4.68 g, 2.4 mL, 20.0 mmol), 1,4-dioxa-8-azaspiro[4.5]decane (6.2 mL, 6.88 g, 48.1 mmol, 2.4 equiv) and sodium tert-butoxide (5.3 g, 55.2 mmol, 2.8 equiv) in dry dioxane (80 mL) were added tris(dibenzylideneacetone)dipalladium(0) (91 mg, 0.1 mmol) and tri-o-tolylphosphine (122 mg, 0.4 mmol) and the reaction was heated at 90° C. for 26 hrs. The resulting reaction mixture was concentrated to remove solvent and the residue was treated with water and extracted with EtOAc. The combined organic extracts were combined, washed with brine, dried over $Na_2SO_4$ and concentrated to give brown oil. This crude product was purified on flash chromatography (hexane/EtOAc, 95/5 to 75/25) to provide the pure product as a slightly yellow solid (3.10 g, 62% yield). MS m/z (M+H), 250 (M+H), Calcd for $C_{14}H_{19}NO_3$, 249.

Step 2:

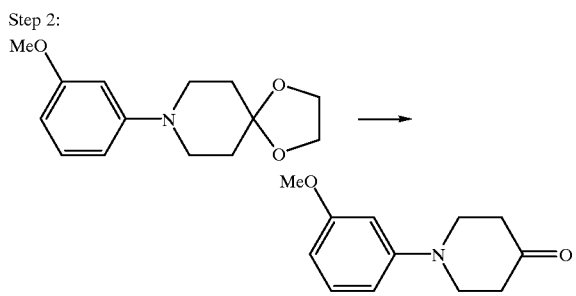

To a solution of the ketal (3.10 g, 12.45 mmol) in acetone (90 mL) was added 6N hydrochloric acid (45 mL) and the reaction was heated at reflux overnight. The resulting reaction was concentrated to remove solvent. The residue was diluted with EtOAc and neutralized with aqueous NaOH (6N). The layers were separated and the aqueous layer was extracted with EtOAc. The combined organic extracts were washed with brine, dried over $Na_2SO_4$ and concentrated. The crude product was purified on flash chromatography hexane/EtOAc, 90/10 to 70/30) to give the product as a yellow oil (2.53 g, 99% yield). $^1$H NMR ($CDCl_3$): 7.20 (m, 1H), 6.58 (d, 1H), 6.39–6.56 (m, 2H), 3.80 (s, 3H), 3.59 (m, 4H) and 2.58 (m, 4H).

Step 3:

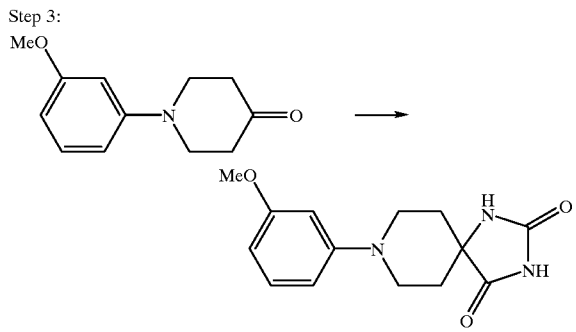

To a solution of the ketone (1.81 g, 8.82 mmol) in ethanol (60 mL) and water (20 mL) in a glass pressure bottle, were added ammonium carbonate (6.77 g, 70.52 mmol, 8 equiv) and potassium cyanide (1.14 g, 17.6 mmol, 2.0 equiv). The mixture was heated at 80–90° C. for 18 hrs. The cooled reaction mixture was added to icy water (200 ml) and stirred vigorously for 30 min. The resulting precipitate was suction filtered, washed thoroughly with water and dried to yield the hydantoin as a white solid (2.23 g, 92% yield). MS m/z 276 (M+H), Calcd for $C_{14}H_{17}N_3O_3$, 275.

Step 4:

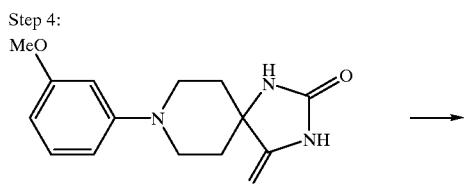

-continued

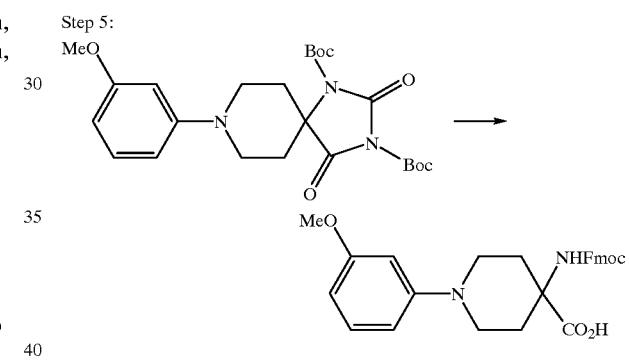

To a suspension of the hydantoin (1.10 g, 4.00 mmol) in dry THF (50 mL) were added di-tert-butyl dicarbonate (2.18 g, 10.0 mmol, 2.5 equiv), triethylamine (0.62 mL, 445 mg, 4.4 mmol, 1.1 equiv) and DMAP (20 mg, 0.164 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with brine (3×30 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin as a white solid (1.90 g, quantitative). $^1$H NMR ($CDCl_3$): 7.16 (t, 1H), 6.57 (d, 1H), 6.24 (s, 1H), 6.19 (d, 1H), 3.77 (s, 3H), 1.58 (s, 9H), 1.42 (s, 9H); MS m/z 476 (M+H), Calcd for $C_{24}H_{33}N_3O_7$, 475.

Step 5:

The bis-Boc hydantoin (1.06 g, 2.23 mmol) was dissolved in DME (20 mL) to give a clear solution. To this solution was added 1N NaOH (20 mL, 20 mmol) and the reaction was stirred overnight at room temperature, giving a fairly clear mixture. HPLC showed completion of the reaction. The reaction mixture was concentrated under reduced pressure to remove DME and extracted with $Et_2O$. Without purification, the resulting aqueous layer containing 4-amino-1-(3-methoxyphenyl)piperidine-4-carboxylic acid (3-MeOAPPC) was treated with 6N HCl to adjust the pH to 11–12. This solution (35 mL) was then diluted with 1,4-dioxane (35 mL) and treated with Fmoc-Cl (755 mg, 2.93 mmol, 1.3 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous $Na_2SO_4$ and concentrated. The crude product was purified through flash chromatography (hexane/EtOAc→$CH_2Cl_2$/MeOH) to give the pure product as a white solid (668 mg, 63% yield from the bis-Boc hydantoin). $^1$H NMR ($CDCl_3$): 7.83 (d, 2H), 7.72 (d, 2H), 7.41 (td, 2H), 7.34 (dt, 2H), 7.16 (t, 1H), 6.52 (d, 1H), 6.42 (s, 1H), 6.36 (d, 1H), 4.25 (m, 3H), 3.68 (s, 3H), 3.23–3.40 (m, 2H), 2.96 (t, 2H) and 1.86–2.18 (m, 4H). HRMS m/z 495.1901 (M+Na), Calcd. for $C_{28}H_{28}N_2O_5Na$, 495.1896.

EXAMPLE 26

Preparation of Fmoc-1-amino-4-cyclohexylcyclohexane-1-carboxylic acid (Fmoc-Achc-OH)

Step 1:

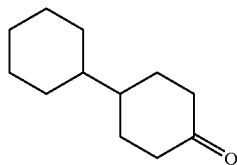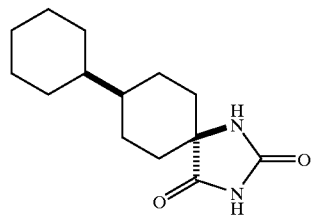

A mixture of 4-cyclohexylcyclohexanone (3.00 g, 16.6 mmole), potassium cyanide (1.63 g, 25.0 mmole), ammonium carbonate (9.59 g, 99.8 mmole), ethanol (75 ml) and water (15 ml) in a sealed, thick walled pressure flask was heated in a 80° C. oil bath for 15 hours. After cooling to room temperature, the white slurry was poured into ice-water and stirred at room temperature for a couple of hours. Filtration and air-drying gave hydantoin (6.10 g, still wet, >100% yield) as a white solid. $^1$H NMR (DMSO-$d_6$) δ10.52 (1H, broad, NH), 8.43 (1H, broad s, NH), 0.80–1.80 (20H, m). LRMS (APCI): $C_{14}H_{22}N_2O_2$, calc. 250; observed: 249 (M−H), 251 (M+H).

Step 2:

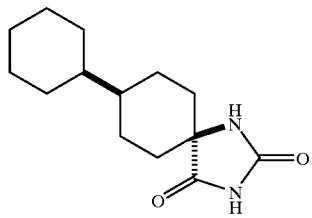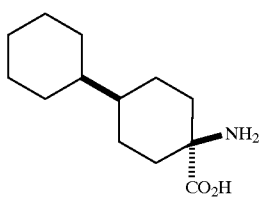

A mixture of hydantoin (1.39 g, 5.55 mmole) and 6N sodium hydroxide solution (50 ml) in a sealed, thick walled pressure flask was heated in a 130° C. oil bath for 2 days. The reaction mixture was cooled in an ice bath, neutralized to ~pH 7 using concentrated hydrochloric acid. The white slurry was filtered and the precipitates rinsed with water to give crude 1-amino-4-cyclohexylcyclohexane-1-carboxylic acid (48.3 g, wet and containing inorganic salts, >100% yield). LRMS (Electrospray): $C_{13}H_{23}NO_2$, calc. 225; observed: 226 (M+H).

Step 3:

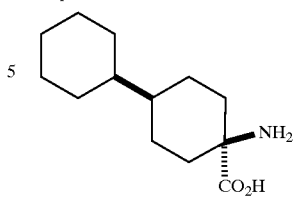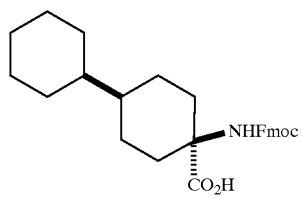

A mixture of crude 1-amino-4-cyclohexylcyclohexane-1-carboxylic acid (48.3 g, 5.55 mmole theoretical), triethylamine (1.0 ml, 7.17 mmole), 9-fluorenylmethyl succinimidyl carbonate (Fmoc-OSu, 2.43 g, 7.20 mmole) in acetonitrile (75 ml) and water (75 ml) was stirred at room temperature for 24 hours. The reaction mixture was concentrated in vacuo to remove most of the acetonitrile, acidified to pH~3 with 10% aqueous citric acid solution, and the white emulsion extracted three times with methylene chloride. The combined organic layers were washed with water, brine, dried over magnesium sulfate. Filtration and concentration gave a crude oil which was purified by column chromatography (eluted with 1→5→8% methanol/methylene chloride) to give Fmoc-1-amino-4-trans-cyclohexylcyclohexane-1-carboxylic acid (250 mg, 10% yield for two steps). HRMS (FAB): $C_{28}H_{34}NO_4$ (M+H) calc. 448.2488; observed: 448.2497.

EXAMPLE 27

Preparation of Fmoc-1-amino-4,4-diphenylcyclohexane-1-carboxylic acid (Fmoc-Adpc-OH)

Step 1:

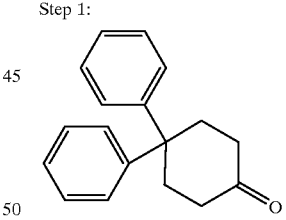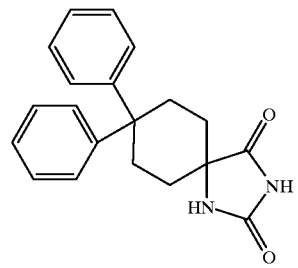

A mixture of 4,4-diphenylcyclohexanone (prepared by hydrogenation of 4,4-diphenylcyclohexenone according to the procedures of Freeman, P. K. et.al. *J. Org. Chem.* 1989, 54, 782–789) (1.55 g, 6.19 mmole), potassium cyanide (0.65 g, 9.97 mmole), ammonium carbonate (3.60 g, 37.5 mmole), ethanol (48 ml) and water (12 ml) in a sealed, thick walled pressure flask was heated in a 80° C. oil bath for 24 hours. After cooling to room temperature, the white slurry was poured into ice-water and stirred at room temperature for a couple of hours. Filtration and air-drying gave hydantoin (1.89 g, 95% yield) as a white solid. $^1$H NMR (DMSO-d$_6$) δ10.57 (1H, broad, NH), 8.59 (1H, broad s, NH), 7.00–7.50 (10H, m, phenyl). LRMS (Electrospray): C$_{20}$H$_{20}$N$_2$O$_2$, calc. 320; observed: 319 (M–H).

Step 2:

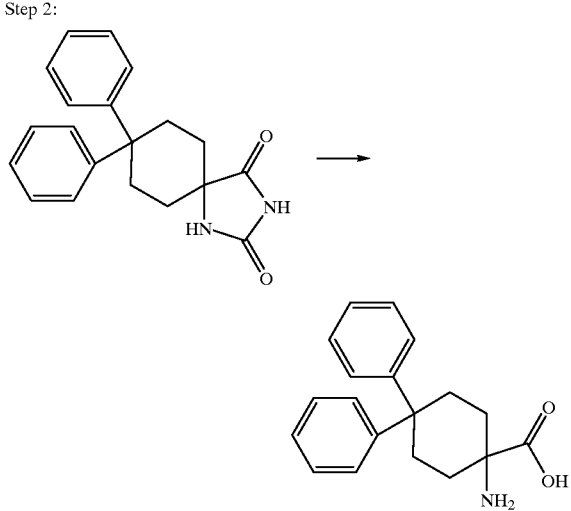

A mixture of hydantoin (1.88 g, 5.87 mmole), barium hydroxide monohydrate (5.60 g, 29.6 mmole) and water (100 ml, too dilute!) in a sealed, thick walled pressure flask was heated in a 105° C. oil bath for 2 days. More barium hydroxide monohydrate (5.60 g, 29.6 mmole) was added and the mixture was heated in a 105° C. oil bath for another 24 hours. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~30 ml. Neutralization with concentrated ammonium hydroxide solution gave white precipitates which were filtered, washed with water and dried in vacuo overnight to give crude 1-amino-4,4-diphenylcyclohexane-1-carboxylic acid (0.52 g, 30% yield) as a white solid. LRMS (Electrospray): C$_{19}$H$_{21}$NO$_2$, calc. 295; observed: 294 (M–H), 296 (M+H).

Step 3:

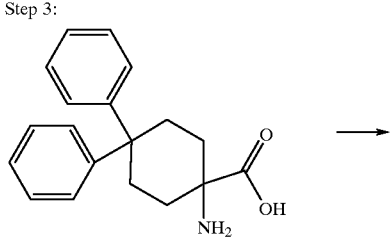

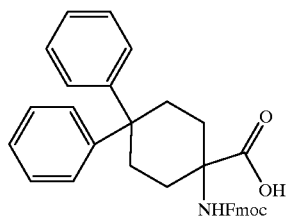

A mixture of crude 1-amino-4,4-diphenylcyclohexane-1-carboxylic acid (510 mg, 1.73 mmole), triethylamine (0.37 ml, 2.65 mmole), 9-fluorenylmethyl succinimidyl carbonate (Fmoc-OSu, 880 mg, 2.61 mmole) in acetonitrile (25 ml) and water (25 ml) was stirred at room temperature overnight. TLC analysis of the reaction indicated the presence of starting material amino acid. 9-fluorenylmethyl succinimidyl carbonate (200 mg) and acetonitrile (5 ml) were added and the mixture was stirred at room temperature for another 24 hours. The reaction mixture was concentrated in vacuo to remove most of the acetonitrile, acidified to pH~3 with 10% aqueous citric acid solution, and the white emulsion extracted three times with ethyl acetate. The combined organic layers were washed with water, brine, dried over sodium sulfate. Filtration and concentration gave a crude oil which was purified by column chromatography (eluted with 1→4→8% methanol/methylene chloride) to give Fmoc-1-amino-4,4-diphenylcyclohexane-1-carboxylic acid (350 mg, 39% yield) as a white solid, HRMS (FAB): C$_{34}$H$_{32}$NO$_4$ (M+H) calc. 518.2331; observed: 518.231

EXAMPLE 28

Preparation of Fmoc-1-amino-4-trans-t-butylcyclohexane-1-carboxylic acid (Fmoc-Abc-OH)

Step 1:

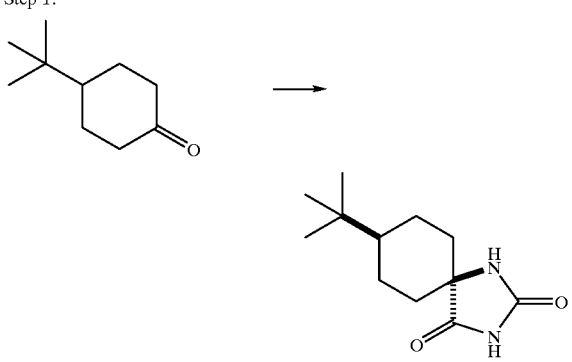

A mixture of 4-t-butylcyclohexanone (2.00 g, 13.0 mmole), potassium cyanide (1.27 g, 19.5 mmole), ammonium carbonate (7.48 g, 77.8 mmole), ethanol (60 ml) and water (12 ml) in a sealed, thick walled pressure flask was heated in a 80° C. oil bath for 15 hours. After cooling to room temperature, the white slurry was poured into ice-water and stirred at room temperature for a couple of hours. Filtration gave hydantoin (2.78 g, 96% yield) as a white solid which was used in the next step as a crude. $^1$H NMR (DMSO-d$_6$) δ10.52 (1H, broad, NH), 8.50 (1H, broad s, NH), 0.81 (9H, s, t-Bu).

Step 2:

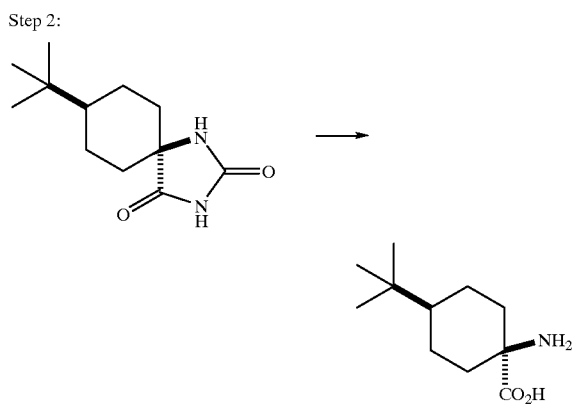

A mixture of hydantoin (2.78 g, 12.4 mmole), barium hydroxide monohydrate (11.74 g, 62.0 mmole) and water (50 ml) in a sealed, thick walled pressure flask was heated in a 120° C. oil bath for 2 days. The reaction mixture was cooled to room temperature, acidified to ~pH 3 using 4N sulfuric acid while being stirred vigorously. The suspension was stirred in a boiling water bath for one hour and cooled to room temperature. The white suspension was filtered and the precipitates rinsed with water. The combined filtrate and washings were concentrated in vacuo to ~30 ml. Neutralization with concentrated ammonium hydroxide solution gave white precipitates which were filtered, washed with water and dried in vacuo overnight to give 1-amino-4-trans-t-butylcyclohexane-1-carboxylic acid (2.10 g, 85% yield) as a white solid.

Step 3:

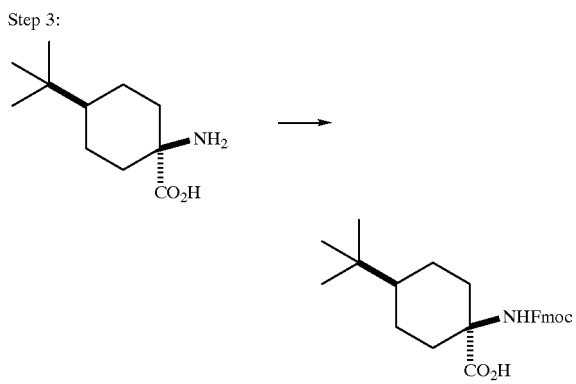

A mixture of crude 1-amino-4-trans-t-butylcyclohexyl-1-carboxylic acid (2.10 g, 10.54 mmole), 9-fluorenylmethyl succinimidyl carbonate (Fmoc-OSu, 6.33 g, 7.20 mmole) in dioxane (150 ml) and 10% sodium carbonate solution (120 ml) was stirred at room temperature for 24 hours. The reaction mixture was concentrated in vacuo to remove most of the dioxane, acidified to pH~3 with 3N HCl, and the white emulsion extracted twice with methylene chloride. The combined organic layers were washed with water, brine, dried over magnesium sulfate. Filtration and concentration gave a crude which was purified by column chromatography (eluted with 1→4→5% methanol/methylene chloride) to give Fmoc-1-amino-4-trans-t-butylcyclohexane-1-carboxylic acid (1.42 g, 32% yield). HRMS (FAB): $C_{26}H_{32}NO_4$ (M+H) calc. 422.2331; observed: 422.23

EXAMPLE 29

Preparation of Fmoc-Linker-BHA Resin

Benzhydrylamine copolystyrene-1% divinylbenzene cross-linked resin (10.0 g, 9.3 mequiv, 100–200 ASTM mesh, Advanced ChemTech) was swelled in 100 mL $CH_2Cl_2$, filtered and washed successively with 100 ml each of $CH_2Cl_2$, 6% DIPEA/$CH_2Cl_2$ (two times), $CH_2Cl_2$ (two times). The resin was treated with p- [(R, S)-α-[1-(9H-fluoren-9-yl) -methoxyformamido]-2,4-dimethoxybenzyl]-phenoxyacetic acid (Fmoc-Linker) (7.01 g, 13.0 mmole), N-hydroxybenzotriazole (2.16 g, 16.0 mmole), and diisopropylcarbodiimide (2.04 ml, 13.0 mmol) in 100 mL 25% DMF/$CH_2Cl_2$ for 24 hours at room temperature. The resin was filtered and washed successively with 100 ml each of $CH_2Cl_2$ (two times), isopropanol (two times), DMF, and $CH_2Cl_2$ (three times). A Kaiser ninhydrin analysis was negative. The resin was dried under vacuum to yield 16.12 g of Fmoc-Linker-BHA resin. A portion of this resin (3.5 mg) was subjected to Fmoc deprotection and quantitative UV analysis indicated a loading of 0.56 mmol/g.

EXAMPLE 30

Preparation of

Bu-His-(D)Phe-Arg-Trp-Gly-NH₂

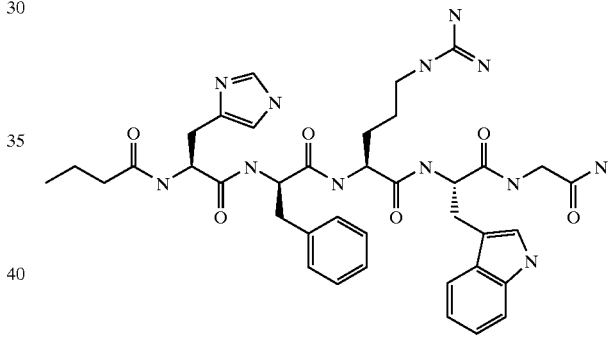

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-His (Trt) (300 mg 0.6 mmol) and HBTU (226 mg, 0.6 mmol). The peptide resin was carried through steps 1–5 of protocol 1, washed with $CH_2Cl_2$ (three times) and treated with 1 mL butyric anhydride in 6% DIPEA/$CH_2Cl_2$ 30 minutes. The resin was filtered and washed successively with 20 ml each of $CH_2Cl_2$ (two times), isopropanol, and $CH_2Cl_2$ (three times). The resin was dried under vacuum to yield 600 mg of Bu-Pentapeptide resin.

The Bu-Pentapeptide resin was treated with 40 μL ethanedithiol, 40 μL dimethylsulfide, 120 μL anisole, and 4 mL trifluoroacetic acid at room temperature for 180 min.

The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 130 mg of an off-white solid.

This crude material was purified by preparative HPLC on a Vydac C18-column (2.5×20 cm) and eluted with a linear gradient of 10–60% B (buffer A: 0.1% $TFA/H_2O$, buffer B: 0.1% $TFA/CH_3CN$) in 60 min., flow rate 8 ml/min, detection 280 nm. The main peak was cut by analytical HPLC analysis of collected fractions, pooled and lyophilized to yield 52 mg (34%) of a white, amorphous powder. This compound was homogeneous by HPLC. LR-Electrospray $C_{38}H_{50}N_{12}O_6$ cal: 770 observed: m/z (771 M+H).

EXAMPLE 31

Penta-Apc-(D)Phe-Arg-Trp-Gly-NH$_2$

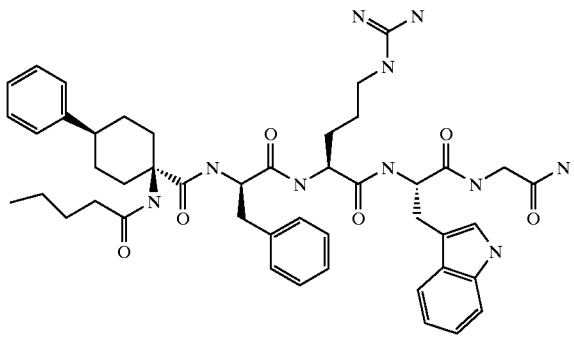

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% $DIPEA/CH_2Cl_2$ 30 minutes. The resin was filtered and washed successively with 20 ml each of $CH_2Cl_2$ (two times), isopropanol, and $CH_2Cl_2$ (three times). The resin was dried under vacuum to yield 580 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% $TFA/H_2O$, buffer B: 0.1% $TFA/CH_3CN$) in 60 min., flow rate 8 ml/min, detection 280 nm. The main peak was cut by analytical HPLC analysis of collected fractions, pooled and lyophilized to yield 61 mg (36%) of a white, amorphous powder. This compound was homogeneous by HPLC. LR-Electrospray: $C_{46}H_{60}N_{10}O_6$, cal: 849 observed: m/z (850 M+H).

EXAMPLE 32

Phenylacetyl-Apc-(D)Phe-Arg-Trp-Gly-NH$_2$

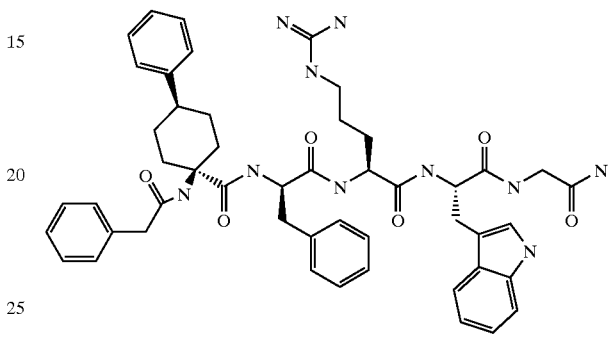

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with phenylacetic acid (82 mg, 0.6 mmole) and HBTU (226 mg, 0.6 mmol) in DMF. The resin was filtered and washed successively with 20 ml each of $CH_2Cl_2$ (two times), isopropanol, and $CH_2Cl_2$ (three times). The resin was dried under vacuum to yield 620 mg of Phenylacetyl-Pentapeptide resin.

The Phenylacetyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 155 mg of an off-white solid.

This crude material was purified by preparative HPLC on a Vydac C18-column (2.5×20 cm) and eluted with a linear gradient of 10–60% B (buffer A: 0.1% $TFA/H_2O$, buffer B: 0.1% $TFA/CH_3CN$) in 60 min, flow rate 8 ml/min, detection 280 nm. The main peak was cut by analytical HPLC analysis of collected fractions, pooled and lyophilized to yield 55 mg (31%) of a white, amorphous powder. This compound was homogeneous by HPLC. LR-Electrospray: $C_{49}H_{58}N_{10}O_6$, cal: 883 observed: m/z (884 M+H).

113
EXAMPLE 33

Bu-Carbamoyl-Apc-(D)Phe-Arg-Trp-Gly-NH$_2$

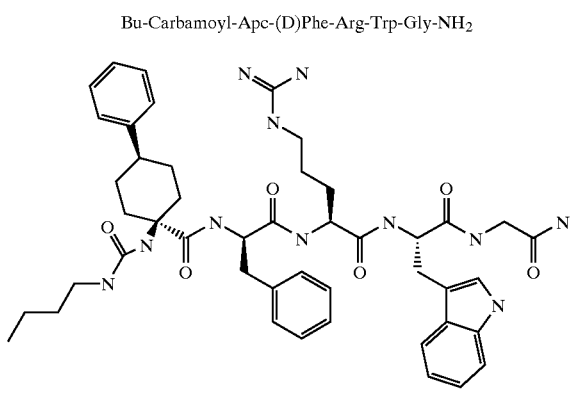

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mal) and HBTU (226 mg, 0.6 mal), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated n-butyl isocyante (5 eq) in 6% DIPEA/DMF for 12 hours. The resin was filtered and washed successively with 20 ml each of CH$_2$Cl$_2$ (two times), isopropanol, and CH$_2$Cl$_2$ (three times). The resin was dried under vacuum to yield 550 mg of Butyl urea-Pentapeptide resin.

The Butyl urea-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 135 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (31%) of a white, amorphous powder. This compound was homogeneous by HPLC. LR-Electrospray: C$_{46}$H$_{61}$N$_{11}$O$_6$, cal: 864 observed: m/z (865 M+H).

114
EXAMPLE 34

Penta-Apc-(D)Phe-Arg-Trp-NH$_2$

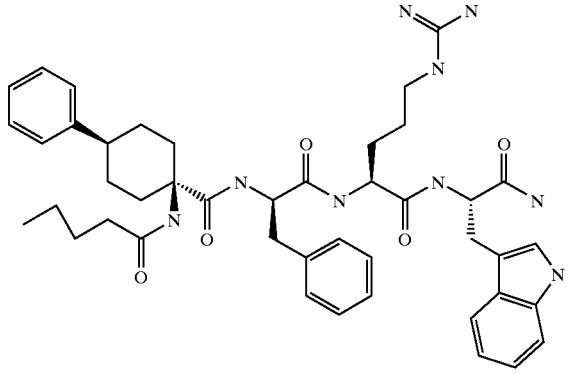

Fmoc-Linker-BHA resin (360 mg, 0.2 mmol) from Example 29 were subjected to solid phase synthesis using Protocol 1 above. All couplings were performed using HBTU in DMF as the coupling agent and DIPEA (3 equiv.) as base. Four coupling cycles were performed of one cycle each with), Fmoc-Trp (260 mg, 0.6 mmol) and HBTU (226 mg, 0.6 mmol), Fmoc-Arg (Cmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of pentyltetrapeptide resin.

The Pentyl-tetra peptide resin was treated with, 40 μL dimethylsulfide, 120 μL anisole, and 4 mL trifluoroacetic acid for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 110 mg of an off-white solid.

This material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 40 mg (25%) of a white powder. This compound was homogeneous by HPLC. LR-Electrospray C$_{44}$H$_{57}$N$_9$O$_5$ cal: 792 observed: m/z (793 M+H)

EXAMPLE 35

Bu-Apc-(D)Phe-Arg-(2)Nal-Gly-NH$_2$

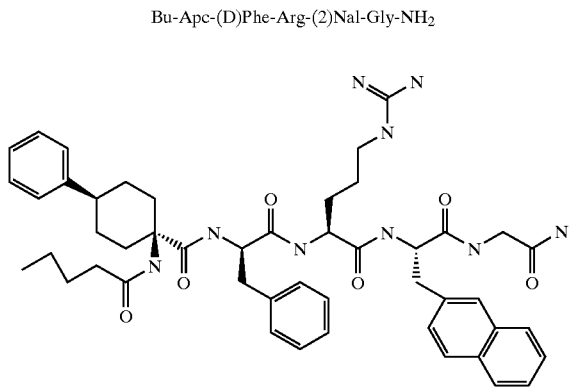

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-2-Nal (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ 30 minutes. The resin was filtered and washed successively with 20 ml each of CH$_2$Cl$_2$ (two times), isopropanol, and CH$_2$Cl$_2$ (three times). The resin was dried under vacuum to yield 580 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 61 mg (36%) of a white, amorphous powder. This compound was homogeneous by HPLC. LR-Electrospray: C$_{48}$H$_{61}$N$_9$O$_6$, cal: 860 observed: m/z (861 M+H).

EXAMPLE 36

Penta-Apc-(D)Phe-Arg-(2)Nal-Gly-NH$_2$

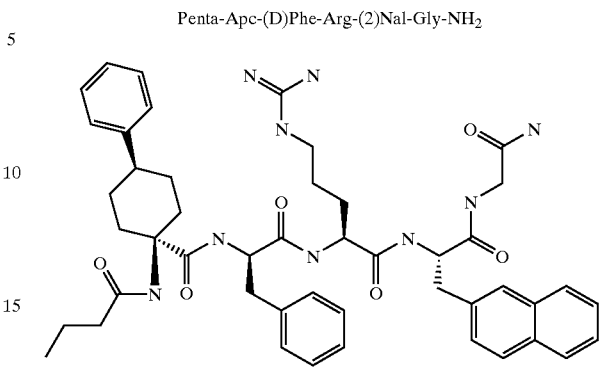

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL acetic anhydride in 6% DIPEA/CH$_2$Cl$_2$ 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of Butyl Pentapeptide resin The butyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 144 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (32%) of a white, amorphous powder. This compound was homogeneous by HPLC. LR-Electrospray: C$_{47}$H$_{59}$N$_9$O$_6$, cal 846 observed: m/z (847 M+H).

EXAMPLE 37

Ac-Apc-(D)Phe-Arg-(2)Nal-Gly-NH$_2$

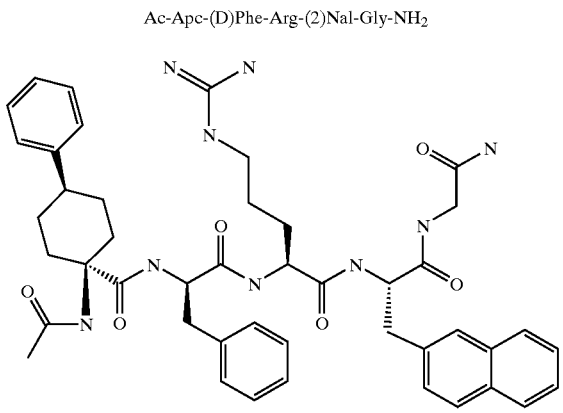

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL acetic anhydride in 6% DIPEA/CH$_2$Cl$_2$ 30 minutes. The resin was filtered and washed successively with 20 ml each of CH$_2$Cl$_2$ (two times), isopropanol, and CH$_2$Cl$_2$ (three times). The resin was dried under vacuum to yield 620 mg of Ac-Pentapeptide resin.

The Ac-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 150 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 62 mg (38%) of a white, amorphous powder. This compound was homogeneous by HPLC. LR-Electrospray: C$_{45}$H$_{55}$N$_9$O$_6$, cal: 818 observed: m/z (819 M+H).

EXAMPLE 38

Bu-Carbamoyl-Apc-(D)Phe-Arg-(2)Nal-Gly-NH$_2$

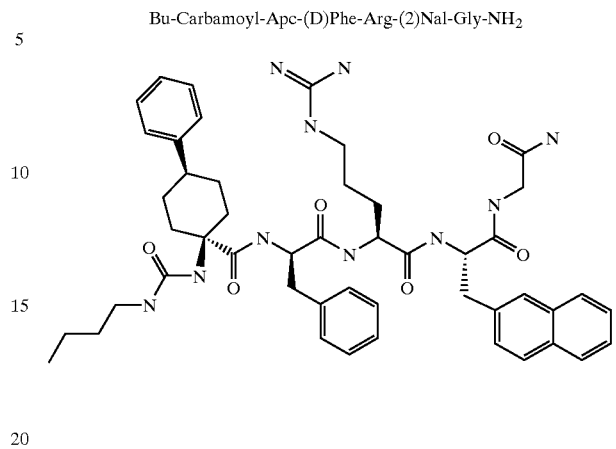

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmo-Gly (180 mg, 0.6 mal) and HBTU (226 mg, 0.6 mal), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated n-butyl isocyante (5 eq) in 6% DIPEA/DMF for 12 hours. The resin was filtered and washed successively with 20 ml each of CH$_2$Cl$_2$ (two times), isopropanol, and CH$_2$Cl$_2$ (three times). The resin was dried under vacuum to yield 550 mg of Butyl carbamoyl-Pentapeptide resin.

The Butyl carbamoyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 135 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (31%) of a white, amorphous powder. This compound was homogeneous by HPLC. LR-Electrospray: C$_{48}$H$_{62}$N$_{10}$O$_6$, cal: 875 observed: m/z (876 M+H).

EXAMPLE 39

Benzol-Apc-(D)Phe-Arg-(2)Nal-Gly-NH$_2$

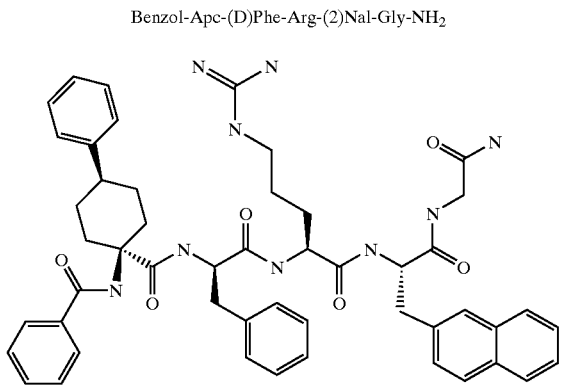

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmo-Gly (180 mg, 0.6 mal) and HBTU (226 mg, 0.6 mal), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated benzoic anhydride in 6% DIPEA/DMF for 12 hours. The resin was filtered and washed successively with 20 ml each of CH$_2$Cl$_2$ (two times), isopropanol, and CH$_2$Cl$_2$ (three times). The resin was dried under vacuum to yield 570 mg of benzoyl-Pentapeptide resin.

The benzoyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 130 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 50 mg (28%) of a white, amorphous powder. This compound was homogeneous by HPLC. LR-Electrospray: C$_{50}$H$_{57}$N$_9$O$_6$, cal: 880 observed: m/z (881 M+H).

EXAMPLE 40

3-carboxylpropanoyl-Apc-(D)Phe-Arg-(2)Nal-Gly-NH$_2$

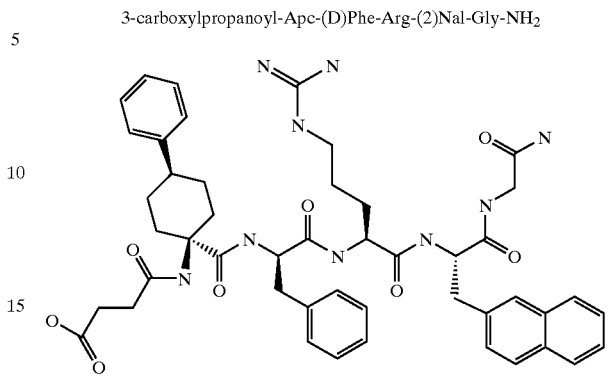

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with succinic acid (71 mg, 0.6 mmol) and HBTU (226 mg, 0.6 mmol) in DMF. The resin was filtered and washed successively with 20 ml each of CH$_2$Cl$_2$ (two times), isopropanol, and CH$_2$Cl$_2$ (three times). The resin was dried under vacuum to yield 550 mg of 3-carboxypropanoyl-Pentapeptide resin.

The 3-carboxypropanoyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 136 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 52 mg (30%) of a white, amorphous powder. This compound was homogeneous by HPLC. LR-Electrospray: C$_{47}$H$_{57}$N$_9$O$_8$, cal: 876 observed: m/z (877 M+H).

EXAMPLE 41

Phenylacetyl-Apc-(D)Phe-Arg-(2)Nal-Gly-NH₂

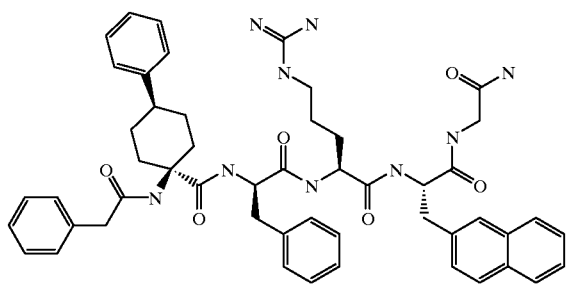

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with phenylacetic acid (82 mg, 0.6 mmol) and HBTU (226 mg, 0.6 mmol) in DMF. The resin was filtered and washed successively with 20 ml each of $CH_2Cl_2$ (two times), isopropanol, and $CH_2Cl_2$ (three times). The resin was dried under vacuum to yield 580 mg of Phenylacetyl-Pentapeptide resin.

The phenylacetyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 132 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 49 mg (29%) of a white, amorphous powder. This compound was homogeneous by HPLC. LR-Electrospray: $C_{51}H_{59}N_9O_6$, cal: 894 observed: m/z (895 M+H).

EXAMPLE 42

Penta-4-ClApc-(D)Phe-Arg-Trp-Gly-NH₂

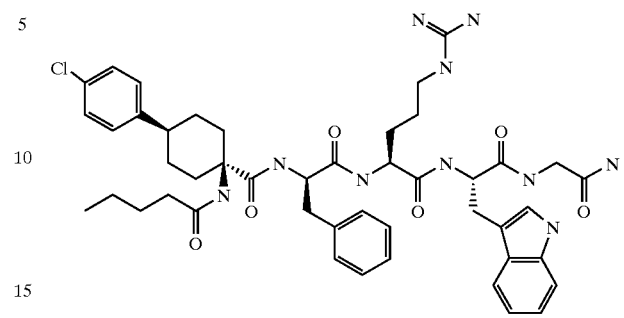

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-ClApe (275 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 620 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 141 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 45 mg (26%) of a white, amorphous powder. This compound was homogeneous by HPLC. LR-Electrospray: $C_{46}H_{59}N_{10}O_6Cl$, cal: 883 observed: m/z (884 M+H).

EXAMPLE 43

Penta-4-HOApc-(D)Phe-Arg-Trp-Gly-NH$_2$

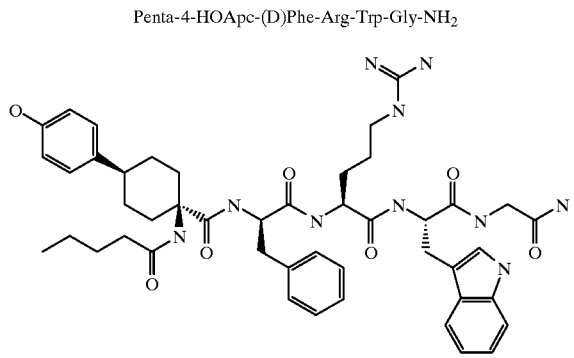

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-HOApc (280 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 620 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 150 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (31%) of a white, amorphous powder. This compound was homogeneous by HPLC. LR-Electrospray: C$_{46}$H$_{60}$N$_{10}$O$_7$, cal: 865 observed: m/z (866 M+H).

EXAMPLE 44

Penta-4-MeOApc-(D)Phe-Arg-Trp-Gly-NH$_2$

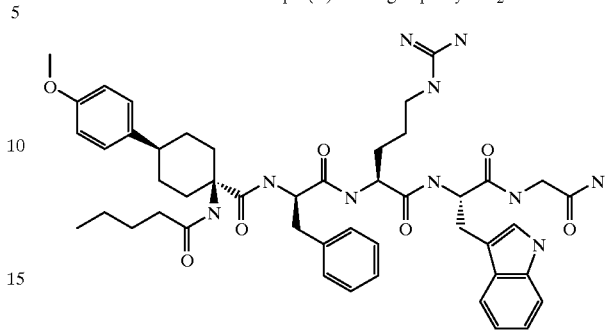

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-MeOApc (300 mg 0.6 mmol) and HBTU (226 mg, 0.6 mmol),. The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 152 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 59 mg (33%) of a white, amorphous powder. This compound was homogeneous by HPLC. LR-Electrospray: C$_{47}$H$_{62}$N$_{10}$O$_7$, cal: 879 observed: 880 m/z (M+H).

EXAMPLE 45

Penta-3-MeOApc-(D)Phe-Arg-Trp-Gly-NH<sub>2</sub>

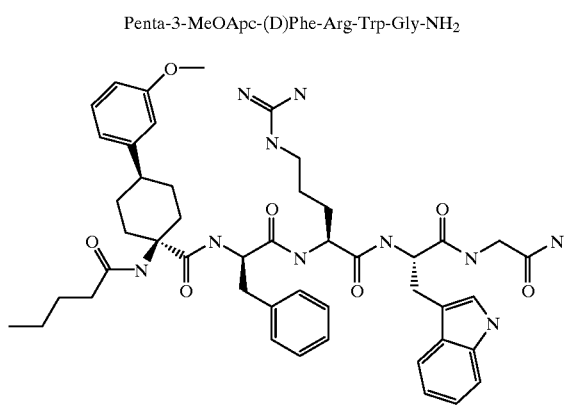

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-3-MeOApc (300 mg 0.6 mmol) and HBTU (226 mg, 0.6 mmol),. The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 610 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 152 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 59 mg (33%) of a white, amorphous powder. This compound was homogeneous by HPLC. LR-Electrospray: $C_{47}H_{62}N_{10}O_7$, cal: 879 observed: 880 m/z (M+H).

EXAMPLE 46

Penta-4-EtOApc-(D)Phe-Arg-Trp-Gly-NH<sub>2</sub>

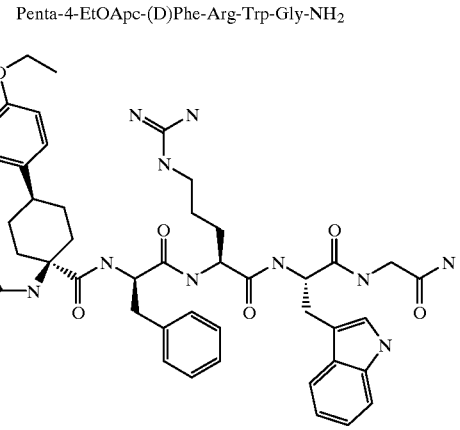

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-EtOApc (320 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 615 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 160 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 63 mg (35%) of a white, amorphous powder. This compound was homogeneous by HPLC. LR-Electrospray: $C_{48}H_{64}N_{10}O_7$, cal: 893 observed: 894 m/z (M+H).

EXAMPLE 47

Penta-4-iPrOApc-(D)Phe-Arg-Trp-Gly-

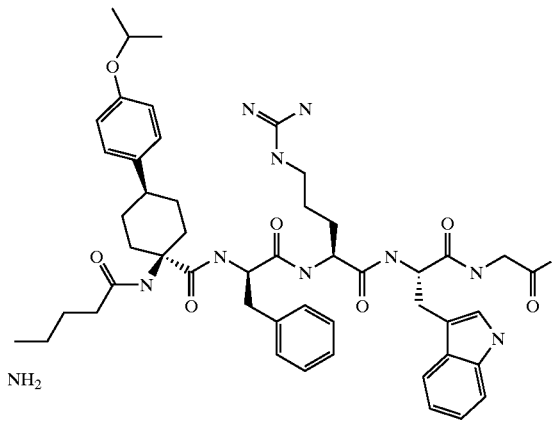

NH2

EXAMPLE 48

Penta-4-MeApc-(D)Phe-Arg-Trp-Gly-NH2

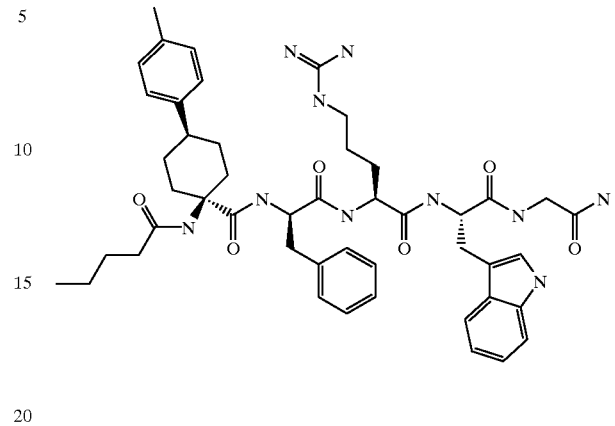

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-iPrOApc (285 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 600 mg of Pentyl-Pentapeptide resin.

The Pentyl-Pentapeptide resin was treated with 40 μL ethanedithiol, 40 μL dimethylsulfide, 120 μL anisole, and 4 L trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 45 mg (26%) of a white, amorphous powder. This compound was homogeneous by HPLC. LR-Electrospray: $C_{49}H_{66}N_{10}O_7$, cal: 907 observed: m/z (908 M+H).

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-MeApc (280 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 590 mg of Pentyl-Pentapeptide resin.

The Pentyl-Pentapeptide resin was treated with 40 μL ethanedithiol, 40 μL dimethylsulfide, 120 μL anisole, and 4 L trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 139 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 51 mg (30%) of a white, amorphous powder. This compound was homogeneous by HPLC. LR-Electrospray: $C_{47}H_{62}N_{10}O_6$, cal: 863 observed: m/z (864 M+H).

EXAMPLE 49

Penta-Apc-(D)Phe-Arg-Trp-Sar-NH₂

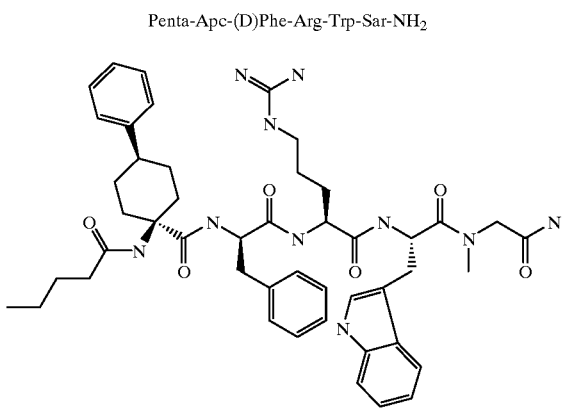

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Sar (187mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH₂Cl₂ (three times) and treated with 1 mL valeric anhydride in 6% DIPEA/CH₂Cl₂ for 30 minutes. The resin was filtered and washed successively with 20 ml each of CH₂Cl₂ (two times), isopropanol, and CH₂Cl₂ (three times). The resin was dried under vacuum to yield 620 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et₂O and recentrifuged and the crude product was dried under vacuum to yield 175 mg of an off-white solid.

This crude material was purified by preparative HPLC on a Vydac C18-column (2.5×20 cm) and eluted with a linear gradient of 10–60% B (buffer A: 0.1% TFA/H₂O, buffer B: 0.1% TFA/CH₃CN) in 60 min., flow rate 8 ml/min, detection 280 nm. The main peak was cut by analytical HPLC analysis of collected fractions, pooled and lyophilized to yield 69 mg (40%) of a white, amorphous powder. This compound was homogeneous by HPLC. LR-Electrospray: $C_{47}H_{62}N_{10}O_6$, cal: 863 observed: 864 m/z (M+H).

EXAMPLE 50

Penta-Apc-(D)Phe-Arg-N-methyl (2)Nal-Gly-NH₂

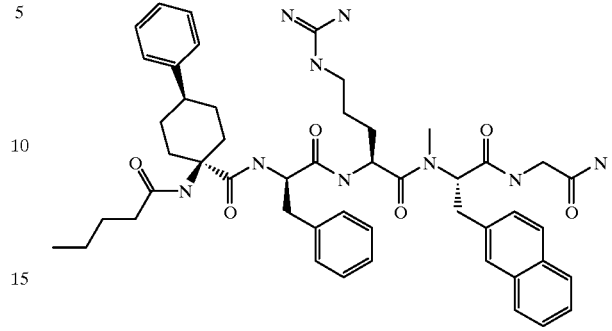

Fmoc-Linker-BHA resin (700 mg, 0.385 mmol) synthesized using the procedure in Example 29 was subjected to solid phase synthesis using DIC/HOBT coupling conditions and washings were performed as shown in protocol 1. All amino acid couplings were performed using DIC (5 eq.), HOBT (2.5 eq.) as the coupling reagents and the Fmoc-amino acid (2.5 eq.). The resin was subjected to washing steps 1–6 as shown in protocol 1, after each peptide coupling. Two coupling cycles were performed, one each with Fmoc-Gly (286 mg, 0.96 mmol) followed by Fmoc-(2)Nal (421 mg, 0.96 mmol). After Fmoc removal from 2-Nal residue, the resulting amine was converted to it's 2-nitrobenzene sulfonyl derivative using 2-nitrobenzenesulfonyl chloride (5 eq., 426 mg, 1.93 mmol) and DIPEA (5 eq.) as the base in DMF. Washings were performed using DMF (6×30 ml) followed by CH₂Cl₂ (3×30 ml) and the resin was dried under vacuum. The sulfonamide obtained was subjected to methylation using triphenylphosphine (5 eq., 505 mg, 1.93 mmol), N,N-diethylazodicarboxylate (5 eq., 303 μl, 1.93 mmol) and methanol (10 eq. 156 μl, 3.85 mmol) in THF. Washings were performed using THF (6×30 ml) followed by CH₂Cl₂ (5×30 ml) and the resin was dried under vacuum. The 2-nitrobenzene sulfonyl group was then removed using 1,8-Diazabicyclo[5.4.0]undec-7-ene (3 eq., 173 μl, 1.16 mmol), 2-mercaptoethanol (5 eq. 135 μl, 1.93 mmol) in DMF. Washings were performed using DMF (3×30 ml), isopropanol (3-×30 ml) followed by ethyl ether (3-×30 ml) and the resin was dried under vacuum. The resulting N-Me-(2)Nal residue was subjected to three coupling cycles, one cycle each with Fmoc-Arg (Pmc) (638 mg, 0.96 mmol), Fmoc-(D)Phe (373 mg, 0.96 mmol) and Fmoc-Apc (170 mg, 0.96 mmol). The peptide resin was carried through steps 1–5 of protocol 1, washed with CH₂Cl₂ (three times) and treated with 300 μl valeric anhydride, 245 μl pyridine in 15 ml DMF for 5 h. The resin was filtered and washed successively with 30 ml each of DMF (three times), isopropanol, CH₂Cl₂ (three times) and ethyl ether (3 times). The resulting pentyl-peptide resin was dried under vacuum and treated with 7 ml of 60% trifluoroacetic acid in CH₂Cl₂, 1% water and 615 ml triethylsilane (10 eq., 3.85 mmol) for 160 minutes. The resin was filtered off, washed with ~5–7 ml CH₂Cl₂, and the filtrates were concentrated on a Savant speed vacuum pump to yield the crude product.

This crude material was purified by preparative HPLC on a Vydac C18-column (2.5×20 cm) and eluted with a linear gradient of 10–60% B (buffer A: 0.1% TFA/H₂O, buffer B: 0.1% TFA/CH₃CN) in 60 min., flow rate 8 ml/min, detection 280 nm. The main peak was cut by analytical HPLC analysis of collected fractions, pooled and lyophilized to yield 30 mg (~10%) of a white, amorphous powder. This compound was homogeneous by HPLC. LR-Electrospray: $C_{49}H_{63}N_9O_6$, cal: 873 observed: m/z (874 M+H).

EXAMPLE 51

Penta-Apc-(D)Phe-Arg-N-methyl (2) Nal-NH$_2$

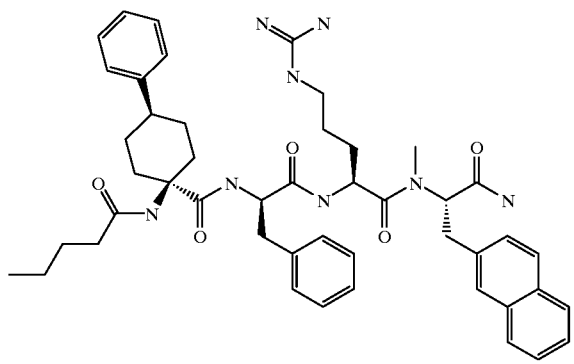

Fmoc-Linker-BHA resin (700 mg, 0.385 mmol) synthesized using the procedure in Example 29 was subjected to solid phase synthesis using DIC/HOBT coupling conditions and washings were performed as shown in protocol 1. All amino acid couplings were performed using DIC (5 eq.), HOBT (2.5 eq.) as the coupling reagents and the Fmoc-amino acid (2.5 eq.) The resin was subjected to washing steps 1–6 as shown in protocol 1, after each peptide coupling. One coupling cycle was performed with Fmoc-(2)Nal (421 mg, 0.96 mmol). After Fmoc removal from (2)Nal residue, the resulting amine was converted to it's 2-nitrobenzene sulfonyl derivative using 2-nitrobenzenesulfonyl chloride (5 eq., 426 mg, 1.93 mmol) and DIPEA (5 eq.) as the base in DMF. Washings were performed using DMF (6×30 ml) followed by $CH_2Cl_2$ (3×30 ml) and the resin was dried under vacuum. The sulfonamide obtained was subjected to methylation using triphenylphosphine (5 eq., 505 mg, 1.93 mmol), N,N-diethylazodicarboxylate (5 eq., 303 µl, 1.93 mmol) and methanol (10 eq. 156 µl, 3.85 mmol) in THF. Washings were performed using THF (6×30 ml) followed by $CH_2Cl_2$ (5×30 ml) and the resin was dried under vacuum. The 2-nitrobenzene sulfonyl group was then removed using 1,8-diazabicyclo[5.4.0]undec-7-ene (3 eq., 173 µl, 1.16 mmol), 2-mercaptoethanol (5 eq. 135 µl, 1.93 mmol) in DMF. Washings were performed using DMF (3×30 ml), isopropanol (3×30 ml) followed by ethyl ether (3×30 ml) and the resin was dried under vacuum. The resulting N-Me-(2)Nal residue was subjected to three coupling cycles, one cycle each with Fmoc-Arg (Pmc) (638 mg, 0.96 mmol), Fmoc-(D)Phe (373 mg, 0.96 mmol) and Fmoc-Apc (170 mg 0.96 mmol). The peptide resin was carried through steps 1–5 of protocol 1, washed with $CH_2Cl_2$ (three times) and treated with 300 µl valeric anhydride, 245 µl pyridine in 15 ml DMF for 5 h. The resin was filtered and washed successively with 30 ml each of DMF (three times), isopropanol, $CH_2Cl_2$ (three times) and ethyl ether (3 times). The resulting pentyl-peptide resin was dried under vacuum and treated with 7 ml of 60% trifluoroacetic acid in $CH_2Cl_2$, 1% water and 615 ml triethylsilane (10 eq., 3.85 mmol) for 160 minutes. The resin was filtered off, washed with ~5–7 ml $CH_2Cl_2$, and the filtrates were concentrated on a Savant speed vacuum pump to yield the crude product.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 43 mg (~14%) of a white, amorphous powder. This compound was homogeneous by HPLC. LR-Electrospray: $C_{47}H_{60}N_8O_5$, cal: 817 observed: m/z (818 M+H).

EXAMPLE 52

Penta-Apc-(D)Phe-Arg-N-methylTrp-Gly-NH$_2$

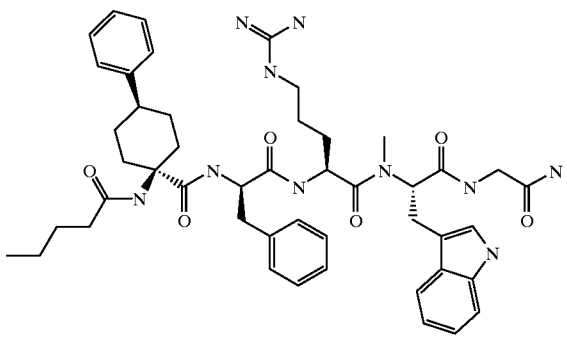

Fmoc-Linker-BHA resin (700 mg, 0.385 mmol) synthesized using the procedure in Example 29 was subjected to solid phase synthesis using DIC/HOBT coupling conditions and washings were performed as shown in the protocol 1. All amino acid couplings were performed using DIC (5 eq.), HOBT (2.5 eq.) as the coupling reagents and the Fmoc-amino acid (2.5 eq.) The resin was subjected to washing steps 1–6 as shown in protocol 1, after each peptide coupling. Two coupling cycles were performed, one each with Fmoc-Gly (286 mg, 0.96 mmol) followed by Fmoc-Trp (461 mg, 0.96 mmol). After Fmoc removal from Trp residue, the resulting amine was converted to its 2-nitrobenzene sulfonyl derivative using 2-nitrobenzenesulfonyl chloride (5 eq., 426 mg, 1.93 mmol) and DIPEA (5 eq.) as the base in DMF. Washings were performed using DMF (6×30 ml) followed by $CH_2Cl_2$ (3×30 ml) and the resin was dried under vacuum. The sulfonamide obtained was subjected to methylation using triphenylphosphine (5 eq., 505 mg, 1.93 mmol), N,N-diethylazodicarboxylate (5 eq., 303 µl, 1.93 mmol) and methanol (10 eq. 156 µl, 3.85 mmol) in THF. Washings were performed using THF (6×30 ml) followed by $CH_2Cl_2$ (5×30 ml) and the resin was dried under vacuum. The 2-nitrobenzene sulfonyl group was then removed using 1,8-diazabicyclo[5.4.0]undec-7-ene (3 eq., 173 µl, 1.16 mmol), 2-mercaptoethanol (5 eq. 135 µl, 1.93 mmol) in DMF. Washings were performed using DMF (3×30 ml), isopropanol (3-×30 ml) followed by ethyl ether (3-×30 ml) and the resin was dried under vacuum. The resulting N-MeTrp residue was subjected to three coupling cycles, one cycle each with Fmoc-Arg (Pmc) (638 mg, 0.96 mmol), Fmoc-(D)Phe (373 mg, 0.96 mmol) and Fmoc-Apc (170 mg 0.96 mmol). The peptide resin was carried through steps 1–5 of protocol 1, washed with $CH_2Cl_2$ (three times) and treated with 300 µl valeric anhydride, 245 µl pyridine in 15 ml DMF for 5 h. The resin was filtered and washed successively with 30 ml each of DMF (three times), isopropanol, $CH_2Cl_2$ (three times) and ethyl ether (3 times). The resulting pentyl-peptide resin was dried under vacuum and treated with 7 ml of 60% trifluoroacetic acid in $CH_2Cl_2$, 1% water and 615 ml triethylsilane (10 eq., 3.85 mmol) for 160 minutes. The resin was filtered off, washed with ~5–7 ml CH₂Cl₂, and the filtrates were concentrated on a Savant speed vacuum pump to yield the crude product.

This crude material was purified by preparative HPLC on a Vydac C18-column (2.5×20 cm) and eluted with a linear gradient of 10–60% B (buffer A: 0.1% TFA/H₂O, buffer B: 0.1% TFA/CH₃CN) in 60 min., flow rate 8 ml/min, detection 280 nm. The main peak was cut by analytical HPLC analysis of collected fractions, pooled and lyophilized to yield 30 mg (~10%) of a white, amorphous powder. This compound was homogeneous by HPLC. LR-Electrospray: $C_{47}H_{62}N_{10}O_6$, cal: 863 observed: m/z (864 M+H).

EXAMPLE 53

Penta-Apc-(D)Phe-Arg-N-methylTrp-NH₂

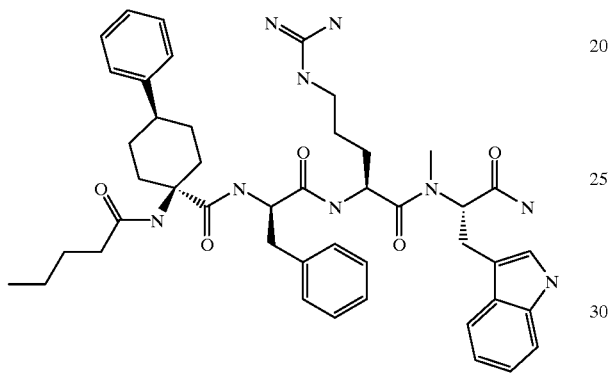

Fmoc-Linker-BHA resin (700 mg, 0.385 mmol) synthesized using the procedure in Example 29 was subjected to solid phase synthesis using DIC/HOBT coupling conditions and washings were performed as shown in the protocol 1. All amino acid couplings were performed using DIC (5 eq.), HOBT (2.5 eq.) as the coupling reagents and the Fmoc-amino acid (2.5 eq.) The resin was subjected to washing steps 1–6 as shown in protocol 1, after each peptide coupling. One coupling cycle was performed with Fmoc-Trp (461 mg, 0.96 mmol). After Fmoc removal from Trp residue, the resulting amine was converted to it's 2-nitrobenzene sulfonyl derivative using 2-nitrobenzenesulfonyl chloride (5 eq., 426 mg, 1.93 mmol) and DIPEA (5 eq.) as the base in DMF. Washings were performed using DMF (6×30 ml) followed by CH₂Cl₂ (3×30 ml) and the resin was dried under vacuum. The sulfonamide obtained was subjected to methylation using triphenylphosphine (5 eq., 505 mg, 1.93 mmol), N, N-diethylazodicarboxylate (5 eq., 303 μl, 1.93 mmol) and methanol (10 eq. 156 μl, 3.85 mmol) in THF. Washings were performed using THF (6×30 ml) followed by CH₂Cl₂ (5×30 ml) and the resin was dried under vacuum. The 2-nitrobenzene sulfonyl group was then removed using 1,8-diazabicyclo[5.4.0]undec-7-ene (3 eq., 173 μl, 1.16 mmol), 2-mercaptoethanol (5 eq. 135 μl, 1.93 mmol) in DMF. Washings were performed using DMF (3×30 ml), isopropanol (3×30 ml) followed by ethyl ether (3×30 ml) and the resin was dried under vacuum. The resulting N-MeTrp residue was subjected to three coupling cycles, one cycle each with Fmoc-Arg (Pmc) (638 mg, 0.96 mmol), Fmoc-(D)Phe (373 mg, 0.96 mmol) and Fmoc-Apc (170 mg 0.96 mmol). The peptide resin was carried through steps 1–5 of protocol 1, washed with CH₂Cl₂ (three times) and treated with 300 μl valeric anhydride, 245 μl pyridine in 15 ml DMF for 5 h. The resin was filtered and washed successively with 30 ml each of DMF (three times), isopropanol, CH₂Cl₂ (three times) and ethyl ether (3 times). The resulting pentyl-peptide resin was dried under vacuum and treated with 7 ml of 60% trifluoroacetic acid in CH₂Cl₂, 1% water and 615 ml triethylsilane (10 eq., 3.85 mmol) for 160 minutes. The resin was filtered off, washed with ~5–7 ml CH₂Cl₂, and the filtrates were concentrated on a Savant speed vacuum pump to yield the crude product.

This crude material was purified by preparative HPLC on a Vydac C18-column (2.5×20 cm) and eluted with a linear gradient of 10–60% B (buffer A: 0.1% TFA/H₂O, buffer B: 0.1% TFA/CH₃CN) in 60 min., flow rate 8 ml/min, detection 280 nm . The main peak was cut by analytical HPLC analysis of collected fractions, pooled and lyophilized to yield 43 mg (14%) of a white, amorphous powder. This compound was homogeneous by HPLC. LR-Electrospray: $C_{45}H_{59}N_9O_5$, cal: 806 observed: m/z (807 M+H).

EXAMPLE 54

Bu-Apc-(D)Phe-Arg-Trp-Ala-NH₂

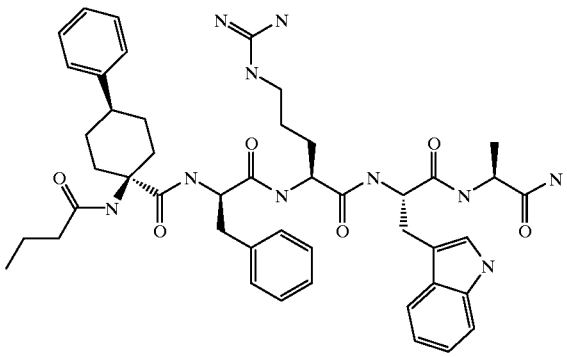

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Ala (187 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH₂Cl₂ (three times) and treated with 1 mL butyric anhydride in 6% DIPEA/CH₂Cl₂ 30 minutes. The resin was filtered and washed successively with 20 ml each of CH₂Cl₂ (two times), isopropanol, and CH₂Cl₂ (three times). The resin was dried under vacuum to yield 580 mg of butyl-Pentapeptide resin.

The butyl-Pentapeptide resin was treated with 40 μL ethanedithiol, 40 μL dimethylsulfide, 120 μL anisole, and 4 μL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 61 mg (36%) of a white, amorphous powder. This compound was homogeneous by HPLC. LR-Electrospray: C$_{46}$H$_{60}$N$_{10}$O$_6$, cal: 849 observed: m/z (850 M+H).

EXAMPLE 55

Bu-carbamoyl-Apc-(D)Phe-Arg-Trp-Ala-NH$_2$

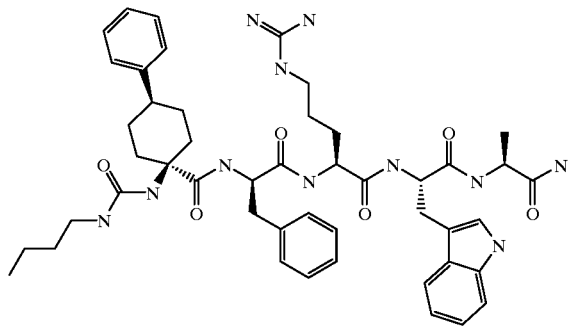

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Ala (187 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with n-butyl isocyanate (5 equ.) in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of Bu-carbamoyl Pentapeptide resin.

The Bu-carbamoyl Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 143 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 65 mg (37%) of a white, amorphous powder. This compound was homogeneous by HPLC. LR-Electrospray: C$_{47}$H$_{63}$N$_{11}$O$_6$, cal: 878 observed: m/z (879 M+H).

EXAMPLE 56

Phenylacetyl-Apc-(D)Phe-Arg-Trp-Ala-NH$_2$

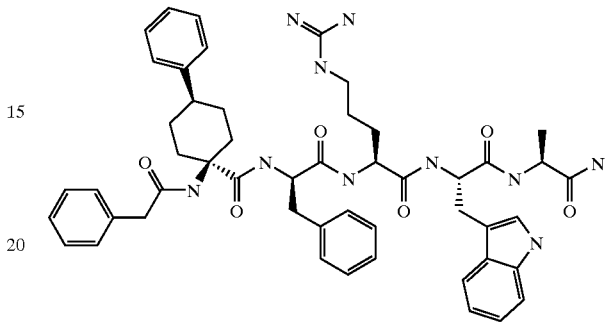

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Ala (187 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with phenylacetic acid (82 mg, 0.6 mmol) and HBTU (226 mg, 0.6 mmol) in DMF. The resin was filtered and washed successively with 20 ml each of CH$_2$Cl$_2$ (two times), isopropanol, and CH$_2$Cl$_2$ (three times). The resin was dried under vacuum to yield 600 mg of phenylacetyl-Pentapeptide resin.

The phenylacetyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 138 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 53 mg (30%) of a white, amorphous powder. This compound was homogeneous by HPLC. LR-Electrospray: C$_{50}$H$_{60}$N$_{10}$O$_6$, cal: 897 observed: m/z (898 M+H).

EXAMPLE 57

Bu-Apc-(D)Phe-Arg-Trp-β-Ala-NH₂

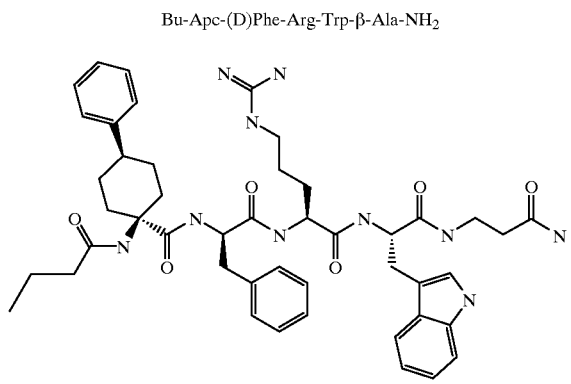

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-β-Ala (186 mg, 0.6 mal) and HBTU (226 mg, 0.6 mal), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with butyric anhydride in 6% DIPEA/DMF for 12 hours. The resin was filtered and washed successively with 20 ml each of $CH_2Cl_2$ (two times), isopropanol, and $CH_2Cl_2$ (three times). The resin was dried under vacuum to yield 550 mg of Butyl-Pentapeptide resin.

The Butyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 135 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 55 mg (32%) of a white, amorphous powder. This compound was homogeneous by HPLC. LR-Electrospray: $C_{46}H_{60}N_{10}O_6$, cal: 848 observed: m/z (850 M+H).

EXAMPLE 58

Bu-Carbamoyl-Apc-(D)Phe-Arg-Trp-β-Ala-NH₂

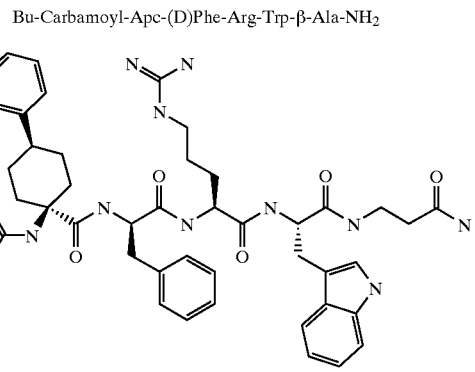

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-β-Ala (186 mg, 0.6 mal) and HBTU (226 mg, 0.6 mal), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated n-butyl isocyanate (5 eq) in 6% DIPEA/DMF for 12 hours. The resin was filtered and washed successively with 20 ml each of $CH_2Cl_2$ (two times), isopropanol, and $CH_2Cl_2$ (three times). The resin was dried under vacuum to yield 550 mg of Butyl carbamoyl-Pentapeptide resin.

The Butyl carbamoyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 135 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 55 mg (31%) of a white, amorphous powder. This compound was homogeneous by HPLC. LR-Electrospray: $C_{47}H_{63}N_{11}O_6$, cal: 878 observed: m/z (879 M+H).

EXAMPLE 59

Phenylacetyl-Apc-(D)Phe-Arg-Trp-β-Ala-NH₂

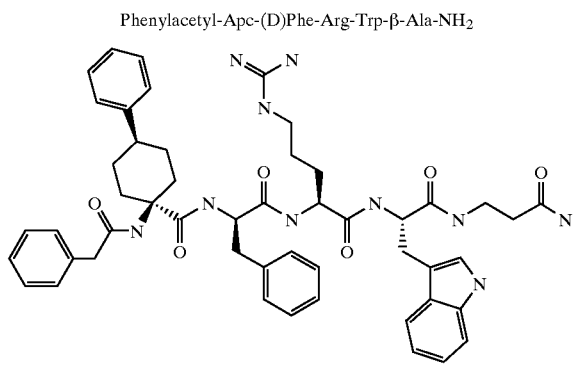

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-β-Ala (186 mg, 0.6 mal) and HBTU (226 mg, 0.6 mal), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with phenylacetic acid (82 mg, 0.6 mmol) and HBTU (226 mg, 0.6 mmol) in DMF. The resin was filtered and washed successively with 20 ml each of $CH_2Cl_2$ (two times), isopropanol, and $CH_2Cl_2$ (three times). The resin was dried under vacuum to yield 550 mg of phenylacetyl-Pentapeptide resin.

The phenylacetyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 129 mg of an off-white solid.

This crude material was purified by preparative HPLC on a Vydac C18-column (2.5×20 cm) and eluted with a linear gradient of 10–60% B (buffer A: 0.1% $TFA/H_2O$, buffer B: 0.1% $TFA/CH_3CN$) in 60 min., flow rate 8 ml/min, detection 280 nm. The main peak was cut by analytical HPLC analysis of collected fractions, pooled and lyophilized to yield 49 mg (27%) of a white, amorphous powder. This compound was homogeneous by HPLC. LR-Electrospray: $C_{50}H_{60}N_{10}O_6$, cal: 897 observed: m/z (898 M+H).

EXAMPLE 60

Bu-Apc-(D)Phe-Arg-Trp-2-Aba-NH₂

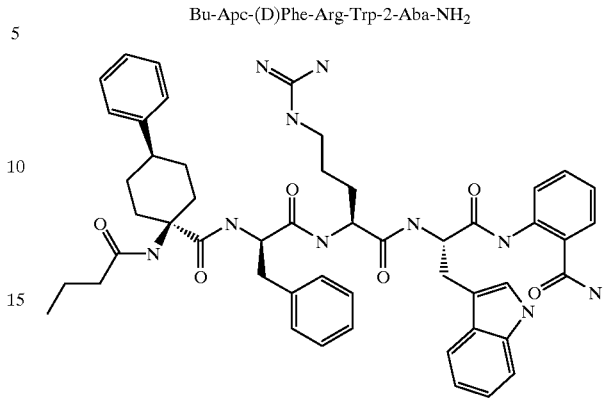

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with 1 mL butyric anhydride in 6% $DIPEA/CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 610 mg of butyl-Pentapeptide resin.

The butyl-Pentapeptide resin was treated with 40 μL ethanedithiol, 40 μL dimethylsulfide, 120 μL anisole, and 4 mL trifluoroacetic acid at room temperature for 180 mm. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% $TFA/H_2O$, buffer B: 0.1% $TFA/CH_3CN$) in 60 min., flow rate 8 ml/min, detection 280 nm. The main peak was cut by analytical HPLC analysis of collected fractions, pooled and lyophilized to yield 47 mg (26%) of a white, amorphous powder. This compound was homogeneous by HPLC. LR-Electrospray: $C_{50}H_{60}N_{10}O_6$, cal: 897 observed: m/z (898 M+H).

EXAMPLE 61

Bu-carbamoyl-Apc-(D)Phe-Arg-Trp-2-Aba-NH$_2$

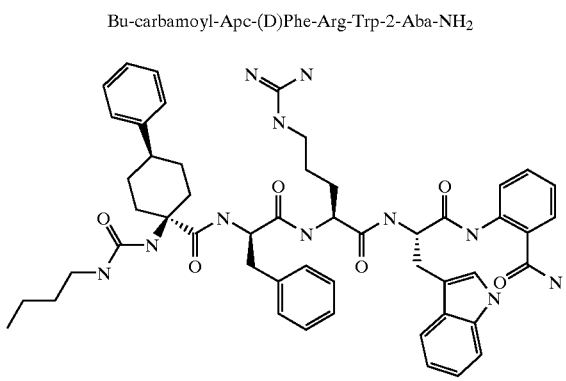

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with n-butyl isocyanate (5 eq) in 6% DIPEA/CH$_2$Cl$_2$ 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of butyl-carbamoyl Pentapeptide resin.

The butyl-carbamoyl Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 152 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (30%) of a white, amorphous powder. This compound was homogeneous by HPLC. LR-Electrospray: C$_{51}$H$_{63}$N$_{11}$O$_6$, cal: 926 observed: m/z (927 M+H).

EXAMPLE 62

Phenylacetyl-Apc-(D)Phe-Arg-Trp-2-Aba-NH$_2$

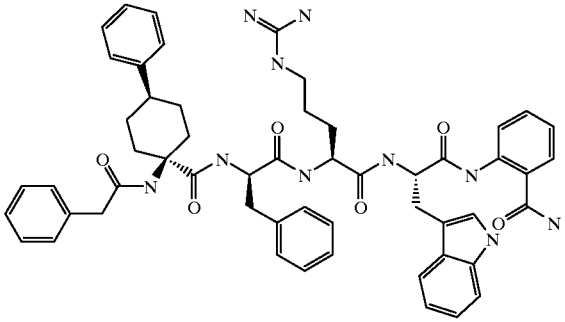

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with phenylacetic acid (82 mg, 0.6 mmol) and HBTU (226 mg, 0.6 mmol) in DMF. The resin was filtered and washed successively with 20 ml each of CH$_2$Cl$_2$ (two times), isopropanol, and CH$_2$Cl$_2$ (three times). The resin was dried under vacuum to yield 615 mg of phenylacetyl-Pentapeptide resin.

The phenylacetyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 142 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 53 mg (29%) of a white, amorphous powder. This compound was homogeneous by HPLC. LR-Electrospray: C$_{54}$H$_{60}$N$_{10}$O$_6$, cal: 945 observed: m/z (955 M+H).

EXAMPLE 63

Bu-Apc-(D)Phe-Arg-Trp-3-Amb-NH$_2$

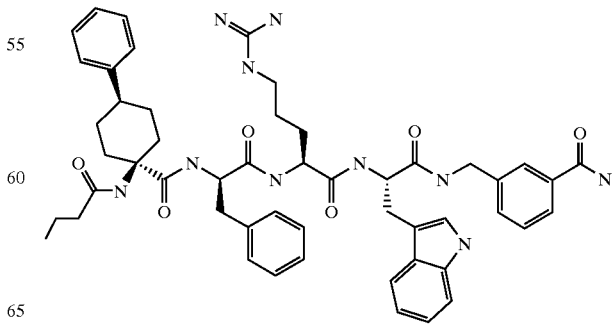

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-3-Amb (230 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with 1 mL of butyric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 590 mg of butyl-Pentapeptide resin.

The butyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 50 mg (27%) of a white, amorphous powder. This compound was homogeneous by HPLC. LR-Electrospray: $C_{51}H_{62}N_{10}O_6$, cal: 911 observed: m/z (912 M+H).

EXAMPLE 64

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-3-Amb (230 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with n-butyl isocyanate (5 eq) in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 600 mg of butyl-carbamoyl Pentapeptide resin.

The butyl-carbamoyl Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 143 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 53 mg (28%) of a white, amorphous powder. This compound was homogeneous by HPLC. LR-Electrospray: $C_{52}H_{65}N_{11}O_6$, cal: 940 observed: m/z (941 M+H).

Bu-carbamoyl-Apc-(D)Phe-Arg-Trp-3-Amb-$NH_2$

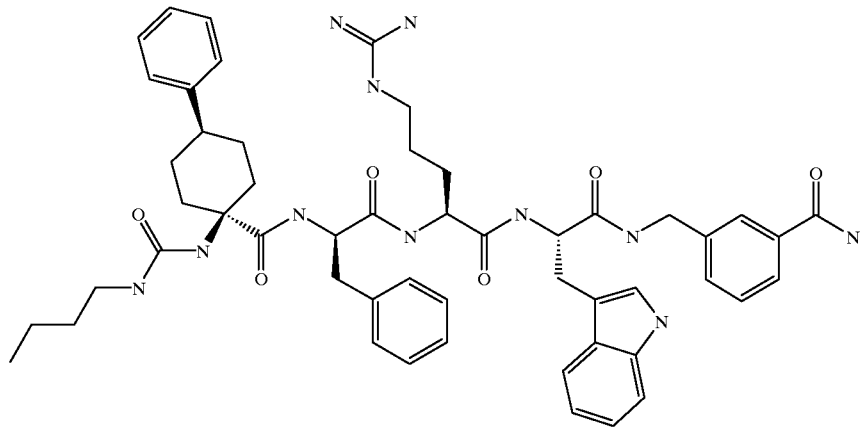

EXAMPLE 65

Phenylacetyl-Apc-(D)Phe-Arg-Trp-3-Amb-NH$_2$

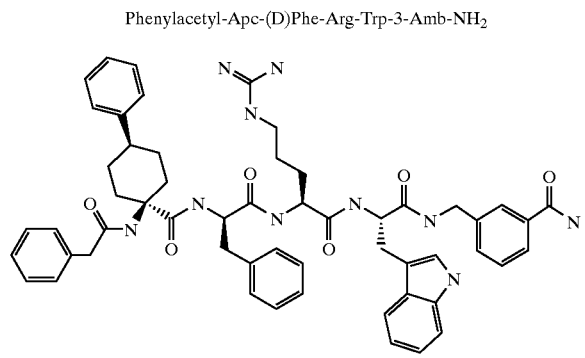

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-3-Amb (230 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with phenylacetic acid (82 mg, 0.6 mmol) and HBTU (226 mg, 0.6 mmol) in DMF. The resin was filtered and washed successively with 20 ml each of CH$_2$Cl$_2$ (two times), isopropanol, and CH$_2$Cl$_2$ (three times). The resin was dried under vacuum to yield 580 mg of phenylacetyl-Pentapeptide resin.

The phenylacetyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 135 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm The main peak was cut by analytical HPLC analysis of collected fractions, pooled and lyophilized to yield 49 mg (26%) of a white, amorphous powder. This compound was homogeneous by HPLC. LR-Electrospray: C$_{55}$H$_{62}$N$_{10}$O$_6$, cal: 959 observed: m/z (960 M+H).

EXAMPLE 66

Bu-Apc-(D)Phe-Arg-Trp-4-Amb-NH$_2$

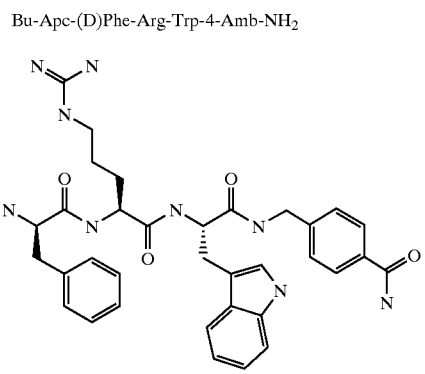

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-4-Amb (230 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 615 mg of butyl-Pentapeptide resin.

The butyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 153 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (30%) of a white, amorphous powder. This compound was homogeneous by HPLC. LR-Electrospray: C$_{51}$H$_{62}$N$_{10}$O$_6$, cal: 911 observed: m/z (912 M+H).

EXAMPLE 67

Phenylacetyl-Apc-(D)Phe-Arg-Trp-4-Amb-NH$_2$

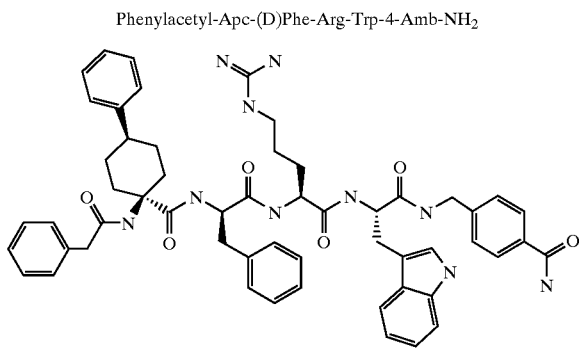

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-4-Amb (230 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with phenylacetic acid (82 mg, 0.6 mmol) and HBTU (226 mg, 0.6 mmol) in DMF. The resin was filtered and washed successively with 20 ml each of CH$_2$Cl$_2$ (two times), isopropanol, and CH$_2$Cl$_2$ (three times). The resin was dried under vacuum to yield 585 mg of phenylacetyl-Pentapeptide resin.

The phenylacetyl-Pentapeptide resin was treated with 40 $\mu$L ethanedithiol, 40 $\mu$L dimethylsulfide, 120 $\mu$L anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 142 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 47 mg (26%) of a white, amorphous powder. This compound was homogeneous by HPLC. LR-Electrospray: C$_{55}$H$_{62}$N$_{10}$O$_6$, cal: 959 observed: m/z (960 M+H).

EXAMPLE 68

Bu-Apc-(D)Phe-Arg-(2)Nal-Ala-NH$_2$

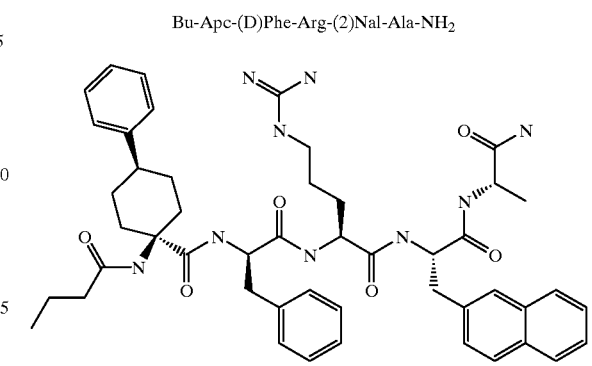

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Ala (187 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL of butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Butyl Pentapeptide resin.

The butyl-Pentapeptide resin was treated with 40 $\mu$L ethanedithiol, 40 $\mu$L dimethylsulfide, 120 $\mu$L anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 149 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 57 mg (33%) of a white, amorphous powder. This compound was homogeneous by HPLC. LR-Electrospray: C$_{48}$H$_{61}$N$_9$O$_6$, cal 860 observed: m/z (861 M+H).

EXAMPLE 69

Bu-Apc-(D)Phe-Arg-(2)Nal-beta-Ala-NH$_2$

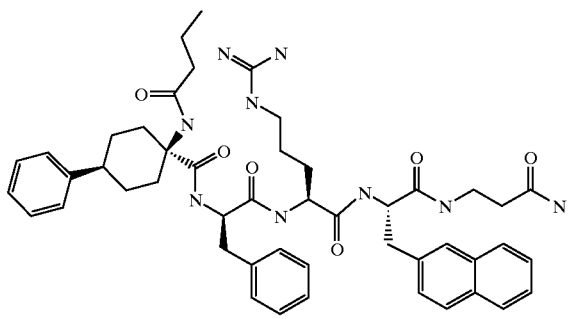

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-beta-Ala (187 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL Butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 605 mg of Butyl Pentapeptide resin.

The butyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 142 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 54 mg (32%) of a white, amorphous powder. This compound was homogeneous by HPLC. LR-Electrospray: C$_{48}$H$_{61}$N$_9$O$_6$, cal 860 observed: m/z (861 M+H).

EXAMPLE 70

Bu-Apc-(D)Phe-Arg-(2)Nal-3-Amb-NH$_2$

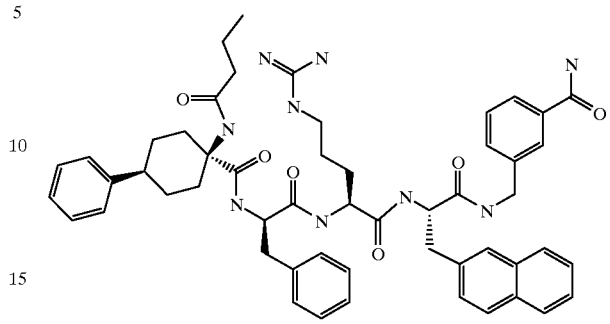

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-3-Amb (230 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL Butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 550 mg of Butyl Pentapeptide resin.

The butyl-Pentapeptide resin was treated with 40 μL ethanedithiol, 40 μL dimethylsulfide, 120 μL anisole, and 4 mL trifluoroacetic acid at room temperature for 180 mm. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 125 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 44 mg (27%) of a white, amorphous powder. This compound was homogeneous by HPLC. LR-Electrospray: C$_{53}$H$_{63}$N$_9$O$_6$, cal 922 observed: m/z (923 M+H).

EXAMPLE 71

Bu-Apc-(D)Phe-Arg-(2)Nal-2-Aba-NH₂

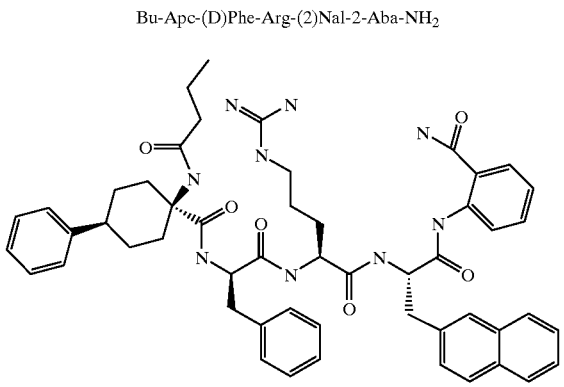

Fmoc-Linker-BHA resin (360 mg, 0.2 mmol) from Example 29 were subjected to solid phase synthesis using protocol 1 described above. All couplings were performed using HBTU in DMF as the 0 coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with 1 mL butyric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 510 mg of Butyl Pentapeptide resin.

The butyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 114 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 36 mg (20%) of a white, amorphous powder. This compound was homogeneous by HPLC. LR-Electrospray: $C_{52}H_{61}N_9O_6$, cal 908 observed: m/z (909 M+H).

EXAMPLE 72

Bu-Apc-(D)Phe-Arg-(2)Nal-4-Amb-NH₂

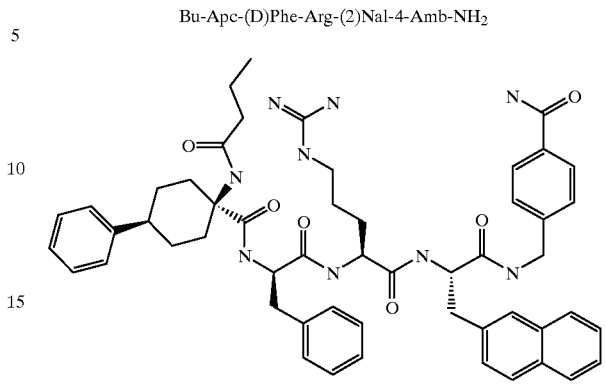

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-4-Amb (230 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with $CH_2Cl_2$ (three times) and treated with 1 mL butyric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 620 mg of Butyl Pentapeptide resin.

The butyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 139 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 56 mg (31%) of a white, amorphous powder. This compound was homogeneous by HPLC. LR-Electrospray: $C_{53}H_{63}N_9O_6$, cal 922 observed: m/z (923 M+H).

EXAMPLE 73

Penta-Apc-(D)Phe-acylguanidine-Trp-Gly-NH$_2$

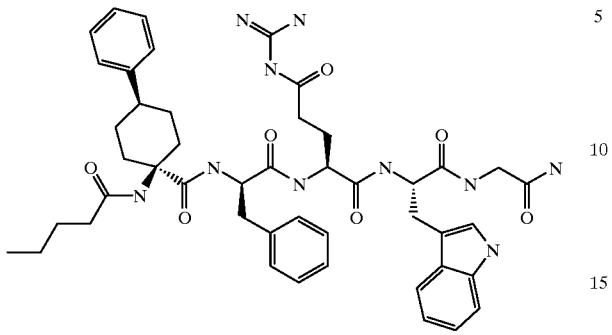

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Glu(allyl) (250 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield Pentyl-Pentapeptide resin.

The allyl protecting group was removed using PdCl$_2$/Triphenylphosphine/tributyltin hydride under Argon in DMF. The guanidinylation was achieved using Boc-Guanidine. HCl (100 mg, 0.6 mmol ) and HBTU (226 mg, 0.6 mmol).

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 mm., flow rate 8 ml/min, detection 280 nm. The main peak was cut by analytical HPLC analysis of collected fractions, pooled and lyophilized to yield 30 mg (15%) of a white, amorphous powder. This compound was homogeneous by HPLC. LR-Electrospray: C$_{46}$H$_{58}$N$_{10}$O$_7$, cal 977 observed: m/z (978 M+H).

EXAMPLE 74

Bu-Apc-(D)Phe-PhenylhomoArg-Trp-Gly-NH2

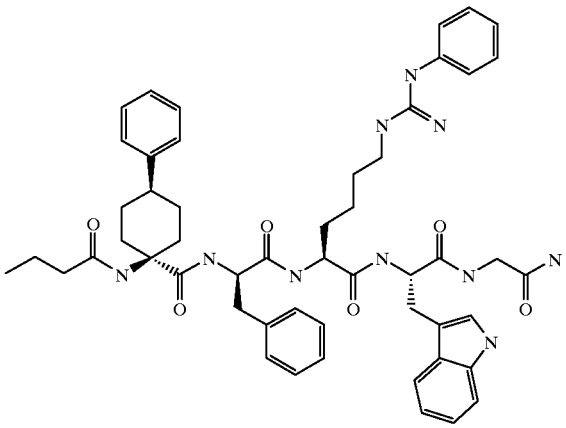

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Phenyl homo Arg (295 mg, 0.6 mmol) and HBTU (226 mg, 0.6 mmol), Fmoc-(D) Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 570 mg of Butyl-Pentapeptide resin.

The Butyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 54 mg (30%) of a white, amorphous powder. This compound was homogeneous by HPLC. LR-Electrospray: C$_{52}$H$_{64}$N$_{10}$O$_6$, cal 925 observed: m/z (926 M+H).

EXAMPLE 75

Penta-Apc-(D)Phe-Cit-Trp-Gly-NH₂

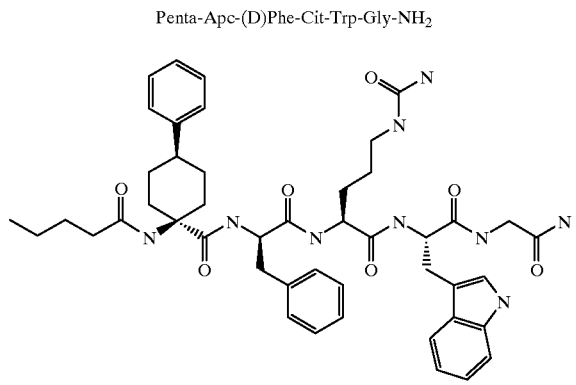

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Cit (240 mg, 0.6 mmol) and HBTU (226 mg, 0.6 mmol), Fmoc-(D)Phe (240 mg, 0.6 mmol) and HBTU (226 mg, 0.6 mmol), Fmoc-Apc (275 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 590 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 152 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 65 mg (38%) of a white, amorphous powder. This compound was homogeneous by HPLC. LR-Electrospray: C$_{46}$H$_{56}$N$_9$O$_7$, cal: 850 observed: m/z (851 M+H).

EXAMPLE 76

Penta-Adpc-(D)Phe-Arg-Trp-Gly-NH₂

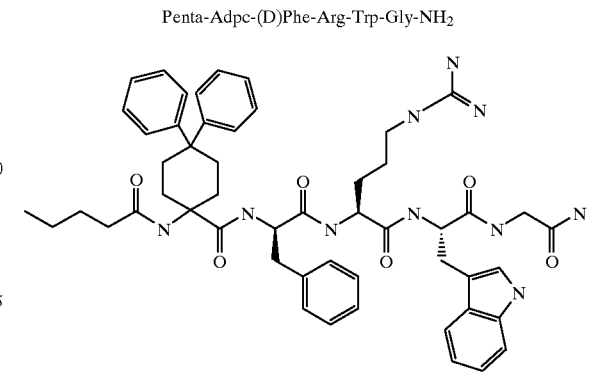

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Adpc (320 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 μL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 142 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 47 mg (26%) of a white, amorphous powder. This compound was homogeneous by HPLC. LR-Electrospray: C$_{52}$H$_{64}$N$_{10}$O$_6$, cal: 925 observed: m/z (926 M+H).

EXAMPLE 77

Penta-Ape-(D)Phe-Arg-Trp-Gly-NH₂ (peak 1)

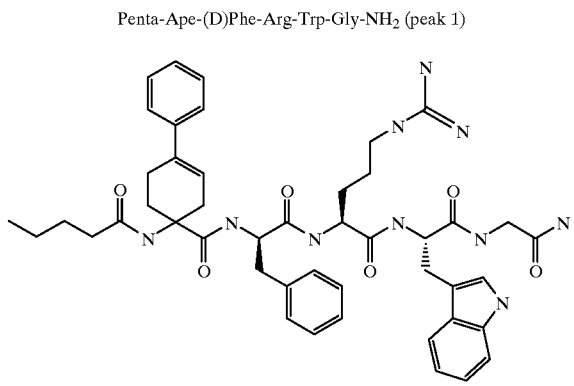

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Ape (275 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The first main peak was cut by analytical HPLC analysis of collected fractions, pooled and lyophilized to yield 25 mg (15%) of a white, amorphous powder. This compound was homogeneous by HPLC. LR-Electrospray: $C_{46}H_{58}N_{10}O_6$, cal: 847 observed: m/z (948 M+H).

EXAMPLE 78

Penta-Ape-(D)Phe-Arg-Trp-Gly-NH₂ (peak 2)

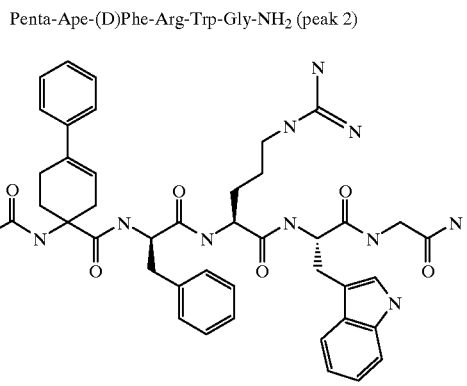

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Ape (275 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The second main peak was cut by analytical HPLC analysis of collected fractions, pooled and lyophilized to yield 22 mg (14%) of a white, amorphous powder. This compound was homogeneous by HPLC. LR-Electrospray: $C_{46}H_{58}N_{10}O_6$, cal: 847 observed: m/z (948 M+H).

EXAMPLE 79

Penta-Abc-(D)Phe-Arg-Trp-Gly-NH2

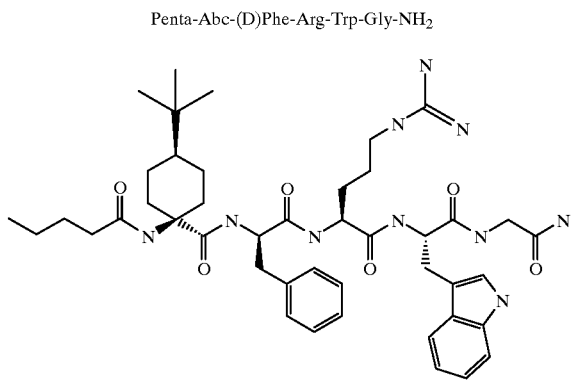

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Abc (270 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 580 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA, and the filtrates precipitated in chilled ethyl ether. The precipitates were centrifuged and the ether layer decanted. The residue was washed with two or three volumes of $Et_2O$ and recentrifuged and the crude product was dried under vacuum to yield 155 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 61 mg (36%) of a white, amorphous powder. This compound was homogeneous by HPLC. LR-Electrospray: $C_{44}H_{64}N_{10}O_6$, cal: 829 observed: m/z (830 M+H).

EXAMPLE 80

Penta-Achc-(D)Phe-Arg-Trp-Gly-NH2

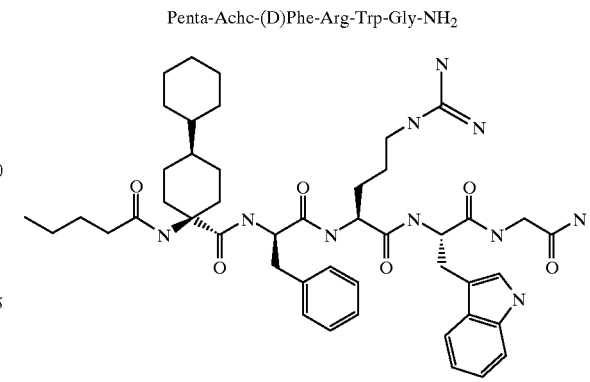

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Achc (278 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 580 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 mm. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 65 mg (38%) of a white, amorphous powder. This compound was homogeneous by HPLC. LR-Electrospray: $C_{46}H_{66}N_{10}O_6$, cal: 855 observed: m/z (856 M+H).

EXAMPLE 81

Bu-Atc-(D)Phe-Arg-Trp-Gly-NH$_2$

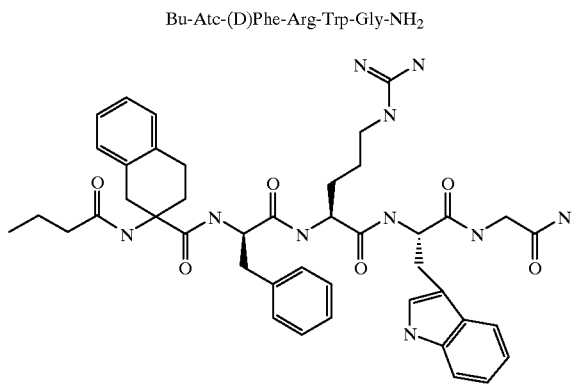

Fmoc-Linker-BHA resin (360 mg, 0.2 mmol) from Example 29 were subjected to solid phase synthesis using Protocol 1 above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)Atc (252 mg 0.6 mmol) and HBTU (226 mg, 0.6 mmol). The peptide resin was carried through steps 1–5 of protocol 1, washed with CH$_2$Cl$_2$ (three times) and treated with 1 mL butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 550 mg of Bu-Pentapeptide resin.

The Bu-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 110 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The second main peak was cut by analytical HPLC analysis of collected fractions, pooled and lyophilized to yield 42 mg (26%) of a white, amorphous powder. This compound was homogeneous by HPLC. LR-Electrospray: C$_{43}$H$_{54}$N$_{10}$O$_6$, cal 807 observed: m/z (808 M+H).

EXAMPLE 82

Penta-5-Br-(D,L)Atc-(D)Phe-Arg-Trp-Gly-NH$_2$

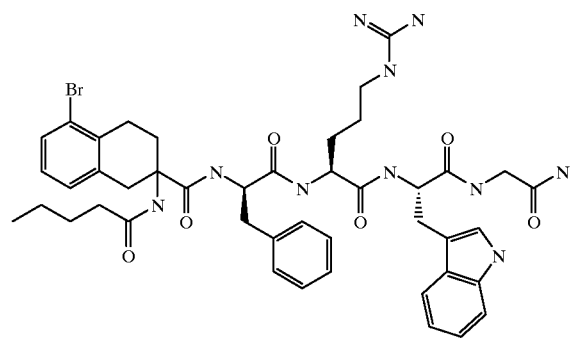

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-Br-(D,L)Atc (310 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 135 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 45 mg (25%) of a white, amorphous powder. This compound was homogeneous by HPLC. LR-Electrospray: C$_{44}$H$_{55}$N$_{10}$O$_6$Br, cal 900 observed: m/z (901 M+H).

EXAMPLE 83

Penta-5-Br-Atc-(D)Phe-Arg-Trp-Gly-NH$_2$ (peak 1)

EXAMPLE 84

Penta-5-BrAtc-(D)Phe-Arg-Trp-Gly-NH$_2$ (peak 2)

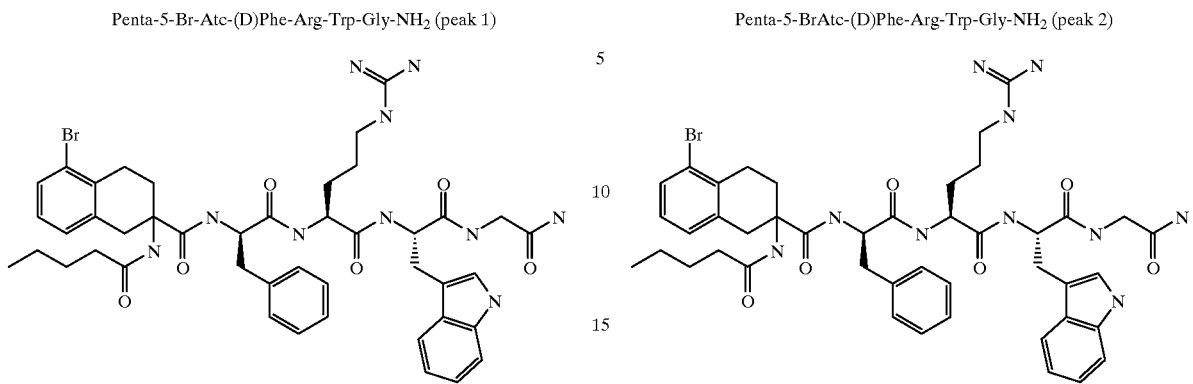

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 590 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 130 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The first main peak was cut by analytical HPLC analysis of collected fractions, pooled and lyophilized to yield 40 mg (22%) of a white, amorphous powder. This compound was homogeneous by HPLC. LR-Electrospray: C$_{44}$H$_{55}$N$_{10}$O$_6$Br, cal 900 observed: m/z (901 M+H).

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 580 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The second main peak was cut by analytical HPLC analysis of collected fractions, pooled and lyophilized to yield 55 mg (30%) of a white, amorphous powder. This compound was homogeneous by HPLC. LR-Electrospray: C$_{44}$H$_{55}$N$_{10}$O$_6$Brr, cal 900 observed: m/z (901 M+H).

EXAMPLE 85

Penta-5-Cl-(D,L)Atc-(D)Phe-Arg-Trp-Gly-NH$_2$

EXAMPLE 86

Penta-5-MeO-(D,L)Atc-(D)Phe-Arg-Trp-Gly-NH$_2$

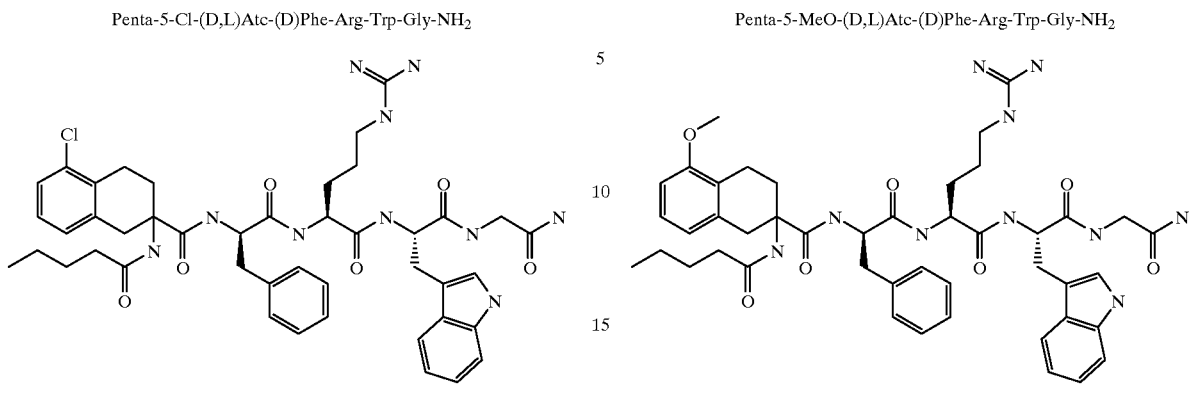

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-ClAtc (290 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 620 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 150 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 48 mg (28%) of a white, amorphous powder. This compound was homogeneous by HPLC. LR-Electrospray: C$_{44}$H$_{55}$N$_{10}$O$_6$Cl, cal 855 observed: m/z (856 M+H).

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-MeO(D,L)Atc (300 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 155 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 46 mg (27%) of a white, amorphous powder. This compound was homogeneous by HPLC. LR-Electrospray: C$_{45}$H$_{58}$N$_{10}$O$_7$, cal 851 observed: m/z (852 M+H).

EXAMPLE 87

Penta-5-EtO-(D,L)Atc-(D)Phe-Arg-Trp-Gly-NH$_2$

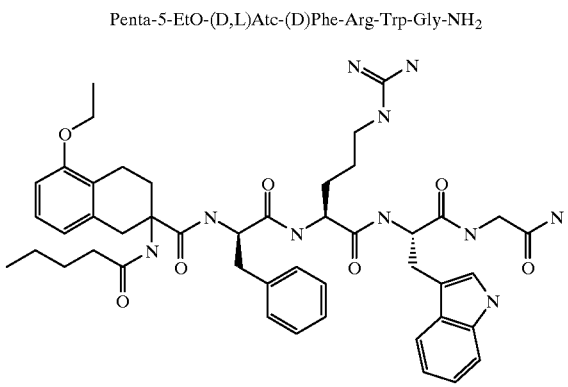

EXAMPLE 88

Penta-5-iPrO-(D,L)Atc-(D)Phe-Arg-Trp-Gly-NH$_2$

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-EtO(D,L)Atc (310 mg 0.6 mmol) and HBTU (226 mg, 0.6 mmol). The peptide resin was carried through steps 1–5 of protocol 1, washed with CH$_2$Cl$_2$ (three times) and treated with 1 μL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 594 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 41 mg (24%) of a white, amorphous powder. This compound was homogeneous by HPLC. LR-Electrospray: C$_{46}$H$_{60}$N$_{10}$O$_7$, cal 865 observed: m/z (866 M+H).

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-iPrO(D,L)Atc (310 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 580 mg of Pentyl-Pentapeptide resin.

The Pentyl-Pentapeptide resin was treated with 40 μL ethanedithiol, 40 μL dimethylsulfide, 120 μL anisole, and 4 μL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 142 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 43 mg (25%) of a white, amorphous powder. This compound was homogeneous by HPLC. LR-Electrospray: C$_{47}$H$_{62}$N$_{10}$O$_7$, cal 879 observed: m/z (880 M+H).

EXAMPLE 89

Penta-5-Me-(D,L)Atc-(D)Phe-Arg-Trp-Gly-NH$_2$

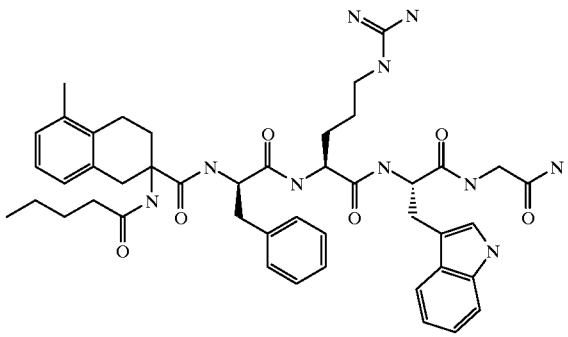

EXAMPLE 90

Penta-5-Et-(D,L)Atc-(D)Phe-Arg-Trp-Gly-NH$_2$

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-Me(D,L)Atc (290 mg, 0.6 mmol) and HBTU (226 mg, 0.6 mmol).The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 143 of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 40 mg (24%) of a white, amorphous powder. This compound was homogeneous by HPLC. LR-Electrospray: C$_{45}$H$_{58}$N$_{10}$O$_6$, cal 835 observed: m/z (836 M+H).

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-Et(D,L)Atc (285 mg, 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 620 mg of Pentyl-Pentapeptide resin The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 154 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 53 mg (31%) of a white, amorphous powder. This compound was homogeneous by HPLC. LR-Electrospray: C$_{46}$H$_{60}$N$_{10}$O$_6$, cal 849 observed: m/z (850 M+H).

EXAMPLE 91

Penta-5-iPr-(D,L)Atc-(D)Phe-Arg-Trp-Gly-NH$_2$

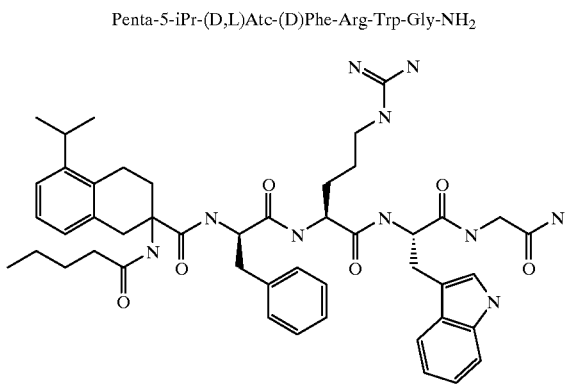

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-iPr(D,L)Atc (300 mg, 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 149 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 47 mg (27%) of a white, amorphous powder. This compound was homogeneous by HPLC. LR-Electrospray: C$_{47}$H$_{62}$N$_{10}$O$_6$, cal 863 observed: m/z (864 M+H).

EXAMPLE 92

Penta-5-DmaAtc-(D)Phe-Arg-Trp-Gly-NH$_2$ (peak 1)

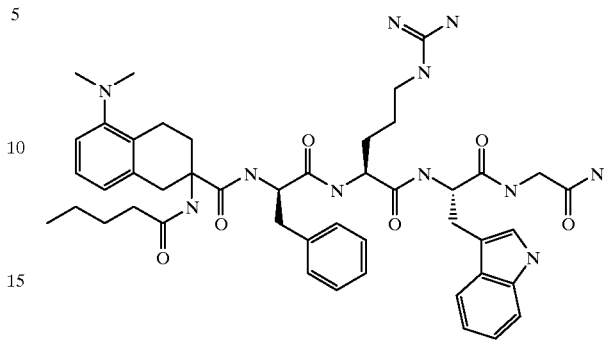

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-Dma(D,L)Atc (300 mg, 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 149 of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The first main peak was cut by analytical HPLC analysis of collected fractions, pooled and lyophilized to yield 22 mg (13%) of a white, amorphous powder. This compound was homogeneous by HPLC. LR-Electrospray: C$_{46}$H$_{61}$N$_{11}$O$_6$, cal 864 observed: m/z (865 M+H).

EXAMPLE 93

Penta-5-DmaAtc-(D)Phe-Arg-Trp-Gly-NH₂ (peak 2)

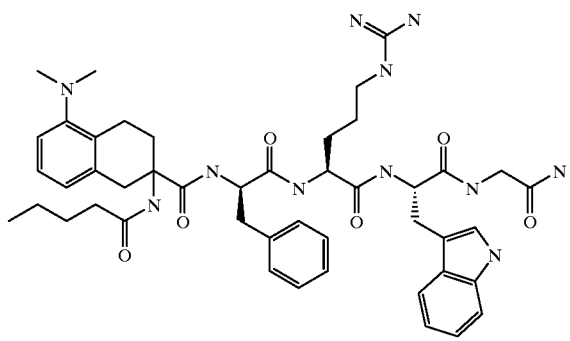

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-5-Dma(D,L)Atc (300 mg, 0.6 mmol) and HBTU (226 mg, 0.6 mmol). The peptide resin was carried through steps 1–5 of protocol 1, washed with CH₂Cl₂ (three times) and treated with 1 mL valeric anhydride in 6% DIPEA/CH₂Cl₂ for 30 minutes. The resin was filtered and washed successively with 20 ml each of CH₂Cl₂ (two times), isopropanol, and CH₂Cl₂ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et₂O and recentrifuged and the crude product was dried under vacuum to yield 149 of an off-white solid.

This crude material was purified by preparative HPLC on a Vydac C18-column (2.5×20 cm) and eluted with a linear gradient of 10–60% B (buffer A: 0.1% TFA/H₂O, buffer B: 0.1% TFA/CH₃CN) in 60 min., flow rate 8 ml/min, detection 280 nm. The second main peak was cut by analytical HPLC analysis of collected fractions, pooled and lyophilized to yield 27 mg (16%) of a white, amorphous powder. This compound was homogeneous by HPLC. LR-Electrospray: $C_{46}H_{61}N_{11}O_6$, cal 864 observed: m/z (865 M+H).

EXAMPLE 94

Bu-(D,L)5-BrAtc-(D)Phe-Arg-Trp-2-Aba-NH₂

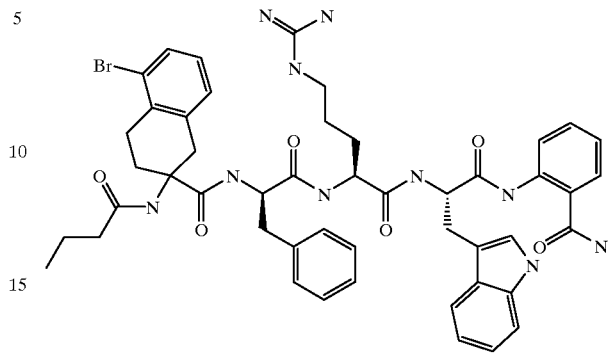

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L) 5-BrAtc (310 mg 0.6 mmol) and HBTU (226 mg, 0.6 mmol). The peptide resin was carried through steps 1–5 of protocol 1, washed with CH₂Cl₂ (three times) and treated with 1 ml of butyric anhydride in 6% DIPEA/CH₂Cl₂ for 30 minutes. The resin was filtered and washed successively with 20 ml each of CH₂Cl₂ (two times), isopropanol, and CH₂Cl₂ (three times). The resin was dried under vacuum to yield 600 mg of butyl Pentapeptide resin.

The butyl Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et₂O and recentrifuged and the crude product was dried under vacuum to yield 141 mg of an off-white solid.

This crude material was purified by preparative HPLC on a Vydac C18-column (2.5×20 cm) and eluted with a linear gradient of 10–60% B (buffer A: 0.1% TFA/H₂O, buffer B: 0.1% TFA/CH₃CN) in 60 min., flow rate 8 ml/min, detection 280 nm. The main peak was cut by analytical HPLC analysis of collected fractions, pooled and lyophilized to yield 35 mg (19%) of a white, amorphous powder. This compound was homogeneous by HPLC. LR-Electrospray: $C_{48}H_{55}N_{10}O_6Br$, cal: 948 observed: m/z (949 M+H).

EXAMPLE 95

Bu-carbamoyl-(D,L)-5-BrAtc-(D)Phe-Arg-Trp-2-Aba-NH$_2$

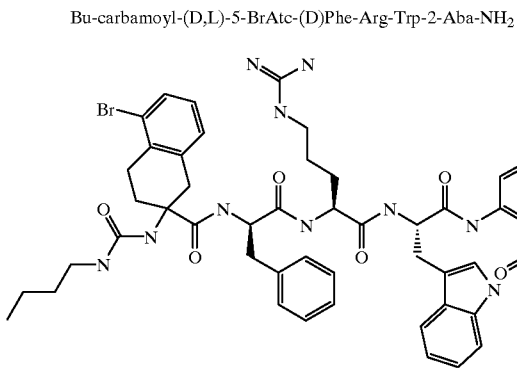

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with n-butyl isocyanate (5 eq) in 6% DIPEA/CH$_2$Cl$_2$ for 12 hours. The resin was filtered and washed successively with 20 ml each of CH$_2$Cl$_2$ (two times), isopropanol, and CH$_2$Cl$_2$ (three times). The resin was dried under vacuum to yield 620 mg of butyl carbamoyl-Pentapeptide resin.

The butyl-carbamoyl Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 153 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 41 mg (21%) of a white, amorphous powder. This compound was homogeneous by HPLC. LR-Electrospray: C$_{49}$H$_{58}$N$_{11}$O$_6$Br, cal: 977 observed: m/z (978 M+H).

EXAMPLE 96

Phenylacetyl-(D,L)-5-BrAtc-(D)Phe-Arg-Trp-2-Aba-NH$_2$

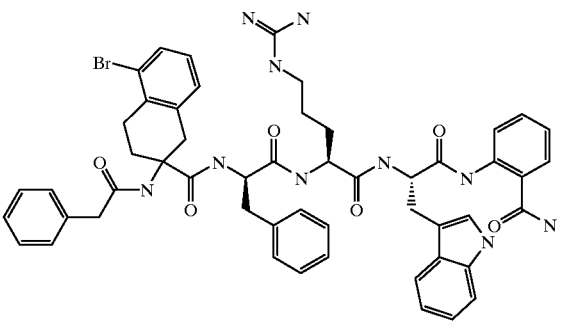

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with phenylacetic acid, HBTU in DMF. The resin was filtered and washed successively with 20 ml each of CH$_2$Cl$_2$ (two times), isopropanol, and CH$_2$Cl$_2$ (three times). The resin was dried under vacuum to yield 610 mg of Phenylacetyl Pentapeptide resin.

The phenylacetyl Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 148 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 38 mg (19%) of a white, amorphous powder. This compound was homogeneous by HPLC. LR-Electrospray: C$_{52}$H$_{55}$N$_{10}$O$_6$Br, cal: 996 observed: m/z (997 M+H).

EXAMPLE 97

Penta-(D,L)-5-BrAtc-(D)Phe-Arg-(2)Nal-Gly-NH$_2$

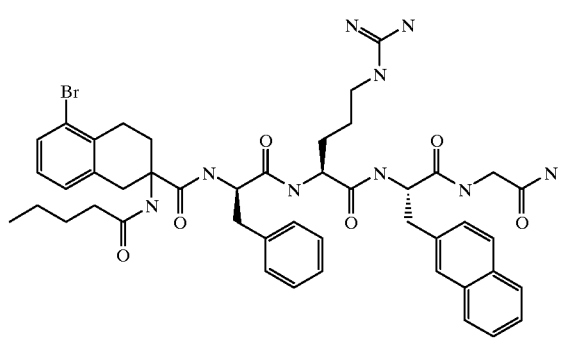

EXAMPLE 98

3-carboxylpropanoyl-(D,L)-5-BrAtc-(D)Phe-Arg-(2)Nal-Gly-NH$_2$

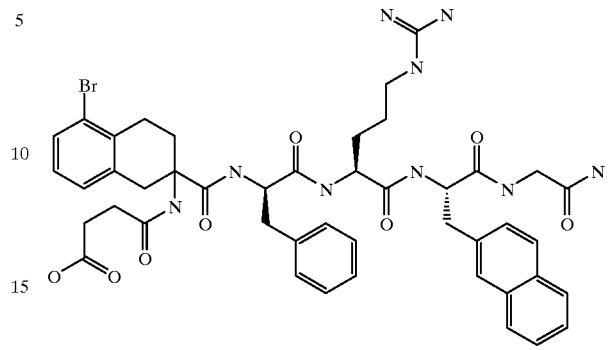

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 620 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 162 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 60 mg (33%) of a white, amorphous powder. This compound was homogeneous by HPLC. LR-Electrospray: C$_{46}$H$_{56}$N$_9$O$_6$Br, cal: 911 observed: m/z (912 M+H).

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with succinic acid, HBTU in DMF. The resin was filtered and washed successively with 20 ml each of CH$_2$Cl$_2$ (two times), isopropanol, and CH$_2$Cl$_2$ (three times). The resin was dried under vacuum to yield 610 mg of 3-carboxylpropanoyl-Pentapeptide resin.

The 3-carboxylpropanoyl Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 158 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (30%) of a white, amorphous powder. This compound was homogeneous by HPLC. LR-Electrospray: C$_{45}$H$_{52}$N$_9$O$_8$Br, cal: 927 observed: m/z (928 M+H).

EXAMPLE 99

Phenylacetyl-(D,L)-5-BrAtc-(D)Phe-Arg-(2)Nal-Gly-NH$_2$

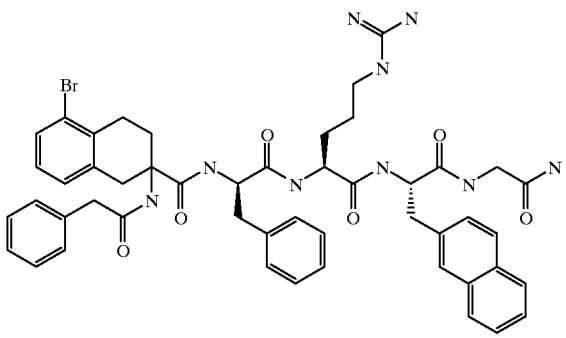

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with phenyl acetic acid, HBTU in DMF. The resin was filtered and washed successively with 20 ml each of CH$_2$Cl$_2$ (two times), isopropanol, and CH$_2$Cl$_2$ (three times). The resin was dried under vacuum to yield 600 mg of phenylacetyl Pentapeptide resin.

The phenylacetyl Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 161 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 58 mg (30%) of a white, amorphous powder. This compound was homogeneous by HPLC. LR-Electrospray: C$_{49}$H$_{54}$N$_9$O$_6$Br, cal: 945 observed: m/z (946 M+H).

EXAMPLE 100

Bu-(D,L)-5-BrAtc-(D)Phe-Arg-(2)Nal-2-Aba-NH$_2$

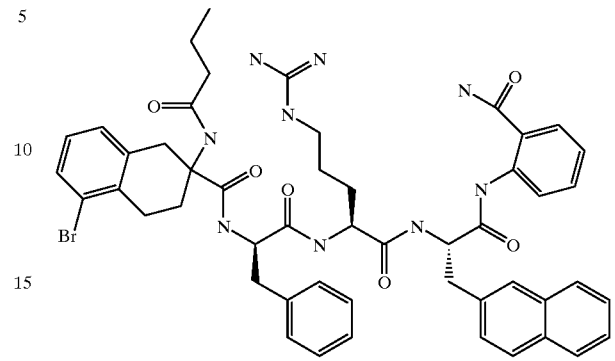

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-2-Aba (215 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-(D,L)-5-BrAtc (310 mg 0.6 mmol) and HBTU (226 mg, 0.6 mmol). The peptide resin was carried through steps 1–5 of protocol 1, washed with CH$_2$Cl$_2$ (three times) and treated with 1 ml of butyric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 590 mg of butyl Pentapeptide resin.

The butyl Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 30 mg (16%) of a white, amorphous powder. This compound was homogeneous by HPLC. LR-Electrospray: C$_{50}$H$_{56}$N$_9$O$_6$Br, cal: 959 observed: m/z (960 M+H).

EXAMPLE 101

Penta-Appc-(D)Phe-Arg-Trp-Gly-NH$_2$

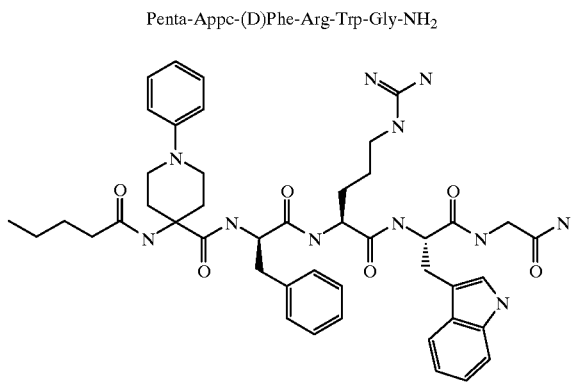

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Appc (275 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 620 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 153 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 65 mg (38%) of a white, amorphous powder. This compound was homogeneous by HPLC. LR-Electrospray: C$_{45}$H$_{59}$N$_{11}$O$_6$, cal: 850 observed: m/z (851 M+H).

EXAMPLE 102

Penta-Appc-(D)Phe-Arg-(2)Nal-Gly-NH$_2$

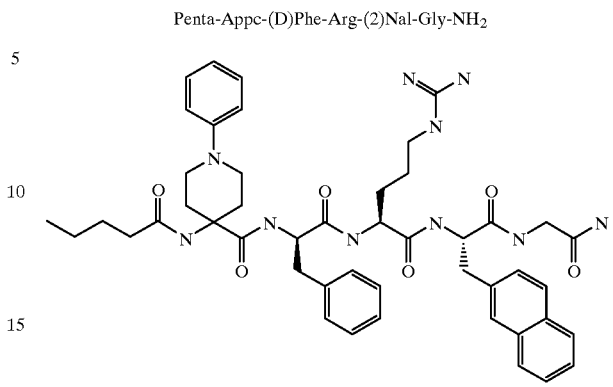

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-(2)Nal (265 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-Appc (275 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 μL ethanedithiol, 40 μL dimethylsulfide, 120 μL anisole, and 4 μL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (32%) of a white, amorphous powder. This compound was homogeneous by HPLC. LR-Electrospray: C$_{47}$H$_{60}$N$_{10}$O$_6$, cal: 861 observed: m/z (862 M+H).

EXAMPLE 103

Penta-2-MeAppc-(D)Phe-Arg-Trp-Gly-NH$_2$

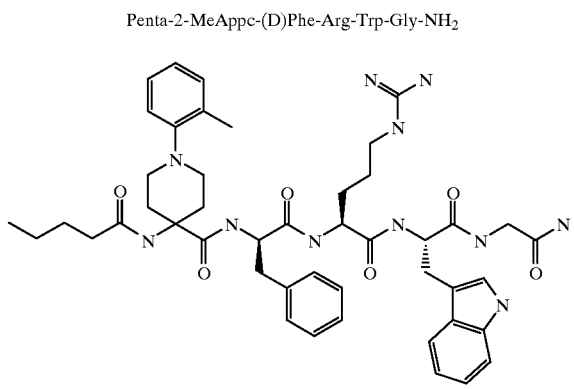

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-2-MeAppc (285 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 580 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 145 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 59 mg (35%) of a white, amorphous powder. This compound was homogeneous by HPLC. LR-Electrospray: C$_{46}$H$_{61}$N$_{11}$O$_6$, cal: 864 observed: m/z (865 M+H).

EXAMPLE 104

Penta-2-iPrAppc-(D)Phe-Arg-Trp-Gly-NH$_2$

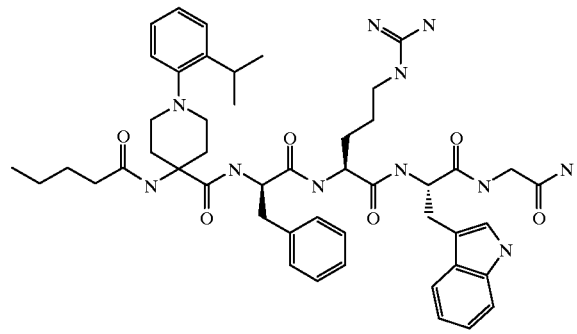

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-2-iPrAppc (295 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of Pentyl-Pentapeptide resin.

The Pentyl-Pentapeptide resin was treated with 40 μL ethanedithiol, 40 μL dimethylsulfide, 120 μL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 147 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 49 mg (27%) of a white, amorphous powder. This compound was homogeneous by HPLC. LR-Electrospray: C$_{48}$H$_{65}$N$_{11}$O$_6$, cal: 892 observed: m/z (893 M+H).

EXAMPLE 105

Penta-3-MeAppc-(D)Phe-Arg-Trp-Gly-NH$_2$

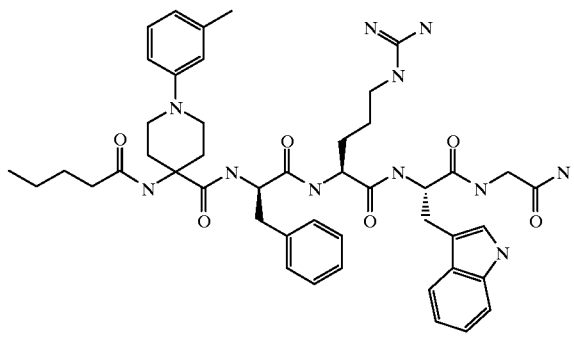

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-3-MeAppc (285 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 595 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 55 mg (32%) of a white, amorphous powder. This compound was homogeneous by HPLC. LR-Electrospray: C$_{46}$H$_{61}$N$_{11}$O$_6$, cal: 864 observed: m/z (865 M+H).

EXAMPLE 106

Penta-3-MeOAppc-(D)Phe-Arg-Trp-Gly-NH$_2$

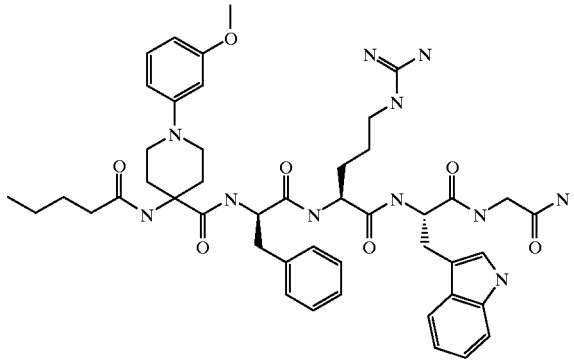

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-3-MeOAppc (290 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 600 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 154 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 50 mg (29%) of a white, amorphous powder. This compound was homogeneous by HPLC. LR-Electrospray: C$_{46}$H$_{61}$N$_{11}$O$_7$, cal: 880 observed: m/z (881 M+H).

EXAMPLE 107

Penta-4-MeAppc-(D)Phe-Arg-Trp-Gly-NH₂

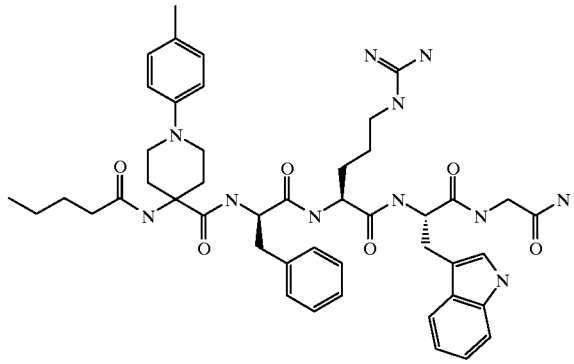

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-MeAppc (285 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 600 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 150 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 57 mg (33%) of a white, amorphous powder. This compound was homogeneous by HPLC. LR-Electrospray: $C_{46}H_{61}N_{11}O_6$, cal: 864 observed: m/z (865 M+H).

EXAMPLE 108

Penta-4-ClAppc-(D)Phe-Arg-Trp-Gly-NH₂

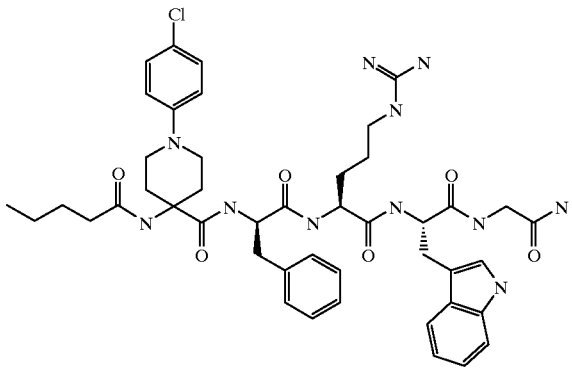

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-ClAppc (290 mg 0.6 mmol) and HBTU (226 mg, 0.6 mmol). The peptide resin was carried through steps 1–5 of protocol 1, washed with $CH_2Cl_2$ (three times) and treated with 1 mL valeric anhydride in 6% DIPEA/$CH_2Cl_2$ for 30 minutes. The resin was filtered and washed successively with 20 ml each of $CH_2Cl_2$ (two times), isopropanol, and $CH_2Cl_2$ (three times). The resin was dried under vacuum to yield 580 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude product was dried under vacuum to yield 140 mg of an off-white solid.

This crude material was purified by preparative HPLC on a Vydac C18-column (2.5×20 cm) and eluted with a linear gradient of 10–60% B (buffer A: 0.1% TFA/$H_2O$, buffer B: 0.1% TFA/$CH_3CN$) in 60 min., flow rate 8 ml/min, detection 280 nm. The main peak was cut by analytical HPLC analysis of collected fractions, pooled and lyophilized to yield 49 mg (28%) of a white, amorphous powder. This compound was homogeneous by HPLC. LR-Electrospray: $C_{45}H_{58}N_{11}O_6Cl$, cal: 884 observed: m/z (885 M+H).

EXAMPLE 109

Penta-4-PhOAppc-(D)Phe-Arg-Trp-Gly-NH$_2$

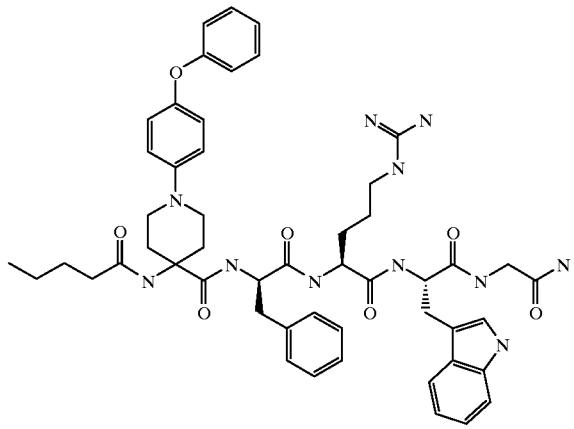

Fmoc-Linker-BHA resin (360 mg, 0.2 mmol) from Example 29 were subjected to solid phase synthesis using protocol 1 described above. All couplings were performed using HBTU in DMF as the coupling agent and DIPEA (3 equiv.) as base. Five coupling cycles were performed of one cycle each with Fmoc-Gly (180 mg, 0.6 mmol) and HBTU (226 mg, 0.6 mmol), Fmoc-Trp (260 mg, 0.6 mmol) and HBTU (226 mg, 0.6 mmol), Fmoc-Arg (Pmc) (400 mg, 0.6 mmol) and HBTU (226 mg, 0.6 mmol), Fmoc-(D)Phe (240 mg, 0.6 mmol) and HBTU (226 mg, 0.6 mmol), Fmoc-4-PhOAppc (325 mg 0.6 mmol) and HBTU (226 mg, 0.6 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 20 ml each of CH$_2$Cl$_2$ (two times), isopropanol, and CH$_2$Cl$_2$ (three times). The resin was dried under vacuum to yield 610 mg of Pentyl-Pentapeptide resin.

The Pentyl-Pentapeptide resin was treated with 40 µL ethanedithiol, 40 µL dimethylsulfide, 120 µL anisole, and 4 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 143 mg of an off-white solid.

This crude material was purified by preparative HPLC on a Vydac C18-column (2.5×20 cm) and eluted with a linear gradient of 10–60% B (buffer A: 0.1% TFA/H$_2$O, buffer B: 0.1% TFA/CH$_3$CN) in 60 min., flow rate 8 ml/min, detection 280 nm. The main peak was cut by analytical HPLC analysis of collected fractions, pooled and lyophilized to yield 41 mg (22%) of a white, amorphous powder. This compound was homogeneous by HPLC. LR-Electrospray: C$_{51}$H$_{63}$N$_{11}$O$_7$, cal: 942 observed: m/z (943 M+H).

Biological Activity Example

Example A

Agonist Assay

Method

Description: 293 cells transfected with either the MC-4 receptor or MC-1 receptor were grown in 96 well plates. The cells were stimulated with either 100 nM NDP-αMSH or screening compounds. Cyclic AMP was extracted from the cells and concentrations were determined using a Biotrak-cAMP SPA assay. Agonists were identified as those compounds causing an increase in cAMP.

Cell Culture: 293MC4 cells (obtained from Dr. Wei Gu, Millenium) were cultured in 75cm$^2$ flasks in D-MEM supplemented with 10% FCS and 500 µg/ml G418. Cells were trypsinized and split 1:3 into 96 well flat-bottom tissue culture treated plates. Cells were stimulated at confluence (day 2–4).

cAMP Response: Compounds serially diluted in 100% DMSO were further diluted 1:200 (2.5 µl compound dilution+500 µl media) in D-MEM containing 10% FBS and 0.1 mM IBMX. For unstimulated cells, 2.5 µl of DMSO was added to 500 µl of media. For NDP-αMSH stimulated cells, 2.5 µl of 20 µM NDP-αMSH in 100% DMSO was added to 500 µl of media (final conc. 100 nM).

Final concentration of DMSO in all wells was 0.5%.

Note: Each sample was run in duplicate on separate plates

Culture medium was removed from confluent 96 well culture plates and replaced with 200 µl of above dilutions into the appropriate wells. The plates were incubated for 1 hr at RT. The media was removed, and the plates were washed 1× with 200"1 well of PBS. CAMP was extracted by the addition of 60 µl 70% ethanol (stored in the refrigerator). After a 30 min extraction period, 10 µl ethanol extract was transferred to the cAMP assay plate or samples were stored at −20° C. until the cAMP assay was performed.

cAMP Assay: The extracted samples and all reagents included in the kit were brought to room temperature. To a 96 well OptiPlate, 10 µl ethanol extract, 40 µl assay buffer, 50 ul [125I]cAMP, 50 µl antiserum and 50 µl SPA beads were added. The total well volume after addition was 200 µl. The plates were sealed and incubated for 15–20 hr at room temperature. [125I]cAMP binding to the SPA beads was determined by counting each plate for 2 minutes on a Packard TopCount™.

Note: Each plate contained samples of controls for unstimulated cells and NDP-αMSH for stimulated cells.

What is claimed is:

1. A compound of the formula:

I

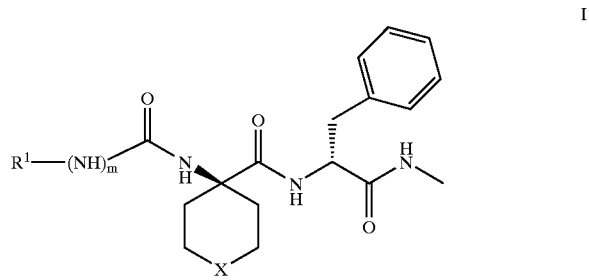

-continued

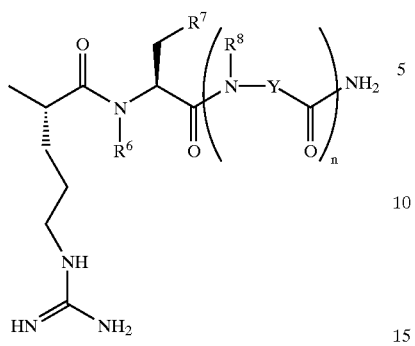

wherein
m is 0 or 1;
n is 0 or 1;
$R^1$ is an unsubstituted linear or branched alkyl having from 1 to 8 carbon atoms; linear or branched alkyl having from 1 to 8 carbon atoms mono-substituted by phenyl or carboxyl; unsubstituted phenyl; or phenyl mono-substituted by fluoro, chloro or linear or branched alkyl having from 1 to 4 carbon atoms;
X is

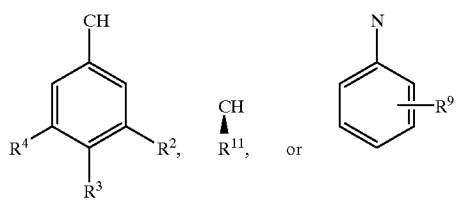

wherein $R^2$, $R^3$ and $R^4$ are independently hydrogen or a linear or branched alkoxy having from 1 to 4 carbon atoms, wherein when $R^3$ is alkoxy, $R^2$ and $R^4$ are both hydrogen;

$R^9$ is hydrogen, linear or branched alkyl having from 1 to 3 carbons, linear or branched alkoxy having from 1 to 3 carbons, or unsubstituted phenoxy;
$R^{11}$ is cyclohexyl, cycloheptyl, or a branched alkyl having from 3 to 8 carbon atoms;
$R^6$ is hydrogen or methyl;
$R^7$ is

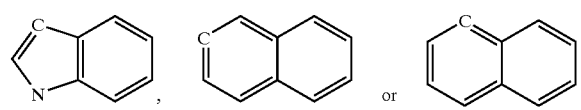

Y is

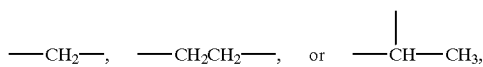

and $R^8$ is hydrogen or methyl; or
Y is

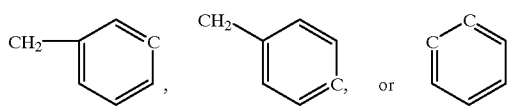

and $R^8$ is hydrogen.

2. The compound of claim 1, wherein $R^6$ is hydrogen and $R^8$ is hydrogen.

3. The compound of claim 1, wherein n is 1.

4. The compound of claim 1, wherein $R^7$ is

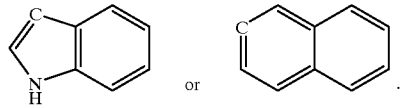

5. The compound of claim 1 of the formula:

IA

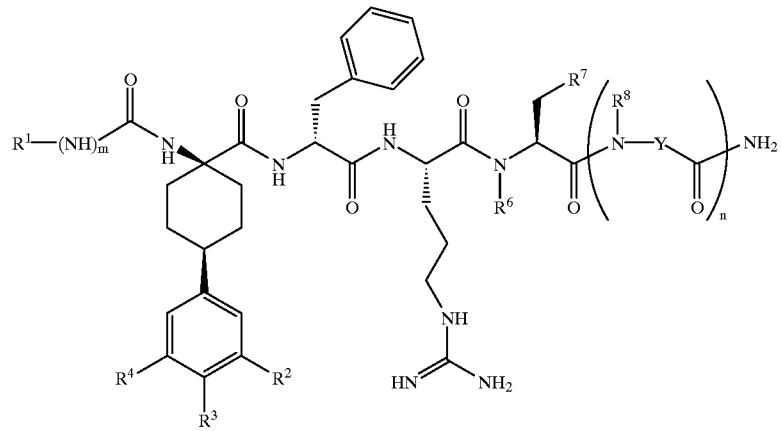

wherein m is 0 or 1;

n is 0 or 1;

R¹ is an unsubstituted linear or branched alkyl having from 1 to 8 carbon atoms; linear or branched alkyl having from 1 to 8 carbon atoms mono-substituted by phenyl or carboxyl; unsubstituted phenyl; or phenyl mono-substituted by fluoro, chloro or linear or branched alkyl having from 1 to 4 carbon atoms;

R², R³ and R⁴ are independently hydrogen; a linear or branched alkyl having from 1 to 4 carbon atoms; hydroxy, a linear or branched alkoxy having from 1 to 4 carbon atoms; or chloro, wherein when R³ is alkyl, hydroxy, alkoxy or chloro, R² and R⁴ are both hydrogen;

R⁶ is hydrogen or methyl;

R⁷ is

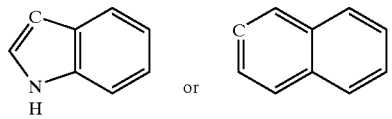 or

Y is

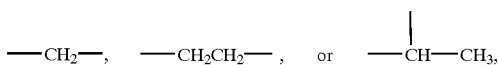

and R⁸ is hydrogen or methyl; or

Y is

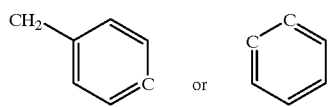 or and R⁸ is hydrogen.

6. The compound of claim 5, wherein R⁷ is

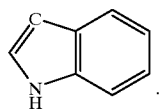

7. The compound of claim 6, wherein n is 0.

8. The compound of claim 7, Penta-1-Amino-4-phenylcyclohexane-1-carboxylic acid-(D)Phe-Arg-Trp-NH₂, wherein Penta is Pentyl.

9. The compound of claim 7, Penta-1-Amino-4-phenylcyclohexane-1-carboxylic acid-(D)Phe-Arg-N-methylTrp-NH₂, wherein Penta is Pentyl.

10. The compound of claim 6, wherein n is 1.

11. The compound of claim 10, wherein Y is —CH₂—, CH₂CH₂—, or

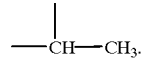

12. The compound of claim 11, wherein m is 1.

13. The compound of claim 12, Bu-Carbamoyl-1-Amino-4-phenylcyclohexane-1-carboxylic acid-(D)Phe-Arg-Trp-Gly-NH₂, wherein Bu is Butyl.

14. The compound of claim 12, Bu-carbamoyl-1-Amino-4-phenylcyclohexane-1-carboxylic acid-(D)Phe-Arg-Trp-Ala-NH₂, wherein Bu is Butyl.

15. The compound of claim 12, Bu-Carbamoyl-1-Amino-4-phenylcyclohexane-1-carboxylic acid-(D)Phe-Arg-Trp-β-Ala-NH₂, wherein Bu is Butyl.

16. The compound of claim 11, wherein m is 0.

17. The compound of claim 16, wherein R², R³ and R⁴ are hydrogen.

18. The compound of claim 17, wherein R¹ is unsubstituted linear alkyl.

19. The compound of claim 18, Penta-1-Amino-4-phenylcyclohexane-1-carboxylic acid-(D)Phe-Arg-Trp-Gly-NH₂, wherein Penta is Pentyl.

20. The compound of claim 18, Penta-1-Amino-4-phenylcyclohexane-1-carboxylic acid-(D)Phe-Arg-Trp-Sarcosine (N-methylglycine)-NH₂, wherein Penta is Pentyl.

21. The compound of claim 18, Penta-1-Amino-4-phenylcyclohexane-1-carboxylic acid-(D)Phe-Arg-N-methylTrp-Gly-NH₂, wherein Penta is Pentyl.

22. The compound of claim 18, Bu-1-Amino-4-phenylcyclohexane-1-carboxylic acid-(D)Phe-Arg-Trp-Ala-NH₂, wherein Bu is Butyl.

23. The compound of claim 18, Bu-1-Amino-4-phenylcyclohexane-1-carboxylic acid-(D)Phe-Arg-Trp-β-Ala-NH₂, wherein Bu is Butyl.

24. The compound of claim 17, wherein R¹ is unsubstituted phenyl.

25. The compound of claim 24, Phenylacetyl-1-Amino-4-phenylcyclohexane-1-carboxylic acid-(D)Phe-Arg-Trp-Gly-NH₂.

26. The compound of claim 24, Phenylacetyl-1-Amino-4-phenylcyclohexane-1-carboxylic acid-(D)Phe-Arg-Trp-Ala-NH₂.

27. The compound of claim 24, Phenylacetyl-1-Amino-4-phenylcyclohexane-1-carboxylic acid-(D)Phe-Arg-Trp-Ala-NH₂.

28. The compound of claim 16, wherein R³ is alkyl, hydroxy, alkoxy or chloro.

29. The compound of claim 28, Penta-4-Cl-1-Amino-4-phenylcyclohexane-1-carboxylic acid-(D)Phe-Arg-Trp-Gly-NH₂, wherein Penta is Pentyl.

30. The compound of claim 28, Penta-4-Me-1-Amino-4-phenylcyclohexane-1-carboxylic acid-(D)Phe-Arg-Trp-Gly-NH₂, wherein Penta is Pentyl.

31. The compound of claim 28, wherein R³ is hydroxy or alkoxy.

32. The compound of claim 31, Penta-1-Amino-4-(4-hydroxyphenyl)cyclohexane-1-carboxylic acid-(D)Phe-Arg-Trp-Gly-NH₂, wherein Penta is Pentyl.

33. The compound of claim 31, Penta-1-Amino-4-(4-methoxyphenyl)cyclohexane-1-carboxylic acid-(D)Phe-Arg-Trp-Gly-NH₂, wherein Penta is Pentyl.

34. The compound of claim 31, Penta-1-Amino-4-(4-ethoxyphenyl)cyclohexane-1-carboxylic acid-(D)Phe-Arg-Trp-Gly-NH₂, wherein Penta is Pentyl.

35. The compound of claim 31, Penta-1-Amino-4-(4-isopropoxyphenyl)cyclohexane-1-carboxylic acid-(D)Phe-Arg-Trp-Gly-NH₂, wherein Penta is Pentyl.

36. The compound of claim 16, wherein R² is alkoxy, R³ is hydrogen and R⁴ is hydrogen.

37. The compound of claim 36, Penta-1-Amino-4-(4-methoxyphenyl)cyclohexane-1-carboxylic acid-(D)Phe-Arg-Trp-Gly-NH₂, wherein Penta is Pentyl.

38. The compound of claim 10, wherein Y is

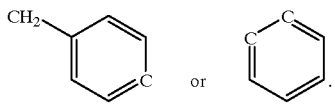

39. The compound of claim 38, wherein m is 1.
40. The compound of claim 39, Bu-carbamoyl-1-Amino-4-phenyl-cyclohexane-1-carboxylic acid-(D)Phe-Arg-Trp-2-Aminobenzoic acid-NH₂, wherein Bu is Butyl.
41. The compound of claim 39, Bu-carbamoyl-1-Amino-4-phenylcyclohexane-1-carboxylic acid-(D)Phe-Arg-Trp-3-Aminomethyl benzoic acid-NH₂, wherein Bu is Butyl.
42. The compound of claim 38, wherein m is 0.
43. The compound of claim 42, Bu-1-Amino-4-phenylcyclohexane-1-carboxylic acid-(D)Phe-Arg-Trp-2-Aminobenzoic acid -NH₂, wherein Bu is Butyl.
44. The compound of claim 42, Phenylacetyl-1-Amino-4-phenylcyclohexane-1-carboxylic acid-(D)Phe-Arg-Trp-2-Aminobenzoic acid-NH₂.
45. The compound of claim 42, Bu-1-Amino-4-phenyl-cyclohexane-1-carboxylic acid-(D)Phe-Arg-Trp-3-Aminomethyl benzoic acid-NH₂, wherein Bu is Butyl.
46. The compound of claim 42, Phenylacetyl-1-Amino-4-phenylcyclohexane-1-carboxylic acid-(D)Phe-Arg-Trp-3-Aminomethyl benzoic acid-NH₂.
47. The compound of claim 42, Bu-1-Amino-4-phenylcyclohexane-1-carboxylic acid-(D)Phe-Arg-Trp-4-Aminomethyl benzoic acid-NH₂, wherein Bu is Butyl.
48. The compound of claim 42, Phenylacetyl-1-Amino-4-phenylcyclohexane-1-carboxylic acid-(D)Phe-Arg-Trp-4-Aminomethyl benzoic acid-NH₂.
49. The compound of claim 5, wherein $R^2$, $R^3$ and $R^4$ are hydrogen and $R^7$ is

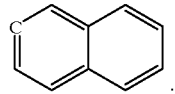

50. The compound of claim 49, Penta-1-Amino-4-phenyl-cyclohexane-1-carboxylic acid-(D)Phe-Arg-N-methyl (2)-Naphthylalanine-NH₂, wherein Penta is Pentyl.
51. The compound of claim 49, Bu-Carbamoyl-1-Amino-4-phenyl-cyclohexane-1-carboxylic acid-(D)Phe-Arg-(2)-Naphthylalanine-Gly-NH₂, wherein Bu is Butyl.
52. The compound of claim 49, wherein n is 1 and m is 0.
53. The compound of claim 52, where Y is —CH₂, —CH₂CH₂—, or

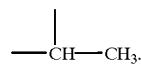

54. The compound of claim 53, wherein $R^1$ is unsubstituted linear alkyl.
55. The compound of claim 54, Penta-1-Amino-4-phenylcyclohexane-1-carboxylic acid-(D)Phe-Arg-(2)-Naphthylalanine-Gly-NH₂, wherein Penta is Pentyl.
56. The compound of claim 54, Bu-1-Amino-4-phenylcyclohexane-1-carboxylic acid-(D)Phe-Arg-(2)-Naphthylalanine-Gly-NH₂, wherein Bu is Butyl.
57. The compound of claim 54, Penta-1-Amino-4-phenylcyclohexane-1-carboxylic acid-(D)Phe-Arg-N-methyl-(2)-Naphthylalanine-Gly-NH₂, wherein Penta is Pentyl.
58. The compound of claim 54, Bu-1-Amino-4-phenylcyclohexane-1-carboxylic acid-(D)Phe-Arg-(2)-Naphthylalanine-Ala-NH₂, wherein Bu is Butyl.
59. The compound of claim 54, Bu-1-Amino-4-phenylcyclohexane-1-carboxylic acid-(D)Phe-Arg-(2)-Naphthylalanine-beta-Ala-NH₂, wherein Bu is Butyl.
60. The compound of claim 53, wherein $R^1$ is unsubstituted phenyl; or alkyl substituted by phenyl or carboxyl.
61. The compound of claim 60, Benzoyl-1-Amino-4-phenylcyclohexane-1-carboxylic acid-(D)Phe-Arg-(2)-Naphthylalanine-Gly-NH₂.
62. The compound of claim 60, 3-carboxylpropanoyl-1-Amino-4-phenylcyclohexane-1-carboxylic acid-(D)Phe-Arg-(2)-Naphthylalanine-Gly-NH₂.
63. The compound of claim 60, 3-carboxylpropanoyl-1-Amino-4-phenylcyclohexane-1-carboxylic acid-(D)Phe-Arg-(2)-Naphthylalanine-Gly-NH₂.
64. The compound of claim 52, wherein $R^1$ is unsubstituted lower alkyl and Y is

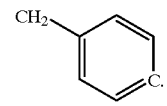

65. The compound of claim 64, Bu-1-Amino-4-phenylcyclohexane-1-carboxylic acid-(D)Phe-Arg-(2)-Naphthylalanine3-Aminomethyl benzoic acid-NH₂, wherein Bu is Butyl.
66. The compound of claim 64, Bu-1-Amino-4-phenylcyclohexane-1-carboxylic acid-(D)Phe-Arg-(2)-Naphthylalanine-2-Aminobenzoic acid-NH₂, wherein Bu is Butyl.
67. The compound of claim 64, Bu-1-Amino-4-phenylcyclohexane-1-carboxylic acid-(D)Phe-Arg-(2)-Naphthylalanine-4-Aminomethyl benzoic acid-NH₂, wherein Bu is Butyl.
68. The compound of claim 1 of the formula:

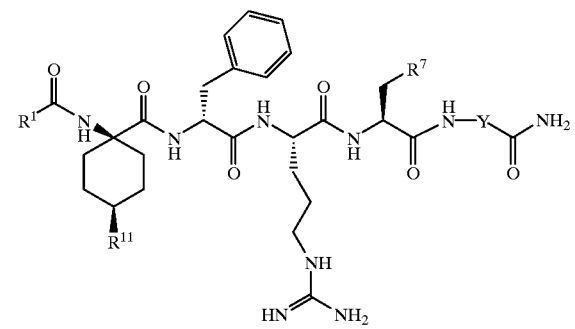

IB $R^1$ is an unsubstituted linear or branched alkyl having from 1 to 8 carbon atoms;
$R^7$ is

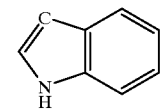

$R^{11}$ is cyclohexyl, or a branched alkyl having from 3 to 8 carbon atoms; and
Y is —CH₂—.

69. The compound of claim 68, Penta-1-Amino-4-tert-butylcyclohexane-1-carboxylic acid-(D)Phe-Arg-Trp-Gly-NH$_2$, wherein Penta is Pentyl.

70. The compound of claim 68, Penta-1-Amino-4-cyclohexylcyclohexane-1-carboxylic acid-(D)Phe-Arg-Trp-Gly-NH$_2$, wherein Penta is Pentyl.

71. The compound of claim 1 of the formula:

IC

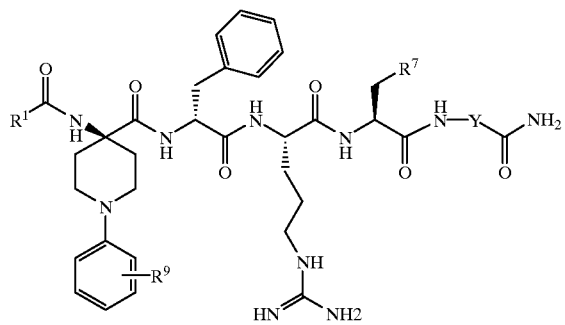

wherein

R$^1$ is an unsubstituted linear or branched alkyl having from 1 to 8 carbon atoms;

R$^7$ is

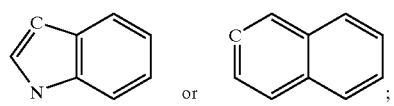

Y is

R$^9$ is hydrogen, a linear or branched alkyl having from 1 to 3 carbon atoms, a linear or branched alkoxy having from 1 to 3 carbon atoms, fluoro, chloro, or unsubstituted phenoxy.

72. The compound of claim 71, wherein R$^9$ is hydrogen.

73. The compound of claim 72, Penta-4-Amino-1-phenylpiperidine-4-carboxylic acid-(D)Phe-Arg-Trp-Gly-NH$_2$, wherein Penta is Pentyl.

74. The compound of claim 72, Penta-4-Amino-1-phenylpiperidine-4-carboxylic acid-(D)Phe-Arg-(2)-Naphthylalanine-Gly-NH$_2$, wherein Penta is Pentyl.

75. The compound of claim 71, wherein R$^9$ is a linear or branched alkyl having from 1 to 3 carbon atoms.

76. The compound of claim 75, Penta-4-Amino-1-(2-methylphenyl)piperidine-4-carboxylic acid-(D)Phe-Arg-Trp-Gly-NH$_2$, wherein Penta is Pentyl.

77. The compound of claim 75, Penta-4-Amino-1-(2-isopropoxyphenyl)piperidine-4-carboxylic acid-(D)Phe-Arg-Trp-Gly-NH$_2$, wherein Penta is Pentyl.

78. The compound of claim 75, Penta-4-Amino-1-(3-methylphenyl)piperidine-4-carboxylic acid-(D)Phe-Arg-Trp-Gly-NH$_2$, wherein Penta is Pentyl.

79. The compound of claim 75, Penta-4-Amino-1-(4-methylphenyl)piperidine-4-carboxylic acid-(D)Phe-Arg-Trp-Gly-NH$_2$, wherein Penta is Pentyl.

80. The compound of claim 71, wherein R$^9$ is a linear or branched alkoxy having from 1 to 3 carbon atoms, or unsubstituted phenoxy.

81. The compound of claim 80, Penta-4-Amino-1-(3-methoxyphenyl)piperidine-4-carboxylic acid-(D)Phe-Arg-Trp-Gly-NH$_2$, wherein Penta is Pentyl.

82. The compound of claim 80, Penta-4-Amino-1-(4-phenoxyphenyl)piperidine-4-carboxylic acid-(D)Phe-Arg-Trp-Gly-NH$_2$, wherein Penta is Pentyl.

83. The compound of claim 71, wherein R$^9$ is chloro.

84. The compound of claim 83, Penta-4-Amino-1-(4-chlorophenyl)piperidine-4-carboxylic acid-(D)Phe-Arg-Trp-Gly-NH$_2$, wherein Penta is Pentyl.

85. A compound of the formula:

II

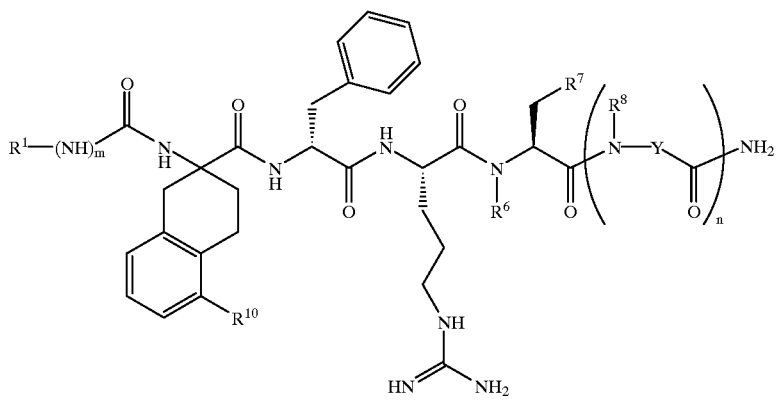

-continued

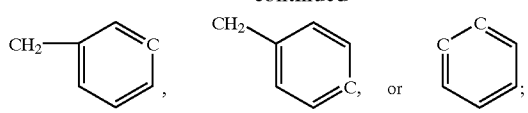

and wherein m is 0 or 1;

n is 0 or 1;

R$^1$ is an unsubstituted linear or branched alkyl having from 4 to 8 carbon atoms; linear or branched alkyl having from 1 to 8 carbon atoms mono-substituted by phenyl or carboxyl; or unsubstituted phenyl; or phenyl mono-substituted by fluoro, chloro or linear or branched alkyl having from 1 to 4 carbon atoms;

R⁷ is

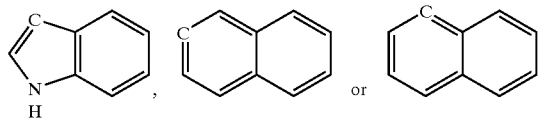

Y is

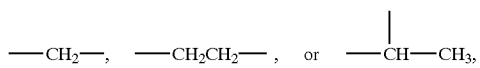

and R⁸ is hydrogen or methyl; or

Y is

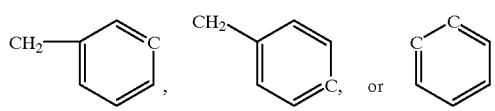

and R⁸ is hydrogen;

R¹⁰ is hydrogen, halo, linear or branched alkyl having from 1 to 3 carbon atoms, linear or branched alkoxy having from 1 to 3 carbon atoms, or —NR¹²R¹³ wherein R¹² and R¹³ are each independently a linear or branched alkyl having from 1 to 3 carbons or together are —(CH₂)$_q$— wherein q is 3,4 or 5.

86. The compound of claim 85, wherein R⁶ and R⁸ are each hydrogen; R⁷ is

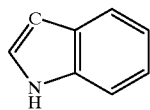

and n is 1.

87. The compound of claim 86, wherein Y is —CH₂— and m is 0.

88. The compound of claim 87, wherein R¹⁰ is hydrogen, or a linear or branched alkyl having from 1 to 3 carbon atoms.

89. The compound of claim 88, Bu-2-Aminotetraline-2-carboxylic acid-(D)Phe-Arg-Trp-Gly-NH₂, wherein Bu is Butyl.

90. The compound of claim 88, Penta-5-Methyl-(D,L)-2-aminotetraline-2-carboxylic acid-(D)Phe-Arg-Trp-Gly-NH₂, wherein Penta is Pentyl.

91. The compound of claim 88, Penta-5-Ethyl-(D,L)-2-aminotetraline-2-carboxylic acid-(D)Phe-Arg-Trp-Gly-NH₂, wherein Penta is Pentyl.

92. The compound of claim 88, Penta-5-Isopropyl-(D,L)-2-aminotetraline-2-carboxylic acid-(D)Phe-Arg-Trp-Gly-NH₂, wherein Penta is Pentyl.

93. The compound of claim 87, wherein R¹⁰ is halo.

94. The compound of claim 93, Penta-5-Bromo-(D,L)-2-aminotetraline-2-carboxylic acid-(D)Phe-Arg-Trp-Gly-NH₂, wherein Penta is Pentyl.

95. The compound of claim 93, Penta-5-Bromo-2-aminotetraline-2-carboxylic acid-(D)Phe-Arg-Trp-Gly-NH₂, wherein Penta is Pentyl.

96. The compound of claim 93, Penta-5-Chloro-(D,L)-2-aminotetraline-2-carboxylic acid-(D)Phe-Arg-Trp-Gly-NH₂, wherein Penta is Pentyl.

97. The compound of claim 87, wherein R¹⁰ is linear or branched alkoxy having from 1 to 3 carbon atoms.

98. The compound of claim 97, Penta-5-Methoxy-(D,L)-2-aminotetraline-2-carboxylic acid-(D)Phe-Arg-Trp-Gly-NH₂, wherein Penta is Pentyl.

99. The compound of claim 97, Penta-5-Ethoxy-(D,L)-2-aminotetraline-2-carboxylic acid-(D)Phe-Arg-Trp-Gly-NH₂, wherein Penta is Pentyl.

100. The compound of claim 97, Penta-5-Isopropoxy-(D,L)-2-aminotetraline-2-carboxylic acid-(D)Phe-Arg-Trp-Gly-NH₂, wherein Penta is Pentyl.

101. The compound of claim 87, wherein R¹⁰ is —NR¹²R¹³ and R¹² and R¹³ are both methyl.

102. The compound of claim 101, Penta-5-Dimethylamino-2-aminotetraline-2-carboxylic acid-(D)Phe-Arg-Trp-Gly-NH₂, wherein Penta is Pentyl.

103. The compound of claim 86, wherein Y is

and R¹⁰ is halo.

104. The compound of claim 103, Bu-(D,L)-5-Bromo-2-aminotetraline-2-carboxylic acid-(D)Phe-Arg-Trp-2-Aminobenzoic acid-NH₂, wherein Bu is Butyl.

105. The compound of claim 103, Bu-carbamoyl-(D,L)-5-Bromo-2-aminotetraline-2-carboxylic acid-(D)Phe-Arg-Trp-2-Aminobenzoic acid-NH₂, wherein Bu is Butyl.

106. The compound of claim 103, Phenylacetyl-(D,L)-5-Bromo-2-aminotetraline-2-carboxylic acid-(D)Phe-Arg-Trp-2-Aminobenzoic acid-NH₂.

107. The compound of claim 85, wherein R⁶ and R⁸ are hydrogen; R⁷ is

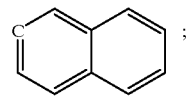

and R¹⁰ is halo.

108. The compound of claim 107, Penta-(D,L)-5-Bromo-2-aminotetraline-2-carboxylic acid-(D)Phe-Arg-(2)-Naphthylalanine-Gly-NH₂, wherein Penta is Pentyl.

109. The compound of claim 107, 3-carboxylpropanoyl-(D,L)-5-Bromo-2-aminotetraline-2-carboxylic acid-(D)Phe-Arg-(2)-Naphthylalanine-Gly-NH₂.

110. The compound of claim 107, Phenylacetyl-(D,L)-5-Bromo-2-aminotetraline-2-carboxylic acid-(D)Phe-Arg-(2)-Naphthylalanine-Gly-NH₂.

111. The compound of claim 107, Bu-(D,L)-5-Bromo-2-aminotetraline-2-carboxylic acid-(D)Phe-Arg-(2)-Naphthylalanine-2-Aminobenzoic acid-NH₂, wherein Bu is Butyl.

112. A compound of the formula:

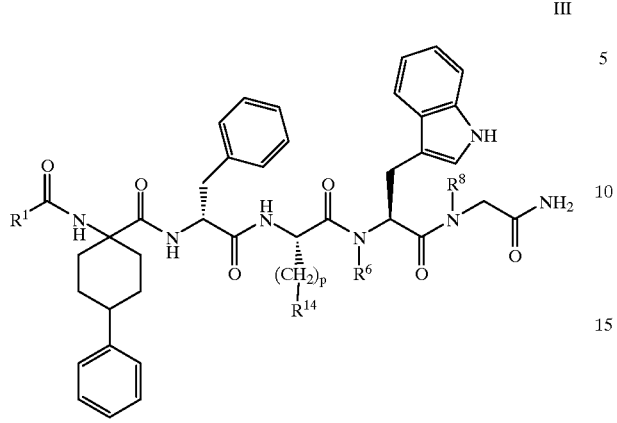

III wherein
R¹ is unsubstituted linear or branched alkyl having from 4 to 8 carbon atoms;
R⁶ is hydrogen or methyl;
R⁸ is hydrogen or methyl;
p is 2, 3 or 4 and R¹⁴ is

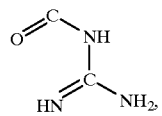

or p is 4 and R¹⁴ is

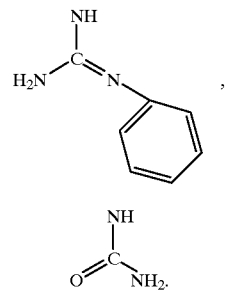

113. The compound of claim 112, Penta-1-Amino-4-phenylcyclohexane-1-carboxylic acid-(D)Phe-acylguanidine-Trp-Gly-NH₂, wherein Penta is Pentyl.

114. The compound of claim 112, Bu-1-Amino-4-phenylcyclohexane-1-carboxylic acid-(D)Phe-PhenylhomoArg-Trp-Gly-NH₂, wherein Bu is Butyl.

115. The compound of claim 112, Penta-1-Amino-4-phenylcyclohexane-1-carboxylic acid-(D)Phe-Citrulline-Trp-Gly-NH₂, wherein Penta is Pentyl.

116. A compound, Penta-1-Amino-4-diphenylcyclohexane-1-carboxylic acid-(D)Phe-Arg-Trp-Gly-NH₂, wherein Penta is Pentyl.

117. A compound, Penta-1-Amino-4-phenylcyclohex-3-ene-1-carboxylic acid-(D)Phe-Arg-Trp-Gly-NH₂, wherein Penta is Pentyl.

* * * * *